United States Patent
Tamayo et al.

(10) Patent No.: US 12,054,476 B2
(45) Date of Patent: *Aug. 6, 2024

(54) KIF18A INHIBITORS

(71) Applicant: AMGEN INC., Thousand Oaks, CA (US)

(72) Inventors: Nuria A. Tamayo, Newbury Park, CA (US); Abhisek Banerjee, Karnataka (IN); James Alexander Brown, Moorpark, CA (US); Michael J Frohn, Thousand Oaks, CA (US); Jian Jeffrey Chen, Camarillo, CA (US); Kexue Li, Newbury Park, CA (US); Qingyian Liu, Camarillo, CA (US); Jonathan Dante Low, Reseda, CA (US); Vu Ma, Oak Park, CA (US); Liping H. Pettus, Thousand Oaks, CA (US); Mary Catherine Walton, Pacifica, CA (US); Ana Elena Minatti, Los Angeles, CA (US); Matthew Paul Bourbeau, Woodland Hills, CA (US); Lei Jia, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 17/551,105

(22) Filed: Dec. 14, 2021

(65) Prior Publication Data
US 2022/0106293 A1 Apr. 7, 2022

Related U.S. Application Data

(63) Continuation of application No. 16/724,119, filed on Dec. 20, 2019, now Pat. No. 11,236,069.

(60) Provisional application No. 62/783,061, filed on Dec. 20, 2018.

(51) Int. Cl.
| | |
|---|---|
| *C07D 401/14* | (2006.01) |
| *C07D 401/12* | (2006.01) |
| *C07D 405/14* | (2006.01) |
| *C07D 413/14* | (2006.01) |
| *C07D 419/14* | (2006.01) |
| *C07D 491/107* | (2006.01) |

(52) U.S. Cl.
CPC ......... *C07D 401/14* (2013.01); *C07D 401/12* (2013.01); *C07D 405/14* (2013.01); *C07D 413/14* (2013.01); *C07D 419/14* (2013.01); *C07D 491/107* (2013.01)

(58) Field of Classification Search
CPC .................................................... C07D 401/14
See application file for complete search history.

(56) References Cited

U.S. PATENT DOCUMENTS

| | | |
|---|---|---|
| 5,100,883 A | 3/1992 | Schiehser |
| 5,118,677 A | 6/1992 | Caufield |
| 5,118,678 A | 6/1992 | Wenling |
| 5,120,842 A | 6/1992 | Failli |
| 5,151,413 A | 9/1992 | Caufield |
| 5,256,790 A | 10/1993 | Nelson |
| 5,258,389 A | 11/1993 | Goulet et al. |
| 5,521,184 A | 5/1996 | Zimmermann |
| 5,650,415 A | 7/1997 | Tang et al. |
| 5,656,643 A | 8/1997 | Spada et al. |
| 5,712,291 A | 1/1998 | D'Amato |
| 5,728,813 A | 3/1998 | Lyman et al. |
| 5,747,498 A | 5/1998 | Schnur et al. |
| 5,770,599 A | 6/1998 | Gibson |
| 5,789,427 A | 8/1998 | Chen et al. |
| 5,792,783 A | 8/1998 | Cho et al. |
| 5,861,510 A | 1/1999 | Piscopio et al. |

(Continued)

FOREIGN PATENT DOCUMENTS

| | | |
|---|---|---|
| AU | 199665580 | 3/1997 |
| AU | 199665580 B2 | 3/1997 |

(Continued)

OTHER PUBLICATIONS

McMahon et al. (2000).*

(Continued)

*Primary Examiner* — Paul V Ward

(74) *Attorney, Agent, or Firm* — MORRISON & FOERSTER LLP

(57) ABSTRACT

Compounds of formula (I):

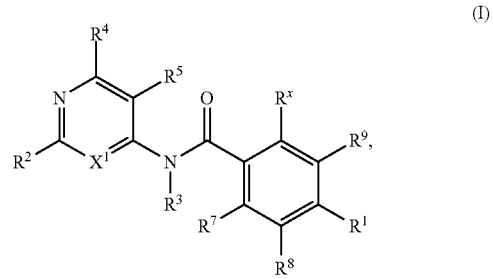

as defined herein, and synthetic intermediates thereof, which are capable of modulating KIF18A protein thereby influencing the process of cell cycle and cell proliferation to treat cancer and cancer-related diseases. The invention also includes pharmaceutical compositions, including the compounds, and methods of treating disease states related to the activity of KIF18A.

31 Claims, No Drawings

(56) References Cited

U.S. PATENT DOCUMENTS

| | | |
|---|---|---|
| 5,863,949 A | 1/1999 | Robinson et al. |
| 5,892,112 A | 4/1999 | Levy et al. |
| 5,969,110 A | 10/1999 | Beckmann et al. |
| 5,981,245 A | 11/1999 | Fox et al. |
| 5,990,141 A | 11/1999 | Hirth et al. |
| 6,057,124 A | 5/2000 | Bartley |
| 6,111,090 A | 8/2000 | Gorman et al. |
| 6,232,447 B1 | 5/2001 | Ceretti |
| 6,235,764 B1 | 5/2001 | Larson et al. |
| 6,258,812 B1 | 7/2001 | Bold et al. |
| 6,413,932 B1 | 7/2002 | Cerretti et al. |
| 6,515,004 B1 | 2/2003 | Misra et al. |
| 6,596,852 B2 | 7/2003 | Cerretti et al. |
| 6,630,500 B2 | 10/2003 | Gingrich |
| 6,656,963 B2 | 12/2003 | Firestone et al. |
| 6,713,485 B2 | 3/2004 | Carter |
| 6,727,225 B2 | 4/2004 | Wiley |
| 7,025,962 B1 | 4/2006 | Gorman et al. |
| 7,423,018 B2 | 9/2008 | Pereira et al. |
| 7,618,632 B2 | 11/2009 | Collins et al. |
| 7,812,135 B2 | 10/2010 | Smith et al. |
| 8,044,057 B2 | 10/2011 | Moss et al. |
| 8,388,967 B2 | 3/2013 | Smith et al. |
| 8,486,950 B2 | 7/2013 | Goodacre et al. |
| 8,586,023 B2 | 11/2013 | Shiku et al. |
| 8,591,886 B2 | 11/2013 | Ponath et al. |
| 11,236,069 B2 * | 2/2022 | Tamayo ............. C07D 491/107 |
| 2002/0042368 A1 | 4/2002 | Fanslow et al. |
| 2003/0105091 A1 | 6/2003 | Riedl et al. |
| 2003/0162712 A1 | 8/2003 | Corretti |
| 2004/0241760 A1 | 12/2004 | Pereira et al. |
| 2006/0287302 A1 | 12/2006 | Coleman et al. |
| 2008/0020461 A1 | 1/2008 | Pereira et al. |
| 2009/0012085 A1 | 1/2009 | Baum |
| 2009/0312365 A1 | 12/2009 | Qian et al. |
| 2010/0021420 A1 | 1/2010 | Lyons et al. |
| 2010/0183550 A1 | 7/2010 | Vennemann et al. |
| 2010/0317643 A1 | 12/2010 | Goodacre et al. |
| 2016/0115128 A1 | 4/2016 | Aida et al. |
| 2021/0226492 A1 | 7/2021 | Chen et al. |
| 2021/0253987 A1 | 8/2021 | Engler et al. |
| 2021/0297759 A1 | 9/2021 | Haller et al. |
| 2022/0002311 A1 | 1/2022 | Tamayo et al. |
| 2022/0056015 A1 | 2/2022 | Tamayo et al. |
| 2022/0073504 A1 | 3/2022 | Tamayo et al. |
| 2022/0267855 A1 | 8/2022 | Han et al. |
| 2022/0281843 A1 | 9/2022 | Tamayo et al. |
| 2022/0289724 A1 | 9/2022 | Tamayo et al. |
| 2022/0372018 A1 | 11/2022 | Tamayo et al. |
| 2023/0147507 A1 | 5/2023 | Cogan |
| 2023/0151432 A1 | 5/2023 | Payton et al. |
| 2023/0382889 A1 | 11/2023 | Cogan |
| 2023/0406860 A1 | 12/2023 | Lanman et al. |

FOREIGN PATENT DOCUMENTS

| | | |
|---|---|---|
| DE | 196 29 652 A1 | 1/1998 |
| DE | 19629652 | 1/1998 |
| EP | 0 039 051 B1 | 7/1985 |
| EP | 0039051 | 7/1985 |
| EP | 0 090 505 B1 | 8/1990 |
| EP | 0090505 | 8/1990 |
| EP | 0 566 226 B1 | 11/1995 |
| EP | 0566226 | 11/1995 |
| EP | 0 818 442 A2 | 1/1996 |
| EP | 0818442 | 1/1996 |
| EP | 0 407 122 B1 | 10/1996 |
| EP | 0407122 | 10/1996 |
| EP | 0 520 722 B1 | 12/1996 |
| EP | 0520722 | 12/1996 |
| EP | 0 606 046 B1 | 10/1997 |
| EP | 0 682 027 B1 | 10/1997 |
| EP | 0606046 | 10/1997 |
| EP | 0682027 | 10/1997 |
| EP | 0 837 063 A1 | 4/1998 |
| EP | 0837063 | 4/1998 |
| EP | 0 770 622 B1 | 2/2000 |
| EP | 0770622 | 2/2000 |
| EP | 1 187 017 A2 | 3/2002 |
| EP | 1187017 | 3/2002 |
| EP | 0 931 788 B1 | 6/2002 |
| EP | 0931788 | 6/2002 |
| EP | 0 780 386 B1 | 10/2002 |
| EP | 0780386 | 10/2002 |
| EP | 0 787 772 B1 | 9/2003 |
| EP | 0787772 | 9/2003 |
| EP | 1 004 578 B1 | 2/2004 |
| EP | 1004578 | 2/2004 |
| EP | 0 970 070 B1 | 10/2004 |
| EP | 0970070 | 10/2004 |
| EP | 1 786 785 B1 | 7/2010 |
| EP | 1786785 | 7/2010 |
| EP | 2295543 | 3/2011 |
| EP | 1 866 339 B1 | 5/2013 |
| EP | 1866339 | 5/2013 |
| EP | 1 947 183 B1 | 7/2013 |
| EP | 1947183 | 7/2013 |
| EP | 3823147 | 5/2021 |
| EP | 3897852 | 10/2021 |
| EP | 3897855 | 10/2021 |
| EP | 3898616 | 10/2021 |
| EP | 4007752 | 6/2022 |
| EP | 4007753 | 6/2022 |
| EP | 4007756 | 6/2022 |
| JP | 02233610 A | 9/1990 |
| JP | H02233610 | 9/1990 |
| JP | 2008503501 A | 1/2006 |
| JP | 2009514866 A | 4/2009 |
| JP | 2012529470 A | 12/2010 |
| JP | 2022513967 A | 6/2020 |
| JP | 2022513971 A | 6/2020 |
| JP | 2022514268 A | 6/2020 |
| WO | 90/05719 A1 | 5/1990 |
| WO | WO 1990/005719 | 5/1990 |
| WO | 92/05179 A1 | 4/1992 |
| WO | WO 1992/005179 | 4/1992 |
| WO | 92/20642 A1 | 11/1992 |
| WO | WO 1992/020642 | 11/1992 |
| WO | 93/11130 A1 | 6/1993 |
| WO | WO 1993/011130 | 6/1993 |
| WO | 94/02136 A1 | 2/1994 |
| WO | 94/02485 A1 | 2/1994 |
| WO | WO 1994/002136 | 2/1994 |
| WO | WO 1994/002485 | 2/1994 |
| WO | 94/09010 A1 | 4/1994 |
| WO | WO 1994/009010 | 4/1994 |
| WO | 95/09847 A1 | 4/1995 |
| WO | WO 1995/009847 | 4/1995 |
| WO | 95/14023 A1 | 5/1995 |
| WO | WO 1995/014023 | 5/1995 |
| WO | 95/16691 A1 | 6/1995 |
| WO | WO 1995/016691 | 6/1995 |
| WO | 95/19774 A1 | 7/1995 |
| WO | 95/19970 A1 | 7/1995 |
| WO | WO 1995/019774 | 7/1995 |
| WO | WO 1995/019970 | 7/1995 |
| WO | 96/27583 A1 | 9/1996 |
| WO | WO 1996/027583 | 9/1996 |
| WO | 96/30347 A1 | 10/1996 |
| WO | 96/31510 A1 | 10/1996 |
| WO | 96/33172 A1 | 10/1996 |
| WO | 96/33980 A1 | 10/1996 |
| WO | WO 1996/030347 | 10/1996 |
| WO | WO 1996/031510 | 10/1996 |
| WO | WO 1996/033172 | 10/1996 |
| WO | WO 1996/033980 | 10/1996 |
| WO | 96/41807 A1 | 12/1996 |
| WO | WO 1996/041807 | 12/1996 |
| WO | 97/02266 A1 | 1/1997 |
| WO | WO 1997/002266 | 1/1997 |
| WO | 97/13771 A1 | 4/1997 |
| WO | WO 1997/013771 | 4/1997 |
| WO | 97/19065 A1 | 5/1997 |
| WO | WO 1997/019065 | 5/1997 |

(56) References Cited

FOREIGN PATENT DOCUMENTS

| | | |
|---|---|---|
| WO | 97/27199 A1 | 7/1997 |
| WO | WO 1997/027199 | 7/1997 |
| WO | 97/30034 A1 | 8/1997 |
| WO | WO 1997/030034 | 8/1997 |
| WO | 97/32880 A1 | 9/1997 |
| WO | 97/32881 A1 | 9/1997 |
| WO | 97/34895 A1 | 9/1997 |
| WO | WO 1997/032880 | 9/1997 |
| WO | WO 1997/032881 | 9/1997 |
| WO | WO 1997/034895 | 9/1997 |
| WO | 97/38983 A1 | 10/1997 |
| WO | 97/38994 A1 | 10/1997 |
| WO | WO 1997/038983 | 10/1997 |
| WO | WO 1997/038994 | 10/1997 |
| WO | 97/49688 A1 | 12/1997 |
| WO | WO 1997/049688 | 12/1997 |
| WO | 98/02434 A1 | 1/1998 |
| WO | 98/02437 A1 | 1/1998 |
| WO | 98/02438 A1 | 1/1998 |
| WO | 98/02441 A2 | 1/1998 |
| WO | 98/03516 A1 | 1/1998 |
| WO | WO 1998/002434 | 1/1998 |
| WO | WO 1998/002437 | 1/1998 |
| WO | WO 1998/002438 | 1/1998 |
| WO | WO 1998/002441 | 1/1998 |
| WO | WO 1998/003516 | 1/1998 |
| WO | 98/07697 A1 | 2/1998 |
| WO | 98/07726 A1 | 2/1998 |
| WO | WO 1998/007697 | 2/1998 |
| WO | WO 1998/007726 | 2/1998 |
| WO | 98/14449 A1 | 4/1998 |
| WO | 98/14450 A1 | 4/1998 |
| WO | 98/14451 A1 | 4/1998 |
| WO | 98/17662 A1 | 4/1998 |
| WO | WO 1998/014449 | 4/1998 |
| WO | WO 1998/014450 | 4/1998 |
| WO | WO 1998/014451 | 4/1998 |
| WO | WO 1998/017662 | 4/1998 |
| WO | 98/30566 A1 | 7/1998 |
| WO | WO 1998/030566 | 7/1998 |
| WO | 98/33768 A1 | 8/1998 |
| WO | 98/33798 A2 | 8/1998 |
| WO | 98/34915 A1 | 8/1998 |
| WO | 98/34918 A1 | 8/1998 |
| WO | WO 1998/033768 | 8/1998 |
| WO | WO 1998/033798 | 8/1998 |
| WO | WO 1998/34915 | 8/1998 |
| WO | WO 1998/34918 | 8/1998 |
| WO | 99/07701 A1 | 2/1999 |
| WO | 99007675 A1 | 2/1999 |
| WO | WO 1999/007675 | 2/1999 |
| WO | WO 1999/007701 | 2/1999 |
| WO | 99/20758 A1 | 4/1999 |
| WO | WO 1999/020758 | 4/1999 |
| WO | 99/29667 A1 | 6/1999 |
| WO | WO 1999/029667 | 6/1999 |
| WO | 99/35132 A1 | 7/1999 |
| WO | 99/35146 A1 | 7/1999 |
| WO | WO 1999/035132 | 7/1999 |
| WO | WO 1999/035146 | 7/1999 |
| WO | 99/40196 A1 | 8/1999 |
| WO | WO 1999/040196 | 8/1999 |
| WO | 99/45009 A1 | 9/1999 |
| WO | WO 1999/045009 | 9/1999 |
| WO | 99/52889 A1 | 10/1999 |
| WO | 99/52910 A1 | 10/1999 |
| WO | WO 1999/052889 | 10/1999 |
| WO | WO 1999/052910 | 10/1999 |
| WO | 99/61422 A1 | 12/1999 |
| WO | WO 1999/061422 | 12/1999 |
| WO | 00/02871 A1 | 1/2000 |
| WO | WO 2000/002871 | 1/2000 |
| WO | 00/12089 A1 | 3/2000 |
| WO | WO 2000/012089 | 3/2000 |
| WO | 00/59509 A1 | 10/2000 |
| WO | WO 2000/059509 | 10/2000 |
| WO | 01/03720 A2 | 1/2001 |
| WO | WO 2001/003720 | 1/2001 |
| WO | 01/14387 A1 | 3/2001 |
| WO | WO 2001/014387 | 3/2001 |
| WO | 01/32651 A1 | 5/2001 |
| WO | 01/37820 A2 | 5/2001 |
| WO | WO 2001/032651 | 5/2001 |
| WO | WO 2001/037820 | 5/2001 |
| WO | WO 2002/012268 | 2/2002 |
| WO | 02/55501 A2 | 7/2002 |
| WO | WO 2002/055501 | 7/2002 |
| WO | 02/59110 A1 | 8/2002 |
| WO | 02/66470 A1 | 8/2002 |
| WO | WO 2002/059110 | 8/2002 |
| WO | WO 2002/066470 | 8/2002 |
| WO | 02/068406 A3 | 9/2002 |
| WO | WO 2002/068406 | 9/2002 |
| WO | 2004/05279 A2 | 1/2004 |
| WO | 2004/07458 A1 | 1/2004 |
| WO | 2004/07481 A2 | 1/2004 |
| WO | 2004/09784 A2 | 1/2004 |
| WO | WO 2004/005279 | 1/2004 |
| WO | WO 2004/007458 | 1/2004 |
| WO | WO 2004/007481 | 1/2004 |
| WO | WO 2004/009784 | 1/2004 |
| WO | WO 2004/039774 | 5/2004 |
| WO | WO 2004/045543 | 6/2004 |
| WO | 2005/005434 A1 | 1/2005 |
| WO | 2005/007190 A1 | 1/2005 |
| WO | WO 2005/005434 | 1/2005 |
| WO | WO 2005/007190 | 1/2005 |
| WO | 2005/011700 A1 | 2/2005 |
| WO | 2005/016252 A2 | 2/2005 |
| WO | WO 2005/011700 | 2/2005 |
| WO | WO 2005/016252 | 2/2005 |
| WO | 2005/055808 A2 | 6/2005 |
| WO | WO 2005/055808 | 6/2005 |
| WO | 2005/115451 A2 | 12/2005 |
| WO | WO 2005/115451 | 12/2005 |
| WO | WO 2006/002236 | 1/2006 |
| WO | 2006/044453 A1 | 4/2006 |
| WO | WO 2006/044453 | 4/2006 |
| WO | 2006/083289 A3 | 8/2006 |
| WO | WO 2006/083289 | 8/2006 |
| WO | 2006/121168 A1 | 11/2006 |
| WO | 2006/122806 A3 | 11/2006 |
| WO | WO 2006/114788 | 11/2006 |
| WO | WO 2006/121168 | 11/2006 |
| WO | WO 2006/122806 | 11/2006 |
| WO | WO 2007/056078 | 5/2007 |
| WO | 2007/133822 A1 | 11/2007 |
| WO | WO 2007/133822 | 11/2007 |
| WO | WO 2008/015265 | 2/2008 |
| WO | 2008/070740 A1 | 6/2008 |
| WO | WO 2008/070740 | 6/2008 |
| WO | 2009/036082 A2 | 3/2009 |
| WO | WO 2009/036082 | 3/2009 |
| WO | 2009/055730 A1 | 4/2009 |
| WO | WO 2009/055730 | 4/2009 |
| WO | 2010/003118 A1 | 1/2010 |
| WO | WO 2010/003118 | 1/2010 |
| WO | 2011/028683 A1 | 3/2011 |
| WO | WO 2011/028683 | 3/2011 |
| WO | 2011/051726 A2 | 5/2011 |
| WO | WO 2011/051726 | 5/2011 |
| WO | 2011/085261 A1 | 7/2011 |
| WO | 2011/090754 A1 | 7/2011 |
| WO | WO 2011/085261 | 7/2011 |
| WO | WO 2011/090754 | 7/2011 |
| WO | WO 2012/159565 | 11/2012 |
| WO | 2013/039954 A1 | 3/2013 |
| WO | WO 2013/039954 | 3/2013 |
| WO | 2015/020184 A1 | 2/2015 |
| WO | WO 2015/183776 | 12/2015 |
| WO | WO 2016/100882 | 6/2016 |
| WO | WO 2016/168660 | 10/2016 |
| WO | WO 2016/187508 | 11/2016 |
| WO | WO 2017/162663 | 9/2017 |

(56) References Cited

FOREIGN PATENT DOCUMENTS

| | | |
|---|---|---|
| WO | WO 2019/140380 | 7/2019 |
| WO | WO 2020/035195 | 2/2020 |
| WO | WO 2020/132648 | 6/2020 |
| WO | WO 2020/132649 | 6/2020 |
| WO | WO 2020/132651 | 6/2020 |
| WO | WO 2020/132653 | 6/2020 |
| WO | WO 2020/206385 | 10/2020 |
| WO | WO 2020/226333 | 11/2020 |
| WO | WO 2021/011634 | 1/2021 |
| WO | WO 2021/026098 | 2/2021 |
| WO | WO 2021/026099 | 2/2021 |
| WO | WO 2021/026100 | 2/2021 |
| WO | WO 2021/026101 | 2/2021 |
| WO | WO 2021/161323 | 8/2021 |
| WO | WO 2021/211549 | 10/2021 |
| WO | WO 2021/231413 | 11/2021 |
| WO | WO 2022/214054 | 10/2022 |
| WO | WO 2022/268230 | 12/2022 |
| WO | WO 2023/004075 | 1/2023 |
| WO | WO 2023/028564 | 3/2023 |
| WO | WO 2023/041055 | 3/2023 |
| WO | WO 2023/061478 | 4/2023 |
| WO | WO 2023/088441 | 5/2023 |
| WO | WO 2023/146979 | 8/2023 |
| WO | WO 2023/198209 | 10/2023 |
| WO | WO 2023/212240 | 11/2023 |
| WO | WO 2023/212714 | 11/2023 |

OTHER PUBLICATIONS

Pinedo et al. (2000).*
Berge, S. M. et al., "Pharmaceutical Salts," *J. Pharm. Sci.*, 66(1):1-19 (1977).
Buur, A., Bundgaard, H. and Falch, E., "Prodrugs of 5-fluorouracil. IV. Hydrolysis kinetics, bioactivation and physicochemical properties of various N-acyloxymethyl derivatives of 5-fluorouracil," *International Journal of Pharmaceutics*, 24(1):43-60, Elsevier (1985).
Goldberg, M.V. et al., "Role of PD-1 and its ligand, B7-H1, in early fate decisions of CD8 T cells," *Blood*, 110(1):186-192 (2007).
Goldstein, N. I. et al., "Biological efficacy of a chimeric antibody to the epidermal growth factor receptor in a human tumor xenograft model," *Clin. Cancer Res.*, 1(11):1311-1318 (1995).
Huang, S. M. et al., "Epidermal Growth Factor Receptor Blockade With C225 Modulates Proliferation, Apoptosis, and Radiosensitivity in Squamous Cell Carcinomas of the Head and Neck," *Cancer Res.* 15:59(8):1935-1940 (1999).
Svensson, Leif-å and Tunek, Anders, "The design and bioactivation of presystemically stable prodrugs," *Drug Metabolism Reviews*, 19:2:165-194 (1988).
Yang, X. et al., "Eradication of established tumors by a fully human monoclonal antibody to the epidermal growth factor receptor without concomitant chemotherapy," *Cancer Res.* 59:1236-1243 (1999).
Yu, Y. et al., "The Role of Kinesin Family Proteins in Tumorigenesis and Progression—Potential Biomarkers and Molecular Targets for Cancer Therapy", *Cancer*, 116:5150-5160 (2010).
Zhang, C. et al., "KIF18A is involved in human breast carcinogenesis," *Carcinogenesis*, 31(9):1676-1684 (2010) doi: 10.1093/carcin/bgq134. Epub Jul. 1, 2010. See also: https://www.proteinatlas.org/ENSG00000121621-KIF18A/pathology.
McMahon, G., "VEGF Receptor Signaling in Tumor Angiogenesis," *The Oncologist*, 5(suppl. 1):3-10 (2000).
Pinedo, H. M. et al., "Translational Research: The Role of VEGF in Tumor Angiogenesis," *The Oncologist*, 5(suppl. 1):1-2 (2000).
Girgis, A. S., "Novel synthesis of nicotinamide derivatives of cytotoxic properties," *Bioorganic & Medicinal Chemistry*, Elsevier, NL, 14(13):4466-4476 (2006).
Braun, Joachim et al., "Synthesis and Biological Evaluation of Optimized Inhibitors of the Mitotic Kinesin KIF18A," ACS Chemical Biology, 10(2):554-560 (2014).
U.S. Appl. No. 18/580,564, filed Jan. 18, 2024, by Wu et al. (Copy not provided). (Copy not submitted herewith pursuant to the waiver of 37 C.F. R. § 1.98(a)(2)(iii) issued by the Office on Sep. 21, 2004).
ATCC Accession No. HB-8508 Mab C225.
Barnett, S. F et al. "Identification and characterization of pleckstrin-homology-domain-dependent and isoenzyme-specific Akt inhibitors," Biochem. J, 385(2):399-408 (2005).
Berge et al., "Pharmaceutical Salts," J Pharmaceutical Sciences (1977) 66(1):1-19.
Braun et al., "Synthesis and biological evaluation of optimized inhibitors of the mitotic kinesin Kif18A," ACS Chem Biol. (2015) 10(2):554-560.
Buur, A. et al., "Prodrugs of 5-fluorouracil. IV. Hydrolysis kinetics, bioactivation and physicochemical properties of various N-acyloxymethyl derivatives of 5-fluorouracil," International Journal of Pharmaceutics, 24(1):43-60, Elsevier (1985).
Dasmahapatra, G. P. et al., "In vitro Combination Treatment with Perifosine and UCN-01 Demonstrates Synergism against Prostate (PC-3) and Lung (A549) Epithelial Adenocarcinoma Cell Lines," Clin. Cancer Res. 10(15):5242-5252 (2004).
Gennaro, Remington's Pharmaceutical Sciences, 18th ed., Mack Publishing Co, Easton, Pennsylvania, 1435-1712 (1990) (Table of Contents Only).
Gills, J. J. and Dennis, P.A., "The development of phosphatidylinositol ether lipid analogues as inhibitors of the serine/threonine kinase, Akt," Expert Opin. Investig. Drugs, 13(7):787-797) (2004).
Girgis et al., "Novel synthesis of nicotinamide derivatives of cytotoxic properties," Bioorganic & Medicinal Chemistry (2006) 14(13):4466-4476.
Goldberg, M.V. et al., "Role of PD-1 and its ligand, B7-HI, in early fate decisions of CD8 T cells," Blood, 110(1): 186-192 (2007).
Goldstein, N. I. et al., "Biological efficacy of a chimeric antibody to the epidermal growth factor receptor in a human tumor xenograft model," Clin. Cancer Res., 1(11): 1311-1318 (1995).
Huang, S. M. et al., "Epidermal Grm\1h Factor Receptor Blockade With C225 Modulates Proliferation, Apoptosis, and Radiosensitivity in Squamous Cell Carcinomas of the Head and Neck," Cancer Res. 15:59(8): 1935-1940 (1999).
Jin, X. et al. "Inhibition of AKT survival pathway by a small molecule inhibitor in human endometrial cancer cells," Br. J. Cancer, 91(10):1808-1812 (2004).
Kim et al., "Decarboxylative acylation of indolines with α-keto acids under palladium catalysis: a facile strategy for the synthesis of 7-substituted indoles," Chem Commun (2014) 50:14249-14252.
Kim et al., "Decarboxylative acylation of indolines with α-keto acids under palladium catalysis: a facile strategy for the synthesis of 7-substituted indoles," Chem Commun (2014) 50:14249-14252, and Supplementary Information, pages S1-S80.
Mayr, M. I., et al., "The Human Kinesin Kif18A Is a Motile Microtubule Depolymerase Essential for Chromosome Congression," Current Biology, 17(6):488-498 (2007).
Modjtahedi, H. et al., Br. J Cancer, 67:247-253 (1993).
Nagahara, M. et al., "Kinesin 18A expression: clinical relevance to colorectal cancer progression", Int. J Cancer, 129:2543-2552 (2011).
Paez, J. G., et al., "EGFR Mutations In Lung Cancer Correlation With Clinical Response To Gefitinib Therapy," Science, 304(5676): 1497-500 (2004).
Rath, O. and Kozielski, F., "Kinesins and cancer," Nature Review Cancer, 12:527-539 (2012).
Sammeta et al., "A New Chemotype of Chemically Tractable Nonsteroidal Estrogens Based on a Thieno[2,3- d]pyrimidine Core," ACS Med Chem Lett (2022) 13(7):1151-1158.
Sammeta et al., "A New Chemotype of Chemically Tractable Nonsteroidal Estrogens Based on a Thieno[2,3- d]pyrimidine Core," ACS Med Chem Lett (2022) 13(7):1151-1158. Supporting Information, compound Z1841446907, p. S3.
Sarkar, F. H. and Li, Y., "Indole-3-Carbinol and Prostate Cancer," International Research Conference on Food, Nutrition, and Cancer, J Nutr. 134(12 Suppl):3493S- 3498S (2004).
STN Registry No. 1449770-19-7, entered Sep. 5, 2013, 4 pages.
STN Registry No. 1578401-55-4, entered Apr. 1, 2014, 3 pages.
STN Registry No. 1582899-72-6, entered Apr. 10, 2014, 3 pages.
STN Registry No. 1632322-51-0, entered Nov. 11, 2014, 4 pages.
STN Registry No. 2184103-96-4, File Registry on STN, entered STN Mar. 4, 2018.

(56) References Cited

OTHER PUBLICATIONS

Svensson, Leif-a and Tunek, Anders, "The design and bioactivation of presystemically stable prodrugs," Drug Metabolism Reviews, 19:2: 165-194 (1988).

Teramoto, T. et al., "Inhibitory effect of anti-epidermal growth factor receptor antibody on a human gastric cancer," Cancer Supplement, 77(8):639-645 (1996).

Thompson, R.H. et al., "PD-1 Is expressed by tumor-infiltrating immune cells and is associated with poor outcome for patients with renal cell carcinoma," Clin. Cancer Res., 13(6): 1757-1761 (2007).

Traxler, P., "Tyrosine kinase inhibitors in cancer treatment (Part II)," Exp. Opin. Ther. Patents, 8(12): 1599-1625 (1998).

Yan, L., et al., "Pharmacogenetics and Pharmacogenomics In Oncology Therapeutic Antibody Development," BioTechniques, 39(4): 565-568 (2005).

Yang, L et al., "Akt/Protein Kinase B Signaling Inhibitor-2, a Selective Small Molecule Inhibitor of Akt Signaling with Antitumor Activity in Cancer Cells Overexpressing Akt," Cancer Res. 64:4394-4399 (2004).

Yang, X. et al., "Eradication of established tumors by a fully human monoclonal antibody to the epidermal grovth factor receptor without concomitant chemotherapy," Cancer Res. 59: 1236-1243 (1999).

Yu, Y. et al., "The Role of Kinesin Fanlily Proteins in Tumorigenesis and Progression-Potential Biomarkers and Molecular Targets for Cancer Therapy", Cancer, 116:5150-5160 (2010).

Zeng et al., "Design, Synthesis and biological activity evaluation of novel N-Acylation substituted isatin derivatives," Advanced Materials Research (2013) 683:34-37.

Zhang, C. et al., "KIF 18A is involved in human breast carcinogenesis," Carcinogenesis, 31(9):1676-1684 (2010) doi: 10.1093/carcin/bgq134. Epub Jul. 1, 2010. See also: http://www.proteinatlas.org/ENSG00000121621-KIF18A/pathology.

* cited by examiner

KIF18A INHIBITORS

RELATED APPLICATION

This application is a continuation application of U.S. Non-Provisional application Ser. No. 16/724,119, having a filing date of Dec. 20, 2019, now allowed, which claims the benefit of U.S. Provisional Application No. 62/783,061, filed Dec. 20, 2018, which specification is incorporated herein by reference in its entirety.

The invention relates to the field of pharmaceutical agents and, more specifically, is directed to compounds and compositions useful for modulating KIF18A, and to uses and methods for managing cell proliferation and for treating cancer.

BACKGROUND OF THE INVENTION

Cancer is one of the most widespread diseases afflicting mankind and a major cause of death worldwide. In an effort to find an effective treatment or a cure for one or more of the many different cancers, over the last couple of decades, numerous groups have invested a tremendous amount of time, effort and financial resources. However, to date, of the available cancer treatments and therapies, only a few offer any considerable degree of success.

Cancer is often characterized by unregulated cell proliferation. Damage to one or more genes, responsible for the cellular pathways, which control progress of proliferation through the cell cycle and centrosome cycle, can cause the loss of normal regulation of cell proliferation. These deregulated genes can code for various tumor suppressor or oncogene proteins, which participate in a cascade of events, leading to unchecked cell-cycling progression and cell proliferation. Various kinase and kinesin proteins have been identified, which play key roles in cell cycle and mitotic regulation and progression of normal dividing cells and cancer cells.

Kinesins are molecular motors that play important roles in cell division and intracellular vesicle and organelle transport. Mitotic kinesin plays roles in several aspects of spindle assembly, chromosome segregation, centrosome separation and dynamics (reviewed in O. Rath and F. Kozielski, *Nature Review Cancer*, 12:527-39, 2012). Human kinesins are categorized into 14 subfamilies based on sequence homology within the socalled "motor domain", this domains ATPase activity drives unidirectional movement along microtubules (MTs). The non-motor domain of these proteins is responsible for cargo attachment; a "cargo" can include any one of a variety of different membranous organelles, signal transduction scaffolding systems, and chromosomes. Kinesins use the energy of ATP hydrolysis to move cargo along polarized microtubules. Thus, kinesins are often called "plus-end" or "minus-end" directed motors.

KLF18A gene belongs to Kinesin-8 subfamily and is a plus-end-directed motor. KIF18A is believed to influence dynamics at the plus end of kinetochore microtubules to control correct chromosome positioning and spindle tension. Depletion of human KIF18A leads to longer spindles, increased chromosome oscillation at metaphase, and activation of the mitotic spindle assembly checkpoint in HeLa cervical cancer cells (MI Mayr et al, *Current Biology* 17, 488-98, 2007). KIF18A appears to be viable target for the treatment of cancer. KIF18A is overexpressed in various types of cancers, including but not limited to colon, breast, lung, pancreas, prostate, bladder, head, neck, cervix, and ovarian cancers. Further, genetic deletion or knockdown, or inhibition of KIF18A effects mitotic spindle apparatus in cancer cell lines. Particularly, inhibition of KIF18A has been found to induce mitotic cell arrest, a known vulnerability that can promote cell death in mitosis via apoptosis, mitotic catastrophe, or multipolarity driven lethality or death after mitotic slippage in interphase. Accordingly, there has been a strong interest in finding inhibitors of KIF18A proteins.

Thus, the inhibition of KIF18A ATPase activity is a promising approach for the development of novel anticancer agents.

SUMMARY OF THE INVENTION

The present invention provides a new class of compounds useful for modulating KIF18A protein alone or in a bound complex with microtubules for treating KIF18A-mediated conditions and/or diseases, including cancer, inflammation, or ciliopathologies.

The compounds provided by the invention have MT-based KIF18A modulatory activity and, in particular, KIF18A inhibitory activity. To this end, the invention also provides the use of these compounds, as well as pharmaceutically acceptable salts thereof, in the preparation and manufacture of a pharmaceutical composition or medicament for therapeutic, prophylactic, acute or chronic treatment of KIF18A mediated diseases and disorders, including without limitation, cancer. Thus, the compounds of the invention are useful in the manufacture of anti-cancer medicaments. The invention also provides processes for making compounds of Formula I, as well as intermediates useful in such processes.

In embodiment 1, the present invention provides a compound of Formula (I), A compound of formula I:

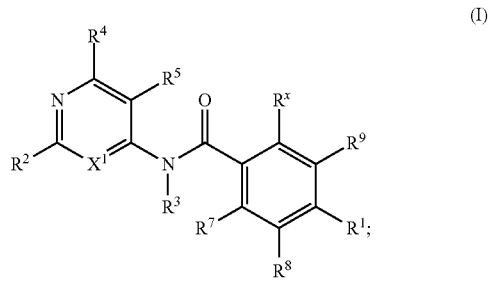

(I)

or any pharmaceutically-acceptable salt thereof, wherein:
$X^1$ is N or —$CR^6$;
$R^1$ is —CN, or a group —Z—$R^{12}$ wherein Z is —$C_{0-4}$alk-, —$NR^{11}$—, —$NR^{11}SO_2$—, —$SO_2NR^{11}$—, —$NR^{11}$—S(=O)(=NH), —S(=O)(=NH)—, —S—, —S(=O)—, —$SO_2$—, $C_{0-4}$alk-O—, —(C=O)—, —(C=O)$NR^{11}$—, —C=N(OH)—, or —$NR^{11}$(C=O); or
the group —Z—$R^{12}$ is —N=S(=O)—$(R^{12})_2$, wherein the two $R^{12}$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S;
$R^2$ is halo or a group —Y—$R^{13}$, wherein Y is —$C_{0-4}$alk-, —N($C_{0-1}$alk)-$C_{0-4}$alk-, —C(=O)$NR^aR^a$($C_{1-4}$alk), —O—$C_{0-4}$alk-, S, S=O, S(=O)$_2$, —$SO_2NR^{13}$, or —S(=O)(=NH)—;
$R^3$ is H, $C_{1-4}$alk, or $C_{1-4}$haloalk;
$R^4$ is H, halo, $R^{4a}$ or $R^{4b}$;
$R^5$ is H, halo, $C_{1-8}$alk, or $C_{1-4}$haloalk;

R⁶ is H, halo, $C_{1-8}$alk, $C_{1-4}$haloalk, —O—$C_{1-8}$alk, or —O—$R^{6a}$; wherein $R^{6a}$ is a saturated or partially-saturated 3-, 4-, 5-, or 6-membered monocyclic ring containing 0, 1, 2 or 3 N atoms and 0, 1, or 2 atoms selected from O and S;

R⁷ is H, halo, $C_{1-8}$alk, or $C_{1-4}$haloalk;

R⁸ is H, halo, $C_{1-8}$alk, $C_{1-4}$haloalk, —OH, —O—$R^{8a}$, or —O—$R^{8b}$;

R⁹ is H, halo, $C_{1-8}$alk, or $C_{1-4}$haloalk;

$R^x$ is selected from the group consisting of

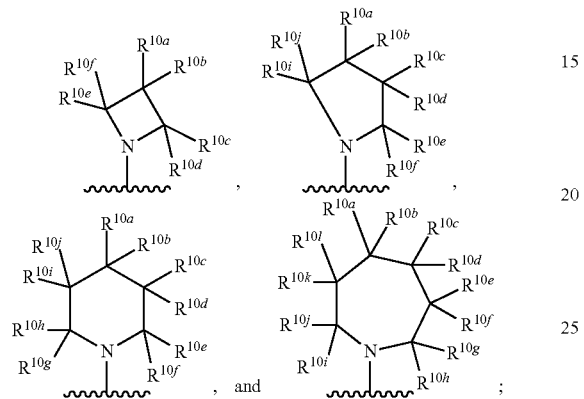

Each of $R^{10a}$, $R^{10b}$, $R^{10c}$, $R^{10d}$, $R^{10e}$, $R^{10f}$, $R^{10g}$, $R^{10h}$, $R^{10i}$, and $R^{10j}$ is H, halo, $R^{10k}$, or $R^{10l}$;

or alternatively, each of $R^{10a}$ and $R^{10b}$ pair, $R^{10c}$ and $R^{10d}$ pair, $R^{10e}$ and $R^{10f}$ pair, $R^{10g}$ and $R^{10h}$ pair, or $R^{10i}$ and $R^{10j}$ pair, independently, can combine with the carbon atom attached to each of them to form a saturated or partially-saturated 3-, 4-, 5-, 6-membered monocyclic ring spiro to the $R^x$ ring; wherein said 3-, 4-, 5-, 6-membered monocyclic ring contains 0, 1, 2 or 3 N atoms and 0, 1, or 2 atoms selected from O and S, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, —OR$^a$, —OC$_{1-4}$haloalk, CN, —NR$^a$R$^a$, or oxo;

R¹¹ is H, $R^{11a}$, or $R^{11b}$;

R¹² is H, $R^{12a}$, or $R^{12b}$;

R¹³ is $R^{13a}$ or $R^{13b}$;

$R^{4a}$, $R^{8a}$, $R^{10k}$, $R^{11a}$, $R^{12a}$, and $R^{13a}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from O and S, which is substituted by 0, 1, 2 or 3 group(s) selected from F, Cl, Br, $C_{1-6}$alk, $C_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, $R^{14}$, and oxo;

$R^{4b}$, $R^{8b}$, $R^{10l}$, $R^{11b}$, $R^{12b}$, and $R^{13b}$ is independently, at each instance, selected from the group consisting of $C_{1-6}$alk substituted by 0, 1, 2, 3, 4, or 5 group(s) selected from F, Cl, Br, —OR$^a$, —OC$_{1-4}$haloalk, or CN;

$R^{14}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo;

$R^a$ is independently, at each instance, H or $R^b$; and $R^b$ is independently, at each instance, $C_{1-6}$alk, phenyl, or benzyl, wherein the $C_{1-6}$alk is being substituted by 0, 1, 2 or 3 substituents selected from halo, —OH, —OC$_{1-4}$alk, —NH$_2$, —NHC$_{1-4}$alk, —OC(=O)C$_{1-4}$alk, or —N(C$_{1-4}$alk)C$_{1-4}$alk; and the phenyl or benzyl is being substituted by 0, 1, 2 or 3 substituents selected from halo, $C_{1-4}$alk, $C_{1-3}$haloalk, —OH, —OC$_{1-4}$alk, —NH$_2$, —NHC$_{1-4}$alk, —OC(=O)C$_{1-4}$alk, or —N(C$_{1-4}$alk)C$_{1-4}$alk.

In embodiment 2, the present invention provides compounds wherein $X^1$ is N; having the formula (Ia):

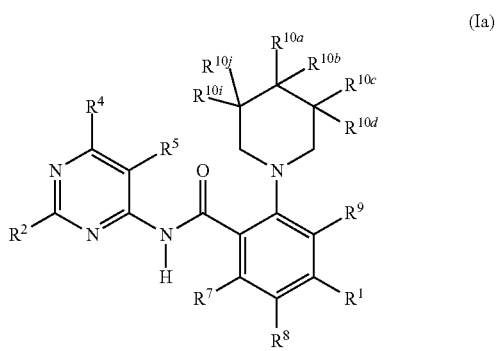

(Ia)

In embodiment 3, the present invention provides compounds wherein $X^1$ is —CR⁶; having the formula (Ib):

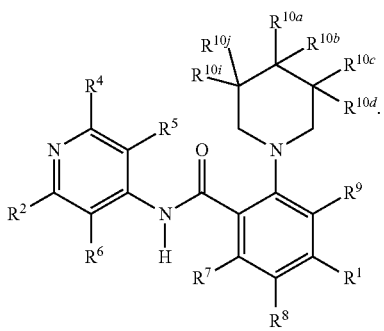

(Ib)

In embodiment 4, the present invention provides compounds wherein $R^3$ is H or methyl. Preferably, $R^3$ is H.

In embodiment 5, the present invention provides compounds wherein each of $R^{10c}$, $R^{10d}$, $R^{10e}$, $R^{10f}$, $R^{10g}$, $R^{10h}$, $R^{10i}$, and $R^{10j}$ is H, halo, $C_{1-6}$alk, or $C_{1-4}$haloalk; and each of $R^{10a}$ and $R^{10b}$ pair combine with the carbon atom attached to each of them form a saturated 3-, 4-, or 5-membered monocyclic ring spiro to the $R^x$ ring; wherein said ring contains 0, 1, 2 or 3 N atoms and 0, 1, or 2 atoms selected from O and S.

In embodiment 6, the present invention provides compounds wherein each of $R^{10c}$, $R^{10d}$, $R^{10e}$, $R^{10f}$, $R^{10g}$, $R^{10h}$, $R^{10i}$, and $R^{10j}$ is H, methyl, or ethyl; and each of $R^{10a}$ and $R^{10b}$ pair combine with the carbon atom attached to each of them form a cyclopropyl, cyclobutyl, or cyclopentyl ring spiro to the $R^x$ ring.

In embodiment 7, the present invention provides compounds in accordance with embodiments 1-6, or pharmaceutically acceptable salts thereof, wherein the group

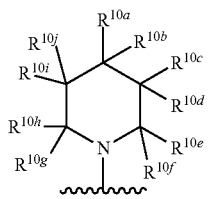

is selected from:

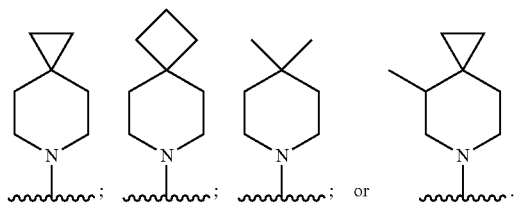

In embodiment 8, the present invention provides compounds in accordance with embodiments 1-7, or pharmaceutically acceptable salts thereof, wherein the group

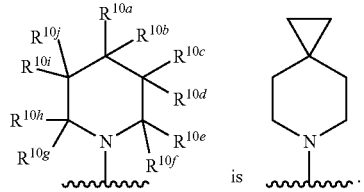

is

In embodiment 9, the present invention provides compounds in accordance with embodiments 1-8, or pharmaceutically acceptable salts thereof, wherein $R^1$ is —CN, or a group —Z—$R^{12}$, wherein Z is a bond, —NH—, —NHSO$_2$—, —SO$_2$NH—, —S(=O)(=NH)—, —S—, —S(=O)—, —SO$_2$—, —(C=O)—, —(C=O)NH—, or —NH(C=O)—; and $R^{12}$ is selected from:
(a) H;
(b) cyclopropyl, cyclobutyl, cyclopentyl, cyclohexyl, oxiranyl, oxetanyl, tetrahydrofuranyl, azetidinyl, imidazolyl, morpholinyl, pyrrolidinyl, piperazinyl,

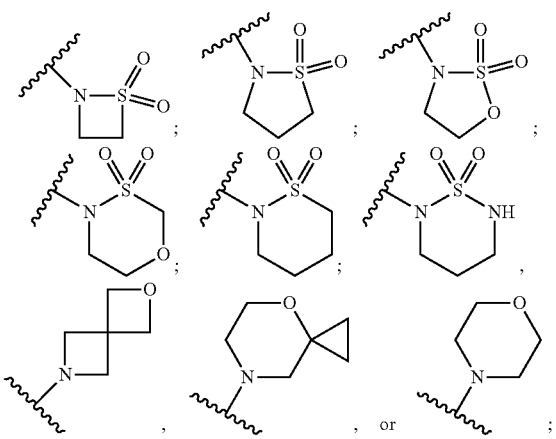

wherein each said ring is substituted by 0, 1, 2 or 3 group(s) selected from OH, F, methyl, —CH$_2$OH, —C(=O)OCH$_3$, —C(=O)OC(CH$_3$)$_3$, NH$_2$, CN, and oxo; or
(c) $C_{1-6}$alk substituted by 0, 1, 2 or 3 OH, F, —C(=O)OCH$_3$, —NH$_2$, —NH(CH$_3$), or —N(CH$_3$)$_2$.

In embodiment 10, the present invention provides compounds in accordance with embodiments 1-9, or pharmaceutically acceptable salts thereof, wherein $R^1$ is —CN, or a group —Z—$R^{12}$, wherein Z is absent, —NH—, —NHSO$_2$—, —SO$_2$NH—, —S(=O)(=NH)—, —S—, —S(=O)—, —SO$_2$—, —(C=O)—, —(C=O)NH—, or —NH(C=O)—; and
(a) $R^{12}$ is H;
(b) $R^{12}$ is oxetanyl, cyclopropyl; or
(c) $R^{12}$ is $C_{1-6}$alk substituted by 0, 1, 2 or 3 OH group(s).

In embodiment 11, the present invention provides compounds in accordance with embodiments 1-10, or pharmaceutically acceptable salts thereof, wherein the group —Z—$R^{12}$ is —N=S(=O)—($R^{12}$)$_2$, wherein the two $R^{12}$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S; which is selected from:

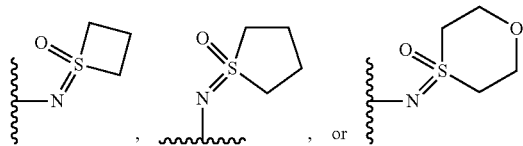

In embodiment 12, the present invention provides compounds in accordance with embodiments 1-11, or pharmaceutically acceptable salts thereof, wherein $R^1$ is a group —Z—$R^{12}$, wherein Z is —NHSO$_2$— or —SO$_2$NH—; and $R^{12}$ is oxetanyl, cyclopropyl, or $R^{12}$ is $C_{1-6}$alk substituted by 0, 1, 2 or 3 OH group(s).

In embodiment 13, the present invention provides compounds in accordance with embodiments 1-12, or pharmaceutically acceptable salts thereof, wherein $R^1$ is a group —Z—$R^{12}$, wherein Z is —NHSO$_2$— and $R^{12}$ is —CH$_2$—CH$_2$—OH.

In embodiment 14, the present invention provides compounds in accordance with embodiments 1-13, or pharmaceutically acceptable salts thereof, wherein $R^2$ is halo or a group —Y—$R^{13}$, wherein Y is a bond, —NH—, —NH—(CH$_2$)$_{0-4}$—, or —O—(CH$_2$)$_{0-4}$; and $R^{13}$ is a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —OH, —O$C_{1-4}$haloalk, CN, $R^{14}$, and oxo; or $R^{13}$ is $C_{1-6}$alk substituted by 0, 1, 2, 3, 4, or 5 group(s) selected from F, Cl, Br, —OH, —O$C_{1-4}$haloalk, or CN.

In embodiment 15, the present invention provides compounds in accordance with embodiments 1-14, or pharmaceutically acceptable salts thereof, wherein $R^2$ is a saturated 5- or 6-membered monocyclic ring wherein each said ring contains 0, 1, or 2 N atoms and 0 or 1 O atom, and wherein each said ring is substituted by 0, 1, 2 or 3 group(s) selected from F, Cl, Br, $C_{1-6}$alk, $C_{1-4}$haloalk, —OH, —O$C_{1-4}$haloalk, CN, $R^{14}$, and oxo.

In embodiment 16, the present invention provides compounds in accordance with embodiments 1-15, or pharmaceutically acceptable salts thereof, wherein $R^2$ is (a) halo; (b) a group —Y—$R^{13}$, wherein Y is a bond; and $R^{13}$ is morpholinyl, piperidinyl, azetidinyl, pyrrolidinyl, cyclopropyl, cyclobutyl, cyclopentyl, cyclohexyl, piperazinyl, tetrahydrofuranyl,

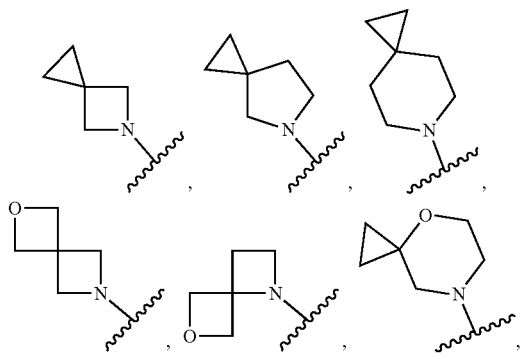

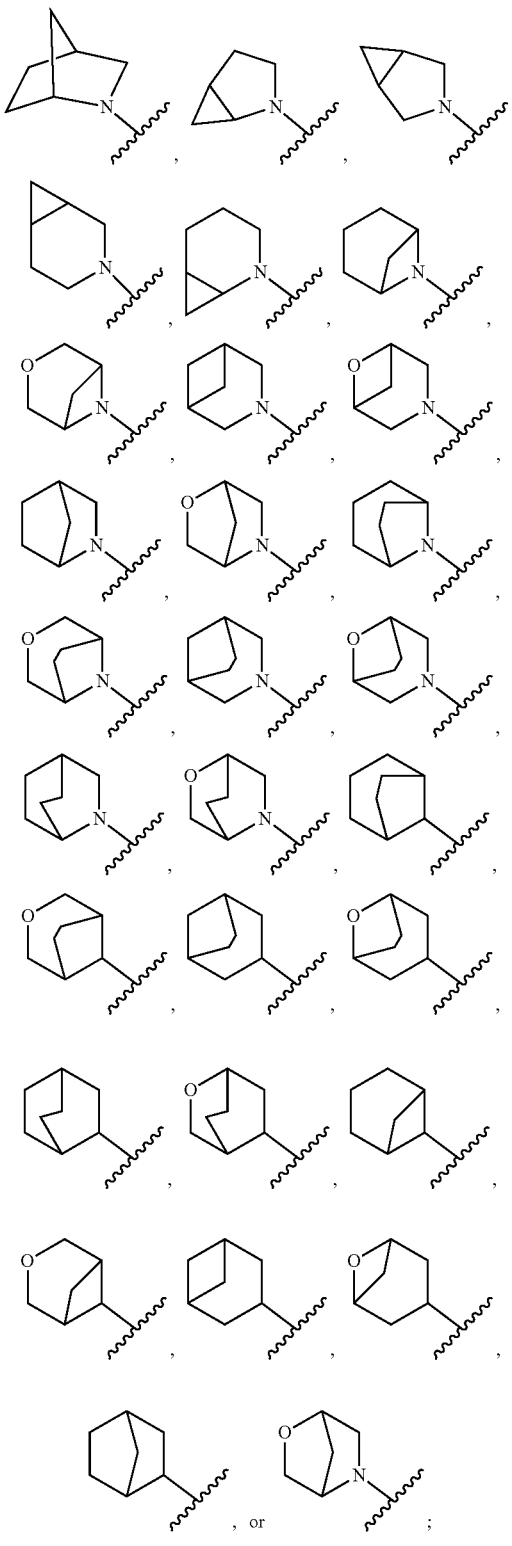

wherein each said ring is substituted by 0, 1, 2 or 3 group(s) selected from F, Cl, Br, methyl, CF$_3$, —OH, —OCHF$_2$, CN, and oxo; or (c) a group —Y—$R^{13}$, wherein Y is NH, —O—, —O—(CH$_2$)—, —O—(CH$_2$)—(CH$_2$)—, or —O—(CH$_2$)—(CH$_2$)—(CH$_2$)—, and wherein $R^{13}$ is

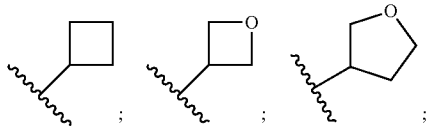 [SMILES: *C1CCC1 ; *C1COC1 ; *C1CCOC1]

or R[13] is $C_{1-6}$alk substituted by 0, 1, 2, 3, 4, or 5 group(s) selected from F, Cl, Br, methyl, $CF_3$, —OH, or CN.

In embodiment 17, the present invention provides compounds in accordance with embodiments 1-16, or pharmaceutically acceptable salts thereof, wherein $R^2$ is morpholinyl or piperidinyl substituted by 0, 1, 2 or 3 group(s) selected from F, Cl, Br, methyl, $CF_3$, —OH, —$OCHF_2$, CN, or oxo In embodiment 18, the present invention provides compounds in accordance with embodiments 1-17, or pharmaceutically acceptable salts thereof, wherein $R^2$ is morpholinyl substituted by 1, 2 or 3 methyl group(s).

In embodiment 19, the present invention provides compounds in accordance with embodiments 1-18, or pharmaceutically acceptable salts thereof, wherein $R^2$ is piperidinyl substituted by 1, 2 or 3 fluoro group(s).

In embodiment 20, the present invention provides compounds in accordance with embodiments 1-19, or pharmaceutically acceptable salts thereof, wherein $R^2$ is

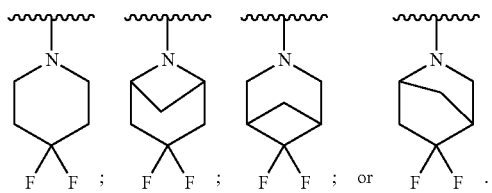

In embodiment 21, the present invention provides compounds in accordance with embodiments 1-20, or pharmaceutically acceptable salts thereof, wherein Z is a bond, —NH—, —$NHSO_2$—, —$SO_2NH$—, —N=S(=O)<$(R^a)_2$ (wherein each $R^{11}$ is independently selected from the group consisting of H, methyl, or isopropyl), —S(=O)(=NH)—, —S—, —S(=O)—, —$SO_2$—, —(C=O)—, —(C=O)NH—, or —NH(C=O)—.

In embodiment 22, the present invention provides compounds in accordance with embodiments 1-21, or pharmaceutically acceptable salts thereof, wherein $R^{12}$ is selected from (a) H; (b) $C_{1-6}$alk substituted by 0, 1, 2 or 3 group(s) selected from F, Cl, Br, —OH, —$OCH_3$, or cyclopropyl; or (c) a saturated, partially-saturated or unsaturated 3-, 4-, 5-, 6-, or 7-membered monocyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —$C_{1-6}$alkOH, —OH, —$OCH_3$, —$NH_2$, or oxo.

In embodiment 23, the present invention provides compounds in accordance with embodiments 1-22, or pharmaceutically acceptable salts thereof, wherein $R^{12}$ is selected from cyclopropyl, cyclobutyl, cyclopentyl, oxetanyl, azetidinyl, tetrahydrofuranyl, or 1,3,4-oxathiazinanyl.

In embodiment 24, the present invention provides compounds in accordance with embodiments 1-23, or pharmaceutically acceptable salts thereof, wherein $R^4$ is selected from (a) H; (b) $C_{1-6}$alk substituted by 0, 1, 2 or 3 OH group(s); or (c) cyclopropyl.

In embodiment 25, the present invention provides compounds in accordance with embodiments 1-24, or pharmaceutically acceptable salts thereof, wherein $R^4$ is methyl.

In embodiment 26, the present invention provides compounds in accordance with embodiments 1-25, or pharmaceutically acceptable salts thereof, wherein $R^5$ is H.

In embodiment 27, the present invention provides compounds in accordance with embodiments 1-26, or pharmaceutically acceptable salts thereof, wherein $R^6$ is H or F.

In embodiment 28, the present invention provides compounds in accordance with embodiments 1-27, or pharmaceutically acceptable salts thereof, wherein $R^7$ is H or F.

In embodiment 29, the present invention provides compounds in accordance with embodiments 1-28, or pharmaceutically acceptable salts thereof, wherein $R^8$ is H.

In embodiment 30, the present invention provides compounds in accordance with embodiments 1-29, or pharmaceutically acceptable salts thereof, wherein $R^9$ is H.

In embodiment 31, the present invention provides a compound, or pharmaceutically acceptable salts thereof, selected from:

| Ex. # | Chemical Structure | Name |
|-------|--------------------|------|
| 1 | 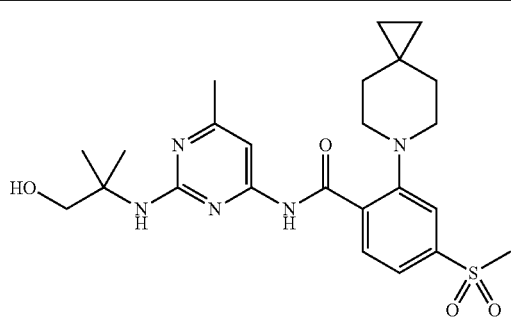 | N-(2-((1-Hydroxy-2-methylpropan-2-yl)amino)-6-methylpyrimidin-4-yl)-4-(methylsulfonyl)-2-(6-azaspiro[2.5]octan-6-yl)benzamide |

| Ex. # | Chemical Structure | Name |
|---|---|---|
| 1-7 | 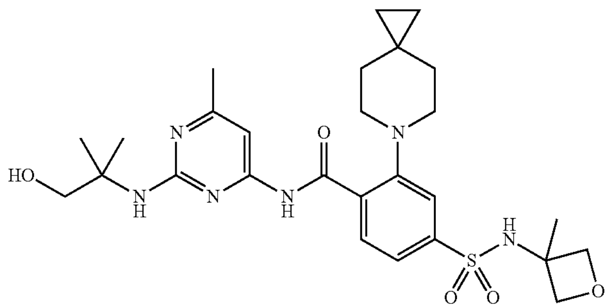 [SMILES: Cc1cc(NC(=O)c2ccc(S(=O)(=O)NC3(C)COC3)cc2N2CCC3(CC2)CC3)nc(NC(C)(C)CO)n1] | N-(2-((1-Hydroxy-2-methylpropan-2-yl)amino)-6-methylpyrimidin-4-yl)-4-(N-(3-methyloxetan-3-yl)sulfamoyl)-2-(6-azaspiro[2.5]octan-6-yl)benzamide |
| 2 | 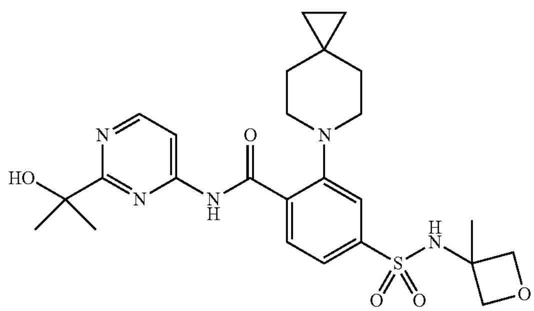 [SMILES: CC1(NS(=O)(=O)c2ccc(C(=O)Nc3ccnc(C(C)(C)O)n3)c(N3CCC4(CC3)CC4)c2)COC1] | N-(2-(2-Hydroxypropan-2-yl)pyrimidin-4-yl)-4-(N-(3-methyloxetan-3-yl)sulfamoyl)-2-(6-azaspiro[2.5]octan-6-yl)benzamide |
| 2-4 | 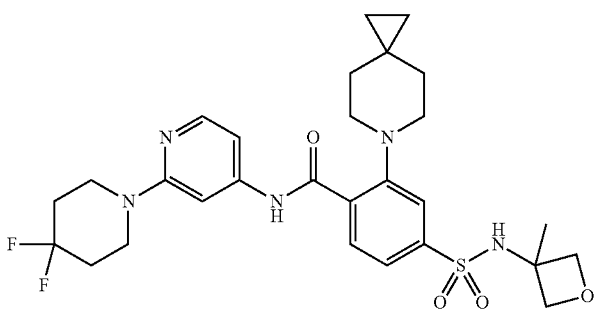 [SMILES: CC1(NS(=O)(=O)c2ccc(C(=O)Nc3ccnc(N4CCC(F)(F)CC4)c3)c(N3CCC4(CC3)CC4)c2)COC1] | N-(2-(4,4-Difluoropiperidin-1-yl)pyridin-4-yl)-4-(N-(3-methyloxetan-3-yl)sulfamoyl)-2-(6-azaspiro[2.5]octan-6-yl)benzamide |
| 2-8 | 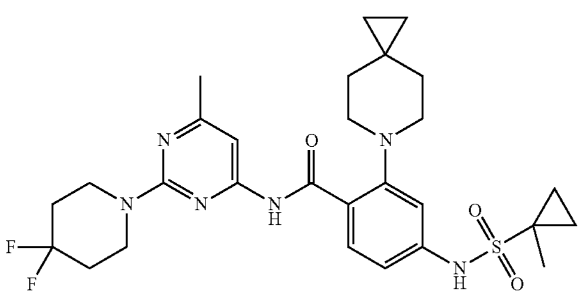 [SMILES: Cc1cc(NC(=O)c2ccc(NS(=O)(=O)C3(C)CC3)cc2N2CCC3(CC2)CC3)nc(N2CCC(F)(F)CC2)n1] | N-(2-(4,4-Difluoropiperidin-1-yl)-6-methylpyrimidin-4-yl)-4-((1-methylcyclopropane)-1-sulfonamido)-2-(6-azaspiro[2.5]octan-6-yl)benzamide |
| 3 | 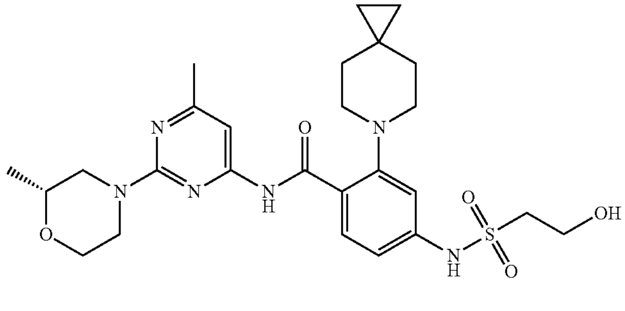 [SMILES: Cc1cc(NC(=O)c2ccc(NS(=O)(=O)CCO)cc2N2CCC3(CC2)CC3)nc(N2CCO[C@H](C)C2)n1] | (R)-4-((2-Hydroxyethyl)sulfonamido)-N-(6-methyl-2-(2-methylmorpholino)pyrimidin-4-yl)-2-(6-azaspiro[2.5]octan-6-yl)benzamide |

| Ex. # | Chemical Structure | Name |
|---|---|---|
| 4 | 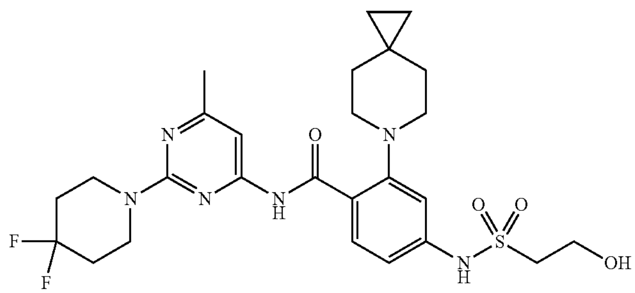 [SMILES: Cc1cc(NC(=O)c2ccc(NS(=O)(=O)CCO)cc2N2CCC3(CC2)CC3)nc(N2CCC(F)(F)CC2)n1] | N-(2-(4,4-Difluoropiperidin-1-yl)-6-methylpyrimidin-4-yl)-4-((2-hydroxyethyl)sulfonamido)-2-(6-azaspiro[2.5]octan-6-yl)benzamide |
| 5-1 | 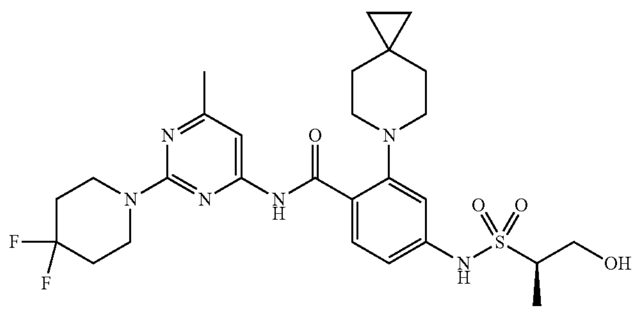 [SMILES: Cc1cc(NC(=O)c2ccc(NS(=O)(=O)[C@H](C)CO)cc2N2CCC3(CC2)CC3)nc(N2CCC(F)(F)CC2)n1] | R)-N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide |
| 5-2 | 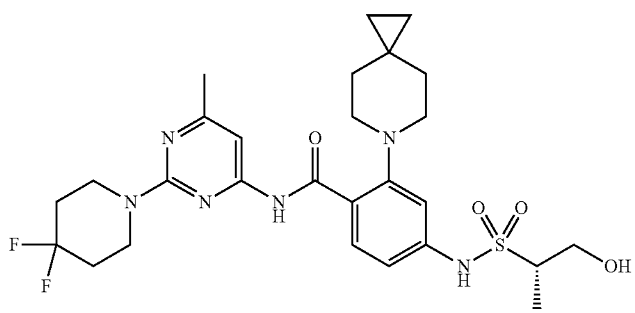 [SMILES: Cc1cc(NC(=O)c2ccc(NS(=O)(=O)[C@@H](C)CO)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide |
| 6-7 | 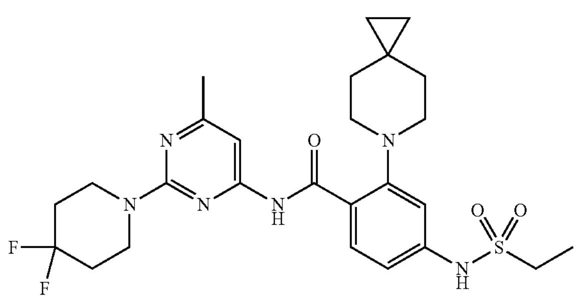 [SMILES: CCS(=O)(=O)Nc1ccc(C(=O)Nc2cc(C)nc(N3CCC(F)(F)CC3)n2)c(N2CCC3(CC2)CC3)c1] | N-(2-(4,4-Difluoropiperidin-1-yl)-6-methylpyrimidin-4-yl)-4-(ethylsulfonamido)-2-(6-azaspiro[2.5]octan-6-yl)benzamide |
| 7 | 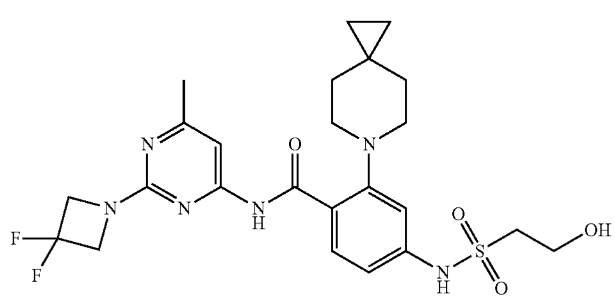 [SMILES: Cc1cc(NC(=O)c2ccc(NS(=O)(=O)CCO)cc2N2CCC3(CC2)CC3)nc(N2CC(F)(F)C2)n1] | N-(2-(3,3-Difluoroazetidin-1-yl)-6-methylpyrimidin-4-yl)-4-((2-hydroxyethyl)sulfonamido)-2-(6-azaspiro[2.5]octan-6-yl)benzamide |

| Ex. # | Chemical Structure | Name |
|---|---|---|
| 8-1 | 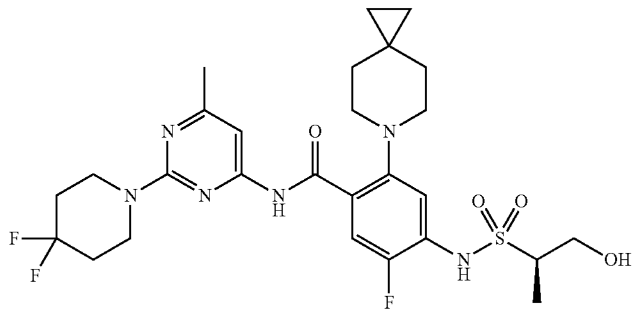 [SMILES: Cc1cc(NC(=O)c2cc(F)c(NS(=O)(=O)[C@H](C)CO)cc2N2CCC3(CC2)CC3)nc(N2CCC(F)(F)CC2)n1] | (R)-N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide |
| 8-2 | 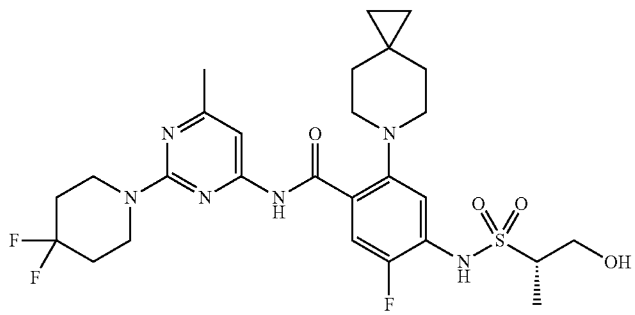 [SMILES: Cc1cc(NC(=O)c2cc(F)c(NS(=O)(=O)[C@@H](C)CO)cc2N2CCC3(CC2)CC3)nc(N2CCC(F)(F)CC2)n1] | (S)-N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide |
| 10-1 | 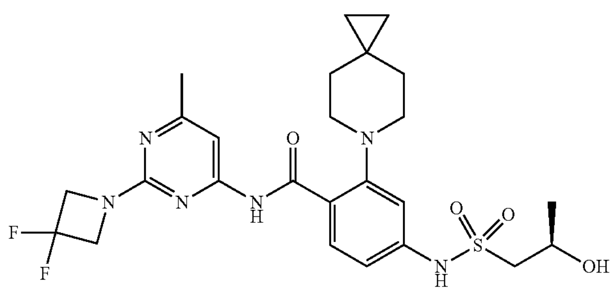 [SMILES: Cc1cc(NC(=O)c2ccc(NS(=O)(=O)C[C@@H](C)O)cc2N2CCC3(CC2)CC3)nc(N2CC(F)(F)C2)n1] | (R)-N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide |
| 10-2 | 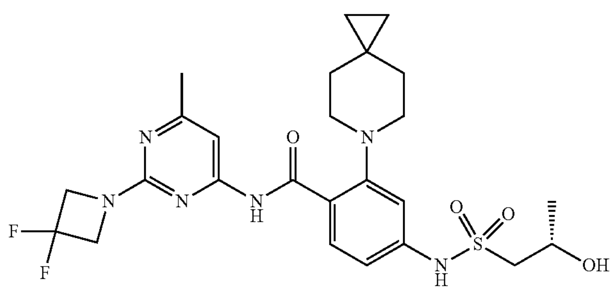 [SMILES: Cc1cc(NC(=O)c2ccc(NS(=O)(=O)C[C@H](C)O)cc2N2CCC3(CC2)CC3)nc(N2CC(F)(F)C2)n1] | (S)-N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide |
| 12 | 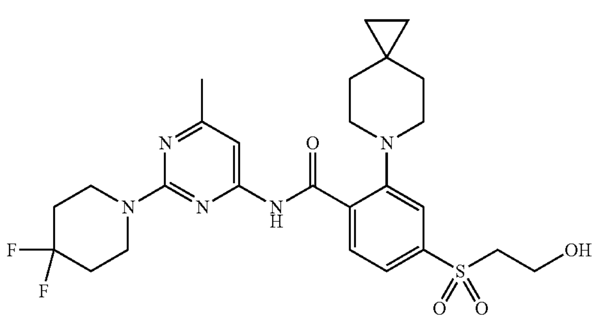 [SMILES: Cc1cc(NC(=O)c2ccc(S(=O)(=O)CCO)cc2N2CCC3(CC2)CC3)nc(N2CCC(F)(F)CC2)n1] | N-(2-(4,4-difluoropiperidin-1-yl)-6-methylpyrimidin-4-yl)-4-((2-hydroxyethyl)sulfonyl)-2-(6-azaspiro[2.5]octan-6-yl)benzamide |

| Ex. # | Chemical Structure | Name |
|---|---|---|
| 13-1 | 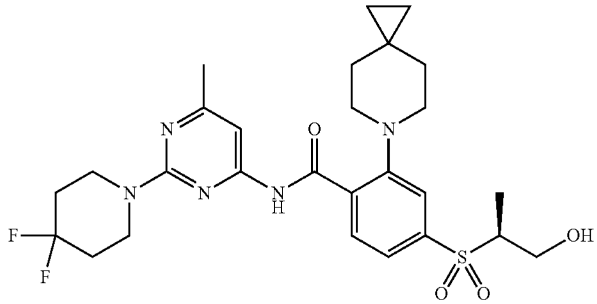 [SMILES: Cc1cc(NC(=O)c2ccc(S(=O)(=O)[C@@H](C)CO)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((1-hydroxypropan-2-yl)sulfonyl)-2-(6-azaspiro[2.5]octan-6-yl)benzamide |
| 13-2 | 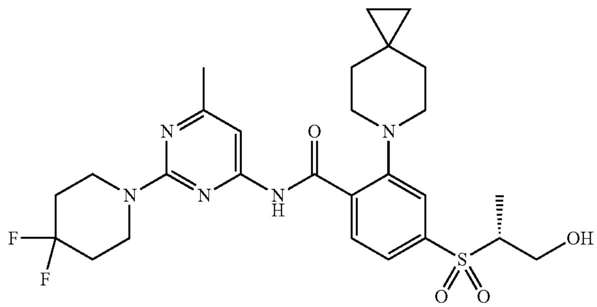 [SMILES: Cc1cc(NC(=O)c2ccc(S(=O)(=O)[C@H](C)CO)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-((1-hydroxypropan-2-yl)sulfonyl)-2-(6-azaspiro[2.5]octan-6-yl)benzamide |
| 14 | 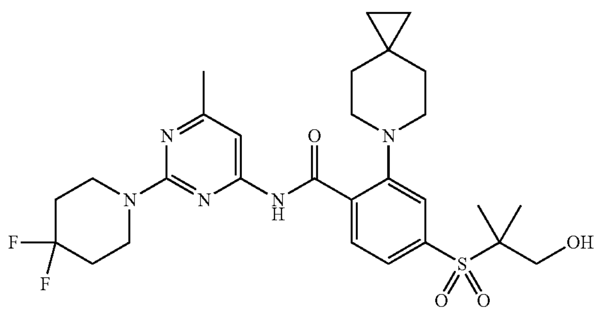 [SMILES: Cc1cc(NC(=O)c2ccc(S(=O)(=O)C(C)(C)CO)cc2N2CCC3(CC2)CC3)nc(N2CCC(F)(F)CC2)n1] | N-(2-(4,4-Difluoropiperidin-1-yl)-6-methylpyrimidin-4-yl)-4-((1-hydroxy-2-methylpropan-2-yl)sulfonyl)-2-(6-azaspiro[2.5]octan-6-yl)benzamide |
| 15 | 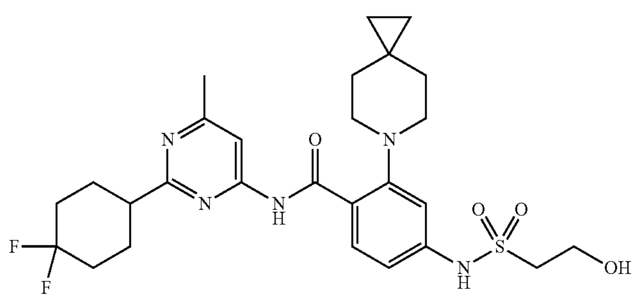 [SMILES: Cc1cc(NC(=O)c2ccc(NS(=O)(=O)CCO)cc2N2CCC3(CC2)CC3)nc(C2CCC(F)(F)CC2)n1] | N-(2-(4,4-Difluorocyclohexyl)-6-methylpyrimidin-4-yl)-4-((2-hydroxyethyl)sulfonamido)-2-(6-azaspiro[2.5]octan-6-yl)benzamide |
| 16-1 | 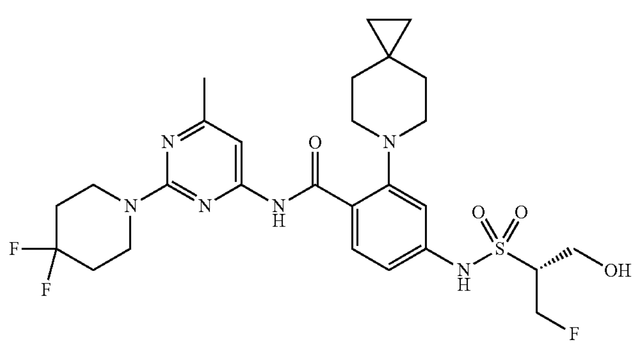 [SMILES: Cc1cc(NC(=O)c2ccc(NS(=O)(=O)[C@H](CO)CF)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide |

| Ex. # | Chemical Structure | Name |
|---|---|---|
| 16-2 | 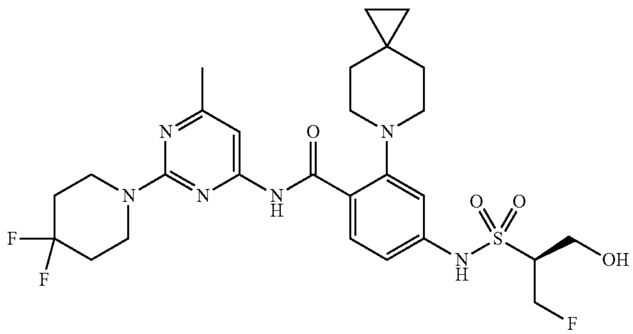 [SMILES: Cc1cc(NC(=O)c2ccc(NS(=O)(=O)[C@@H](CO)CF)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide |
| 17 | 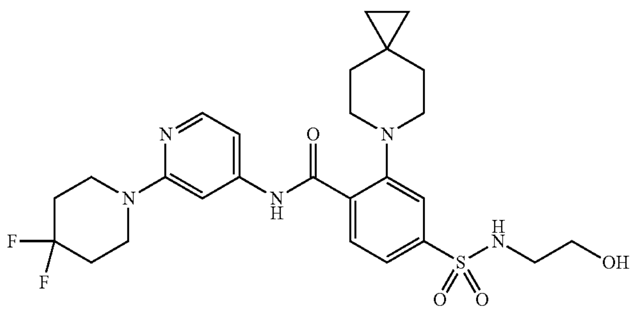 [SMILES: O=C(Nc1ccnc(N2CCC(F)(F)CC2)c1)c1ccc(S(=O)(=O)NCCO)cc1N1CCC2(CC1)CC2] | N-(2-(4,4-Difluoropiperidin-1-yl)pyridin-4-yl)-4-(N-(2-hydroxyethyl)sulfamoyl)-2-(6-azaspiro[2.5]octan-6-yl)benzamide |
| 18-1 | 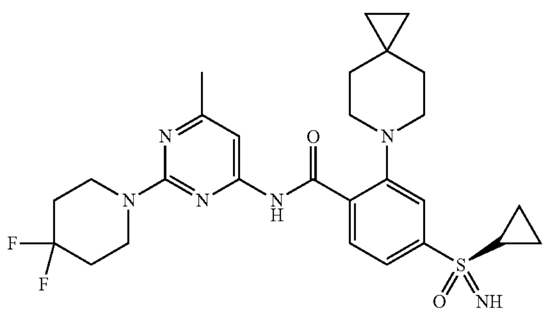 [SMILES: Cc1cc(NC(=O)c2ccc([S@](=N)(=O)C3CC3)cc2N2CCC3(CC2)CC3)nc(N2CCC(F)(F)CC2)n1] | 2-(6-Azaspiro[2.5]octan-6-yl)-4-(R-cyclopropylsulfonimidoyl)-N-(2-(4,4-difluoro-1-piperidinyl)-6-methyl-4-pyrimidinyl)benzamide |
| 18-2 | 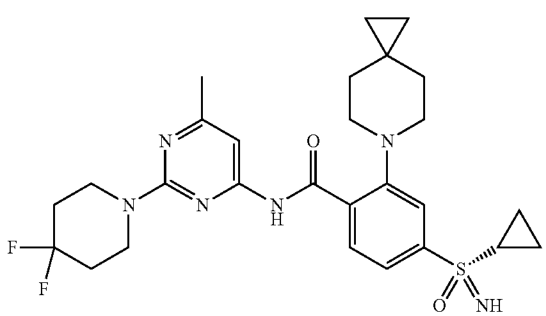 [SMILES: Cc1cc(NC(=O)c2ccc([S@@](=N)(=O)C3CC3)cc2N2CCC3(CC2)CC3)nc(N2CCC(F)(F)CC2)n1] | 2-(6-Azaspiro[2.5]octan-6-yl)-4-(S-cyclopropylsulfonimidoyl)-N-(2-(4,4-difluoro-1-piperidinyl)-6-methyl-4-pyrimidinyl)benzamide |
| 20 | 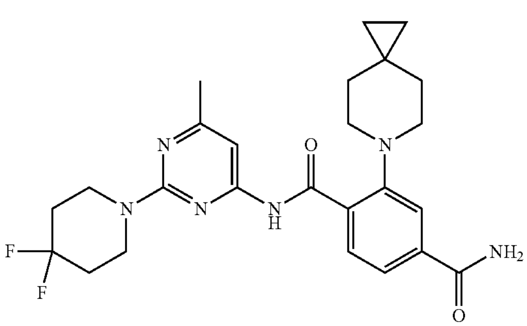 [SMILES: Cc1cc(NC(=O)c2ccc(C(N)=O)cc2N2CCC3(CC2)CC3)nc(N2CCC(F)(F)CC2)n1] | ($N^1$-(2-(4,4-Difluoropiperidin-1-yl)-6-methylpyrimidin-4-yl)-2-(6-azaspiro[2.5]octan-6-yl)terephthalamide |

| Ex. # | Chemical Structure | Name |
|---|---|---|
| 21 | 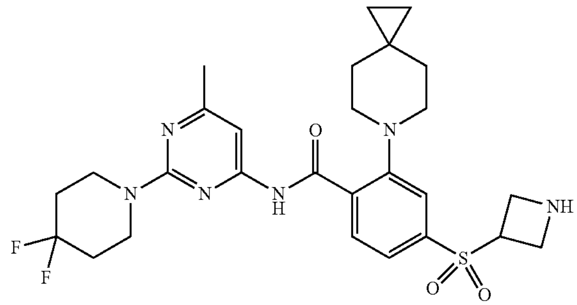 [SMILES: Cc1cc(NC(=O)c2ccc(S(=O)(=O)C3CNC3)cc2N2CCC3(CC2)CC3)nc(N2CCC(F)(F)CC2)n1] | 4-(Azetidin-3-ylsulfonyl)-N-(2-(4,4-difluoropiperidin-1-yl)-6-methylpyrimidin-4-yl)-2-(6-azaspiro[2.5]octan-6-yl)benzamide |
| 22 | | N-(2-(4,4-Difluoropiperidin-1-yl)-6-methylpyrimidin-4-yl)-4-((1-methylazetidin-3-yl)sulfonyl)-2-(6-azaspiro[2.5]octan-6-yl)benzamide | or any pharmaceutically-acceptable salt thereof.

In sub-embodiment 31a, the present invention provides N-(2-((1-Hydroxy-2-methylpropan-2-yl)amino)-6-methylpyrimidin-4-yl)-4-(methylsulfonyl)-2-(6-azaspiro[2.5]octan-6-yl)benzamide, or the pharmaceutically acceptable salt thereof.

In sub-embodiment 31b, the present invention provides N-(2-((1-Hydroxy-2-methylpropan-2-yl)amino)-6-methylpyrimidin-4-yl)-4-(N-(3-methyloxetan-3-yl)sulfamoyl)-2-(6-azaspiro[2.5]octan-6-yl)benzamide, or the pharmaceutically acceptable salt thereof.

In sub-embodiment 31c, the present invention provides N-(2-(2-Hydroxypropan-2-yl)pyrimidin-4-yl)-4-(N-(3-methyloxetan-3-yl)sulfamoyl)-2-(6-azaspiro[2.5]octan-6-yl)benzamide, or the pharmaceutically acceptable salt thereof.

In sub-embodiment 31d, the present invention provides N-(2-(4,4-Difluoropiperidin-1-yl)pyridin-4-yl)-4-(N-(3-methyloxetan-3-yl)sulfamoyl)-2-(6-azaspiro[2.5]octan-6-yl)benzamide, or the pharmaceutically acceptable salt thereof.

In sub-embodiment 31e, the present invention provides N-(2-(4,4-Difluoropiperidin-1-yl)-6-methylpyrimidin-4-yl)-4-((1-methylcyclopropane)-1-sulfonamido)-2-(6-azaspiro[2.5]octan-6-yl)benzamide, or the pharmaceutically acceptable salt thereof.

In sub-embodiment 31f, the present invention provides (R)-4-((2-Hydroxyethyl)sulfonamido)-N-(6-methyl-2-(2-methylmorpholino)pyrimidin-4-yl)-2-(6-azaspiro[2.5]octan-6-yl)benzamide, or the pharmaceutically acceptable salt thereof.

In sub-embodiment 31g, the present invention provides N-(2-(4,4-Difluoropiperidin-1-yl)-6-methylpyrimidin-4-yl)-4-((2-hydroxyethyl)sulfonamido)-2-(6-azaspiro[2.5]octan-6-yl)benzamide, or the pharmaceutically acceptable salt thereof.

In sub-embodiment 31h, the present invention provides (R)—N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide, or the pharmaceutically acceptable salt thereof.

In sub-embodiment 31i, the present invention provides (S)—N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide, or the pharmaceutically acceptable salt thereof.

In sub-embodiment 31j, the present invention provides N-(2-(4,4-Difluoropiperidin-1-yl)-6-methylpyrimidin-4-yl)-4-(ethylsulfonamido)-2-(6-azaspiro[2.5]octan-6-yl)benzamide, or the pharmaceutically acceptable salt thereof.

In sub-embodiment 31k, the present invention provides N-(2-(3,3-Difluoroazetidin-1-yl)-6-methylpyrimidin-4-yl)-4-((2-hydroxyethyl)sulfonamido)-2-(6-azaspiro[2.5]octan-6-yl)benzamide, or the pharmaceutically acceptable salt thereof.

In sub-embodiment 31l, the present invention provides (R)—N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide, or the pharmaceutically acceptable salt thereof.

In sub-embodiment 31m, the present invention provides (S)—N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide, or the pharmaceutically acceptable salt thereof.

In sub-embodiment 31n, the present invention provides (R)—N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide, or the pharmaceutically acceptable salt thereof.

In sub-embodiment 31o, the present invention provides (S)—N-(2-(3,3-Difluoroazetidin-1-yl)-6-methylpyrimidin- 4-yl)-4-((2-hydroxypropyl)sulfonamido)-2-(6-azaspiro[2.5]octan-6-yl)benzamide, or the pharmaceutically acceptable salt thereof.

In sub-embodiment 31p, the present invention provides N-(2-(4,4-difluoropiperidin-1-yl)-6-methylpyrimidin-4-yl)-4-((2-hydroxyethyl)sulfonyl)-2-(6-azaspiro[2.5]octan-6-yl)benzamide, or the pharmaceutically acceptable salt thereof.

In sub-embodiment 31q, the present invention provides (S)—N-(2-(4,4-Difluoropiperidin-1-yl)-6-methylpyrimidin-4-yl)-4-((l-hydroxypropan-2-yl)sulfonyl)-2-(6-azaspiro[2.5]octan-6-yl)benzamide, or the pharmaceutically acceptable salt thereof.

In sub-embodiment 31r, the present invention provides (R)—N-(2-(4,4-Difluoropiperidin-1-yl)-6-methylpyrimidin-4-yl)-4-((l-hydroxypropan-2-yl)sulfonyl)-2-(6-azaspiro[2.5]octan-6-yl)benzamide, or the pharmaceutically acceptable salt thereof.

In sub-embodiment 31s, the present invention provides N-(2-(4,4-Difluoropiperidin-1-yl)-6-methylpyrimidin-4-yl)-4-((l-hydroxy-2-methylpropan-2-yl)sulfonyl)-2-(6-azaspiro[2.5]octan-6-yl)benzamide, or the pharmaceutically acceptable salt thereof.

In sub-embodiment 3 It, the present invention provides N-(2-(4,4-Difluorocyclohexyl)-6-methylpyrimidin-4-yl)-4-((2-hydroxyethyl)sulfonamido)-2-(6-azaspiro[2.5]octan-6-yl)benzamide, or the pharmaceutically acceptable salt thereof.

In sub-embodiment 31u, the present invention provides (R)—N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide, or the pharmaceutically acceptable salt thereof.

In sub-embodiment 31v, the present invention provides (S)—N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide, or the pharmaceutically acceptable salt thereof.

In sub-embodiment 31w, the present invention provides N-(2-(4,4-Difluoropiperidin-1-yl)pyridin-4-yl)-4-(N-(2-hydroxyethyl)sulfamoyl)-2-(6-azaspiro[2.5]octan-6-yl)benzamide, or the pharmaceutically acceptable salt thereof.

In sub-embodiment 31x, the present invention provides 2-(6-Azaspiro[2.5]octan-6-yl)-4-(R-cyclopropylsulfonimidoyl)-N-(2-(4,4-difluoro-1-piperidinyl)-6-methyl-4-pyrimidinyl)benzamide, or the pharmaceutically acceptable salt thereof.

In sub-embodiment 31y, the present invention provides 2-(6-Azaspiro[2.5]octan-6-yl)-4-(S-cyclopropylsulfonimidoyl)-N-(2-(4,4-difluoro-1-piperidinyl)-6-methyl-4-pyrimidinyl)benzamide, or the pharmaceutically acceptable salt thereof.

In sub-embodiment 31z, the present invention provides (N$^1$-(2-(4,4-Difluoropiperidin-1-yl)-6-methylpyrimidin-4-yl)-2-(6-azaspiro[2.5]octan-6-yl)terephthalamide, or the pharmaceutically acceptable salt thereof.

In sub-embodiment 31aa, the present invention provides 4-(Azetidin-3-ylsulfonyl)-N-(2-(4,4-difluoropiperidin-1-yl)-6-methylpyrimidin-4-yl)-2-(6-azaspiro[2.5]octan-6-yl)benzamide, or the pharmaceutically acceptable salt thereof.

In sub-embodiment 31ab, the present invention provides N-(2-(4,4-Difluoropiperidin-1-yl)-6-methylpyrimidin-4-yl)-4-((1-methylazetidin-3-yl)sulfonyl)-2-(6-azaspiro[2.5]octan-6-yl)benzamide, or the pharmaceutically acceptable salt thereof.

In embodiment 32, the present invention provides pharmaceutical compositions comprising a compound, or pharmaceutically acceptable salts thereof, in accordance with any one of embodiments 1 to 31, and a pharmaceutically acceptable diluent or carrier.

In embodiment 33, the present invention provides a method of treating a condition that may be treated with KIF18a inhibitors, the method comprising administering to a patient in need thereof a therapeutically effective amount of the compound in accordance with embodiments 1 to 31, or the composition according to embodiment 31.

In embodiment 34, the present invention provides the method of embodiment 33, wherein said condition is cancer selected from the group consisting of (a) a solid or hematologically derived tumor selected from cancer of the bladder, endometrial, lung squamous cell, breast, colon, kidney, liver, lung, small cell lung cancer, esophagus, gall-bladder, brain, head and neck, ovary, pancreas, stomach, cervix, thyroid, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, or (f) a melanoma, seminoma, teratocarcinoma, osteosarcoma, xeroderma pigmentosum, keratoactanthoma, thyroid follicular cancer or Kaposi's sarcoma.

In a sub-embodiment 34a, the present invention provides the method of embodiment 33, wherein said condition is cancer selected from the group consisting of melanoma, prostate cancer, cervical cancer, breast cancer, colon cancer, sarcoma, or leukemia. See: Zhang C. et. al., "Kif18A is involved in human breast carcinogenesis", Carcinogenesis, 2010 September; 31(9): 1676-84. doi: 10.1093/carcin/bgq134. Epub 2010 Jul. 1. See also: (1) https://www.proteinatlas.org/ENSG00000121621-KIF18A/pathology; (2) Nagahara, M. et. al., "Kinesin 18A expression: clinical relevance to colorectal cancer progression", Int. J. Cancer: 129, 2543-2552 (2011) VC 2011 UIC; and (3) Yu, Y. et. al., "The Role of Kinesin Family Proteins in Tumorigenesis and Progression—Potential Biomarkers and Molecular Targets for Cancer Therapy", Cancer 2010; 116:5150-60. VC 2010 American Cancer Society. In a sub-embodiment 34b, the present invention provides the method of embodiment 33, wherein said condition is any one of the cancer specified in embodiments (a), (b), (c), (d), (e), or (f).

In embodiment 35, the present invention provides a method of reducing the size of a solid tumor in a subject, the method comprising administering to the subject in need thereof a therapeutically effective amount of the compound in accordance with any one of embodiments 1 to 31, or the composition according to embodiment 32.

In embodiment 36, the present invention provides a method of treating a cell proliferation disorder in a subject, the method comprising administering to the subject in need thereof a therapeutically effective amount of the compound in accordance with any one of embodiments 1 to 31, or the composition according to embodiment 32.

In embodiment 37, the present invention provides a method of inhibiting KIF18A in a cell, comprising contacting the cell with a compound, or pharmaceutically acceptable salts thereof, in accordance with any one of embodiments 1 to 31, or the composition according to embodiment 32.

In embodiment 38, the invention provides use of the compound or the pharmaceutically acceptable salt of said compound according to any one of embodiments 1 to 31, or the pharmaceutical composition according to embodiment 32, in the preparation of a medicament for treating a condition that may be treated with KIF18a inhibitors.

In embodiment 39, the invention provides use of embodiments 38, wherein the condition is cancer selected from the group consisting of (a) a solid or hematologically derived tumor selected from cancer of the bladder, endometrial, lung squamous cell, breast, colon, kidney, liver, lung, small cell lung cancer, esophagus, gall-bladder, brain, head and neck, ovary, pancreas, stomach, cervix, thyroid, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, or (f) a melanoma, seminoma, teratocarcinoma, osteosarcoma, xeroderma pigmentosum, keratoactanthoma, thyroid follicular cancer or Kaposi's sarcoma.

In a sub-embodiment 39a, the present invention provides the use of embodiment 33, wherein said condition is any one of the cancer specified in embodiments (a), (b), (c), (d), (e), or (f).

In embodiment 40, the invention provides use of the compound or the pharmaceutically acceptable salt of said compound according to any one of embodiments 1 to 31, or the pharmaceutical composition according to embodiment 32, in the preparation of a medicament for reducing the size of a solid tumor in a subject.

In embodiment 41, the invention provides use of the compound or the pharmaceutically acceptable salt of said compound according to any one of embodiments 1 to 31, or the pharmaceutical composition according to embodiment 32, in the preparation of a medicament for treating a cell proliferation disorder in a subject.

In embodiment 42, the invention provides use of the compound or the pharmaceutically acceptable salt of said compound according to any one of embodiments 1 to 31, or the pharmaceutical composition according to embodiment 32, in the preparation of a medicament for inhibiting KIF18A in a cell.

In embodiment 43, the invention provides a method of preparing a compound of Formula (I) as described herein.

In embodiment 44, the invention provides an intermediate compound used in the method of preparing a compound of Formula (I) as described herein.

It is to be understood that the above reference to any embodiment is intended to include any and all its sub-embodiment thereof. For example, reference to embodiment 31 includes reference to sub-embodiments 31a-31ab.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof.

Unless otherwise specified, the following definitions apply to terms found in the specification and claims:

"C$_{\alpha-\beta}$alk" means an alkyl group comprising a minimum of α and a maximum of β carbon atoms in a branched or linear relationship or any combination of the three, wherein α and β represent integers. The alkyl groups described in this section may also contain one or two double or triple bonds. A designation of C$_0$alk indicates a direct bond. Examples of C$_{1-6}$alkyl include, but are not limited to the following:

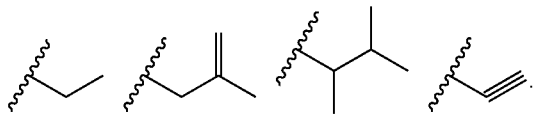

"Benzo group", alone or in combination, means the divalent radical C$_4$H$_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atom selected from F, Cl, Br and I.

"$C_{\alpha-\beta}$haloalk" means an alk group, as described above, wherein any number—at least one—of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

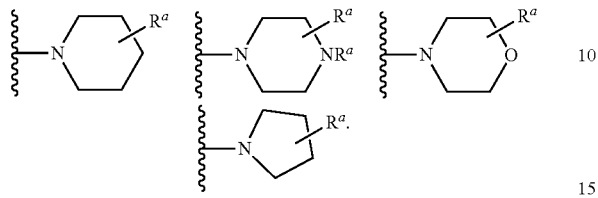

The group $N(C_{\alpha-\beta}alk) C_{\alpha-\beta}alk$, wherein $\alpha$ and $\beta$ are as defined above, include substituents where the two $C_{\alpha-\beta}alk$ groups together form a ring, optionally including a N, O or S atom, and include groups such as

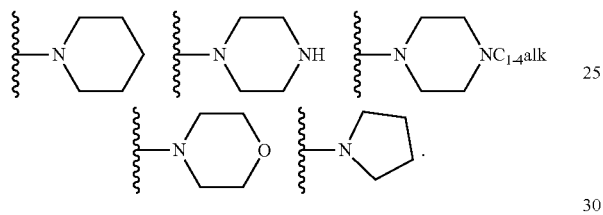

"Bicyclic ring" means a group that features two joined rings. A bicyclic ring can be carbocyclic (all of the ring atoms are carbons), or heterocyclic (the rings atoms consist, for example, 1, 2 or 3 heteroatoms, such as N, O, or S, in addition to carbon atoms). The two rings can both be aliphatic (e.g. decalin and norbornane), or can be aromatic (e.g. naphthalene), or a combination of aliphatic and aromatic (e.g. tetralin). Bicyclic rings include (a) spirocyclic compounds, wherein the two rings share only one single atom, the spiro atom, which is usually a quaternary carbon. Examples of spirocyclic compound include, but are not limited to:

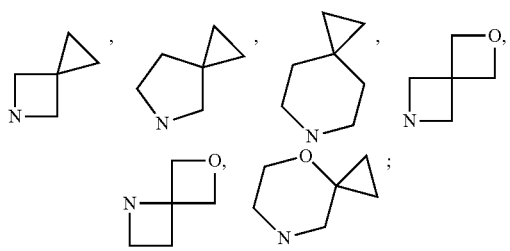

(b) fused bicyclic compounds, wherein two rings share two adjacent atoms. In other words, the rings share one covalent bond, i.e. the bridgehead atoms are directly connected (e.g. α-thujene and decalin). Examples of fused bicyclic rings include, but are not limited to:

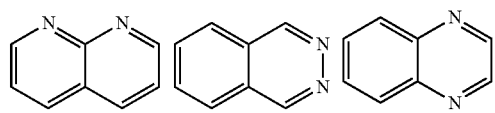

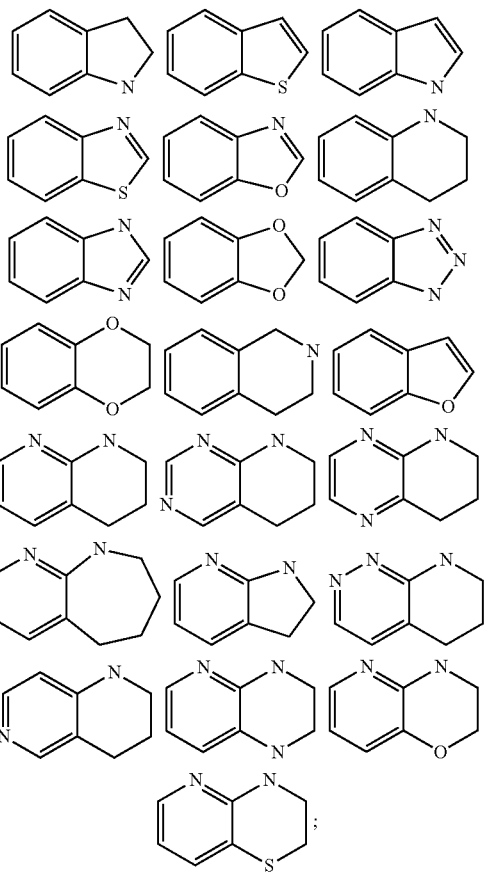

and (c) bridged bicyclic compounds, wherein the two rings share three or more atoms, separating the two bridgehead atoms by a bridge containing at least one atom. For example, norbornane, also known as bicyclo[2.2.1]heptane, can be thought of as a pair of cyclopentane rings each sharing three of their five carbon atoms. Examples of bridged bicyclic rings include, but are not limited to:

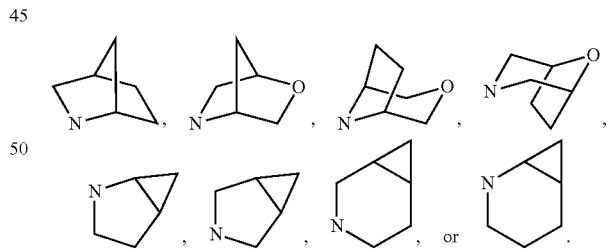

"Carbocycle" or "Carbocyclic" means a ring comprising by itself or in combination with other terms, represents, unless otherwise stated, cyclic version of "$C_{\alpha-\beta}alk$". Examples of carbocycle include cyclopentyl, cyclohexyl, 1-cyclohexenyl, 3-cyclohexenyl, cycloheptyl, cyclobutylene, cyclohexylene and the like.

"Heterocycle" or "Heterocyclic" means a ring comprising at least one carbon atom and at least one other atom selected from N, O and S. Examples of heterocycles that may be found in the claims include, but are not limited to, the following:

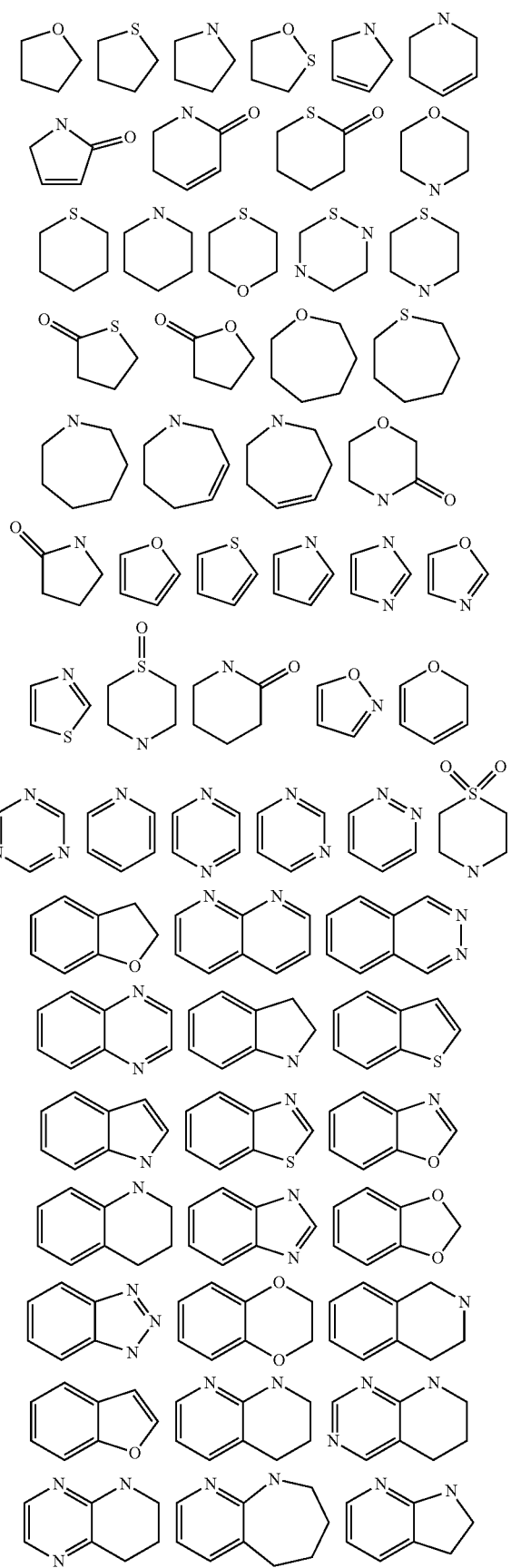
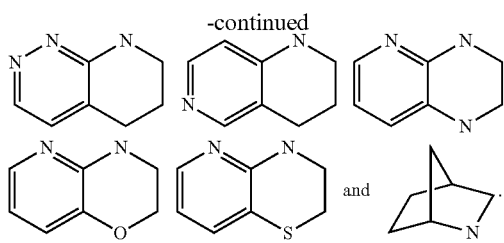

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluene sulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

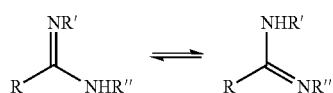

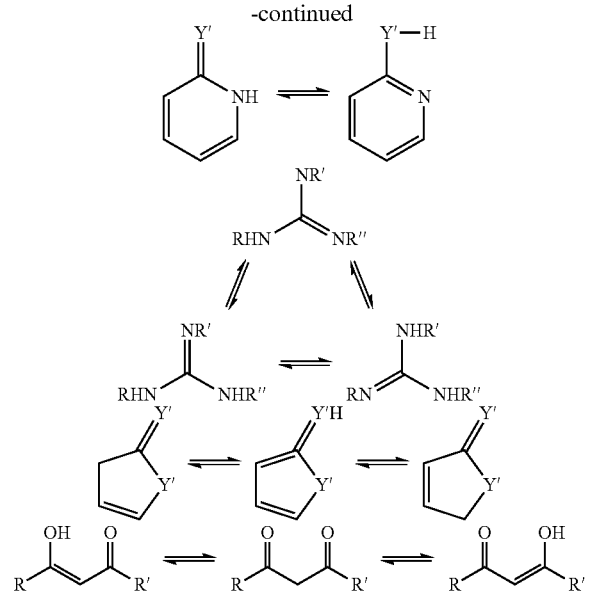

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pennsylvania, 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable e" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, F-leucine, calcium phosphate tribasic, F-tyrosine, F-proline, F-lysine acetate, DATEM (an emulsifier), F-glutamine, F-valine, potassium phosphate dibasic, F-isoleucine, F-arginine, F-alanine, glycine, F-asparagine monohydrate, F-serine, potassium citrate, F-threonine, sodium citrate, magnesium chloride, F-histidine, F-methionine, ascorbic acid, calcium carbonate, F-glutamic acid, F-cystine dihydrochloride, F-tryptophan, F-aspartic acid, choline chloride, taurine, m-inositol, ferrous sulfate, ascorbyl palmitate, zinc sulfate, F-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methane sulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KIF18A-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KIF18A activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. While individual needs vary, determination of optimal ranges of effective amounts of the compound is within the skill of the art. Such doses may be administered in a single dose or it may be divided into multiple doses.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer, ovarian cancer, and endometrial cancer. While the term "cancer" as used herein is not limited to any one specific form of the disease, it is believed that the methods of the invention will be particularly effective for cancers which are found to be accompanied by unregulated levels of KIF18A or dependent on KIF18A for proper chromosome segregation and survival in the mammal.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "patient", "subject", or "mammal" as used herein refers to any "patient", "subject", or "mammal" including humans, cows, horses, dogs and cats. In one embodiment of the invention, the mammal is a human.

The term "comprising" is meant to be open ended, including the indicated component(s) but not excluding other elements.

The terms "Formula I" include any sub formulas, such as (Ia), (Ib), (Ic), (Id), etc.

Methods of Using Kif18A Inhibitors

The present disclosure provides compounds having MT-based KIF18A modulatory activity in general, and inhibitory activity in particular. In one embodiment of the invention, there is provided a method of modulating KIF18A protein in a subject, the method comprising administering to the subject an effective dosage amount of a compound of Formulas I. As such, the compounds of the invention may be used to treat cellular proliferation disorders, including uncontrolled cell growth, aberrant cell cycle regulation, centrosome abnormalities (structural and or numeric, fragmentation). Other diseases or disorders associated with the accumulation of extra centrosomes (>2) include human papillomavirus (HPV) infection, including HPV-associated neoplasias. The compounds are also useful for cilia-related diseases as well as ablating haploid germ cell population which could be used as a male contraceptive.

In addition, compounds of the invention are useful for, but not limited to, the prevention or treatment of cancer and other KIF18A-mediated diseases or disorders. For example, compounds of the invention would be useful for the treatment of various solid and hematologically derived tumors, such as carcinomas, including, without limitation, cancer of the bladder, breast, colon, kidney, liver, lung (including squamous cell and small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderma pigmentosum, keratoctanthoma, thyroid follicular cancer and Kaposi's sarcoma).

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

Based on the ability to modulate kinesin impacting angiogenesis, the compounds of the invention are also useful in treatment and therapy of proliferative diseases. Particularly, these compounds can be used for the treatment of an inflammatory disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy, small molecule targeted agents (e.g. PARP inhibitors, kinase inhibitors), therapeutic antibodies (e.g. naked and drug-conjugate) immunotherapy antibodies (checkpoint inhibitors, bi-specific T-cell engagers) with neoplastic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

There are large numbers of anticancer agents available in commercial use, in clinical evaluation and in pre-clinical development, which would be selected for treatment of neoplasia by combination drug chemotherapy. Such agents fall into several major categories such as antibiotic-type agents, alkylating and alkylating-like agents, antimitotic agents, targeted small molecule agents, antimetabolite agents, hormonal agents, immunological agents, anti-angiogenic agents, interferon-type agents and a category of miscellaneous agents.

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, targeted small molecule agents, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of antimitotic agents, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel, Nab-paclitaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin, oxaliplatin, carboplatin; etoposide (VP-16); ifosfamide; mitomycin C; mitoxantrone; vinblastine vincristine; vinorelbine; navelbine; novantrone; teniposide; daunomycin; aminopterin; xeloda; ibandronate; topotecan; camptothecin-11 (CPT-11); topoisomerase inhibitor RFS 2000; difluoromethylornithine (DMFO), Where desired, the compounds or pharmaceutical composition of the present disclosure can be used in combination with commonly prescribed anti-cancer drugs such as Herceptin®, Avastin®, Erbitux®, Rituxan®, Taxol®, Abraxane, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Talazoparib, Niraparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar, CDK4/6 inhibitors (Palbociclib, Ibrance; Ribociclib, Kisqali; Abemaciclib, Verzenio).

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No. EP1181017, United States Publication No. US20090012085, United States Publication U.S. Pat. No. 5,863,949, United States Publication U.S. Pat. No. 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafirr, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aetema), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728, 813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (KyowaHakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aetema, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafdomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfdgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., FY2127399), IKK inhibitors, p38MAPK inhibitors, anti-IL-6 (e.g., CNT0328), telomerase inhibitors (e.g., GRN 163F), aurora kinase inhibitors (e.g., MFN8237, AMG 900, AZD-1152), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zamestra™), anti-CD138 (e.g., BT062), Torc1/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib, Talazoparib, Niraparib veliparib (ABT-888)), BCF-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds or pharmaceutical compositions of the disclosure can also be used in combination with an amount of one or more substances selected from EGFR inhibitors, MEK inhibitors, PI3K inhibitors, AKT inhibitors, TOR inhibitors, and immune therapies, including anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., Pharmacogenetics and Pharmacogenomics In Oncology Therapeutic Antibody Development, BioTechniques 2005; 39(4): 565-8, and Paez J G, et. al., EGFR Mutations In Lung Cancer Correlation With Clinical Response To Gefitinib Therapy, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 1997; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12): 1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8): 1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) Biochem. J., 385 (Pt. 2), 399-408); Akt-1-1,2 (inhibits Ak1 and 2) (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

Immune therapies include, but are not limited to, anti-PD-1 agents, anti-PDL-1 agents, anti-CTLA-4 agents, anti-LAG1 agents, and anti-OX40 agents. Exemplary anti-PD-1 antibodies and methods for their use are described by Goldberg et al., Blood 110(1): 186-192 (2007), Thompson et al., Clin. Cancer Res. 13(6): 1757-1761 (2007), and Korman et al., International Application No. PCT/JP2006/309606 (publication no. WO 2006/121168 A1), each of which are expressly incorporated by reference herein, include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090 box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXPERIMENTAL

Abbreviations: The following abbreviations may be used herein:

| | |
|---|---|
| ACN or MeCN | Acetonitrile |
| AcOH | acetic acid |
| aq or aq. | Aqueous |
| BOC or Boc | tert-butyloxycarbonyl |
| cataCXium ® A | rac-((3R,5R,7R)-adamantan-1-yl)((3S,5S,7S)-adamantan-1-yl)(butyl)phosphane |
| DABSO | 1,4-diazabicyclo[2.2.2]octane bis(sulfur dioxide) adduct |
| DCE | 1,2-dichloroethane |
| DCM | Dichloromethane |
| DMAP | 4-dimethylaminopyridine |
| DMF | N,N-dimethylformamide |
| DMSO | dimethyl sulfoxide |
| Dppf, DPPF or dppf | 1,1'-bis(diphenylphosphino)ferrocene |
| dppp | 1,3-bis(diphenylphosphino)propane |
| eq or eq. or equiv. | Equivalent |
| ESI or ES | electrospray ionization |
| Et | Ethyl |
| Et$_2$O | diethyl ether |
| EtOH | ethyl alcohol |

| | |
|---|---|
| EtOAc | ethyl acetate |
| G | Grams |
| H | Hour |
| HATU | 1-[bis(dimethylamino)methylene]-1H-1,2,3-triazolo[4,5-b]pyridinium 3-oxid hexafluorophosphate |
| HPLC | high pressure liquid chromatography |
| IPA | Isopropanol |
| iPr | Isopropyl |
| iPr$_2$NEt or DIPEA | N-ethyl diisopropylamine (Hünig's base) |
| KOAc | potassium acetate |
| LDA | lithium diisopropylamide |
| LC MS, LCMS, LC-MS or LC/MS | liquid chromatography mass spectroscopy |
| LG | leaving group (e.g., halogen, mesylate, triflate) |
| m/z | mass divided by charge |
| Me | Methyl |
| MeOH | Methanol |
| Met | metal species for cross-coupling (e.g., MgX, ZnX, SnR$_3$, SiR$_3$, B(OR)$_2$) |
| Mg | milligrams |
| min | minutes |
| mL | milliliters |
| MS | mass spectra |
| MsCl | methanesulfonyl chloride |
| MTBE | tert-butyl methyl ether |
| NMP | 1-methyl-2-pyrrolidine |
| n-BuLi | N-butyllithium |
| NMR | nuclear magnetic resonance |
| Pd$_2$(dba)$_3$ | tris(dibenzylideneacetone)dipalladium(0) |
| Pd(dppf)Cl$_2$ · DCM | [1,1'-Bis(diphenylphosphino)ferrocene]dichloropalladium(II), complex with dichloromethane |
| Pd(PPh$_3$)$_4$ | tetrakis(triphenylphosphine)palladium(0) |
| Ph | phenyl |
| Phen | 1,10-phenanthroline |
| PR or PG or Prot. group | protecting group |
| rbf | round-bottom flask |
| RP-HPLC | reverse phase high pressure liquid chromatography |
| RT or rt | room temperature |
| sat. or satd. | saturated |
| SFC | supercritical fluid chromatography |
| SPhos Pd G3 or SPhos G3 | (2-Dicyclohexylphosphino-2',6'-dimethoxybiphenyl) [2-(2'-amino-1,1'-biphenyl)]palladium(II) methanesulfonate |
| TBAF | tetra-n-butylammonium fluoride |
| t-BuOH | tert-butanol |
| TEA or Et$_3$N | trimethylamine |
| TFA | trifluoroacetic acid |
| THF | tetrahydrofuran |
| TLC | thin layer chromatography |
| T$_3$P | 2,4,6-tripropyl-1,3,5,2,4,6-trioxatriphosphinane 2,4,6-trioxide |
| UV | ultraviolet |
| Xantphos | 4,5-bis(diphenylphosphino)-9,9-dimethylxanthene |
| XtalFluor-M | difluoro(morpholino)sulfonium tetrafluoroborate |

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 µm, 5 to 100% CH$_3$CN in H$_2$O with 0.1% TFA for 15 min at 1.5 mL/min; System B: Zorbax SB-C8, 4.6×75 mm, 10 to 90% CH$_3$CN in H$_2$O with 0.1% formic acid for 12 min at 1.0 mL/min) (Agilent Technologies, Santa Clara, CA). Silica gel chromatography was generally performed with prepacked silica gel cartridges (Biotage, Uppsala, Sweden or Teledyne-Isco, Lincoln, NE). $^1$H NMR spectra were recorded on a Bruker AV-400 (400 MHz) spectrometer (Bruker Corporation, Madison, WI) or a Varian (Agilent Technologies, Santa Clara, CA) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, CA) LC/MS with UV detection at 254 nm and 215 nm and a low resonance electrospray mode (ESI).

For the purpose of clarity in this general synthesis section, Compounds of Formula (I) as defined in the summary of the inventions can be schematically drawn to contain Ring $Ar^1$ and Ring $Ar^2$ as follows:

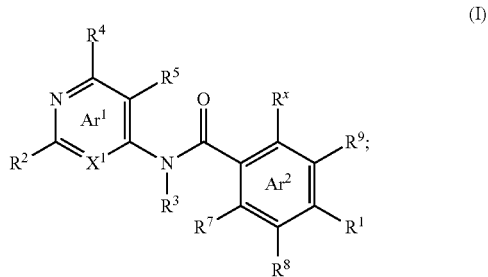

wherein the group $-NR^3-(C=O)-$ is a linker, Ring $Ar^1$ is located to the left of the linker, and ring $Ar^2$ is located to the right of linker.

Generally, compounds of Formula (I), can be synthesized via three general steps as follows:
Step 1: Preparation of Ring $Ar^1$ compound.
Step 2: Preparation of Ring $Ar^2$ compound.
Step 3: Coupling of Ring $Ar^1$ compound to Ring $Ar^2$ compound The generic Schemes A-E below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

Scheme A

According to Scheme A, in one embodiment a compound of Formula (I) as disclosed herein can be synthesized as follows:
Step 1a: Preparation of Ring $Ar^1$ Compound:

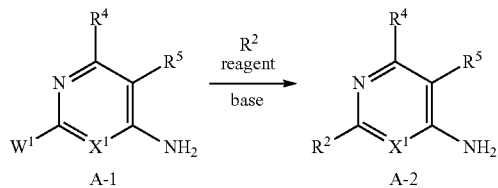

Step 1a: Preparation of Ring $Ar^1$ compound: Compound A-1, wherein $W^1$ is a halogen, for example fluoro or chloro, can be reacted with an $R^2$ group containing agent in the presence of a suitable base, in a suitable organic solvent such as NMP, dioxane, acetonitrile, tetrahydrofuran, DMF, methylene chloride, and the like, to form compound A-2. Compound A-1 is commercially available or can be synthesized by known methods by those skilled in the art. Examples of compound A-1 include, but are not limited to, 2-chloropyrimidin-4-amine, 2-chloro-6-methylpyrimidin-4-amine, 2-fluoro-6-methylpyridin-4-amine, 2-chloropyridin-4-amine, 2-chloro-6-methylpyridin-4-amine, 2-chloro-6-ethylpyrimidin-4-amine, or 2-chloro-6-cyclopropylpyrimidin-4-amine. Examples of $R^2$ reagents include, but not limited to (1) (R)-2-methylmorpholine, (2) 4,4-difluoropiperidine hydrochloride, (3) 3,3-difluoroazetidine hydrochloride, or (4) 3,3,3-trifluoropropan-1-ol. Examples of bases include, but are not limited to diisopropylethyl amine, potassium carbonate, or sodium hydride.

Step 1b: Preparation of Ring $Ar^1$ Compound:

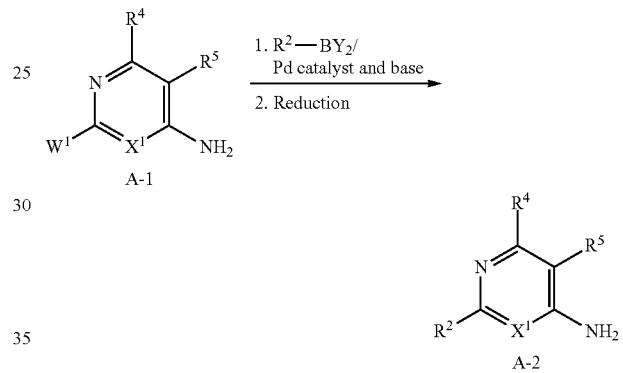

Alternatively, compound A-1 as defined in step 1a, can be converted to compound A-2, as defined in step 1a, via Suzuki cross coupling reaction with a suitable organoboron $R^2$ reagent ($R^2$—$BY_2$, wherein Y is an organic functional group) such as 2-(4,4-difluorocyclohex-1-en-1-yl)-4,4,5,5-tetramethyl-1,3,2-dioxaborolane or 2-(4-fluorocyclopent-1-en-1-yl)-4,4,5,5-tetramethyl-1,3,2-dioxaborolane, and a suitable palladium catalyst and a base, such as $PdCl_2$(dppf)-DCM adduct and potassium phosphate tribasic. This step is followed by a reduction with a suitable palladium catalyst and a hydrogen source, such as Pd/C in the presence of hydrogen gas, to form compound A-2. This alternative Suzuki reaction can be used when the group $R^2$ is linked to the $Ar^1$ ring via a carbon-carbon bond.

Step 2a: Preparation of Ring $Ar^2$ Compound:

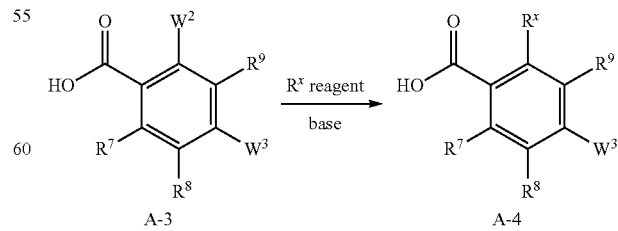

In Step 2a, Compound A-3, wherein each of $W^2$ and $W^3$ is independently a halogen, for example fluoro, chloro, bromo, or iodo, can be reacted with an $R^x$ reagent, such as (1) 6-azaspiro[2.5]octane hydrochloride, (2) 4,4-dimethylpiperidine hydrochloride, (3) 3,4,4-trimethylpiperidine hydrochloride, (4) 4-methyl-6-azaspiro[2.5]octane hydrochloride, or (5) 7-azaspiro[3.5]nonane hydrochloride, in a suitable organic solvent such as NMP, acetonitrile, tetrahydrofuran, DMF, methylene chloride, DMSO, and the like, to form Compound A-4.

Step 3a: Coupling of Ring $Ar^1$ Compound to Ring $Ar^2$ Compound Followed by Introduction of $R^1$:

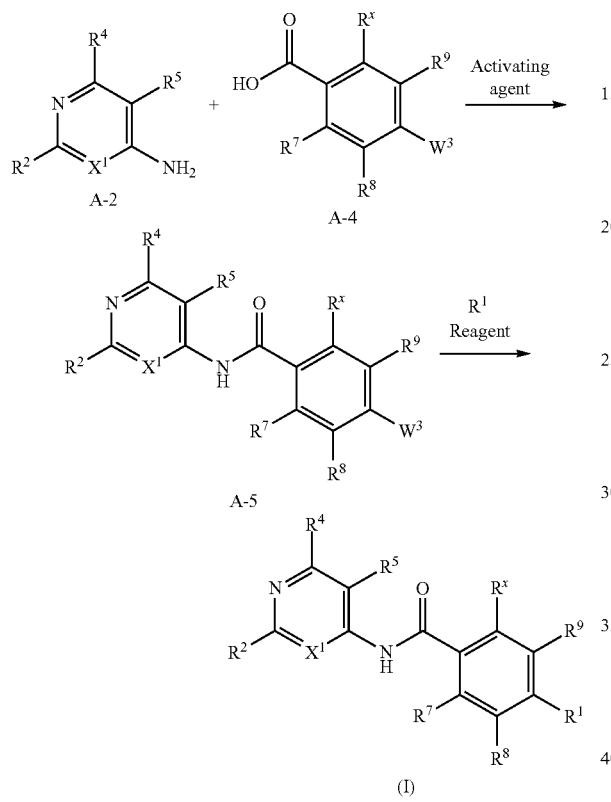

In Step 3a, compound A-4, which was obtained from Step 2a, can be reacted with an activating agent such as acid chloride $(COCl)_2$ or $SOCl_2$, in a suitable organic solvent such as tetrahydrofuran, methylene chloride, and the like, to form an acid chloride derivative, which can then react with compound A-2 to form compound A-5. Alternatively, compound A-2 can be directly coupled with compound A-4, which was obtained from Step 2a, in a suitable organic solvent such as acetonitrile, tetrahydrofuran, DMF, methylene chloride, and the like, in the presence of a coupling reagent, such as N,N'-diisopropylcarbodiimide, N-(3-dimethylaminopropyl)-N'-ethylcarbodiimide, benzotriazol-1-yloxytripyrrolidinophosphonium hexafluorophosphate, O-(benzotriazol-1-yl)-N,N,N',N'-tetramethyluronium hexafluorophosphate, carbonyl diimidazole, and polyphosphonic anhydride. Those ordinary skilled synthetic chemists will readily understand that other coupling agents can be used. Further manipulation of halogen group $W^3$ by transformation reactions such as, metal-catalyzed sulfoamidation, sulfmation, or sulfonylation, in a suitable organic solvent such as DMSO, acetonitrile, tetrahydrofuran, DMF, and the like, in the presence of a metal catalyst and an $R^1$ reagent, such as (1) 1-methylcyclopropane-1-sulfonamide, (2) 3-methyloxetan-3-amine, (3) tert-butyl 3-mercaptoazetidine-1-carboxylate, (4) ethyl 2-sulfamoylpropanoate, (5) 2-hydroxypropane-1-sulfonamide, (6) 2-hydroxyethane-1-sulfonamide, (7) ethyl iodoacetate, (8) 2-mercaptopropan-1-ol, (9) 2-mercapto-2-methylpropan-1-ol, (10) 2-aminoethan-1-ol, or (11) cyclopropanethiol can be used to form Compound (I). Those ordinary skilled chemists will readily understand that coupling reaction such as shown in Step 3a can be performed under various known conditions.

Scheme B

Step 1a or 1b: Preparation of Ring $Ar^1$ Compound: See SCHEME A Above
Step 2b: Preparation of Ring $Ar^2$ Compound:

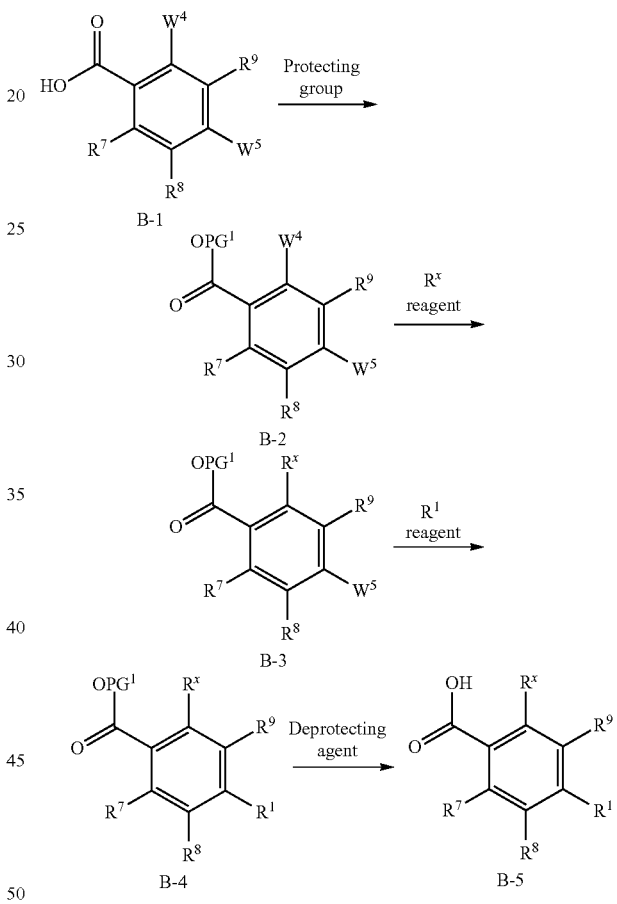

Scheme B provides an alternative method for formation of compounds of Formula (I) as disclosed herein. After Step 1a or Step 1b as described in Scheme A, the group $R^1$ can alternatively be introduced to Ring $Ar^2$ in Step 2b rather that in Step 3a as in Scheme A. According to Step 2b, compound B-1, wherein each of $W^4$ and $W^5$ is independently a halogen, for example fluoro, chloro, bromo, or iodo, can be reacted with an appropriate carboxylic acid protecting group ($PG_1$ reagent), such as methyl iodide in the presence of a base such as potassium carbonate, to form a methyl ester, or other appropriate protecting group to form other ester such as benzyl ester, in a suitable organic solvent such as NMP, acetonitrile, tetrahydrofuran, DMF, methylene chloride and the like, to form compound B-2, wherein each of $W^4$ and $W^5$ are as defined in compound B-1. Compound B-2 can then be reacted with an $R^x$ reagent, such as 6-azaspiro[2.5]octane, in a suitable organic solvent such as NMP, acetonitrile, tetrahydrofuran, DMF, methylene chloride, DMSO, and the like, to form compound B-3, wherein $W^5$ is as defined in compound B-1. Compound B-3 can then be reacted with an $R^1$ reagent by a transformation reaction such as, metal-catalyzed sulfoamidation, sulfmation, or sulfonylation, in a suitable organic solvent such as DMSO, acetonitrile, tetrahydrofuran, DMF, and the like, in the presence of a metal catalyst, such as copper iodide, $Pd_2(dba)_3$ to form compound B-4, which can then be reacted further with an appropriate carboxylic acid deprotecting agent to form compound B-5. Appropriate carboxylic acid protecting groups and deprotection agents are known to those skilled in the art, e.g., as discussed in Greene's Protective Groups in Organic Synthesis.

Step 3b: Coupling of Ring $Ar^1$ Compound to Ring $Ar^2$ Compound:

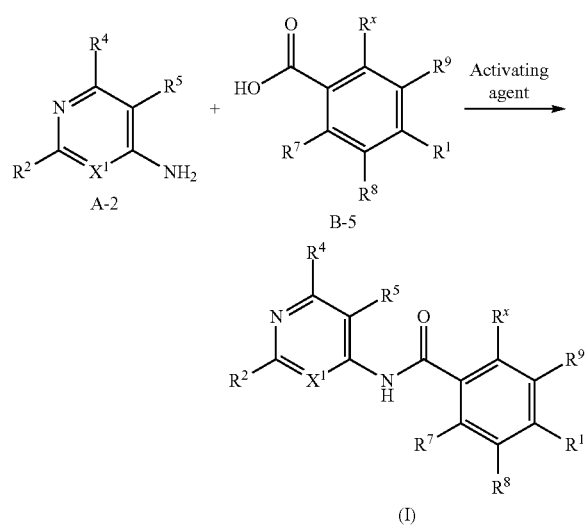

Step 3b is similar to the coupling reaction as described above in Step 3a.

Scheme C

Scheme C provides yet another alternative method for formation of compounds of Formula (I) as disclosed herein. According to Scheme C, Step 1a can be performed as described in Scheme C, followed by Step 2b as described in Scheme B.

Step 3c: Coupling of Ring $Ar^1$ Compound to Ring $Ar^2$ Compound:

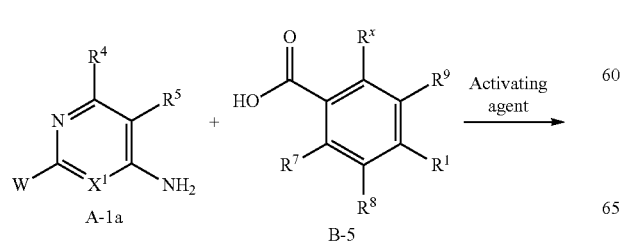

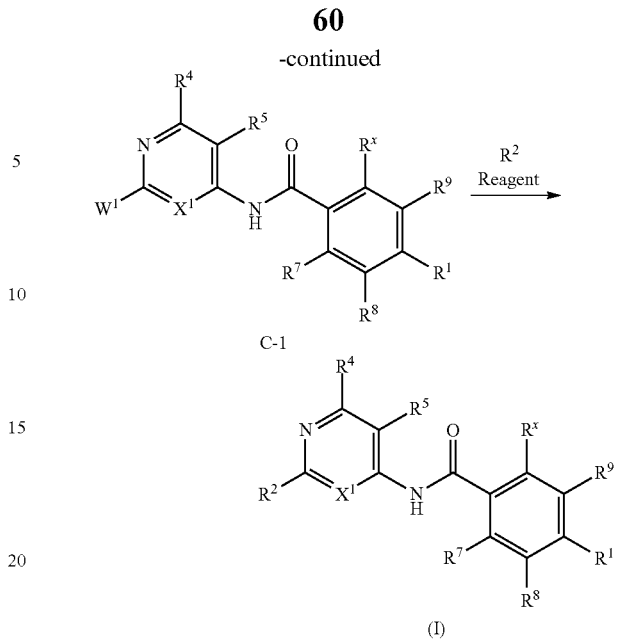

In Step 3c, compound A-1a, which is compound A-1 of Scheme A, wherein $X^1$ is N and $W^1$ is a halogen, for example fluoro or chloro, can be reacted with compound B-5 obtained from step 2b of scheme B, in the presence of an activating agents under conditions similar to step 3a and 3b above, to form compound C-1, wherein $W^1$ is as defined in compound A-1a, which then can be reacted with an $R^2$ group containing agent, such as (1) (R)-2-methylmorpholine, (2) 4,4-difluoropiperidine hydrochloride, (3) 3,3-difluoroazetidine hydrochloride, or (4) 3,3,3-trifluoropropan-1-ol, in the presence of a suitable base, such as diisopropylethyl amine, potassium carbonate, or sodium hydride, in a suitable organic solvent such as NMP, dioxane, acetonitrile, tetrahydrofuran, DMF, methylene chloride, and the like, to form compound of formula (I).

Scheme D

Scheme D provides yet another alternative method for formation of compounds of Formula (I) as disclosed herein. According to Scheme D, Step 1a or 1b can be performed as described in Scheme A, followed by Step 2b as described in Scheme B.

Step 3d: Coupling of Ring $Ar^1$ Compound to Ring $Ar^2$ Compound:

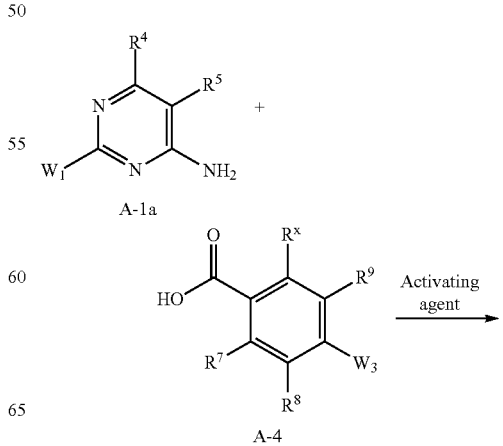

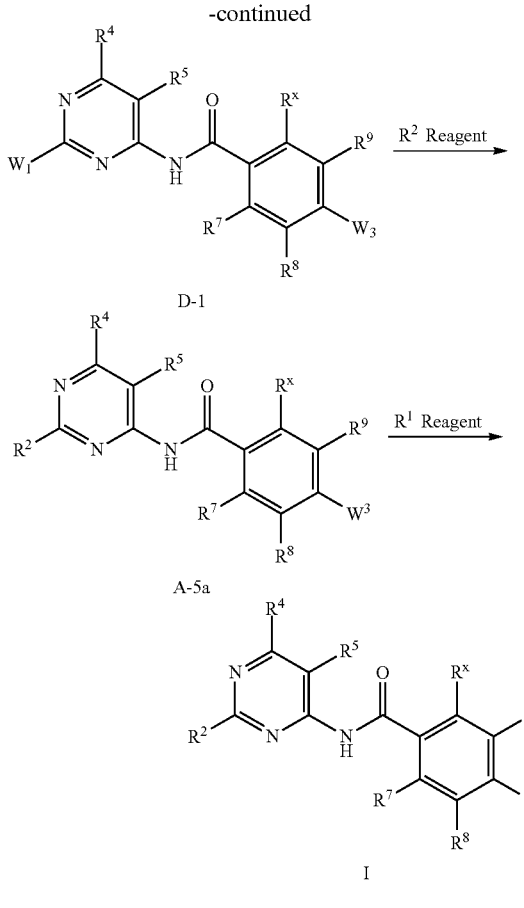

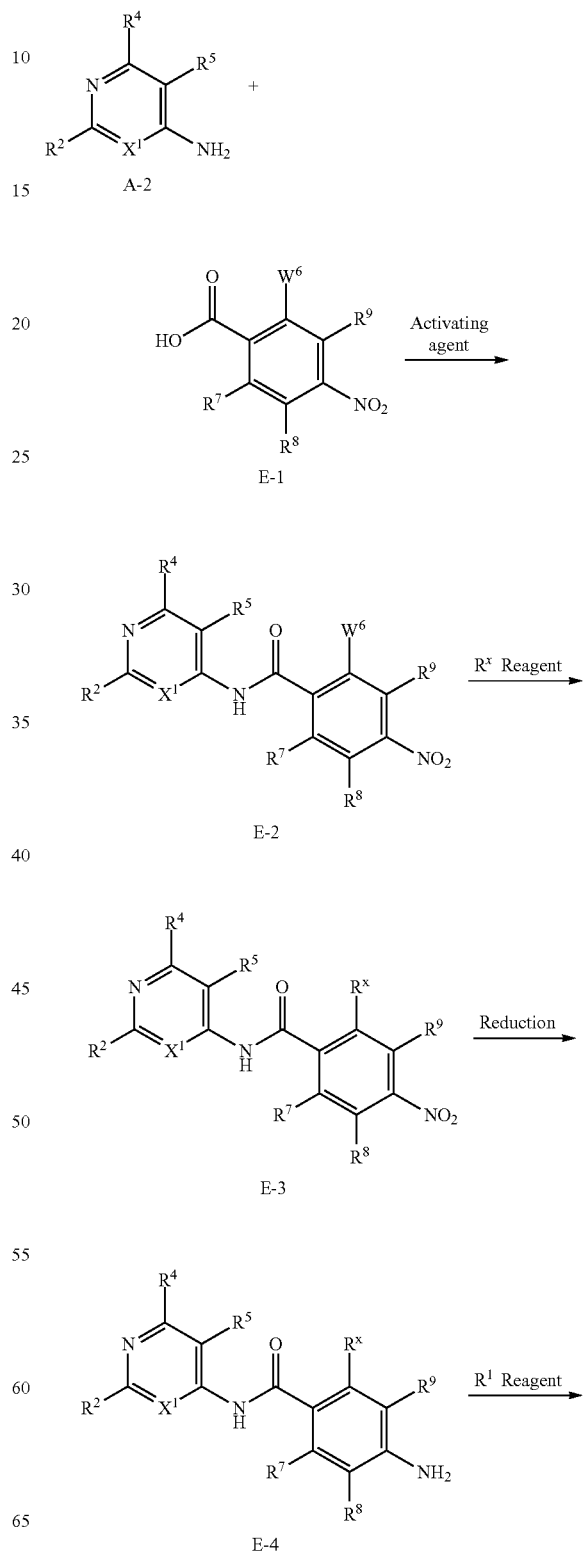

In Step 3d, compound A-1a, which is compound A-1 of Scheme A, wherein $X^1$ is N and $W^1$ is a halogen, for example fluoro or chloro, can be reacted with compound B-5 obtained from step 2a of scheme A, in the presence of a activating agent under conditions similar to step 3a and 3b above, to form compound D-1, wherein $W^1$ is as defined in compound A-1a and $W^3$ is as defined in compound B-5, which then can be reacted with an $R^2$ group containing agent, such as (1) (R)-2-methylmorpholine, (2) 4,4-difluoropiperidine hydrochloride, (3) 3,3-difluoroazetidine hydrochloride, or (4) 3,3, 3-trifluoropropan-1-ol, optionally in the presence of a suitable base, such as diisopropylethyl amine, potassium carbonate, or sodium hydride, in a suitable organic solvent such as NMP, dioxane, acetonitrile, tetrahydrofuran, DMF, methylene chloride, and the like, to form compound A-5a, which is compound A-5, wherein $X^1$ is N and $W^3$ is as defined in compound B-5, which can then be reacted with an $R^1$ group containing agent by a transformation reaction such as, metal-catalyzed sulfoamidation, sulfination, or sulfonylation, in a suitable organic solvent such as DMSO, acetonitrile, tetrahydrofuran, DMF, and the like, in the presence of a metal catalyst, to form compound formula (I).

Scheme E

Scheme E provides yet another alternative method for formation of compounds of Formula (I) as disclosed herein. According to Scheme E, Step 1a or 1b can be performed as described in Scheme A to prepare compound A-2. Compound E-1, wherein $W^6$ is a halogen, for example fluoro or chloro, which includes but is not limited to 2-fluoro-4-nitrobenzoic acid, 2,5-difluoro-4-nitrobenzoic acid, or 2,6-difluoro-4-nitrobenzoic acid, is commercially available or can be synthesized according to known methods by those skilled in the art.

Step 3e: Coupling of Ring $Ar^1$ Compound to Ring $Ar^2$ Compound

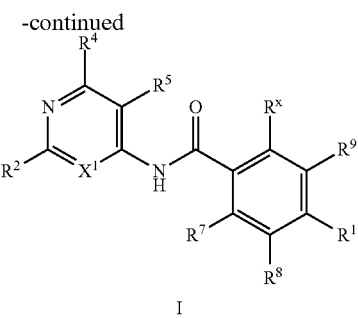

I

In step 3e, compound A-2 can be reacted with compound E-1, the presence of an activation reagent under conditions similar to step 3a and 3b above, to form compound E-2, which then can be reacted with an $R^x$ reagent in a similar way as described in Step 2a to form compound E-3. The nitro group on compound E-3 can then be converted into an amino group by reacting with a reducing agent, which includes but is not limited to palladium on carbon and hydrogen gas, to form compound E-4, which can then be reacted with an $R^1$ reagent, such as (1) 1-methylcyclopropane-1-sulfonamide, (2) 3-methyloxetan-3-amine, (3) tert-butyl 3-mercaptoazetidine-1-carboxylate, (4) ethyl 2-sulfamoylpropanoate, (5) 2-hydroxypropane-1-sulfonamide, (6) 2-hydroxyethane-1-sulfonamide, (7) ethyl iodoacetate, (8) 2-mercaptopropan-1-ol, (9) 2-mercapto-2-methylpropan-1-ol, (10) 2-aminoethan-1-ol, or (11) cyclopropanethiol, by a transformation reaction such as, metal-catalyzed sulfoamidation, sulfmation, or sulfonylation, in a suitable organic solvent such as DMSO, acetonitrile, tetrahydrofuran, DMF, and the like, in the presence of a metal catalyst, to form compound (I).

EXAMPLES

Preparation of Synthetic Intermediates

Ring $Ar^1$ Intermediates

Intermediate 1: (R)-2-(2-Methylmorpholino)pyrimidin-4-amine

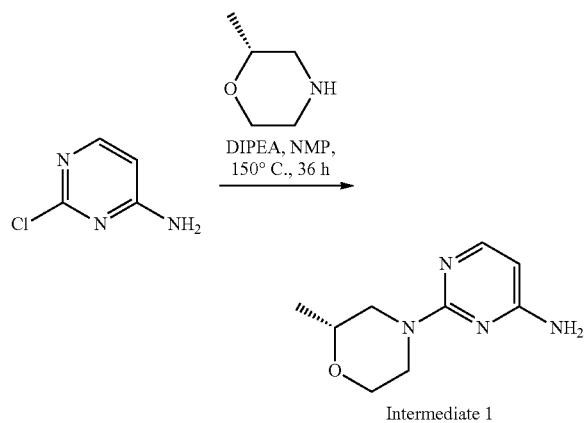

Intermediate 1

A mixture of 2-chloropyrimidin-4-amine (60.0 g, 463 mmol, Combi-Blocks, San Diego, CA), (R)-2-methylmorpholine (65.6 g, 648 mmol, Wuxi Apptec) and DIPEA (243 mL, 1389 mmol) in NMP (600 mL) was taken in an autoclave and heated at 150° C. for 36 h. The reaction mixture was cooled to room temperature and quenched with water (1 L) and extracted with ethyl acetate (3×500 mL). The organic layer was washed with brine solution (500 mL), dried ($Na_2SO_4$), filtered and concentrated under reduced pressure to give the crude material as a tan oil. The crude material was adsorbed onto a plug of silica gel and purified by column chromatography over silica gel (60-120 mesh), eluting with a gradient of 50% to 100% ethyl acetate in hexanes to give a yellow solid. This solid was further triturated with hexanes (300 mL), filtered and dried under vacuum to give the title compound (70 g, 78% yield) as a pale yellow solid. $^1$H NMR (400 MHz, DMSO-$d_6$) δ ppm 7.75 (d, J=5.6 Hz, 1H), 6.42 (s, 2H), 5.75 (d, J=5.6 Hz, 1H), 4.26-4.49 (m, 2H), 3.83 (ddd, J=11.4, 3.6, 1.4 Hz, 1H), 3.31-3.50 (m, 2H), 2.78 (ddd, J=13.2, 11.8, 3.5 Hz, 1H), 2.42-2.48 (m, 1H), 1.11 (d, J=6.2 Hz, 3H). m/z (ESI): 195.2 $(M+H)^+$.

Intermediate 2: (R)-6-Methyl-2-(2-methylmorpholino)pyrimidin-4-amine

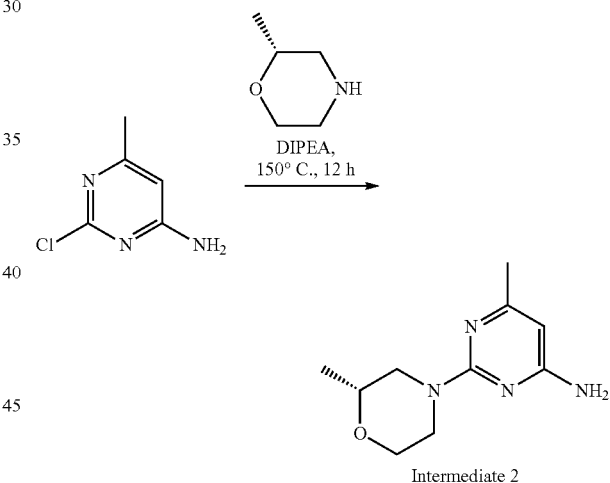

Intermediate 2

A mixture of 2-chloro-6-methylpyrimidin-4-amine (30.0 g, 209 mmol, Combi-Blocks, San Diego, CA), (R)-2-methylmorpholine (40.3 g, 293 mmol, Wuxi Apptec, PR China), and DIPEA (109 mL, 627 mmol) was taken in an autoclave (600 mL) and heated at 150° C. for 12 h. The reaction mixture was quenched with water (500 mL) and extracted with ethyl acetate (2×1500 mL). The organic layer was washed with brine solution (500 mL), dried ($Na_2SO_4$), filtered and concentrated under reduced pressure. The crude residue was purified by column chromatography over silica gel (60-120 mesh) using 50% ethyl acetate in hexanes as an eluent to give the title compound (25.0 g, 57% yield) as a yellow solid. $^1$H NMR (400 MHz, DMSO-$d_6$) δ 6.28 (s, 2H), 5.62 (s, 1H), 4.45-4.31 (m, 2H), 3.83 (ddd, J=11.4, 3.5, 1.3 Hz, 1H), 3.42 (ddt, J=14.4, 9.7, 2.8 Hz, 2H), 2.78-2.70 (m, 1H), 2.43 (dd, J=13.0, 10.3 Hz, 1H), 2.05 (s, 3H), 1.11 (d, J=6.2 Hz, 3H). m/z (ESI): 209.2 $(M+H)^+$.

Intermediate 3: 2-(4,4-Difluoropiperidin-1-yl)pyrimidin-4-amine

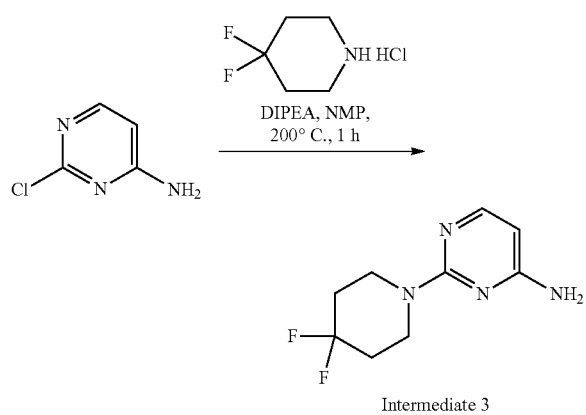

Intermediate 3

A glass microwave reaction vessel was successively charged with 2-chloro-4-aminopyrimidine (1.0 g, 7.7 mmol, Combi-Blocks, San Diego, CA), 4,4-difluoropiperidine hydrochloride (1.82 g, 11.58 mmol, Combi-Blocks, San Diego, CA) and DIPEA (4.04 mL, 23.2 mmol) in NMP (12 mL). The reaction mixture was stirred and heated in a microwave at 200° C. for 1 h. Reaction mixture was diluted with water (50 mL), extracted with ethyl acetate (30×2 mL). The organic extract was washed with brine (30×mL), dried over Na$_2$SO$_4$, concentrated in vacuo to give the crude material as a brownish sticky liquid. The crude material was absorbed onto a plug of silica gel and purified by flash chromatography through a Redi-Sep pre-packed silica gel column (40 g), eluting with 0% to 100% ethyl acetate in heptane to provide the title compound as an off-white solid (6.02 g, 91%). $^1$H NMR (300 MHz, DMSO-d$_6$) δ ppm 7.21 (d, J=5.6 Hz, 1H), 6.46 (br s, 2H), 5.77 (d, J=5.6 Hz, 1H), 3.80 (t, J=5.6 Hz, 4H), 1.85-1.90 (m, 4H). m/z (ESI): 215.2 (M+H)$^+$.

Intermediate 4: 2-(4,4-Difluoropiperidin-1-yl)-6-methylpyrimidin-4-amine

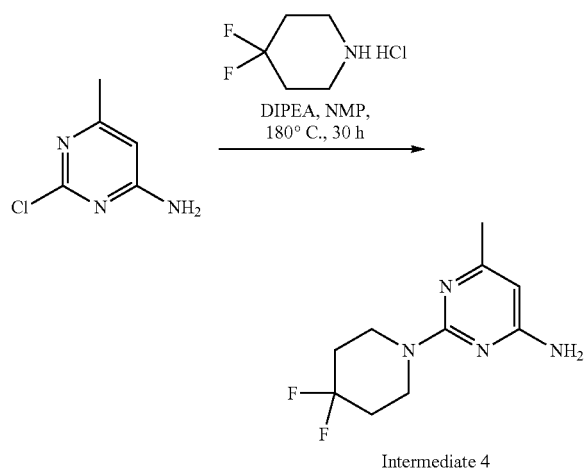

Intermediate 4

A mixture of 2-chloro-6-methylpyrimidin-4-amine (46 g, 320 mmol, Combi-Blocks, San Diego, CA), 4,4-difluoropiperidine hydrochloride (76 g, 481 mmol, Combi-Blocks, San Diego, CA) and DIPEA (166 mL, 961 mmol) in NMP (460 mL, 10.00 mL/g) was taken in an autoclave (1 L) and heated at 180° C. for 30 h. The reaction mixture was cooled to room temperature and quenched with water (500 mL), extracted with ethyl acetate (2×1000 mL). The organic layer was washed with brine (500 mL), dried (Na$_2$SO$_4$), filtered and concentrated under reduced pressure. The crude material was adsorbed onto a plug of silica gel and purified by column chromatography over silica gel (60-120 mesh), eluting with 50% to 100% ethyl acetate in hexanes as an eluent to give the product. This was re-dissolved in ethyl acetate (500 mL), washed with water (2×500 mL). The organic layer was dried (Na$_2$SO$_4$), filtered and concentrated under reduced pressure. The yellow solid was once again suspended in hexanes (400 mL) and stirred for 30 min. The slurry was filtered, washed with hexanes (100 mL), dried under vacuum to provide the title compound (58 g, 79% yield) as a pale yellow solid. $^1$H NMR (400 MHz, DMSO-d$_6$) δ ppm 6.33 (s, 2H), 5.63 (s, 1H), 3.80-3.78 (dd, J=6.8, 4.7 Hz, 4H), 2.06 (s, 3H), 1.95-1.85 (tt, J=14.2, 5.7 Hz, 4H). m/z (ESI): 229.2 (M+H)$^+$.

Intermediate 5: 2-(3,3-Difluoroazetidin-1-yl)pyrimidin-4-amine

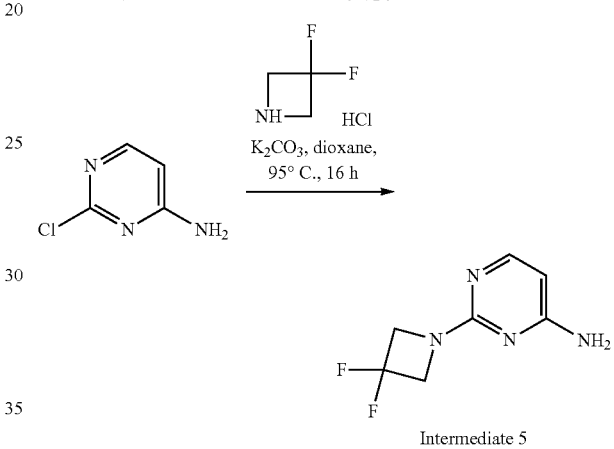

Intermediate 5

A mixture of 2-chloro-4-aminopyrimidine (5.0 g, 38.6 mmol, Combi-Blocks, San Diego, CA), 3,3-difluoroazetidine hydrochloride (7.50 g, 57.9 mmol, Combi-Blocks, San Diego, CA) and potassium carbonate (5.33 g, 38.6 mmol) in dioxane (25 mL) was heated at 95° C. for 16 h. The reaction mixture was cooled to room temperature and the suspension was filtered. The crude material was absorbed onto a plug of silica gel and purified by flash chromatography through a Redi-Sep pre-packed silica gel column (40 g), eluting with 10% MeOH in DCM to provide the title compound as light brown solid (6.1 g, 85%). $^1$H NMR (300 MHz, DMSO-d$_6$) δ ppm 8.29-8.66 (m, 2H), 7.81 (d, J=7.05 Hz, 1H), 6.22 (d, J=7.26 Hz, 1H), 4.61 (t, J=12.23 Hz, 4H). m/z (ESI): 187.2 (M+H)$^+$.

Intermediate 6: 2-(4,4-Difluorocyclohexyl)-6-methylpyrimidin-4-amine

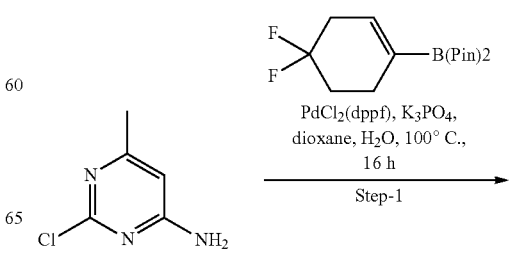

Step-1

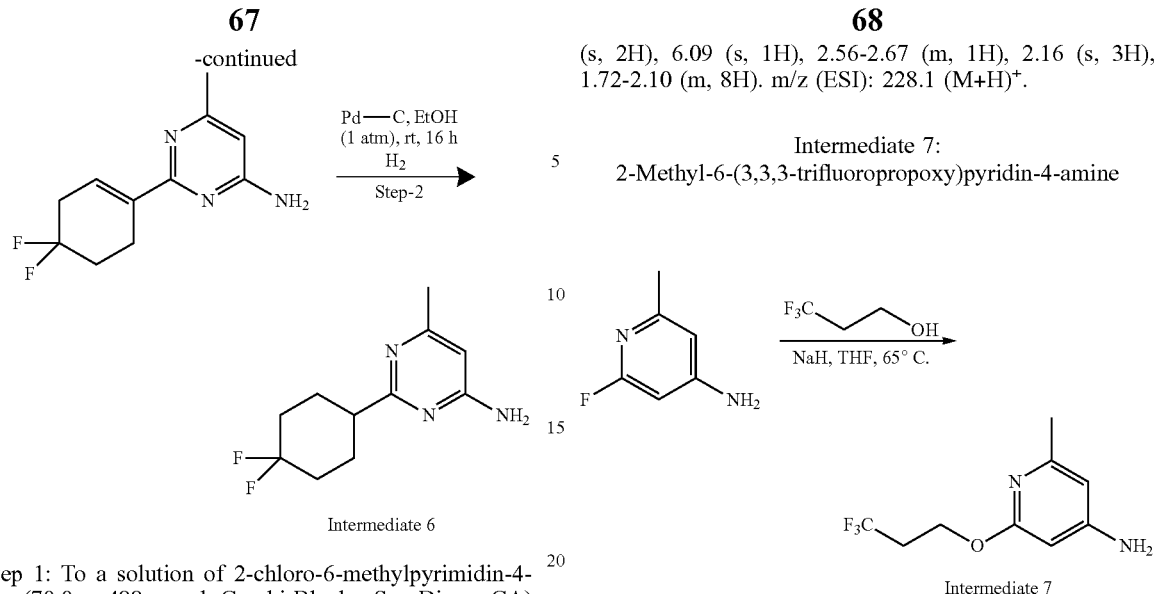

Step 1: To a solution of 2-chloro-6-methylpyrimidin-4-amine (70.0 g, 488 mmol, Combi-Blocks, San Diego, CA) in 1,4-dioxane (560 mL) and water (210 mL) were added 2-(4,4-difluorocyclohex-1-en-1-yl)-4,4,5,5-tetramethyl-1,3,2-dioxaborolane (119 g, 488 mmol, Combi-Blocks, San Diego, CA) and potassium phosphate tribasic (310 g, 1463 mmol). The reaction mixture was degassed and purged with nitrogen for 5 min. PdCl$_2$(dppf)-DCM adduct (39.8 g, 48.8 mmol) was added to the reaction mixture and stirred at 100° C. for 16 h. The dark heterogeneous mixture was filtered through a CELITE® bed and the filter cake was washed with ethyl acetate (2×1000 mL). The filtrate was washed with 1N NaOH solution (300 mL), followed by water (500 mL). The organic layer was dried (Na$_2$SO$_4$), filtered and concentrated under reduced pressure. The crude residue was adsorbed onto a plug of silica gel and purified by column chromatography over silica gel (60-120 mesh), eluting with a gradient of 50% to 60% ethyl acetate in hexanes, to give 2-(4,4-difluorocyclohex-1-en-1-yl)-6-methylpyrimidin-4-amine (70 g, 64% yield) as a pale yellow solid. $^1$H NMR (400 MHz, DMSO-d$_6$) δ ppm 6.85 (br s, 1H), 6.59 (br s, 2H), 6.13 (s, 1H), 2.62-2.80 (m, 4H), 2.19 (s, 3H), 2.04-2.17 (m, 2H). m/z (ESI): 226.2 (M+H)$^+$.

Step 2: To a solution of 2-(4,4-difluorocyclohex-1-en-1-yl)-6-methylpyrimidin-4-amine (70.0 g, 311 mmol) in EtOH (700 mL) was added 10% Pd on carbon (33.1 g, 155 mmol) under nitrogen. The reaction mixture was stirred at room temperature under hydrogen pressure (1 atm) for 16 h. The reaction mixture was filtered through a CELITE® bed and washed with a mixture of ethyl acetate and ethanol (1:1, 500 mL). The filtrate was concentrated under reduced pressure. The crude product was purified by column chromatography over silica gel (60-120 mesh) using 50% ethyl acetate in hexanes to give the title compound (58.5 g, 83% yield) as an off white solid. $^1$H NMR (400 MHz, DMSO-d$_6$) δ ppm 6.61 (s, 2H), 6.09 (s, 1H), 2.56-2.67 (m, 1H), 2.16 (s, 3H), 1.72-2.10 (m, 8H). m/z (ESI): 228.1 (M+H)$^+$.

Intermediate 7:
2-Methyl-6-(3,3,3-trifluoropropoxy)pyridin-4-amine

To a solution of 3,3,3-trifluoropropan-1-ol (1.99 g, 17.44 mmol, Combi-Blocks) in 30 mL of THF at 0° C. was added sodium hydride (60% wt. in mineral oil, 0.79 g, 19.82 mmol). The mixture was stirred at RT for 30 min then treated with 2-fluoro-6-methylpyridin-4-amine (1.00 g, 7.93 mmol, AstaTech Inc). The mixture was heated at 65° C. in an oil bath for 5 h. It was cooled to RT, quenched with water (10 mL) and extracted with EtOAc (2×50 mL). The organic solution was dried over Na$_2$SO$_4$, filtered and concentrated in vacuo to give the crude material as a yellow oil. The crude material was absorbed onto a plug of silica gel and purified on a silica gel column (15% to 30% EtOAc in heptane) to give 2-methyl-6-(3,3,3-trifluoropropoxy)pyridin-4-amine (0.47 g, 2.13 mmol, 27% yield) as a light-yellow oil. m/z (ESI): 221.1 (M+H)$^+$.

TABLE 1

The intermediate below was prepared following a similar procedure for Intermediate 7:

| Int. # | Chemical Structure | Name | LRMS: (ESI + ve ion) m/z |
|---|---|---|---|
| 7-1 | 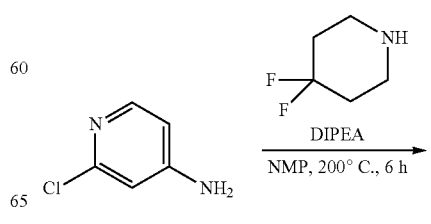 | 6-Methyl-2-(3,3,3-trifluoropropoxy)pyrimidin-4-amine | 222.0 |

Intermediate 8:
2-(4,4-Difluoropiperidin-1-yl)pyridin-4-amine

-continued

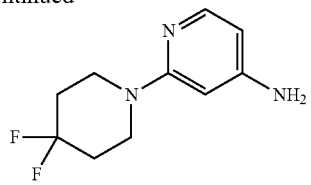

Intermediate 8

A mixture of 2-chloropyridin-4-amine (2.00 g, 15.56 mmol, Combi Blocks), DIPEA (6.03 g, 46.70 mmol, Sigma-Aldrich) and 4,4-difluoropiperidin (2.45 g, 20.22 mmol, Enamine) in NMP (6 mL) was heated in a microwave at 200° C. for 6 h. The reaction mixture was diluted with water (20 mL) and extracted with EtOAc (2×50 mL). The organic extracts were concentrated. The residue was purified by silica gel chromatography (20% to 70% EtOAc in heptane) to provide 2-(4,4-difluoropiperidin-1-yl)pyridin-4-amine (2.91 g. 13.65 mmol. 88% yield) as a light yellow solid, m/z (ESI): (M+H)$^+$214.1.

TABLE 2

Intermediates below were prepared following a similar procedure as described for Intermediate 8

| Int. # | Chemical Structure | Name | LRMS: (ESI + ve ion) m/z |
|---|---|---|---|
| 8-1 | 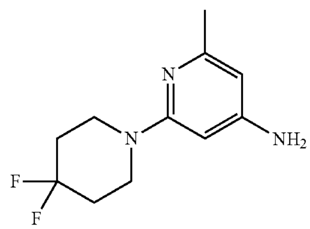 [SMILES: Cc1cc(N)cc(N2CCC(F)(F)CC2)n1] | 2-(4,4-Difluoropiperidin-1-yl)-6-methylpyridin-4-amine | 228.2 |
| 8-2 | 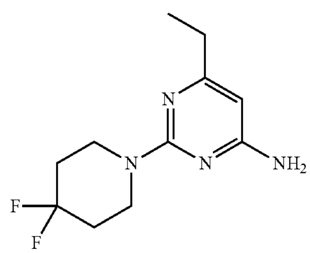 [SMILES: CCc1cc(N)nc(N2CCC(F)(F)CC2)n1] | 2-(4,4-Difluoropiperidin-1-yl)-6-ethylpyrimidin-4-amine | 243.1 |
| 8-3 | 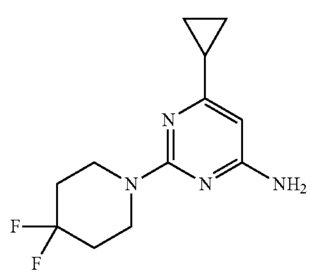 [SMILES: Nc1cc(C2CC2)nc(N2CCC(F)(F)CC2)n1] | 6-Cyclopropyl-2-(4,4-difluoropiperidin-1-yl)pyrimidin-4-amine | 255.1 |

Intermediate 9: 2-(4,4-Difluoropiperidin-1-yl)-3-fluoro-6-methylpiperidin-4-amine

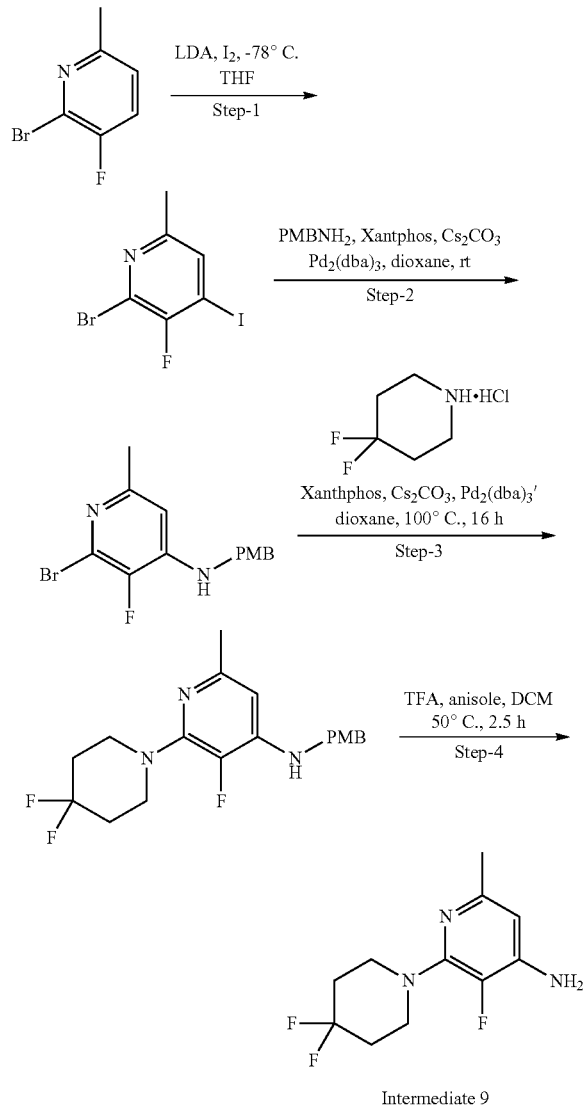

Intermediate 9

Step 1: To a solution of diisopropylamine (5.85 mL, 41.0 mmol) in tetrahydrofuran (50 mL) was added n-butyllithium (2M solution in hexanes, 20.52 mL, 41.0 mmol) dropwise at −60° C. The reaction mixture was slowly warmed to 0° C. and was stirred at the same temperature for 45 minutes. In another round bottom flask, to a solution of 2-bromo-3-fluoro-6-methylpyridine (3.9 g, 20.52 mmol) in tetrahydrofuran (50 mL) was added the above prepared LDA solution dropwise at −78° C. The reaction resultant reaction mixture was stirred for 45 minutes at the same temperature and then iodine (10.42 g, 41.0 mmol) in THF (40 mL) was added dropwise. The reaction mixture was stirred at same temperature for 1 h. After completion of the reaction, it was quenched with a saturated solution of ammonium chloride and was extracted in ethyl acetate. The organic layer was washed with sodium thiosulfate solution, water, and brine, dried over Na$_2$SO$_4$, filtered and concentrated to afford 2-bromo-3-fluoro-4-iodo-6-methylpyridine (6 g, 18.99 mmol, 93% yield) as yellow solid. The product was taken for next step without further purification. $^1$H NMR (400 MHz, Chloroform-d) δ ppm 7.53 (d, J=3.8 Hz, 1H), 2.52 (s, 3H). m/z (ESI): 315.8, 317.8 (M+H)$^+$.

Step 2: A mixture of 2-bromo-3-fluoro-4-iodo-6-methylpyridine (1.5 g, 4.75 mmol), (4-methoxyphenyl)methanamine (0.782 g, 5.70 mmol), cesium carbonate (4.64 g, 14.24 mmol), Xantphos (0.549 g, 0.950 mmol) and Pd$_2$(dba)$_3$ (0.065 g, 0.071 mmol) in 1,4-dioxane (30 mL) was stirred at ambient temperature for 16 h. Then the reaction mixture was filtered through a plug of CELITE® and filtrate was diluted with EtOAc. The resulting solution was washed with water, brine, dried over Na$_2$SO$_4$, filtered and concentrated. The concentrate was purified by flash column chromatography using a gradient of 0-18% ethyl acetate in petroleum ether to afford 2-bromo-3-fluoro-N-(4-methoxybenzyl)-6-methylpyridin-4-amine (0.7 g, 2.15 mmol, 45% yield) as pale-yellow solid. $^1$H NMR (300 MHz, DMSO-d$_6$) δ ppm 7.38 (s, 1H), 7.21-7.31 (m, 2H), 6.84-6.95 (m, 2H), 6.52 (d, J=6.0 Hz, 1H), 4.32 (d, J=6.3 Hz, 2H), 3.72 (s, 3H), 2.20 (s, 3H). m/z (ESI): 325.0, 327.0 (M+H)$^+$.

Step 3: A mixture of 2-bromo-3-fluoro-N-(4-methoxybenzyl)-6-methylpyridin-4-amine (0.7 g, 2.153 mmol), 4,4-difluoropiperidine hydrochloride (0.407 g, 2.58 mmol), cesium carbonate (2.81 g, 8.61 mmol), Xantphos (0.249 g, 0.431 mmol) and Pd$_2$(dba)$_3$ (0.030 g, 0.032 mmol) in 1,4-dioxane (15 mL) was stirred in a sealed tube at 100° C. for 16 h. Then the reaction mixture was filtered through a plug of CELITE® and filtrate was diluted with EtOAc. The resulting solution was washed with water, brine, dried over Na$_2$SO$_4$, filtered, and concentrated. The concentrate was purified by flash column chromatography using a gradient of 0-6% ethyl acetate in petroleum ether to afford 2-(4,4-difluoropiperidin-1-yl)-3-fluoro-N-(4-methoxybenzyl)-6-methylpyridin-4-amine (0.67 g, 1.83 mmol, 85% yield) as pale-yellow solid. $^1$H NMR (300 MHz, DMSO-d$_6$) δ ppm 7.19-7.29 (m, 2H), 6.83-6.93 (m, 2H), 6.75 (m, 1H), 6.13 (d, J=5.4 Hz, 1H), 4.26 (d, J=6.3 Hz, 2H), 3.72 (s, 3H), 3.40 (d, J=11.5 Hz, 4H), 1.92-2.14 (m, 7H). m/z (ESI): 366.1 (M+H)$^+$.

Step 4: To a solution of 2-(4,4-difluoropiperidin-1-yl)-3-fluoro-N-(4-methoxybenzyl)-6-methylpyridin-4-amine (0.3 g, 0.821 mmol) in dichloromethane (3 mL) were added anisole (0.179 mL, 1.642 mmol) and TFA (1.5 mL, 19.47 mmol) at ambient temperature and the reaction mixture was stirred at 50° C. for 2.5 h. Then the reaction mixture quenched with water and pH was adjusted to 8 with 10% sodium bicarbonate solution before it was extracted with ethyl acetate. The organic layer was washed with water and brine, dried over Na$_2$SO$_4$, filtered and concentrated. The concentrate was purified by flash column chromatography using a gradient of 20% ethyl acetate in petroleum ether to afford 2-(4,4-difluoropiperidin-1-yl)-3-fluoro-6-methylpyridin-4-amine (0.17 g, 0.69 mmol, 84% yield) as yellow oil. $^1$H NMR (400 MHz, DMSO-d$_6$) δ ppm 6.15 (d, J=5.5 Hz, 1H), 5.79 (s, 2H), 3.40 (t, J=5.6 Hz, 4H), 2.13 (s, 3H), 2.02 (tt, J=14.2, 5.6 Hz, 4H). m/z (ESI): 246.2 (M+H)$^+$.

Intermediate 10: 2-(6-Amino-2-(4,4-difluoropiperidin-1-yl)pyrimidin-4-yl)propan-2-ol

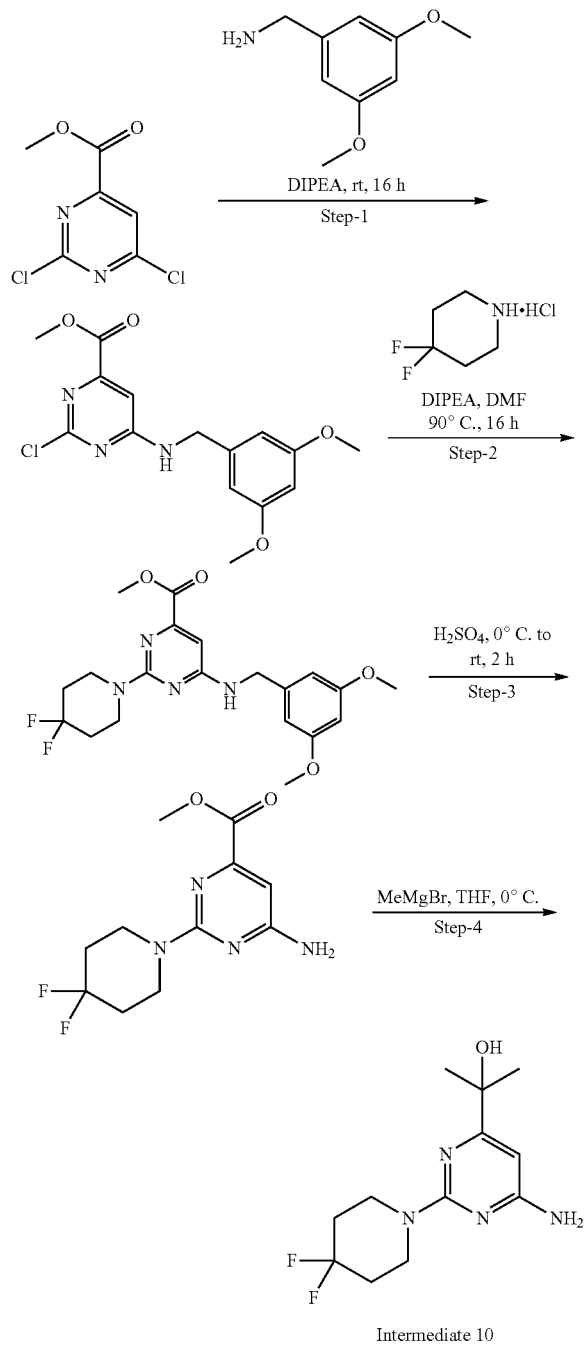

Intermediate 10

Step 1: To a solution of methyl 2,6-dichloropyrimidine-4-carboxylate (20.00 g, 97 mmol), in tetrahydrofuran (200 mL) were added (3,5-dimethoxyphenyl)methanamine (19.39 g, 116 mmol) and DIPEA (33.7 mL, 193 mmol) at 0° C. Then the reaction mixture was stirred at ambient temperature for 16 h before it was quenched with water and was extracted with EtOAc. The organic layer was washed with brine, and dried over $Na_2SO_4$, filtered and concentrated. The concentrate was triturated with DCM and hexane to afford methyl 2-chloro-6-((3,5-dimethoxybenzyl)amino)pyrimidine-4-carboxylate (19.5 g, 57.7 mmol, 59.8% yield) as off white solid. $^1H$ NMR (400 MHz, DMSO-$d_6$) δ ppm 8.52 (t, J=5.5 Hz, 1H), 7.16 (d, J=8.9 Hz, 2H), 6.59 (d, J=2.4 Hz, 1H), 6.50 (dd, J=8.4, 2.4 Hz, 1H), 4.40 (d, J=5.4 Hz, 2H), 3.82 (d, J=14.5 Hz, 6H), 3.75 (d, J=5.8 Hz, 3H). m/z (ESI): 338.1 (M+H)$^+$.

Step 2: A solution of methyl 2-chloro-6-((3,5-dimethoxybenzyl)amino)pyrimidine-4-carboxylate (3 g, 8.88 mmol), 4,4-difluoropiperidine hydrochloride (2.10 g, 13.32 mmol) and DIPEA (3.44 g, 26.6 mmol) in DMF (30 mL) was stirred in a sealed tube at 90° C. for 16 h. Then the reaction mixture was quenched with water and was extracted with ethyl acetate. The organic layer was washed with brine, dried over $Na_2SO_4$, filtered, and concentrated. The crude material was purified by flash column chromatography using a gradient of 50% to 60% ethyl acetate in petroleum ether to provide methyl 2-(4,4-difluoropiperidin-1-yl)-6-((3,5-dimethoxybenzyl)amino)pyrimidine-4-carboxylate (2.6 g, 6.15 mmol, 69.3% yield) as pale yellow solid. $^1H$ NMR (300 MHz, DMSO-$d_6$) δ ppm 7.74 (s, 1H), 7.13 (d, J=8.3 Hz, 1H), 6.55 (d, J=2.4 Hz, 1H), 6.47 (dd, J=8.3, 2.4 Hz, 2H), 4.39 (s, 2H), 3.82 (s, 3H), 3.79 (s, 3H), 3.73 (s, 3H), 3.33 (m, 4H), 1.85-2.00 (m, 4H).

Step 3: To a solution of methyl 2-(4,4-difluoropiperidin-1-yl)-6-((3,5-dimethoxybenzyl)amino)pyrimidine-4-carboxylate (1 g, 2.367 mmol) in DCM (10 mL) was dropwise added sulfuric acid (0.126 mL, 2.37 mmol) at 0° C. Then the mixture was allowed to warm to RT and the progress of the reaction was monitored by TLC. Upon completion of starting material, the reaction mixture was quenched with ice-water and pH was adjusted to 9 by using 10% NaHCCf solution. Then, the reaction mixture was extracted with ethyl acetate and the organic layer was washed with brine, dried over $Na_2SO_4$, filtered and concentrated to provide methyl 6-amino-2-(4,4-difluoropiperidin-1-yl)pyrimidine-4-carboxylate (0.45 g, 1.653 mmol, 69.8% yield) as off-white solid. $^1H$ NMR (300 MHz, DMSO-$d_6$) δ ppm 6.90 (br s, 2H), 6.39 (s, 1H), 3.85-3.83 (m, 4H), 3.79 (s, 3H), 1.99-1.35 (m, 4H). m/z (ESI): 273.1 (M+H)$^+$.

Step 4: To a solution of methyl 6-amino-2-(4,4-difluoropiperidin-1-yl)pyrimidine-4-carboxylate (0.45 g, 1.653 mmol) in tetrahydrofuran (5 mL) was added methyl magnesium bromide (2.0 M diethyl ether) (2.07 mL, 4.13 mmol) at 0° C. and was stirred at room temperature for 2 h. Upon consumption of starting material, the reaction mixture was quenched with ice water and was extracted with ethyl acetate. The organic layer was washed with brine, dried over $Na_2SO_4$, filtered and concentrated. The concentrate was purified by flash column chromatography using a gradient of 0%-90% ethyl acetate in petroleum ether to provide 2-(6-amino-2-(4,4-difluoropiperidin-1-yl)pyrimidin-4-yl)propan-2-ol (0.35 g, 1.28 mmol, 78% yield) as pale yellow solid. m/z (ESP: 273.1 (M+H)$^+$.

TABLE 3

The intermediate below was prepared following a similar procedure as described for intermediate 10

| Int. # | Chemical Structure | Name | LRMS: (ESI + ve ion) m/z |
|---|---|---|---|
| 10-1 | 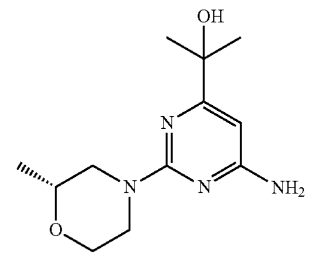 [SMILES: C[C@@H]1CN(c2nc(N)cc(C(C)(C)O)n2)CCO1] | (R)-2-(6-Amino-2-(2-methylmorpholino)pyrimidin-4-yl)propan-2-ol | 252.2 |

Intermediate 11:
2-(4-Amino-6-methylpyrimidin-2-yl)propan-2-ol

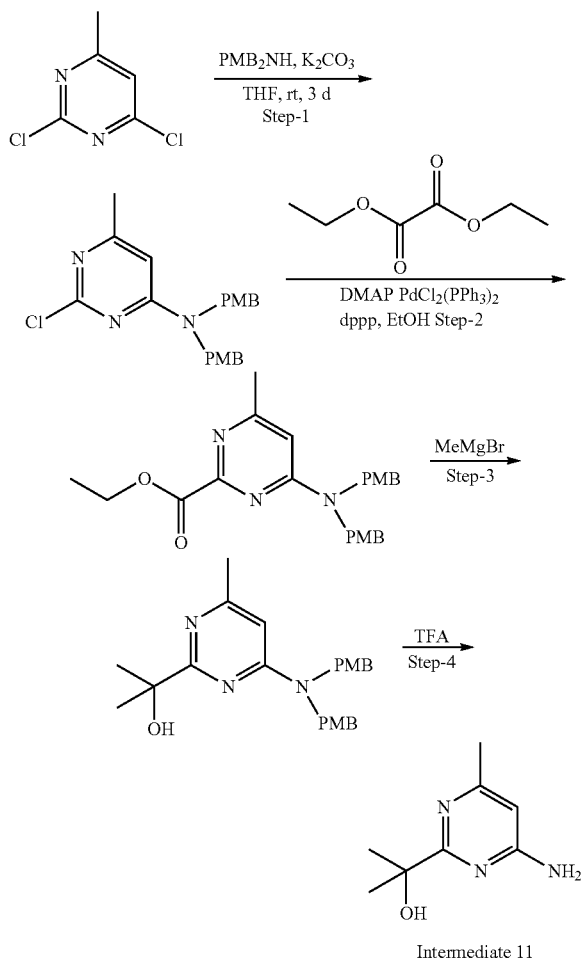

Intermediate 11

Step 1: A mixture of 2,4-dichloro-6-methylpyrimidine (3.0 g, 18.40 mmol, Aldrich, St. Louis, MO, USA), bis(4-methoxybenzyl)-amine (7.10 g, 27.6 mmol, Combi-Blocks Inc., San Diego, CA, USA), and potassium carbonate (7.63 g, 55.2 mmol, Aldrich, St. Louis, MO, USA) in tetrahydrofuran (100 mL) was stirred at room temperature for 72 h. Then, the mixture was diluted with water (50 mL) and was then extracted with EtOAc (2×100 mL). The combined organic extracts were then dried over $MgSO_4$ and concentrated in vacuo. Chromatographic purification of the residue (silica gel, 0%-100% EtOAc/heptane) provided 2-chloro-N,N-bis(4-methoxybenzyl)-6-methylpyrimidin-4-amine (3.11 g, 8.10 mmol, 44.0% yield) as an off white solid. $^1$H NMR (DMSO-d6) δ ppm 7.16 (br d, J=6.2 Hz, 4H), 6.89 (d, J=8.7 Hz, 4H), 6.60 (s, 1H), 4.39-4.84 (m, 4H), 3.73 (s, 6H), 2.20 (s, 3H). m/z (ESI): 384.2 (M+H)+.

Step 2: A mixture of 2-chloro-A/V-bis(4-methoxybenzyl)-6-methylpyrimidin-4-amine (1.0 g, 2.61 mmol), 1,3-bis(diphenylphosphino)propane (64.5 mg, 0.156 mmol, Aldrich, St. Louis, MO, USA), diethyl oxalate (0.529 mL, 3.91 mmol, Aldrich, St. Louis, MO, USA), trans-dichlorobis (triphenyl-phosphine)palladium (ii) (54.9 mg, 0.078 mmol, Strem Chemicals Inc., Newburyport, MA, USA), and 4-(dimethylamino) pyridine (477 mg, 3.91 mmol, Aldrich, St. Louis, MO, USA) in ethanol (0.5 mL) was subjected to a microwave irradiation at 140° C. for 20 min. Then, the mixture was diluted with water (50 mL) and was then extracted with EtOAc (2×50 mL). The combined organic extracts were then dried over MgSO4 and concentrated in vacuo. Chromatographic purification of the residue (silica gel, 0%-100% EtOAc/heptane) provided ethyl 4-(bis(4-methoxybenzyl)amino)-6-methylpyrimidine-2-carboxylate (274 mg, 0.650 mmol, 24.95% yield) as a light yellow solid. $^1$H NMR (Methanol-d4) δ ppm 7.29 (br s, 4H), 6.97 (d, J=8.5 Hz, 4H), 6.68 (s, 1H), 4.78-4.93 (m, 4H), 4.54 (q, J=7.2 Hz, 2H), 3.88 (s, 6H), 2.43 (s, 3H), 1.53 (t, 7=7.0 Hz, 3H). m/z (ESI): 422.1 (M+H)+.

Step 3: To a solution of ethyl 4-(bis(4-methoxybenzyl)amino)-6-methylpyrimidine-2-carboxylate (396 mg, 0.940 mmol) in 2-methyltetrahydrofuran (7 mL) at 0° C. under $N_2$ was added methylmagnesium bromide, 3.4M in 2-methyl-tetrahydrofuran (0.829 mL, 2.82 mmol, Aldrich, St. Louis, MO, USA) dropwise. After addition, the mixture was then stirred at 0° C. for 3.5 hours. Then, the mixture was quenched with saturated $NH_4Cl$ (10 mL) and was then extracted with EtOAc (2×50 mL). The combined organic extracts were then dried over $MgSO_4$ and concentrated in vacuo. Chromatographic purification of the residue (silica gel, 0%-100% EtOAc/heptane) provided 2-(4-(bis(4-methoxybenzyl)amino)-6-methylpyrimidin-2-yl)propan-2-ol (307 mg, 0.753 mmol, 80% yield) as a yellow solid, m/z (ESI): 408.2 (M+H)+.

Step 4: A solution of 2-(4-(bis(4-methoxybenzyl)amino)-6-methylpyrimidin-2-yl)propan-2-ol (300 mg, 0.736 mmol)

in trifluoroacetic acid (10 mL, Aldrich, St. Louis, MO, USA) was subjected to a microwave irradiation at 110° C. for 30 min. Then, the mixture was concentrated under reduced pressure. The crude was then dissolved in DCM (10 mL) and was then quenched with saturated Na2CO3 (15 mL). The mixture was then extracted with EtOAc (2×50 mL). The combined organic extracts were then dried over MgSO4 and concentrated in vacuo. Chromatographic purification of the residue (silica gel, 0%-100% EtOAc:EtOH (3:1)/heptane) provided 2-(4-amino-6-methylpyrimidin-2-yl)propan-2-ol (123 mg) as a light yellow solid, m/z (ESI): 168.2 (M+H)+.

Preparation of Ring Ar² Intermediates

Intermediate 12: 4-Iodo-2-(6-azaspiro[2.5]octan-6-yl)benzoic acid

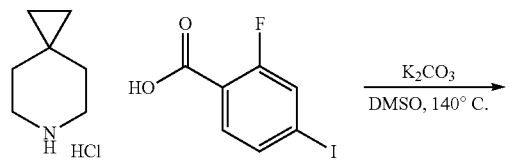

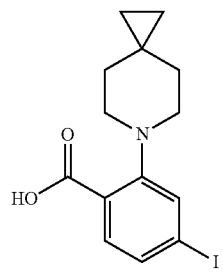

Intermediate 12

To a solution of 2-fluoro-4-iodobenzoic acid (300 g, 1.13 mol, Combi-Blocks, San Diego, CA) in DMSO (2.10 L) was added 6-azaspiro[2.5]octane hydrochloride (216 g, 1.47 mol, Wuxi AppTec) at 20° C. Then K₂CO₃ (468 g, 3.38 mol) was added and the reaction solution was stirred at 140° C. for 48 hours under N₂. The reaction solution was slowly poured into ice water (4.20 L), then extracted with hexanes (2.00 L×3). The water phase was separated and adjusted to pH=6 with HCl (2.00 mol/L, aq). Solid was precipitated out and collected. The solid was washed with water (700 mL×3) and filtered. The moist solid was spread out on a large watch glass and dried in the air at 25° C. for 72 hours. 4-Iodo-2-(6-azaspiro[2.5]octan-6-yl)benzoic acid (280 g, 777 mmol, 68.9% yield) was obtained as a light yellow solid. 400 MHz DMSO-d₆ δ ppm 8.07 (s, 1H), 7.76-7.66 (m, 2H), 3.10 (t, J=5.2 Hz, 4H), 1.55 (br s, 4H), 0.41 (s, 4H).

TABLE 4

Intermediates below were prepared following a similar procedure for Int. 12:

| Int. # | Chemical Structure | Name | LRMS: (ESI + ve ion) m/z |
|---|---|---|---|
| 12-1 | 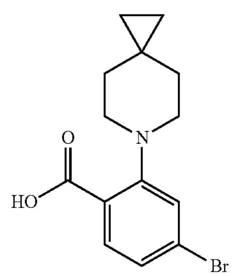 [SMILES: O=C(O)c1ccc(Br)cc1N1CCC2(CC1)CC2] | 4-Bromo-2-(6-azaspiro[2.5]octan-6-yl)benzoic acid | 310.2/312.2 |
| 12-2 | 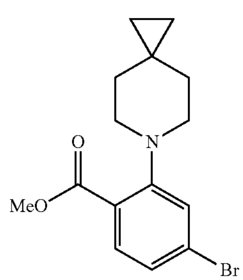 [SMILES: COC(=O)c1ccc(Br)cc1N1CCC2(CC1)CC2] | Methyl 4-bromo-2-(6-azaspiro[2.5]octan-6-yl)benzoate | 324.0/326.0 |

TABLE 4-continued

Intermediates below were prepared following a similar procedure for Int. 12:

| Int. # | Chemical Structure | Name | LRMS: (ESI + ve ion) m/z |
|---|---|---|---|
| 12-3 | 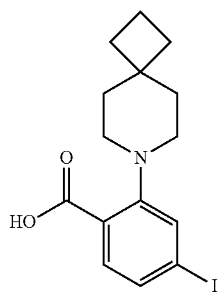 [SMILES: O=C(O)c1ccc(I)cc1N1CCC2(CCC2)CC1] | 4-Iodo-2-(7-azaspiro[3.5]nonan-7-yl)benzoic acid | 372.0 |
| 12-4 | 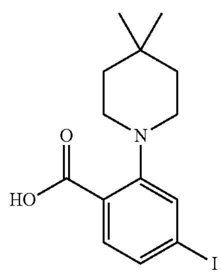 [SMILES: CC1(C)CCN(c2cc(I)ccc2C(=O)O)CC1] | 2-(4,4-Dimethylpiperidin-1-yl)-4-iodobenzoic acid | 360.0 |

Intermediate 13: 4-(Methylsulfonyl)-2-(6-azaspiro[2.5]octan-6-yl)benzoic

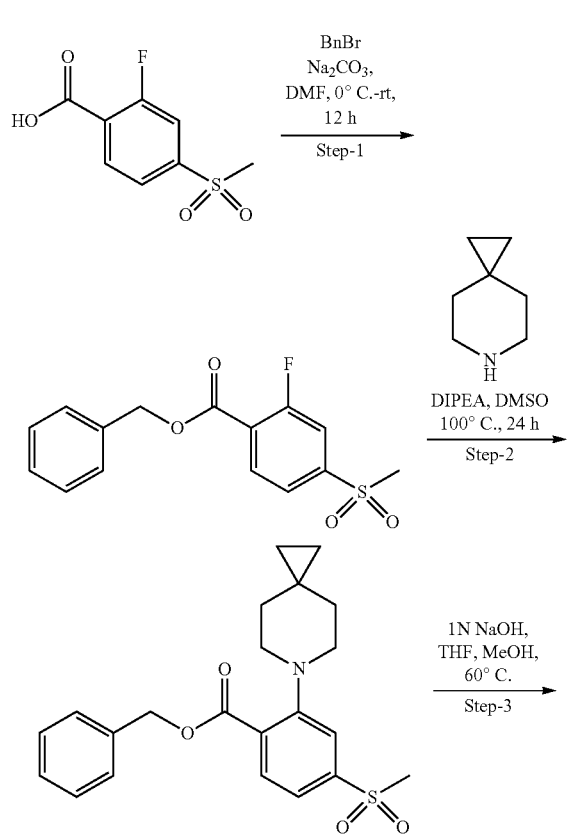

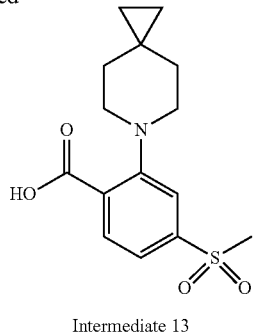

Intermediate 13

Step 1: To a solution of 2-fluoro-4-(methylsulfonyl)benzoic acid (90.0 g, 412.1 mmol) in N,N-dimethylformamide (1.0 L) were added benzyl bromide (78.1 g, 454.0 mmol) and sodium carbonate (52.5 g, 495 mmol) at 0° C. The reaction mixture was stirred for 12 h at room temperature. The reaction mixture was quenched with water (1 L) and extracted with MTBE (3×1 L). The combined organic layer was washed with brine (1 L), dried over $Na_2SO_4$, filtered and concentrated under reduced pressure. The crude residue was purified by column chromatography over silica gel using 0 to 30% ethyl acetate in hexanes as an eluent to give benzyl 2-fluoro-4-(methylsulfonyl)benzoate (100 g, 79% yield) as a white solid. $^1$H NMR (300 MHz, DMSO-$d_6$) 3 ppm 8.16 (dd, J=8.2, 6.9 Hz, 1H), 7.98-7.86 (m, 2H), 7.48-7.31 (m, 5H), 5.40 (s, 2H), 3.33 (s, 3H).

Step 2: To a solution of benzyl 2-fluoro-4-(methylsulfonyl)benzoate (55 g, 178 mmol) in dimethyl sulfoxide (550 mL) was added DIPEA (57.6 g, 446 mmol) followed by 6-azaspiro[2.5]octane (29.8 g, 268 mmol) and the reaction mixture was stirred at 100° C. for 24 h. The reaction mixture was quenched with water (1 L) and extracted with MTBE (3×1 L). The combined organic layer was washed with brine solution (1 L), dried over Na$_2$SO$_4$, filtered and concentrated under reduced pressure. The crude product was purified by column chromatography over silica gel (230-400 mesh) using 0 to 10% ethyl acetate in hexanes as an eluent to give benzyl 4-(methylsulfonyl)-2-(6-azaspiro[2.5]octan-6-yl)benzoate (55 g, 77% yield) as a white solid. $^1$H NMR (400 MHz, DMSO-d$_6$) 3 ppm 7.76 (d, J=8.0 Hz, 1H), 7.52-7.45 (m, 4H), 7.43-7.35 (m, 3H), 5.35 (s, 2H), 3.25 (s, 3H), 3.05 (t, J=5.3 Hz, 4H), 1.36 (t, J=5.3 Hz, 4H), 0.30 (s, 4H). m/z (ESI): 400.1 (M+H)$^+$.

Step 3: To a solution of benzyl 4-(methylsulfonyl)-2-(6-azaspiro[2.5]octan-6-yl)benzoate (65 g, 163 mmol) in tetrahydrofuran (108 mL) and methanol (36 mL) was added 1N aqueous sodium hydroxide solution (407 mL, 407 mmol) and the reaction mixture was stirred for 12 h at 60° C. The reaction mixture was concentrated under reduced pressure to remove THF and methanol. The remaining aqueous solution was acidified to pH ~2 with 1.5 N HCl solution. The precipitated solid was filtered, washed with water (200 mL) followed by hexanes (200 mL), dried under vacuum for 12 h to give 4-(methylsulfonyl)-2-(6-azaspiro[2.5]octan-6-yl)benzoic acid (42 g, 83% yield) as an off white solid. $^1$H NMR (400 MHz, DMSO-d$_6$) δ ppm 16.13 (s, 1H), 8.04 (d, J=8.0 Hz, 1H), 7.99 (s, 1H), 7.75 (d, J=8.0 Hz, 1H), 3.29 (s, 3H), 3.17 (b s, 4H), 1.55 (b s, 4H), 0.41 (s, 4H). m/z (ESI): 310.1 (M+H)$^+$.

Intermediate 14: 4-((1-Methylcyclopropane)-1-sulfonamido)-2-(6-azaspiro[2.5]octan-6-yl)benzoic acid

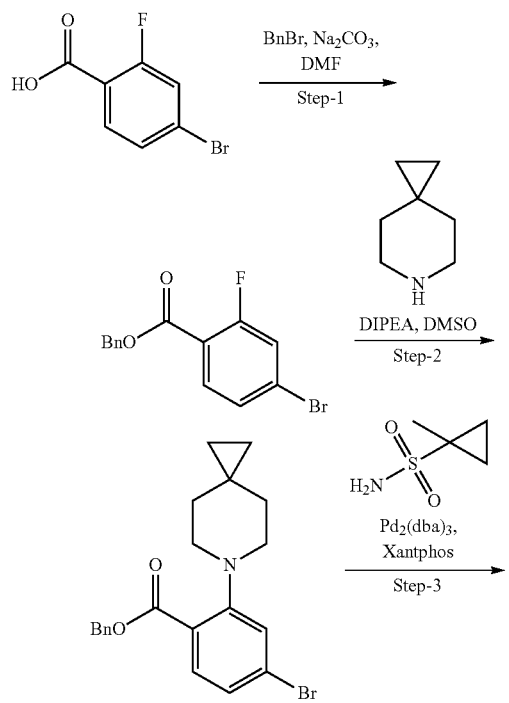

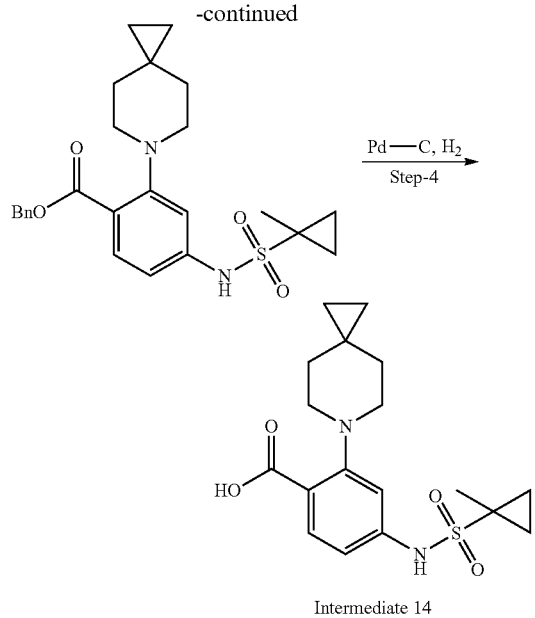

Intermediate 14

Step 1: To a solution of 4-bromo-2-fluorobenzoic acid (50.0 g, 228 mmol, F Chemicals, China) in DMF (500 mL) was added sodium carbonate (31.5 g, 297 mmol) followed by benzyl bromide (43.0 g, 251 mmol) at 0° C. and the reaction mixture was stirred for 24 h at room temperature. The reaction mixture was quenched with water (1000 mL) and extracted with ethyl acetate (3×2000 mL). The organic layer was dried over sodium sulfate, filtered and concentrated under reduced pressure. The crude residue was purified by column chromatography over silica gel using 10% ethyl acetate in hexanes as an eluent to give benzyl 4-bromo-2-fluorobenzoate (65 g, 92% yield) as a colorless viscous oil. $^1$H NMR (400 MHz, Chloroform-d) δ ppm 7.91 (t, J=8.4 Hz, 1H), 7.47 (dt, J=6.0, 1.5 Hz, 2H), 7.43 (dd, J=6.8, 1.8 Hz, 1H), 7.41 (q, J=1.5 Hz, 1H), 7.39-7.35 (m, 1H), 7.02 (dd, J=8.7, 2.1 Hz, 1H), 6.79 (s, 1H), 5.38 (s, 2H). m/z (ESI): 310.2 (MH)$^+$.

Step 2: To a solution of benzyl 4-bromo-2-fluorobenzoate (60.0 g, 194 mmol) in DMSO (200 mL) were added 6-azaspiro[2.5]octane (32.4, 291 mmol, Wuxi Appec) in DMSO (200 mL) and DIPEA (30 g, 291 mmol) and stirred at 100° C. for 12 h. The reaction mixture was quenched with water (2000 mL) and extracted with ethyl acetate (3×2000 mL). The organic layer was dried over sodium sulfate, filtered and concentrated under reduced pressure. The crude residue was purified by column chromatography over silica gel using 10% ethyl acetate in hexanes to give benzyl 4-bromo-2-(6-azaspiro[2.5]octan-6-yl)benzoate (70 g, 90% yield) as a yellow oil. $^1$H NMR (400 MHz, Chloroform-d) δ ppm 7.60 (dd, J=8.4, 1.9 Hz, 1H), 7.50-7.45 (m, 2H), 7.49-7.28 (m, 3H), 7.20 (d, J=1.9 Hz, 1H), 7.07 (dd, J=8.3, 1.9 Hz, 1H), 5.36 (s, 2H), 3.12-3.02 (m, 4H), 1.47 (t, J=5.3 Hz, 4H), 0.33 (d, J=1.8 Hz, 4H). m/z (ESI): 398.1, 400.1 (M+H)$^+$.

Step 3: To a 250-mL sealed tube were added benzyl 4-bromo-2-(6-azaspiro[2.5]octan-6-yl)benzoate (9 g, 22.48 mmol), 1-methylcyclopropane-1-sulfonamide (3.95 g, 29.2 mmol, Combi-Blocks, San Diego, CA) and K$_2$CO$_3$ (6.21 g, 45.0 mmol) in 1,4-dioxane (90 mL) and the reaction was degassed and purged with nitrogen for 5 min. To this reaction mixture was added Xantphos (1.301 g, 2.248 mmol)

followed by Pd$_2$(dba)$_3$ (1.03 g, 1.12 mmol) and the sealed tube was closed and stirred at 110° C. for 18 h. The reaction mixture was quenched with water (250 mL) and extracted with ethyl acetate (2×150 mL). The organic layer was washed with water (100 mL), dried over Na$_2$SO$_4$, filtered and concentrated under reduced pressure. The crude residue was purified by column chromatography over silica gel eluting with a gradient of 0% to 15% EtOAc in hexanes to give benzyl 4-((l-methylcyclopropane)-1-sulfonamido)-2-(6-azaspiro[2.5]octan-6-yl)benzoate (6.1 g, 59% yield) as an orange oil. $^1$H NMR (400 MHz, DMSO-d$_6$) δ ppm 10.06 (s, 1H), 7.62 (d, J=8.5 Hz, 1H), 7.48-7.31 (m, 5H), 6.98 (s, 1H), 6.81 (d, J=8.5 Hz, 1H), 5.27 (s, 2H), 2.92 (t, J=4.96 Hz, 4H), 1.40-1.30 (m, 7H), 1.16 (dd, J=6.4, 4.7 Hz, 2H), 0.81 (dd, J=6.4, 4.7 Hz, 2H), 0.28 (s, 4H). m/z (ESI): 455.2 (M+H)$^+$.

Step 4: To a solution of benzyl 4-((1-methylcyclopropane)-1-sulfonamido)-2-(6-azaspiro[2.5]octan-6-yl)benzoate (2.1 g, 4.62 mmol) in methanol (20 mL) and ethyl acetate (10 mL) was added 10% Pd—C(1.05 g, 50% wt/wt) under nitrogen atmosphere. The reaction mixture was degassed and stirring under hydrogen pressure (1 atm, balloon pressure) for 4 h. The reaction mixture was filtered through a CELITE® bed and washed with methanol (20 mL). The filtrate was concentrated under reduced pressure. The residue was triturated with Et$_2$O (50 mL) to give 4-((1-methylcyclopropane)-1-sulfonamido)-2-(6-azaspiro[2.5]octan-6-yl)benzoic acid (1.2 g, 71% yield) as an off white solid. $^1$H NMR (400 MHz, DMSO-d$_6$) δ ppm 13.20 (s, 1H), 10.33 (s, 1H), 7.95 (d, J=8.6 Hz, 1H), 7.41 (s, 1H), 7.20 (d, J=8.6 Hz, 1H), 2.99 (s, 4H), 1.56 (s, 4H), 1.39 (s, 3H), 1.18 (t, J=4.8 Hz, 2H), 0.83 (t, J=4.7 Hz, 2H), 0.42 (s, 4H). m/z (ESI): 363.2 (M−H)$^+$.

Intermediate 15: 4-(N-(3-Methyloctan-3-yl)sulfamoyl)-2-(6-azaspiro[2.5]octan-6-yl)benzoic acid

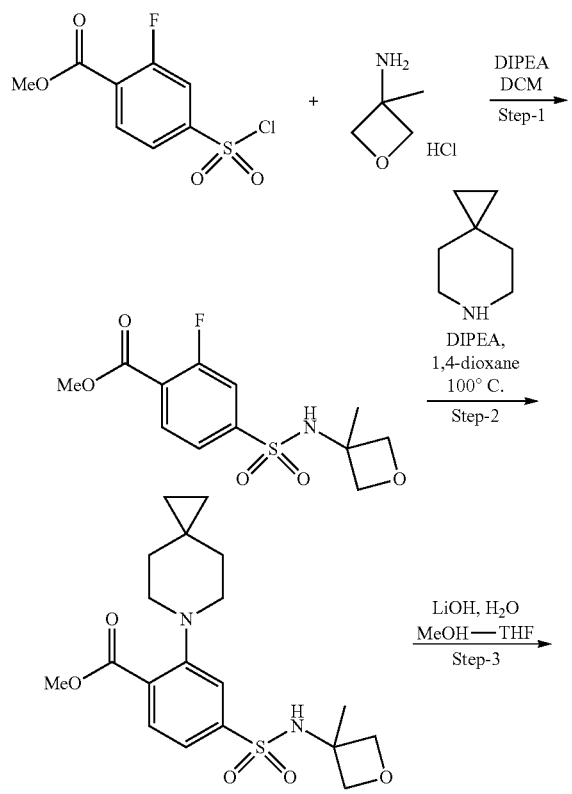

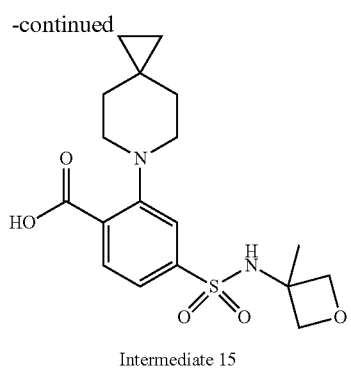

Intermediate 15

Step 1: To a solution of 3-methyl-3-oxetanamine hydrochloride (5.50 g, 44.5 mmol) and N,N-diisopropylethylamine (23.26 mL, 134 mmol) in DCM (200 mL) at 0° C., methyl 4-(chlorosulfonyl)-2-fluorobenzoate (12.37 g, 49.0 mmol) was added and the mixture stirred from 0° C. to room temperature for 1 h. The mixture was diluted with 1.0 N HCl (200 mL) and extracted with dichloromethane (150 mL×2). The combined organic layers were washed with brine, dried with anhydrous sodium sulfate, filtered and concentrated under reduced pressure to afford crude product. The crude product was purified with Biotage SNAP 100 g column eluting with 0-30% 3:1 EtOAc-EtOH in heptane to afford methyl 2-fluoro-4-(N-(3-methyloxetan-3-yl)sulfamoyl)benzoate (13.59 g, 44.8 mmol, 100% yield) as a white solid. $^1$H NMR (500 MHz, DMSO-d$_6$) δ ppm 8.67 (s, 1H), 8.11 (t, J=7.37 Hz, 1H), 7.76-7.82 (m, 1H), 7.69-7.76 (m, 1H), 4.56 (d, J=6.23 Hz, 2H), 4.18 (d, J=6.75 Hz, 2H), 3.90 (s, 3H), 1.42 (s, 3H).

Step 2: A mixture of N,N-diisopropylethylamine (16.23 mL, 93 mmol), 6-azaspiro[2.5]octane (6.22 g, 55.9 mmol), and methyl 2-fluoro-4-(A-(3-methyloxetan-3-yl)sulfamoyl)benzoate (14.13 g, 46.6 mmol) in anhydrous 1,4-dioxane was stirred at 100° C. for 20 h. The mixture was cooled down to room temperature, quenched with water and extracted with ethyl acetate. The combined organic phases were washed with brine, dried and evaporated to dryness under reduced pressure. The crude product was purified using the Biotage SNAP 340 g column eluting with 0-40% 3:1 EtOAc-EtOH in heptane to get methyl 4-(N-(3-methyloxetan-3-yl)sulfamoyl)-2-(6-azaspiro[2.5]octan-6-yl)benzoate (14.15 g, 35.9 mmol, 77% yield) as an off-white solid. $^1$H NMR (500 MHz, DMSO-d$_6$) δ ppm 8.42 (s, 1H), 7.72 (d, J=8.04 Hz, 1H), 7.47 (d, J=1.56 Hz, 1H), 7.36 (dd, J=1.82, 8.04 Hz, 1H), 4.55 (d, J=5.97 Hz, 2H), 4.14 (d, J=6.49 Hz, 2H), 3.85 (s, 3H), 3.02-3.09 (m, 4H), 1.44-1.50 (m, 4H), 1.42 (s, 3H), 0.35 (s, 4H).

Step 3: A mixture of methyl 4-(N-(3-methyloxetan-3-yl)sulfamoyl)-2-(6-azaspiro[2.5]octan-6-yl)benzoate (14.15 g, 35.9 mmol) and lithium hydroxide monohydrate (22.58 g, 538 mmol) in THF-water-MeOH (1:1:1, 300 mL) was stirred at room temperature overnight. The mixture was concentrated under reduced pressure to partially remove the organic solvent. The solution was acidified with 2N HCl to reach pH<3. The precipitated solid was filtered and dried in air to give 4-(N-(3-methyloxetan-3-yl)sulfamoyl)-2-(6-azaspiro[2.5]octan-6-yl)benzoic acid (9.94 g, 26.1 mmol, 72.8% yield) as a white solid. $^1$H NMR (500 MHz, DMSO-J$_6$) δ ppm 8.51 (s, 1H), 8.04 (d, J=8.04 Hz, 1H), 7.89 (d, J=1.30 Hz, 1H), 7.66 (dd, J=1.69, 8.17 Hz, 1H), 4.55 (d, J=6.23 Hz, 2H), 4.09-4.17 (m, 2H), 3.06-3.19 (m, 4H), 1.56 (t, J=5.19 Hz, 4H), 1.40 (s, 3H), 0.36-0.46 (s, 4H).

Intermediate 16: 4-((1-(tert-Butoxycarbonyl)azetidin-3-yl)sulfonyl)-2-(6-azaspiro[2.5]octan-6-yl)benzoic acid

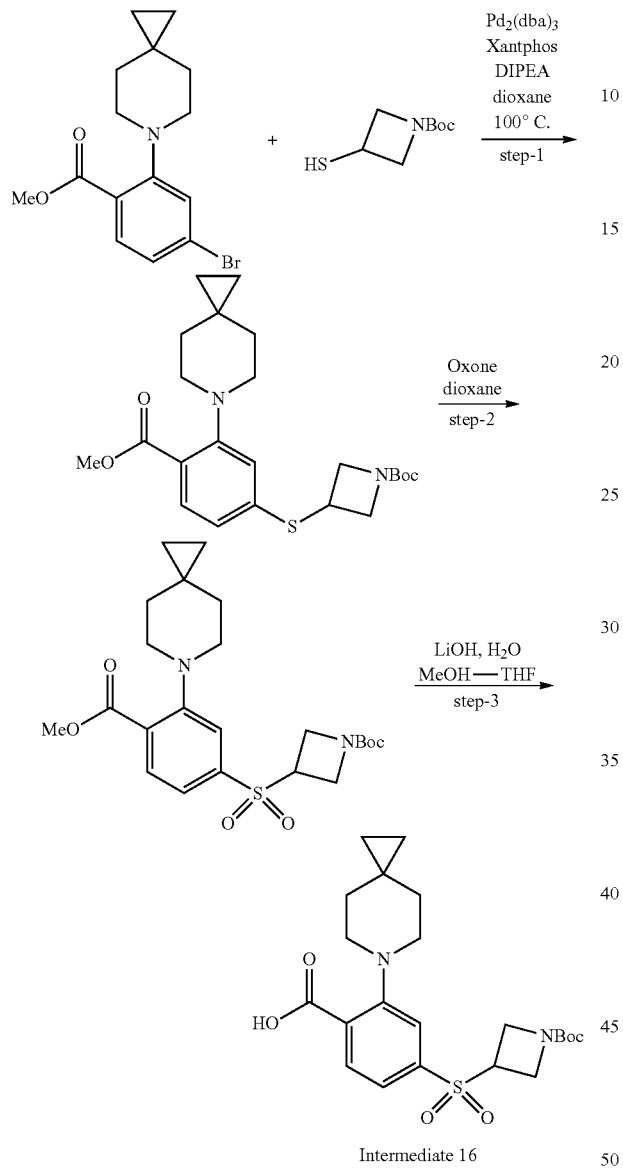

Intermediate 16

Step 1: A mixture of methyl 4-bromo-2-(6-azaspiro[2.5]octan-6-yl)benzoate (10.50 g, 32.4 mmol, Int. 12-2), DIPEA (8.37 mL, 64.8 mmol), Xantphos (1.874 g, 3.24 mmol) and Pd$_2$(dba)$_3$ (2.97 g, 3.24 mmol) in 1,4-dioxane was bubbled with argon flow, then was added tert-butyl 3-mercaptoazetidine-1-carboxylate (7.66 mL, 40.5 mmol). The mixture was stirred at 100° C. for 18 h. The mixture was cooled down to room temperature, concentrated and purified through a Biotage SNAP eluting with a gradient of 0% to 25% 3:1 EtOAc-EtOH in heptane to provide tert-butyl 3-((4-(methoxycarbonyl)-3-(6-azaspiro[2.5]octan-6-yl)phenyl)thio)azetidine-1-carboxylate (13.85 g, 32.0 mmol, 99% yield) as a light-yellow sticky solid. $^1$H NMR (500 MHz, DMSO-d$_6$) δ ppm 7.55 (d, J=8.04 Hz, 1H), 6.79 (s, 1H), 6.76 (d, J=8.14 Hz, 1H), 4.34-4.43 (m, 2H), 4.27-4.34 (m, 1H), 3.79 (s, 3H), 3.70 (dd, J=4.67, 8.56 Hz, 2H), 2.97-3.04 (m, 4H), 1.41-1.51 (m, 4H), 1.38 (s, 9H), 0.29-0.37 (m, 4H).

Step 2: To a solution of tert-butyl 3-((4-(methoxycarbonyl)-3-(6-azaspiro[2.5]octan-6-yl)phenyl)thio)azetidine-1-carboxylate (13.85 g, 32.0 mmol) in 1,4-dioxane (300 mL) was added Oxone monopersulfate (39.4 g, 64.0 mmol) in 150 mL water. The mixture was stirred at room temperature for 5 h and added 150 mL of ethyl acetate and 150 mL of water and the mixture was stirred for 10 minutes. The organic layer was separated, the aqueous layer was extracted with ethyl acetate. The combined organics were washed with brine, dried, filtered and concentrated. The crude material was purified through a Biotage SNAP 340 g column eluting with a gradient of 0% to 25% EtOAc-EtOH (3:1) in heptane to give tert-butyl 3-((4-(methoxycarbonyl)-3-(6-azaspiro[2.5]octan-6-yl)phenyl)sulfonyl)azetidine-1-carboxylate (12.77 g, 27.5 mmol, 86% yield) as an off-white solid. $^1$H NMR (500 MHz, DMSO-d$_6$) δ 7.75 (d, J=8.04 Hz, 1H), 7.44-7.50 (m, 2H), 4.48-4.55 (m, 1H), 4.09 (br s, 2H), 3.97-4.02 (m, 2H), 3.86 (s, 3H), 3.04-3.17 (m, 4H), 1.42-1.51 (m, 4H), 1.38 (s, 9H), 0.35 (s, 4H).

Step 3: A mixture of tert-butyl 3-((4-(methoxycarbonyl)-3-(6-azaspiro[2.5]octan-6-yl)phenyl)sulfonyl) azetidine-1-carboxylate (12.77 g, 27.5 mmol) and lithium hydroxide monohydrate (11.53 g, 275 mmol) in THF-water-MeOH (1:1:1, 230 mL) was stirred at room temperature for 15 h. The mixture was concentrated under reduced pressure to remove some organic solvent. The solution was acidified with 2N HCl to pH<3. The precipitated solid was filtered and dried to give 4-((1-(tert-butoxycarbonyl)azetidin-3-yl)sulfonyl)-2-(6-azaspiro[2.5]octan-6-yl)benzoic acid (10.6 g, 23.53 mmol, 86% yield) as an off-white solid. $^1$H NMR (500 MHz, DMSO-d$_6$) δ ppm 8.03 (d, J=8.30 Hz, 1H), 7.93 (d, J=1.82 Hz, 1H), 7.72 (dd, J=1.69, 8.17 Hz, 1H), 4.48-4.60 (m, 1H), 4.10 (br. s., 2H), 3.99-4.06 (m, 3H), 3.14-3.22 (m, 4H), 1.49-1.59 (m, 4H), 1.38 (s, 9H), 0.41 (s, 4H).

Intermediates Compounds Having Ar$^1$ and Ar$^2$ Rings

Intermediate 17: N-(2-Chloro-6-methylpyrimidin-4-yl)-4-iodo-2-(6-azaspiro[2.5]octan-6-yl)benzamide

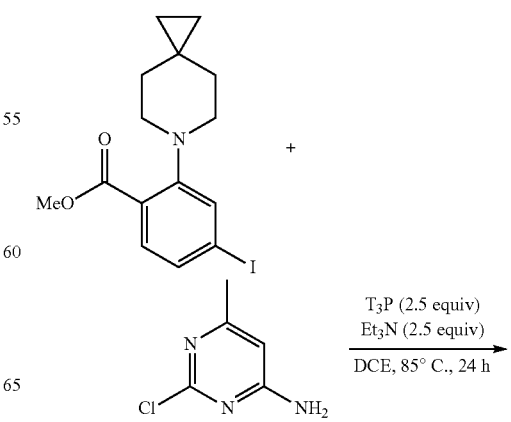

87

-continued

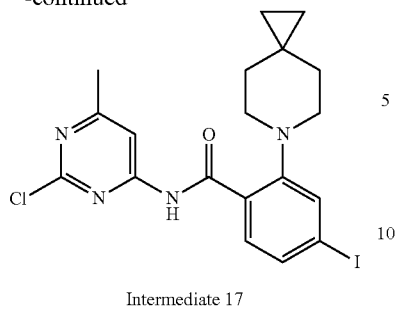

Intermediate 17

2,4,6-Tripropyl-1,3,5,2,4,6-trioxatriphosphinane 2,4,6-trioxide (50 wt % solution in EtOAc, 12.50 mL, 21.00 mmol) and triethylamine (2.93 mL, 21.00 mmol) were added to a suspension of 4-iodo-2-(6-azaspiro[2.5]octan-6-yl)benzoic acid (3.0 g, 8.40 mmol, Int. 12) and 2-chloro-6-methylpyrimidin-4-amine (1.45 g, 10.08 mmol, Aurum Pharmtech Inc.) in DCE (20 mL). The mixture was heated to 85° C. for 24 h, then cooled to room temperature. Water (10 mL) was added, the layers were separated, and the aqueous layer was extracted with DCM (1×10 mL). The combined organic extracts were dried over anhydrous MgSO$_4$, filtered, and concentrated in vacuo to give a solid. The solid was suspended in 1:1 EtOAc/heptane and filtered to provide N-(2-chloro-6-methylpyrimidin-4-yl)-4-iodo-2-(6-azaspiro[2.5]octan-6-yl)benzamide (3.61 g, 7.48 mmol, 89% yield) as an off white solid. $^1$H NMR (400 MHz, CHLOROFORM-d) δ ppm 13.53 (br s, 1H) 8.11 (s, 1H) 7.92 (d, J=8.29 Hz, 1H) 7.70 (s, 1H) 7.65-7.69 (m, 1H) 3.05 (t, J=5.39 Hz, 4H) 2.53 (s, 3H) 1.61-1.88 (m, 4H) 0.44 (s, 4H). m/z (ESI): 483.0 (M+H)$^+$.

Intermediate 18: (R)-4-Bromo-N-(6-methyl-2-(2-methylmorpholino)pyrimidin-4-yl)-2-(6-azaspiro[2.5]octan-6-yl)benzamide

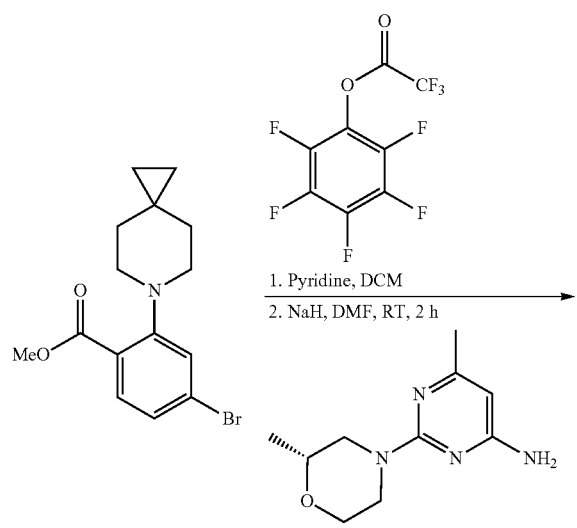

88

-continued

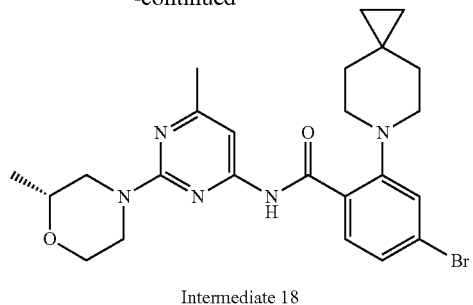

Intermediate 18

Step 1: To a 100-mL round-bottomed flask was added 4-bromo-2-(6-azaspiro[2.5]octan-6-yl)benzoic acid (0.9 g, 2.90 mmol, Int. 12-1), pyridine (0.657 mL, 8.12 mmol) and perfluorophenyl 2,2,2-trifluoroacetate (0.717 g, 3.77 mmol) in DCM (8 mL). The resultant mixture was stirred at rt for 16 h and the solvent was removed under vacuum to get crude product which was used for the next step without purification, m/z (ESI): 476 and 478 (M+1).

Step 2: To a 50-mL round-bottomed flask was added (R)-6-methyl-2-(2-methylmorpholino)pyrimidin-4-amine (0.223 g, 1.15 mmol, Int. 2) dissolved in N,N-dimethylformamide (6 mL) followed by sodium hydride (0.084 g, 2.1 mmol) at rt under nitrogen atmosphere. The reaction mixture was stirred for 10 min and then it was treated with perfluorophenyl 4-bromo-2-(6-azaspiro[2.5]octan-6-yl)benzoate (0.5 g, 1.050 mmol) at RT under nitrogen atmosphere. The resultant reaction mixture was stirred at rt for additional 2 h. Reaction mixture was extracted with DCM (2×30 mL), separated, dried over anhydrous sodium sulphate and evaporated to dryness to get crude material. It was then absorbed onto a plug of silica gel and purified by silica gel flash column chromatography eluting with 30% to 50% EtOAc/hexanes, to provide the title compound (0.20 g, 0.40 mmol, 38% yield) as white solid. $^1$H NMR (300 MHz, DMSO-d$_6$) δ ppm 13.19 (bs, 1H), 7.99 (d, J=8.4 Hz, 1H), 7.69 (s, 1H), 7.55 (d, J=8.4 Hz, 1H), 7.36 (s, 1H), 4.45 (t, J=12 Hz, 2H), 3.88 (m, 1H), 3.52-3.48 (m, 2H) 3.10-2.90 (m, 6H), 2.30 (s, 3H), 1.71-1.62 (m, 4H), 1.14 (d, J=6 Hz, 3H), 0.36 (s, 4H). m/z (ESI): 500 and 502 (M+1).

Intermediate 19: N-(2-(4,4-Difluoropiperidin-1-yl)-6-methylpyrimidin-4-yl)-4-iodo-2-(6-azaspiro[2.5]octan-6-yl)benzamide 13.38 (br s, 1H) 7.72-7.87 (m, 3H) 7.39 (s, 1H) 3.91 (br s, 4H) 2.99-3.06 (m, 4H) 2.32 (s, 3H) 1.92-2.07 (m, 4H) 1.62-1.85 (m, 4H) 0.38 (s, 4H). m/z (ESI): 568.0 (M–H)⁺.

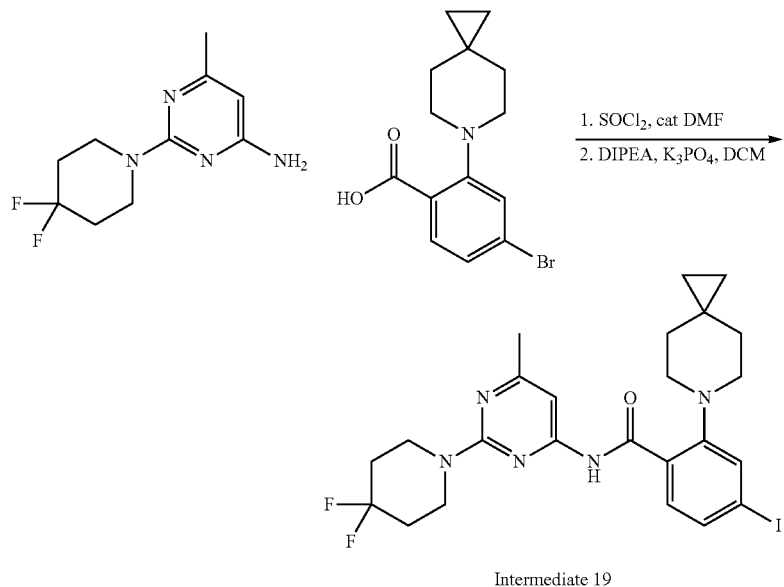

Intermediate 19

4-Iodo-2-(6-azaspiro[2.5]octan-6-yl)benzoic acid (150.0 g, 420 mmol, Int. 12) was suspended in dichloromethane (1000 mL) under argon. Catalytic DMF (1.0 mL) was added followed by dropwise addition of a solution of thionyl chloride (54.6 g, 28 mL, 459 mmol, Sigma-Aldrich Corporation) in dichloromethane (500 mL) over 10 minutes. After stirring at ambient temperature for 30 minutes, the mixture was evaporated to dryness under reduced pressure. The crude was azeotroped with toluene (2×300 mL) and suspended in dichloromethane (300 mL) under argon. Tribasic potassium phosphate (267 g, 1.26 mol, Sigma-Aldrich Corporation) was added followed by a solution of 2-(4,4-difluoropiperidin-1-yl)-6-methylpyrimidin-4-amine (100 g, 438 mmol, Int. 4) and N,N-diisopropylethylamine (200 mL, 1.14 mol, Sigma-Aldrich Corporation) in DCM (300 mL, added over 5 minutes). The yellow mixture was stirred at ambient temperature for 3 hours then evaporated to dryness under reduced pressure. The crude solids were suspended in dichloromethane (1 L) and stirred for 10 minutes. The mixture was filtered through a frit and the solids washed with additional dichloromethane (2×100 mL). The solids were discarded, and the filtrate was evaporated to dryness under reduced pressure. The crude residue was suspended in acetonitrile (750 mL) and stirred at ambient temperature for 15 minutes. The suspension was filtered through a glass frit and the solids washed with additional acetonitrile (75 mL). The solids were dried under a stream of nitrogen to give N-(2-(4,4-difluoropiperidin-1-yl)-6-methylpyrimidin-4-yl)-4-iodo-2-(6-azaspiro[2.5]octan-6-yl)benzamide (186 g, 328 mmol, 78% yield). ¹H NMR (400 MHz, DMSO-d₆) δ ppm Intermediate 20: 4-Bromo-N-(2-(4,4-difluoropiperidin-1-yl)-6-methylpyrimidin-4-yl)-2-fluoro-6-(6-azaspiro[2.5]octan-6-yl)benzamide

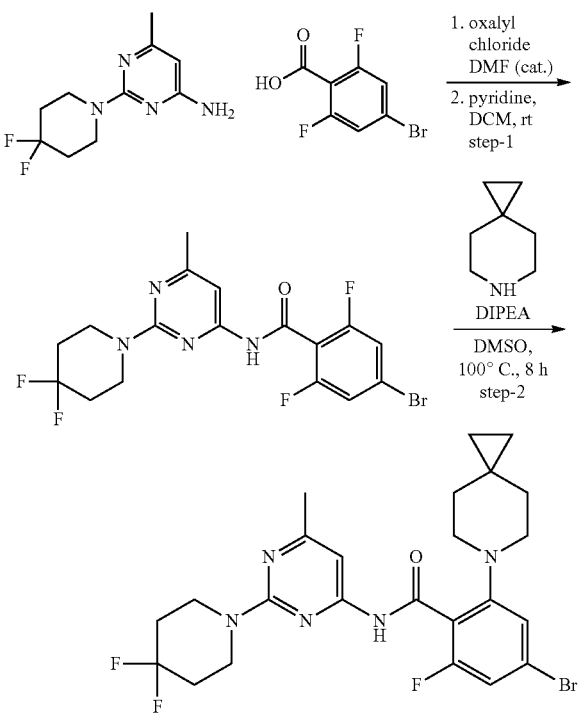

Intermediate 20

Step 1: To a solution of 4-bromo-2,6-difluorobenzoic acid (3.0 g, 12.7 mmol, Apollo Scientific Ltd.) in THF (50 mL)

was oxalyl chloride (1.7 mL, 19.0 mmol) followed by 1 drop of DMF. The mixture was stirred for 1 h then the solvent was removed in vacuo to give a solid that was taken directly to the next stage without further characterization. The solid was dissolved in DCM (50 mL) and anhydrous pyridine (4.31 mL, 50.6 mmol) followed by 2-(4,4-difluoropiperidin-1-yl)-6-methylpyrimidin-4-amine (2.89 g, 12.7 mmol, Int. 4) were added and the mixture was stirred for 16 h at room temperature. EtOAc (200 mL) was added and the mixture was washed with saturated NH$_4$Cl (1×), water (1×), brine (1×), dried over anhydrous MgSO$_4$, filtered and concentrated in vacuo to give an oil. The oil was purified by silica gel chromatography, eluting with 0 to 40% EtOAc/heptane, to provide 4-bromo-N-(2-(4,4-difluoropiperidin-1-yl)-6-methylpyrimidin-4-yl)-2,6-difluorobenzamide (1.36 g, 3.04 mmol, 24% yield) as a white solid. $^1$H NMR (400 MHz, DMSO-d$_6$) δ ppm 11.24 (s, 1H) 7.64 (d, J=7.05 Hz, 2H) 7.19-7.37 (m, 1H) 3.86 (br s, 4H) 2.32 (s, 3H) 1.98 (br d, J=11.40 Hz, 4H). m/z (ESI): 447.0, 449.0 (M+H)$^+$.

Step 2: A mixture of 4-bromo-N-(2-(4,4-difluoropiperidin-1-yl)-6-methylpyrimidin-4-yl)-2,6-difluorobenzamide (0.65 g, 1.45 mmol), 6-azaspiro[2.5]octane (0.18 g, 1.60 mmol, Wuxi App Tech), and DIPEA (0.31 mL, 1.74 mmol) in DMSO (2.5 mL) was heated to 100° C. for 8 h then cooled to room temperature. Water was added, and the resulting suspension was filtered and the solid obtained was dried. This solid was purified by silica gel chromatography, eluting with 0 to 15% EtOAc/heptane, to provide 4-bromo-N-(2-(4,4-difluoropiperidin-1-yl)-6-methylpyrimidin-4-yl)-2-fluoro-6-(6-azaspiro[2.5]octan-6-yl)benzamide (0.23 g, 0.43 mmol, 28.2% yield) as a white solid. $^1$H NMR (400 MHz, DMSO-d$_6$) δ ppm 10.86 (br s, 1H) 7.30 (br s, 1H) 7.21 (br d, J=9.12 Hz, 1H) 7.10 (br s, 1H) 3.88 (br s, 4H) 3.05 (br s, 4H) 2.32 (br s, 3H) 1.77-2.04 (m, 4H) 1.36 (br s, 4H) 0.27 (s, 4H). $^{19}$F NMR (376 MHz, DMSO-d$_6$) δ ppm −94.88 (s, 1F) −113.60 (s, 1F). m/z (ESI): 538.2, 540.2 (M+H)$^+$.

Intermediate 21: 4-Amino-N-(2-(4,4-difluoropiperidin-1-yl)-6-methylpyrimidin-4-yl)-5-fluoro-2-(6-azaspiro[2.5]octan-6-yl)benzamide

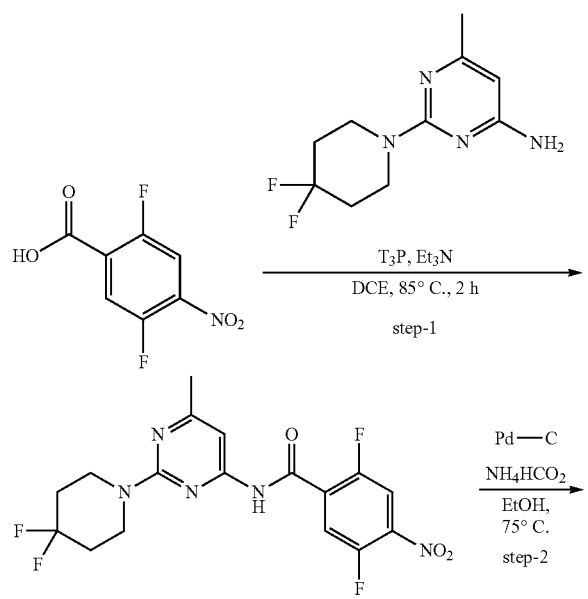

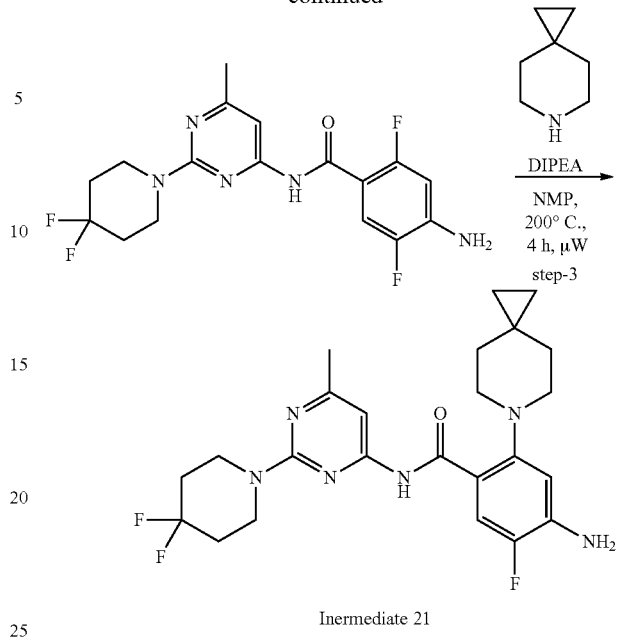

Inermediate 21

Step 1: Triethylamine (3.11 mL, 22.2 mmol) and 2,4,6-tripropyl-1,3,5,2,4,6-trioxatriphosphinane 2,4,6-trioxide (50 wt % in EtOAc, 13.2 mL, 22.2 mmol) were added to a solution of 2,5-difluoro-4-nitrobenzenecarboxylic acid (1.5 g, 7.39 mmol, Combi-Blocks Inc.) and 2-(4,4-difluoropiperidin-1-yl)-6-methylpyrimidin-4-amine (1.69 g, 7.39 mmol, Int. 4) in DCE (15 mL) and the mixture was heated to 85° C. for 2 h then cooled to room temperature. Water (15 mL) was added, the resulting biphasic mixture was separated, and the organic layer was dried over anhydrous MgSO$_4$, filtered, and concentrated in vacuo to give a solid. The solid was suspended in DCM (15 mL), filtered, and dried to provide N-(2-(4,4-difluoropiperidin-1-yl)-6-methylpyrimidin-4-yl)-2,5-difluoro-4-nitrobenzamide (3.05 g, 4.55 mmol, 62% yield) as a yellow solid. $^1$H NMR (400 MHz, DMSO-d$_6$) δ ppm 11.15 (s, 1H) 8.27 (dd, J=8.81, 5.91 Hz, 1H) 7.99 (dd, J=10.57, 5.39 Hz, 1H) 7.23 (br s, 1H) 3.85 (br s, 3H) 2.33 (s, 4H) 1.89-2.05 (m, 4H). $^{19}$F NMR (376 MHz, DMSO-d$_6$) δ ppm −95.11 (s, 1F) −123.35 (s, 1F) −123.40 (s, 1F). m/z (ESI): 414.2 (M+H)$^+$.

Step 2: A mixture of N-(2-(4,4-difluoropiperidin-1-yl)-6-methylpyrimidin-4-yl)-2,5-difluoro-4-nitrobenzamide (1.0 g, 2.42 mmol) and palladium (10 wt. % on activated carbon, 0.45 g, 0.42 mmol) was placed under argon atmosphere and then EtOH (15 mL) was added, followed by ammonium formate (0.76 g, 12.1 mmol). The mixture was stirred at 75° C. for 10 min, then cooled to room temperature. The palladium was filtered off using CELITE® and the filtrate was concentrated in vacuo. The resulting residue was dissolved in EtOAc (10 mL) and the solution was washed with water (2×10 mL), brine (1×10 mL), dried over anhydrous MgSO$_4$, filtered, and concentrated in vacuo to provide 4-amino-N-(2-(4,4-difluoropiperidin-1-yl)-6-methylpyrimidin-4-yl)-2,5-difluorobenzamide (0.93 g, 2.19 mmol, 91% yield) as a white solid. $^1$H NMR (400 MHz, DMSO-d$_6$) δ ppm 9.68-9.80 (m, 1H) 7.40 (dd, J=11.61, 6.84 Hz, 1H) 7.28 (s, 1H) 6.54 (dd, J=13.48, 7.26 Hz, 1H) 6.26 (s, 2H) 3.83-3.90 (m, 4H) 2.30 (s, 3H) 1.92-2.05 (m, 4H). $^{19}$F NMR (376 MHz, DMSO-d$_6$) δ ppm −95.07 (s, 1F) −116.10 (s, 1F) −140.24 (s, 1F). m/z (ESI): 384.2 (M+H)$^+$.

Step 3: A mixture of 4-amino-N-(2-(4,4-difluoropiperidin-1-yl)-6-methylpyrimidin-4-yl)-2,5-difluorobenzamide (0.80 g, 2.09 mmol), 6-azaspiro[2.5]octane (0.70 g, 6.26 mmol, Wuxi App Tech), and DIPEA (1.1 mL, 6.26 mmol) in NMP (4 mL) was heated to 200° C. in a microwave reactor for 4 h. Water (4 mL) was added and the resulting suspension was stirred for 30 min, filtered, and the collected solid was dried to give a white solid. This solid was dissolved in DCM, fused to silica gel and purified by silica gel chromatography, eluting with 0 to 50% EtOAc/heptane, to provide 4-amino-N-(2-(4,4-difluoropiperidin-1-yl)-6-methylpyrimidin-4-yl)-5-fluoro-2-(6-azaspiro[2.5]octan-6-yl)benzamide (702 mg, 1.48 mmol, 70.9% yield) as a white solid. $^1$H NMR (400 MHz, DMSO-d$_6$) δ ppm 13.77 (s, 1H) 7.64 (d, J=12.85 Hz, 1H) 7.38 (s, 1H) 6.83 (d, J=8.09 Hz, 1H) 6.04 (s, 2H) 3.90 (br t, J=5.39 Hz, 4H) 2.91 (br s, 4H) 2.29 (s, 3H) 1.88-2.04 (m, 4H) 0.37 (s, 4H). (Note: 4 protons not observed). $^{19}$F NMR (376 MHz, DMSO-d$_6$) δ ppm −94.73 (s, 1F) −138.31 (s, 1F). m/z (ESI): 475.2 (M+H)$^+$.

TABLE 5

Intermediates 21-1 to 21-20 were prepared following similar procedures for Int. 17 to 21:

| Int. # | Chemical Structure | Name | LRMS: (ESI + ve ion) m/z |
|---|---|---|---|
| 21-1 | 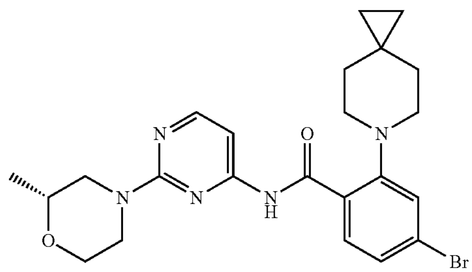 [SMILES: C[C@@H]1CN(c2nccc(NC(=O)c3ccc(Br)cc3N3CCC4(CC3)CC4)n2)CCO1] | (R)-4-Bromo-N-(2-(2-methylmorpholino)pyrimidin-4-yl)-2-(6-azaspiro[2.5]octan-6-yl)benzamide | 486.1/488.1 |
| 21-2 | 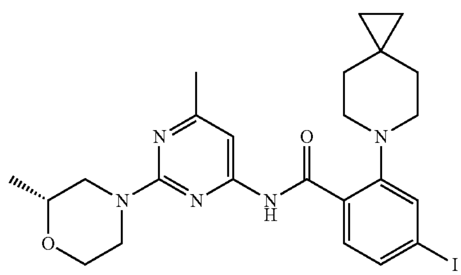 [SMILES: Cc1cc(NC(=O)c2ccc(I)cc2N2CCC3(CC2)CC3)nc(N2CCO[C@H](C)C2)n1] | (R)-4-Iodo-N-(6-methyl-2-(2-methylmorpholino)pyrimidin-4-yl)-2-(6-azaspiro[2.5]octan-6-yl)benzamide | 548.2 |
| 21-3 | 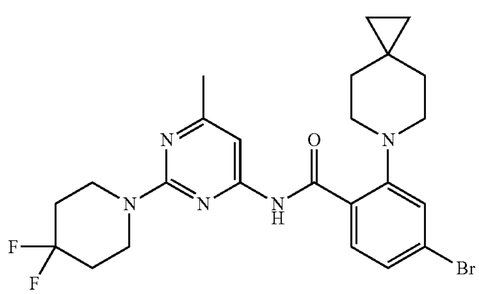 [SMILES: Cc1cc(NC(=O)c2ccc(Br)cc2N2CCC3(CC2)CC3)nc(N2CCC(F)(F)CC2)n1] | 4-Bromo-N-(2-(4,4-difluoropiperidin-1-yl)-6-methylpyrimidin-4-yl)-2-(6-azaspiro[2.5]octan-6-yl)benzamide | 520.1/522.1 |
| 21-4 | 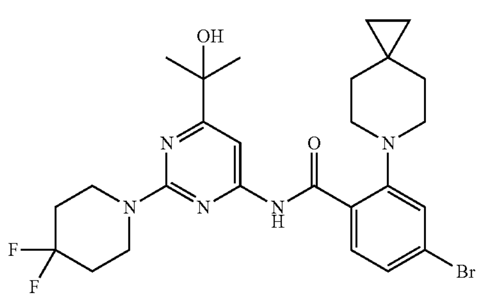 [SMILES: CC(C)(O)c1cc(NC(=O)c2ccc(Br)cc2N2CCC3(CC2)CC3)nc(N2CCC(F)(F)CC2)n1] | 4-Bromo-N-(2-(4,4-difluoropiperidin-1-yl)-6-(2-hydroxypropan-2-yl)pyrimidin-4-yl)-2-(6-azaspiro[2.5]octan-6-yl)benzamide | 564.1/566.1 |

TABLE 5-continued

Intermediates 21-1 to 21-20 were prepared following similar procedures for Int. 17 to 21:

| Int. # | Chemical Structure | Name | LRMS: (ESI + ve ion) m/z |
|---|---|---|---|
| 21-5 | 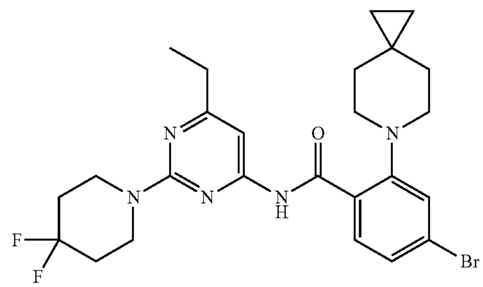 [SMILES: CCc1cc(NC(=O)c2ccc(Br)cc2N2CCC3(CC2)CC3)nc(N2CCC(F)(F)CC2)n1] | 4-Bromo-N-(2-(4,4-difluoropiperidin-1-yl)-6-ethylpyrimidin-4-yl)-2-(6-azaspiro[2.5]octan-6-yl)benzamide | 534.2/536.2 |
| 21-6 | 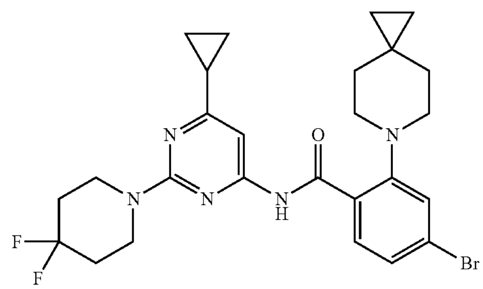 [SMILES: O=C(Nc1cc(C2CC2)nc(N2CCC(F)(F)CC2)n1)c1ccc(Br)cc1N1CCC2(CC1)CC2] | 4-Bromo-N-(6-cyclopropyl-2-(4,4-difluoropiperidin-1-yl)pyrimidin-4-yl)-2-(6-azaspiro[2.5]octan-6-yl)benzamide | 546.1/548.1 |
| 21-7 | 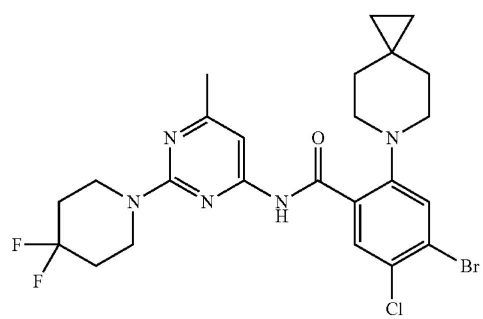 [SMILES: Cc1cc(NC(=O)c2cc(Cl)c(Br)cc2N2CCC3(CC2)CC3)nc(N2CCC(F)(F)CC2)n1] | 4-Bromo-5-chloro-N-(2-(4,4-difluoropiperidin-1-yl)-6-methylpyrimidin-4-yl)-2-(6-azaspiro[2.5]octan-6-yl)benzamide | 553.0/555.0 |
| 21-8 | 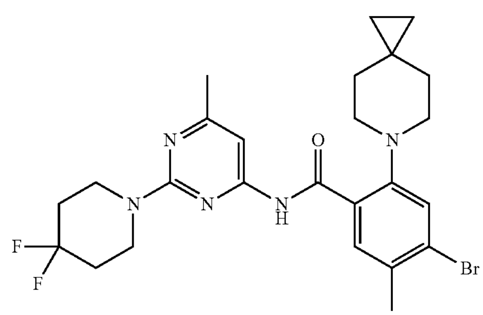 [SMILES: Cc1cc(NC(=O)c2cc(C)c(Br)cc2N2CCC3(CC2)CC3)nc(N2CCC(F)(F)CC2)n1] | 4-Bromo-N-(2-(4,4-difluoropiperidin-1-yl)-6-methylpyrimidin-4-yl)-5-methyl-2-(6-azaspiro[2.5]octan-6-yl)benzamide | 534.2/536.2 |
| 21-9 | 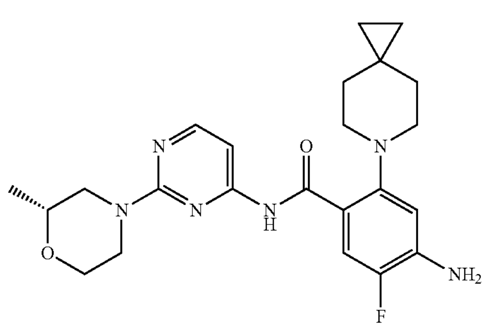 [SMILES: C[C@@H]1CN(c2nccc(NC(=O)c3cc(F)c(N)cc3N3CCC4(CC3)CC4)n2)CCO1] | (R)-4-Amino-5-fluoro-N-(2-(2-methylmorpholino)pyrimidin-4-yl)-2-(6-azaspiro[2.5]octan-6-yl)benzamide | 441.2 |

TABLE 5-continued

Intermediates 21-1 to 21-20 were prepared following similar procedures for Int. 17 to 21:

| Int. # | Chemical Structure | Name | LRMS: (ESI + ve ion) m/z |
|---|---|---|---|
| 21-10 | 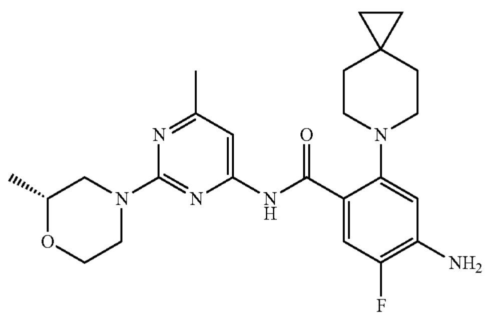 [SMILES: Cc1cc(NC(=O)c2cc(F)c(N)cc2N2CCC3(CC2)CC3)nc(N2CCO[C@H](C)C2)n1] | (R)-4-Amino-5-fluoro-N-(6-methyl-2-(2-methylmorpholino)pyrimidin-4-yl)-2-(6-azaspiro[2.5]octan-6-yl)benzamide | 455.2 |
| 21-11 | 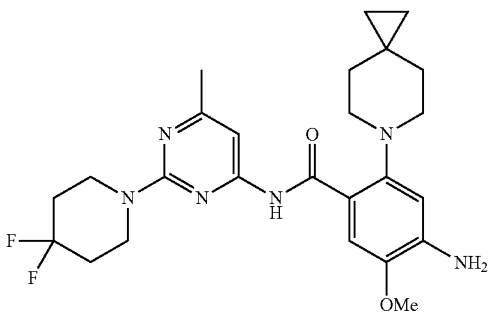 [SMILES: COc1cc(C(=O)Nc2cc(C)nc(N3CCC(F)(F)CC3)n2)c(N2CCC3(CC2)CC3)cc1N] | 4-Amino-N-(2-(4,4-difluoropiperidin-1-yl)-6-methylpyrimidin-4-yl)-5-methoxy-2-(6-azaspiro[2.5]octan-6-yl)benzamide | 487.4 |
| 21-12 | 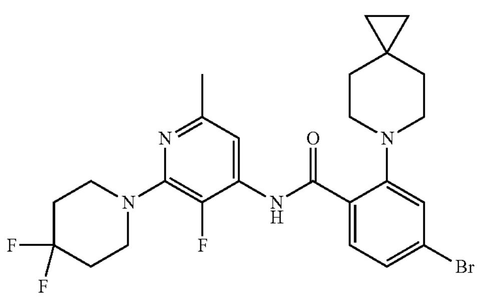 [SMILES: Cc1cc(NC(=O)c2ccc(Br)cc2N2CCC3(CC2)CC3)c(F)c(N2CCC(F)(F)CC2)n1] | 4-Bromo-N-(2-(4,4-difluoropiperidin-1-yl)-3-fluoro-6-methylpyridin-4-yl)-2-(6-azaspiro[2.5]octan-6-yl)benzamide | 537.1/539.1 |
| 21-13 | 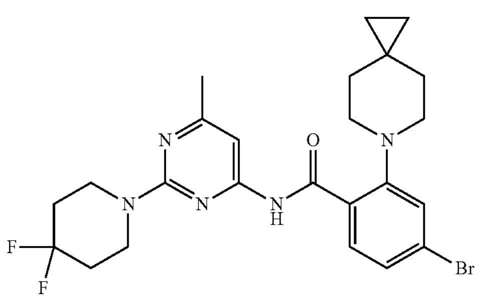 [SMILES: Cc1cc(NC(=O)c2ccc(Br)cc2N2CCC3(CC2)CC3)nc(N2CCC(F)(F)CC2)n1] | 4-Bromo-N-(2-(4,4-difluorocyclohexyl)-6-methylpyrimidin-4-yl)-2-(6-azaspiro[2.5]octan-6-yl)benzamide | 519.1/521.1 |
| 21-14 | 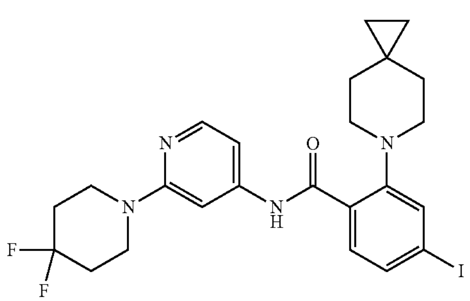 [SMILES: O=C(Nc1ccnc(N2CCC(F)(F)CC2)c1)c1ccc(I)cc1N1CCC2(CC1)CC2] | N-(2-(4,4-Difluoropiperidin-1-yl)pyridin-4-yl)-4-iodo-2-(6-azaspiro[2.5]octan-6-yl)benzamide | 553.1 |

TABLE 5-continued

Intermediates 21-1 to 21-20 were prepared following similar procedures for Int. 17 to 21:

| Int. # | Chemical Structure | Name | LRMS: (ESI + ve ion) m/z |
|---|---|---|---|
| 21-15 | 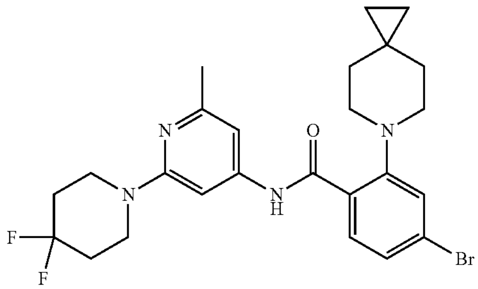 [SMILES: Cc1cc(NC(=O)c2ccc(Br)cc2N2CCC3(CC2)CC3)cc(N2CCC(F)(F)CC2)n1] | 4-Bromo-N-(2-(4,4-difluoropiperidin-1-yl)-6-methylpyridin-4-yl)-2-(6-azaspiro[2.5]octan-6-yl)benzamide | 519.1/521.1 |
| 21-16 | 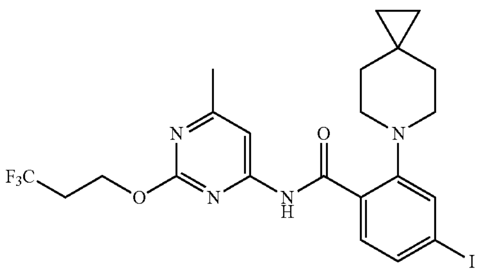 [SMILES: Cc1cc(NC(=O)c2ccc(I)cc2N2CCC3(CC2)CC3)nc(OCCC(F)(F)F)n1] | 4-Iodo-N-(6-methyl-2-(3,3,3-trifluoropropoxy)pyrimidin-4-yl)-2-(6-azaspiro[2.5]octan-6-yl)benzamide | 561.0 |
| 21-17 | 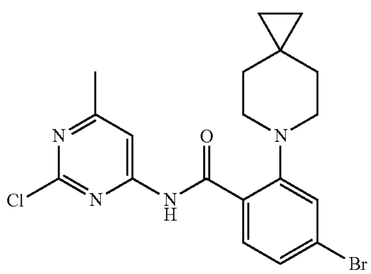 [SMILES: Cc1cc(NC(=O)c2ccc(Br)cc2N2CCC3(CC2)CC3)nc(Cl)n1] | 4-Bromo-N-(2-chloro-6-methylpyrimidin-4-yl)-2-(6-azaspiro[2.5]octan-6-yl)benzamide | 435.0/437.0 |
| 21-18 | 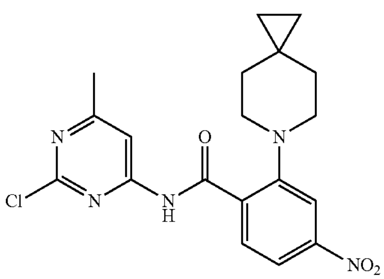 [SMILES: Cc1cc(NC(=O)c2ccc([N+](=O)[O-])cc2N2CCC3(CC2)CC3)nc(Cl)n1] | N-(2-Chloro-6-methylpyrimidin-4-yl)-4-nitro-2-(6-azaspiro[2.5]octan-6-yl)benzamide | 402.2 |
| 21-19 | 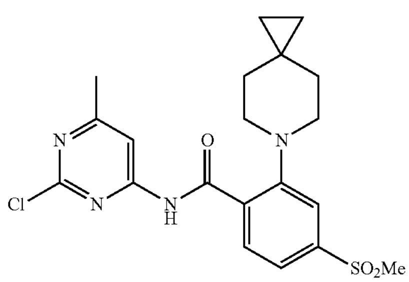 [SMILES: Cc1cc(NC(=O)c2ccc(S(C)(=O)=O)cc2N2CCC3(CC2)CC3)nc(Cl)n1] | N-(2-Chloro-6-methylpyrimidin-4-yl)-4-(methylsulfonyl)-2-(6-azaspiro[2.5]octan-6-yl)benzamide | 434.4 |

TABLE 5-continued

Intermediates 21-1 to 21-20 were prepared following similar procedures for Int. 17 to 21:

| Int. # | Chemical Structure | Name | LRMS: (ESI + ve ion) m/z |
|---|---|---|---|
| 21-20 | 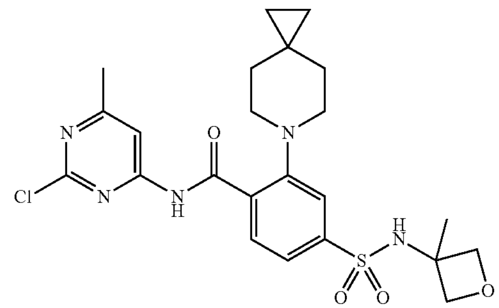 [SMILES: Cc1cc(NC(=O)c2ccc(S(=O)(=O)NC3(C)COC3)cc2N2CCC3(CC2)CC3)nc(Cl)n1] | N-(2-Chloro-6-methylpyrimidin-4-yl)-4-(N-(3-methyloxetan-3-yl)sulfamoyl)-2-(6-azaspiro[2.5]octan-6-yl)benzamide | 506.1 |

Intermediate 22: Ethyl 2-sulfamoylpropanoate

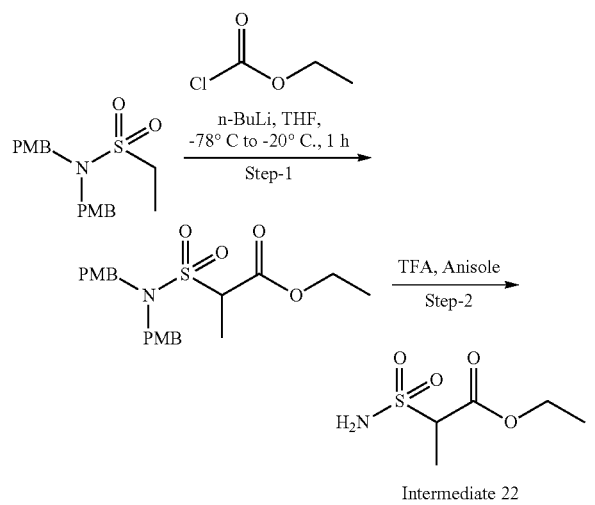

Intermediate 22

Step 1: To a solution of N,N-bis(4-methoxybenzyl)ethanesulfonamide (200.0 g, 572.0 mmol) in tetrahydrofuran (4000 mL) was added nBuLi (1.6 M in hexane, 608.0 mL, 973.0 mmol) at −78° C. slowly and stirred for 30 min. Ethyl carbonochloridate (92.0 mL, 973.0 mmol) in THF (50 mL) was added to the reaction mixture and stirred at −78° C. for 1 h. The reaction mixture was quenched with HCl (1.5 N, 3000 mL) and extracted with EtOAc (2×3000 mL). The organic extract was dried over sodium sulphate, filtered and concentrated in reduced pressure to give the crude material of ethyl 2-(N,N-bis(4-methoxybenzyl)sulfamoyl)propanoate (250.0 g, 60% pure) as yellow oil. The $^1$H-NMR showed desired peaks and proceeded to next step without any purification.

Step 2: To solution of ethyl 2-(N,N-bis(4-methoxybenzyl) sulfamoyl)propanoate (600.0 g, 1.4 mol) in trifluoroacetic acid (2.50 L, 32.45 mol) was added anisole (500.0 mL, 4.57 mol) and stirred at room temperature for 3 h. The reaction mixture was concentrated under reduced pressure, quenched with 10% cold aqueous NaHCO$_3$ solution (3 L) and extracted with EtOAc (2×3 L). The organic layer was dried over sodium sulfate, filtered and concentrated under reduced pressure. The crude residue was purified by column chromatography over silica gel using 25% ethyl acetate in hexanes to give a pale yellow solid (168 g) which was dissolved in DCM (1 L) and precipitated by the addition of hexanes (3000 mL). The solid was filtered, dried under vacuum to give the title compound (109.0 g, 42% yield) as a white solid. $^1$H NMR (400 MHz, DMSO-d$_6$) δ ppm 7.14 (s, 2H), 4.15 (q, J=7.1 Hz, 2H), 3.98 (q, J=7.0 Hz, 1H), 1.45 (d, J=7.0 Hz, 3H), 1.21 (t, J=7.1 Hz, 3H). m/z (ESI): 180.1 (M−H)$^+$.

Intermediate 23: 2-Hydroxypropane-1-sulfonamide

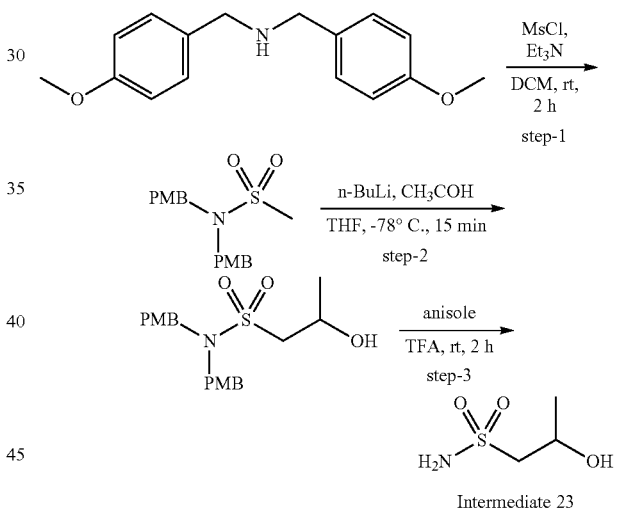

Intermediate 23

Step 1: Methanesulfonyl chloride (1.73 mL, 22.3 mmol) was added dropwise over 5 min to a 0° C. solution of bis(4-methoxylbenzyl)amine (5.0 g, 19.4 mmol, Combi-Blocks Inc.) and triethylamine (8.12 mL, 58.3 mmol) in DCM (40 mL). The mixture was then stirred for 2 h at room temperature and then 1N HCl (50 mL) was added. The layers were separated, and the organic layer was washed with brine (1×50 mL), dried over anhydrous MgSO$_4$, filtered, and then concentrated in vacuo to give a brown oil. The oil was dissolved in MeOH (50 mL) and partially concentrated in vacuo until a thick suspension formed. The suspension was stirred for 30 min, filtered, and the collected solid was dried in vacuo to provide N,N-bis(4-methoxybenzyl)methanesulfonamide (5.11 g, 15.2 mmol, 78% yield) as a white solid. $^1$H NMR (400 MHz, DMSO-t4) δ ppm 7.19 (d, J=8.50 Hz, 4H) 6.90 (d, J=8.50 Hz, 4H) 4.19 (s, 4H) 3.75 (s, 6H) 2.89 (s, 3H).

Step 2: n-Butyllithium (4.10 mL, 6.56 mmol) was added dropwise to a solution of N,N-bis(4-methoxybenzyl)methanesulfonamide (2.0 g, 5.96 mmol) in THF (15 mL) at −78°

C. The mixture was stirred for 10 min before acetaldehyde (0.37 mL, 6.56 mmol) was added dropwise. This mixture was stirred at −78° C. for 5 min, and then the −78° C. bath was replaced with a 0° C. bath. The mixture was stirred for 15 min and then the reaction was quenched with saturated $NH_4Cl$. EtOAc was added, the resulting biphasic mixture was separated, and the organic layer was dried over anhydrous $MgSO_4$, filtered, and concentrated in vacuo to give an oil. The oil was purified by silica gel chromatography, eluting with 0 to 70% EtOAc/heptane gradient, to provide 2-hydroxy-N,N-bis(4-methoxybenzyl)propane-1-sulfonamide (1.84 g, 4.85 mmol, 81% yield) as an oil. $^1$H NMR (400 MHz, DMSO-$d_6$) δ ppm 7.16 (d, J=8.50 Hz, 4H) 6.80-6.92 (m, 4H) 4.99 (d, J=5.18 Hz, 1H) 4.15-4.28 (m, 4H) 4.01-4.13 (m, 1H) 3.74 (s, 6H) 3.16 (dd, J=13.99, 6.53 Hz, 1H) 3.04 (dd, J=13.89, 5.39 Hz, 1H) 1.12-1.27 (m, 3H). m/z (ESI): 402.2 (M+Na)$^+$.

Step 3: A mixture of 2-hydroxy-N,N-bis(4-methoxybenzyl)propane-1-sulfonamide (1.84 g, 4.85 mmol) and anisole (1.06 mL, 9.70 mmol) in TFA (10 mL) was stirred at room temperature for 2 h, then the volatiles were removed in vacuo. The resulting oil was purified by silica gel chromatography, eluting with 0 to 100% EtOAc/heptane gradient, to provide 2-hydroxypropane-1-sulfonamide (592 mg, 4.25 mmol, 88% yield) as a colorless oil. $^1$H NMR (400 MHz, DMSO-$d_6$) δ ppm 6.70 (s, 2H) 4.02-4.13 (m, 1H) 3.50-3.25 (br s, 1H) 3.07-3.15 (m, 1H) 2.98-3.06 (m, 1H) 1.20 (d, J=6.22 Hz, 3H).

Example 1: N-(2-((1-Hydroxy-2-methylpropan-2-yl)amino)-6-methylpyrimidin-4-yl)-4-(methylsulfonyl)-2-(6-azaspiro[2.5]octan-6-yl)benzamide

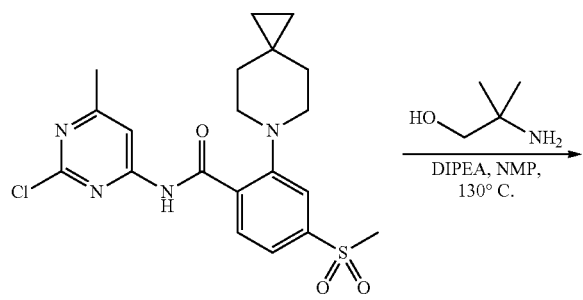

A mixture of N-(2-chloro-6-methylpyrimidin-4-yl)-4-(methylsulfonyl)-2-(6-azaspiro[2.5]octan-6-yl)benzamide (200 mg, 0.46 mmol, Int. 21-19), 2-amino-2-methyl-1-propanol (180 uL, 1.80 mmol, Sigma-Aldrich, St Louis, MO), and DIPEA (200 uL, 1.14 mmol) in NMP (1 mL) was heated at 130° C. for 60 h. The reaction mixture was cooled to room temperature and quenched with water (10 mL), extracted with ethyl acetate (2×10 mL). The organic layer was washed with brine (500 mL), dried ($Na_2SO_4$), filtered and concentrated under reduced pressure. The crude material was adsorbed onto a plug of silica gel and purified by column chromatography over silica gel (60-120 mesh), eluting with 0% to 70% ethyl acetate in heptane to give the title compound (111 mg, 49%) as an off white solid. $^1$H NMR (400 MHz, DMSO-$d_6$) δ ppm 11.65-11.96 (m, 1H), 8.07-8.25 (m, 1H), 7.82-7.87 (m, 1H), 7.75-7.81 (m, 1H), 7.32-7.41 (m, 1H), 6.13-6.24 (m, 1H), 4.73-4.91 (m, 1H), 3.42-3.54 (m, 2H), 3.30-3.33 (m, 3H), 3.01-3.16 (m, 4H), 2.18-2.28 (m, 3H), 1.55-1.75 (m, 4H), 1.25-1.42 (m, 6H), 0.27-0.40 (m, 4H). m/z (ESI): 487.4 (M+H)$^+$.

TABLE 6

Examples 1-1 to 1-7 were prepared following a similar procedure as described for Example 1:

| Ex. # | Chemical Structure | Name | LRMS: (ESI +ve ion) m/z |
|---|---|---|---|
| 1-1 | 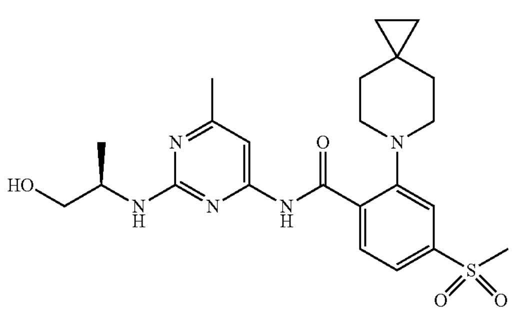 [SMILES: Cc1cc(NC(=O)c2ccc(S(C)(=O)=O)cc2N2CCC3(CC2)CC3)nc(N[C@H](C)CO)n1] | (R)-N-(2-((1-Hydroxypropan-2-yl)amino)-6-methylpyrimidin-4-yl)-4-(methylsulfonyl)-2-(6-azaspiro[2.5]octan-6-yl)benzamide | 474.0 |

TABLE 6-continued

Examples 1-1 to 1-7 were prepared following a similar procedure as described for Example 1:

| Ex. # | Chemical Structure | Name | LRMS: (ESI + ve ion) m/z |
|---|---|---|---|
| 1-2 | 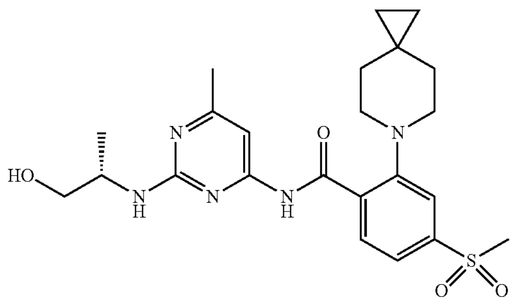 [SMILES: Cc1cc(NC(=O)c2ccc(S(C)(=O)=O)cc2N2CCC3(CC2)CC3)nc(N[C@@H](C)CO)n1] | (S)-N-(2-((1-Hydroxypropan-2-yl)amino)-6-methylpyrimidin-4-yl)-4-(methylsulfonyl)-2-(6-azaspiro[2.5]octan-6-yl)benzamide | 474.0 |
| 1-3 | 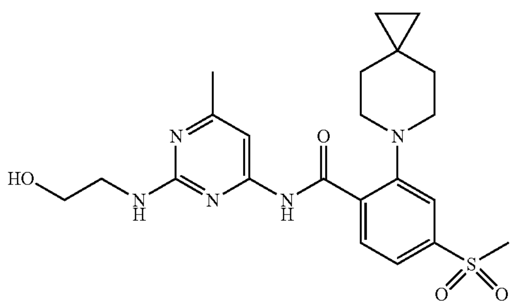 [SMILES: Cc1cc(NC(=O)c2ccc(S(C)(=O)=O)cc2N2CCC3(CC2)CC3)nc(NCCO)n1] | N-(2-((2-Hydroxyethyl)amino)-6-methylpyrimidin-4-yl)-4-(methylsulfonyl)-2-(6-azaspiro[2.5]octan-6-yl)benzamide | 460.4 |
| 1-4 | 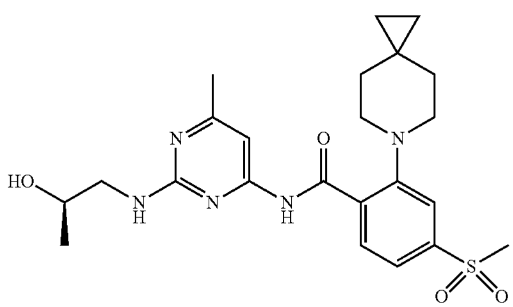 [SMILES: Cc1cc(NC(=O)c2ccc(S(C)(=O)=O)cc2N2CCC3(CC2)CC3)nc(NC[C@@H](C)O)n1] | (R)-N-(2-((2-Hydroxypropyl)amino)-6-methylpyrimidin-4-yl)-4-(methylsulfonyl)-2-(6-azaspiro[2.5]octan-6-yl)benzamide | 474.4 |
| 1-5 | 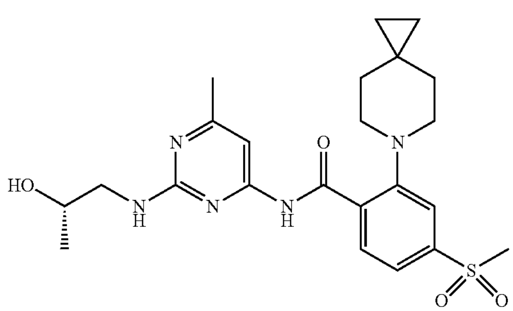 [SMILES: Cc1cc(NC(=O)c2ccc(S(C)(=O)=O)cc2N2CCC3(CC2)CC3)nc(NC[C@H](C)O)n1] | (S)-N-(2-((2-Hydroxypropyl)amino)-6-methylpyrimidin-4-yl)-4-(methylsulfonyl)-2-(6-azaspiro[2.5]octan-6-yl)benzamide | 474.4 |

TABLE 6-continued

Examples 1-1 to 1-7 were prepared following a similar procedure as described for Example 1:

| Ex. # | Chemical Structure | Name | LRMS: (ESI + ve ion) m/z |
|---|---|---|---|
| 1-6 | 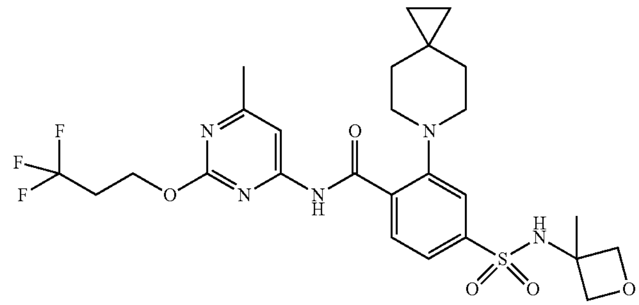 [SMILES: Cc1cc(NC(=O)c2ccc(S(=O)(=O)NC3(C)COC3)cc2N2CCC3(CC2)CC3)nc(OCCC(F)(F)F)n1] | N-(6-Methyl-2-(3,3,3-trifluoropropoxy)pyrimidin-4-yl)-4-(N-(3-methyloxetan-3-yl)sulfamoyl)-2-(6-azaspiro[2.5]octan-6-yl)benzamide | 584.2 |
| 1-7 | 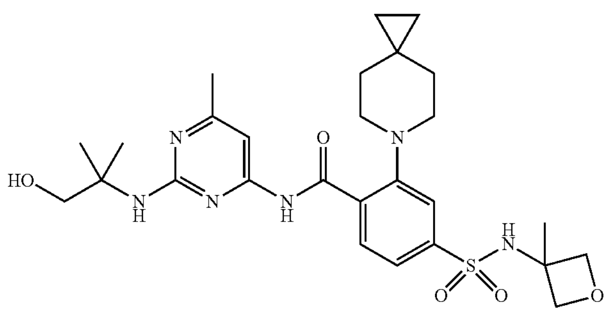 [SMILES: Cc1cc(NC(=O)c2ccc(S(=O)(=O)NC3(C)COC3)cc2N2CCC3(CC2)CC3)nc(NC(C)(C)CO)n1] | N-(2-((1-Hydroxy-2-methylpropan-2-yl)amino)-6-methylpyrimidin-4-yl)-4-(N-(3-methyloxetan-3-yl)sulfamoyl)-2-(6-azaspiro[2.5]octan-6-yl)benzamide | 559.4 |

Example 2: N-(2-(2-Hydroxypropan-2-yl)pyrimidin-4-yl)-4-(N-(3-methyloxetan-3-yl)sulfamoyl)-2-(6-azaspiro[2.5]octan-6-yl)benzamide

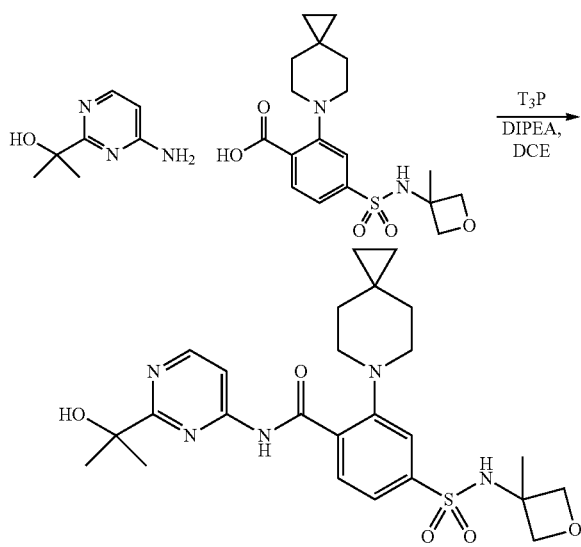

To a solution of 4-(N-(3-methyloxetan-3-yl)sulfamoyl)-2-(6-azaspiro[2.5]octan-6-yl)benzoic acid (150 mg, 0.394 mmol, Int. 15) and 2-(4-aminopyrimidin-2-yl)propan-2-ol (91 mg, 0.591 mmol, AstaTech, Bristol, PA, USA) in dichloromethane (2.6 mL) at 0° C. was added 1-propanephosphonic anhydride (50% in ethyl acetate, 0.469 mL, 0.789 mmol, Aldrich) followed by DIPEA (0.207 mL, 1.18 mmol, Aldrich). The resulting mixture was then stirred at room temperature overnight. Then, the mixture was then diluted with saturated NaHCO$_3$ (2 mL) followed by saturated NH$_4$Cl (7 mL). The mixture was then extracted with EtOAc (2×15 mL). The combined organic extracts were then dried over MgSO$_4$ and concentrated. Chromatographic purification of the residue (silica gel, 0%-100% EtOAc/heptane) provided N-(2-(2-hydroxypropan-2-yl)pyrimidin-4-yl)-4-(N-(3-methyloxetan-3-yl)sulfamoyl)-2-(6-azaspiro[2.5]octan-6-yl)benzamide (45 mg, 0.087 mmol) as a light yellow solid. $^1$H NMR (DMSO-d$_6$) δ ppm 13.52 (brs, 1H), 8.76 (d, J=5.6 Hz, 1H), 8.54 (br d, J=3.5 Hz, 1H), 8.24 (d, J=8.1 Hz, 1H), 8.08 (br d, J=5.4 Hz, 1H), 7.86 (d, J=1.0 Hz, 1H), 7.74 (dd, J=8.1, 1.5 Hz, 1H), 4.96 (s, 1H), 4.55 (d, J=6.0 Hz, 2H), 4.13 (d, J=6.4 Hz, 2H), 3.08 (br t, J=5.2 Hz, 4H), 1.70 (brs, 4H), 1.51 (s, 6H), 1.41 (s, 3H), 0.38 (s, 4H). m/z (ESI): 516.2 (M+H)+.

TABLE 7

Examples 2-1 to 2-8 were prepared following a similar procedure as described for example 2:

| Ex. # | Chemical Structure | Name | LRMS: (ESI + ve ion) m/z |
|---|---|---|---|
| 2-1 | 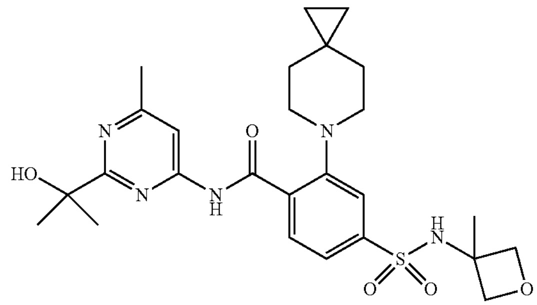 [SMILES: Cc1cc(NC(=O)c2ccc(S(=O)(=O)NC3(C)COC3)cc2N2CCC3(CC2)CC3)nc(C(C)(C)O)n1] | N-(2-(2-Hydroxypropan-2-yl)-6-methylpyrimidin-4-yl)-4-(N-(3-methyloxetan-3-yl)sulfamoyl)-2-(6-azaspiro[2.5]octan-6-yl)benzamide | 530.2 |
| 2-2 | 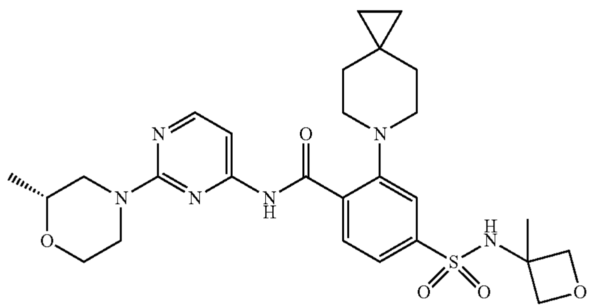 [SMILES: C[C@@H]1CN(c2nccc(NC(=O)c3ccc(S(=O)(=O)NC4(C)COC4)cc3N3CCC4(CC3)CC4)n2)CCO1] | (R)-N-(2-(2-Methylmorpholino)pyrimidin-4-yl)-4-(N-(3-methyloxetan-3-yl)sulfamoyl)-2-(6-azaspiro[2.5]octan-6-yl)benzamide | 557.2 |
| 2-3 | 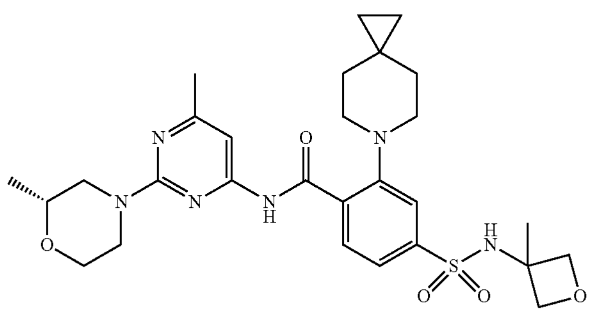 [SMILES: Cc1cc(NC(=O)c2ccc(S(=O)(=O)NC3(C)COC3)cc2N2CCC3(CC2)CC3)nc(N2CCO[C@H](C)C2)n1] | (R)-N-(6-Methyl-2-(2-methylmorpholino)pyrimidin-4-yl)-4-(N-(3-methyloxetan-3-yl)sulfamoyl)-2-(6-azaspiro[2.5]octan-6-yl)benzamide | 571.2 |
| 2-4 | 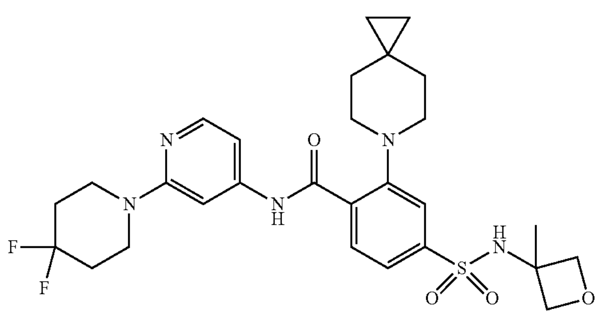 [SMILES: CC1(NS(=O)(=O)c2ccc(C(=O)Nc3ccnc(N4CCC(F)(F)CC4)c3)c(N3CCC4(CC3)CC4)c2)COC1] | N-(2-(4,4-Difluoropiperidin-1-yl)pyridin-4-yl)-4-(N-(3-methyloxetan-3-yl)sulfamoyl)-2-(6-azaspiro[2.5]octan-6-yl)benzamide | 576.2 |
| 2-5 | 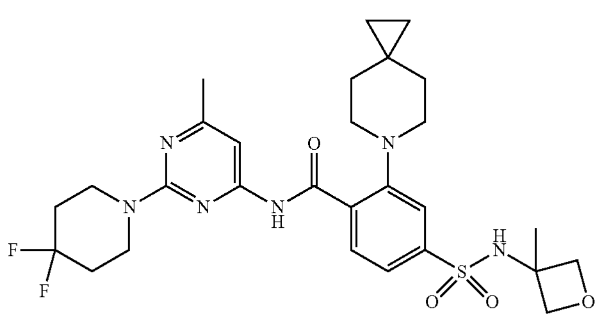 [SMILES: Cc1cc(NC(=O)c2ccc(S(=O)(=O)NC3(C)COC3)cc2N2CCC3(CC2)CC3)nc(N2CCC(F)(F)CC2)n1] | N-(2-(4,4-Difluoropiperidin-1-yl)-6-methylpyrimidin-4-yl)-4-(N-(3-methyloxetan-3-yl)sulfamoyl)-2-(6-azaspiro[2.5]octan-6-yl)benzamide | 591.2 |

TABLE 7-continued

Examples 2-1 to 2-8 were prepared following a similar procedure as described for example 2:

| Ex. # | Chemical Structure | Name | LRMS: (ESI + ve ion) m/z |
|---|---|---|---|
| 2-6 | 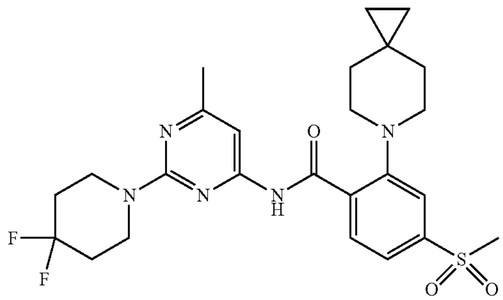 [SMILES: Cc1cc(NC(=O)c2ccc(S(C)(=O)=O)cc2N2CCC3(CC2)CC3)nc(N2CCC(F)(F)CC2)n1] | N-(2-(4,4-Difluoropiperidin-1-yl)-6-methylpyrimidin-4-yl)-4-(methylsulfonyl)-2-(6-azaspiro[2.5]octan-6-yl)benzamide | 520.0 |
| 2-7 | 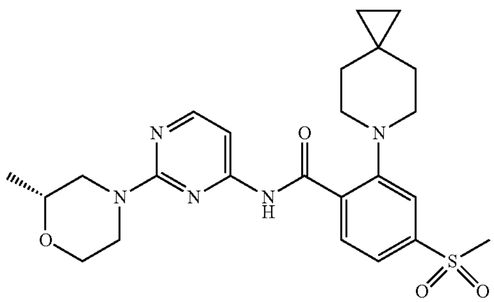 | (R)-N-(2-(2-Methylmorpholino)pyrimidin-4-yl)-4-(methylsulfonyl)-2-(6-azaspiro[2.5]octan-6-yl)benzamide | 486.1 |
| 2-8 | 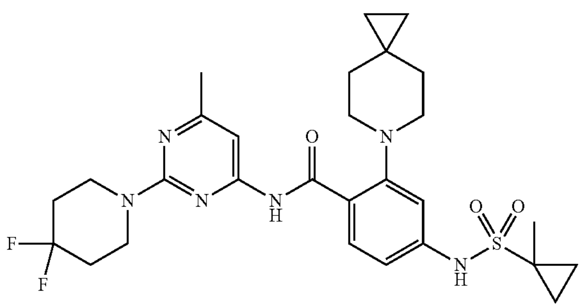 [SMILES: Cc1cc(NC(=O)c2ccc(NS(=O)(=O)C3(C)CC3)cc2N2CCC3(CC2)CC3)nc(N2CCC(F)(F)CC2)n1] | N-(2-(4,4-Difluoropiperidin-1-yl)-6-methylpyrimidin-4-yl)-4-((1-methylcyclopropane)-1-sulfonamido)-2-(6-azaspiro[2.5]octan-6-yl)benzamide | 575.4 |

Example 3: (R)-4-((2-Hydroxyethyl)sulfonamido)-N-(6-methyl-2-(2-methylmorpholino)pyrimidin-4-yl)-2-(6-azaspiro[2.5]octan-6-yl)benzamide

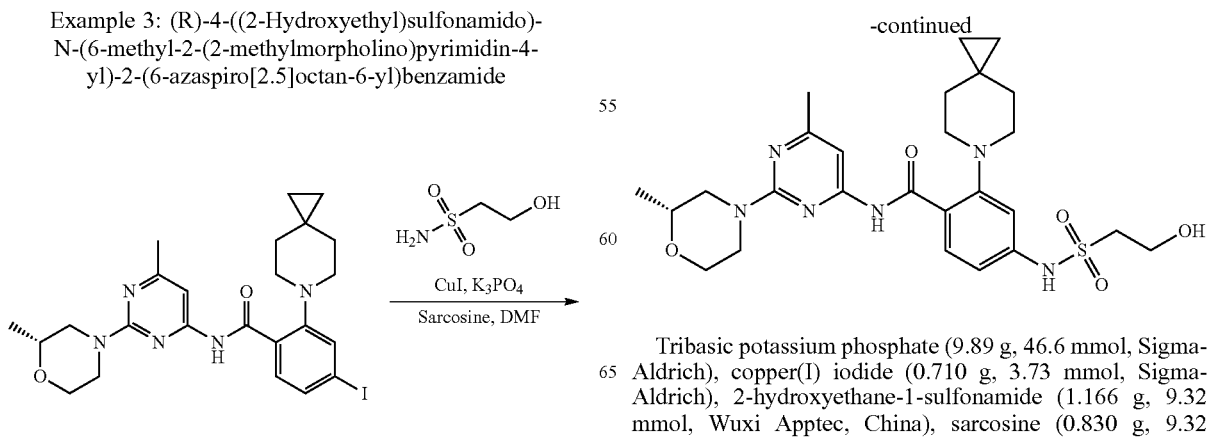

Tribasic potassium phosphate (9.89 g, 46.6 mmol, Sigma-Aldrich), copper(I) iodide (0.710 g, 3.73 mmol, Sigma-Aldrich), 2-hydroxyethane-1-sulfonamide (1.166 g, 9.32 mmol, Wuxi Apptec, China), sarcosine (0.830 g, 9.32 mmol), and (R)-4-iodo-N-(6-methyl-2-(2-methylmorpholino)pyrimidin-4-yl)-2-(6-azaspiro[2.5]octan-6-yl)benzamide (5.1 g, 9.32 mmol, Int. 21-2) were combined in a three neck flask under argon. Dry, degassed DMF (20 mL) was added and the mixture heated to 110° C. with overhead stirring for 45 minutes. The reaction was cooled to ambient temperature and saturated ammonium chloride (75 mL), water (200 mL) and ethyl acetate (200 mL) were added. The phases were mixed and separated and the organic dried with brine (75 mL) before evaporating to dryness under reduced pressure. The crude solids were stirred in boiling ethanol (15 mL) for 10 minutes then cooled to ambient temperature and filtered through a sintered glass frit. The solids were dried on the frit then suspended in water (75 mL) and heated to 80° C. After 10 minutes, the mixture was cooled to ambient temperature and filtered through a sintered glass frit. The solids were dried under a stream of nitrogen to give the title compound (3.3 g, 6.06 mmol, 65.0% yield) as an off-white solid. ¹H NMR (400 MHz, DMSO-d₆) δ ppm 13.23 (bs, 1H), 10.26 (bs, 1H), 8.05 (m, 1H), 7.37 (s, 1H), 7.26 (s, 1H), 7.13 (s, 1H), 4.95 (bs, 1H), 4.50-4.42 (m, 2H), 3.84 (m, 1H), 3.76-3.74 (m, 2H), 3.51-3.45 (m, 2H), 3.00-2.82 (m, 6H), 2.61-2.58 (m, 2H), 2.31 (s, 3H), 1.91-1.65 (m, 4H), 1.17 (d, J=6.0 Hz, 3H), 0.39 (s, 4H). m/z (ESI): 545.2 (M+H)+.

Example 4: N-(2-(4,4-Difluoropiperidin-1-yl)-6-methylpyrimidin-4-yl)-4-((2-hydroxyethyl)sulfonamido)-2-(6-azaspiro[2.5]octan-6-yl)benzamide

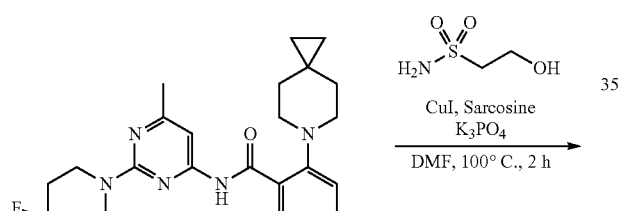

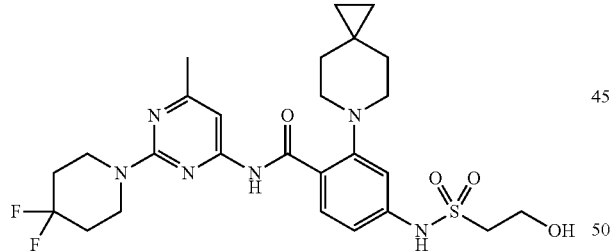

A mixture of 2-hydroxyethane-1-sulfonamide (1.28 g, 10.3 mmol, Wuxi AppTec), copper(I) iodide (0.49 g, 2.56 mmol), potassium phosphate tribasic (5.44 g, 25.6 mmol), and Sarcosine (0.48 g, 5.13 mmol) in a 100 mL round bottom flask was placed under argon atmosphere. Anhydrous DMF (20 mL) was added and the mixture was warmed to 50° C. for 5 minutes. N-(2-(4,4-difluoropiperidin-1-yl)-6-methylpyrimidin-4-yl)-4-iodo-2-(6-azaspiro[2.5]octan-6-yl)benzamide (2.91 g, 5.13 mmol, Int. 19) was added as a solid and the mixture was heated to 100° C. and stirred for 2 h, then cooled to room temperature. EtOAc (20 mL) and water (20 mL) were added, the resulting biphasic mixture was separated, and the aqueous layer was extracted with EtOAc (3×). The combined organic extracts were then washed with water (2×), 9:1 NH₄Cl/NH₄OH (aq), brine, dried over anhydrous MgSO₄, filtered, and concentrated in vacuo to give an oil. The oil was purified by silica gel chromatography, eluting with 0 to 50% EtOAc/heptane gradient, then 50% EtOAc/heptane isocratic elution, to provide an off-white solid. This solid was suspended in methanol, filtered, and dried to give a white solid. This solid was then suspended in water, stirred for 24 h, filtered, and dried in vacuo to provide N-(2-(4,4-difluoropiperidin-1-yl)-6-methylpyrimidin-4-yl)-4-((2-hydroxyethyl)sulfonamido)-2-(6-azaspiro[2.5]octan-6-yl)benzamide (1.55 g, 2.75 mmol, 54% yield) as a white solid. ¹H NMR (400 MHz, DMSO-d₆) δ ppm 13.37 (s, 1H) 10.03-10.52 (m, 1H) 8.06 (d, J=8.71 Hz, 1H) 7.41 (s, 1H) 7.28 (d, J=1.87 Hz, 1H) 7.15 (dd, J=8.71, 1.87 Hz, 1H) 4.73-5.14 (m, 1H) 3.92 (br t, J=5.39 Hz, 4H) 3.77 (t, J=6.43 Hz, 2H) 3.34-3.40 (m, 2H) 2.98 (br t, J=4.56 Hz, 4H) 2.32 (s, 3H) 1.93-2.07 (m, 4H) 1.58-1.85 (m, 4H) 0.40 (s, 4H). ¹⁹F NMR (376 MHz, DMSO-d₆) δ ppm −94.74 (s, 1F). m/z (ESI): 565.2 (M+H)⁺.

Examples 5-1 and 5-2: (R)—N-(2-(4,4-difluoropiperidin-1-yl)-6-methylpyrimidin-4-yl)-4-((2-hydroxy-1-methylethyl)sulfonamido)-2-(6-azaspiro[2.5]octan-6-yl)benzamide and (S)—N-(2-(4,4-difluoropiperidin-1-yl)-6-methylpyrimidin-4-yl)-4-((2-hydroxy-1-methylethyl)sulfonamido)-2-(6-azaspiro[2.5]octan-6-yl)benzamide

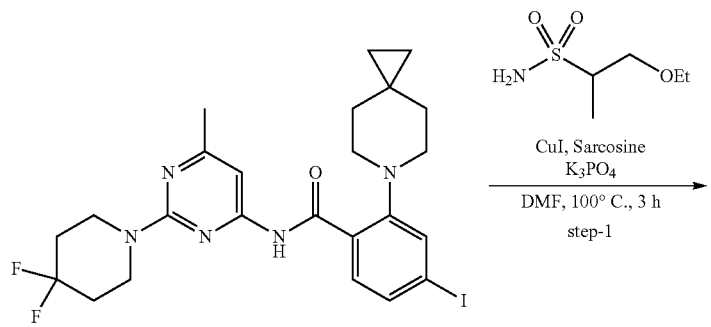

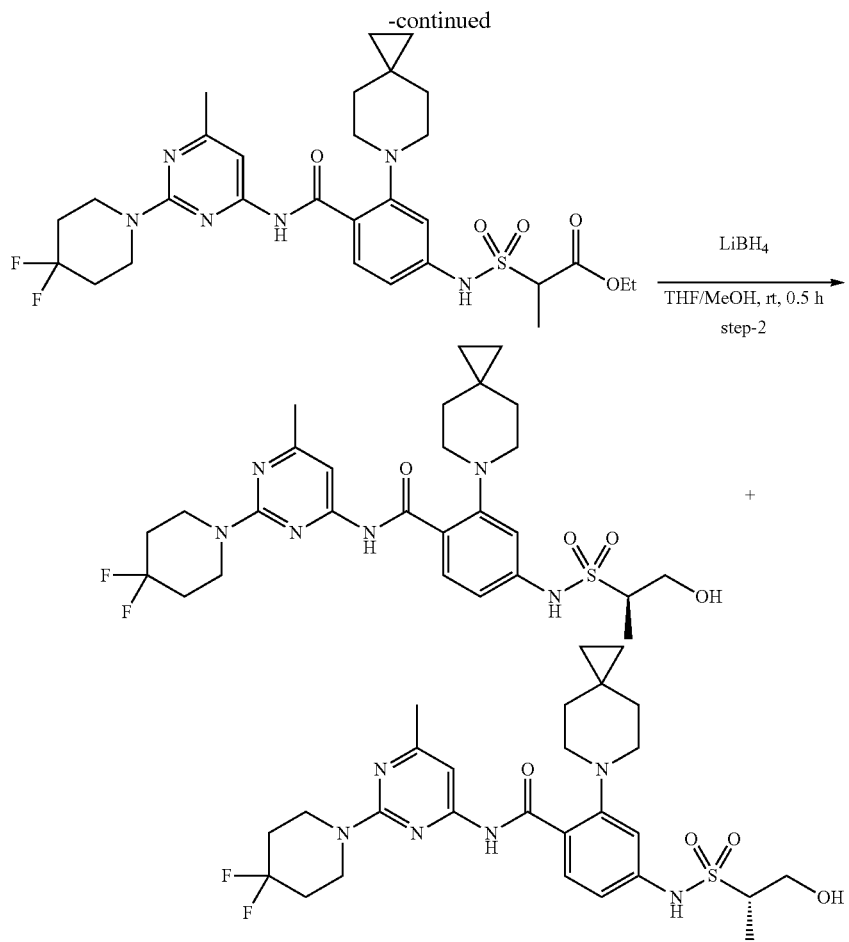

Step 1: A mixture of ethyl 2-sulfamoylpropanoate (1.44 g, 7.93 mmol, Int. 22), copper(I) iodide (0.503 g, 2.64 mmol, Strem), sarcosine (0.47 g, 5.29 mmol, Sigma-Aldrich Corporation), and potassium phosphate (4.49 g, 21.2 mmol) in DMF (15 mL) was placed under argon atmosphere and warmed to 50° C. for 5 min. N-(2-(4,4-difluoropiperidin-1-yl)-6-methylpyrimidin-4-yl)-4-iodo-2-(6-azaspiro[2.5]octan-6-yl)benzamide (3.0 g, 5.29 mmol, Int. 19) was added and the mixture was heated to 100° C. for 3 h, then cooled to room temperature. EtOAc (50 mL), IPA (5 mL) and water (50 mL) were added and the mixture was stirred vigorously for 5 min. The resulting biphasic mixture was transferred to a separatory funnel and the layers were separated. The aqueous layer was extracted with EtOAc (2×20 mL) and the combined extracts were then washed with water (2×50 mL), 9:1 NH$_4$Cl/NH$_4$OH (1×50 mL), dried over anhydrous MgSO$_4$, filtered, and concentrated in vacuo to give an oil. The crude oil was purified by silica gel chromatography using a Redi-Sep pre-packed silica gel column (80 g), eluting with 0 to 50% EtOAc/heptane gradient, to provide ethyl 2-(N-(4-((2-(4,4-difluoropiperidin-1-yl)-6-methylpyrimidin-4-yl)carbamoyl)-3-(6-azaspiro[2.5]octan-6-yl)phenyl)sulfamoyl)propanoate (2.76 g, 4.45 mmol, 84% yield) as a white solid. $^1$H NMR (400 MHz, DMSO-d$_6$) δ ppm 13.35 (s, 1H) 10.69 (br s, 1H) 8.07 (d, J=8.71 Hz, 1H) 7.40 (s, 1H) 7.31 (d, J=1.87 Hz, 1H) 7.17 (dd, J=8.60, 1.97 Hz, 1H) 4.06 (qd, J=7.08, 4.87 Hz, 2H) 3.92 (br t, J=5.49 Hz, 4H) 2.98 (br t, J=4.77 Hz, 4H) 2.32 (s, 3H) 1.85-2.06 (m, 5H) 1.73 (br s, 4H) 1.48 (d, J=6.84 Hz, 3H) 1.14 (t, J=7.05 Hz, 3H) 0.39 (s, 4H). $^{19}$F NMR (376 MHz, DMSO-d$_6$) δ ppm −94.75 (s, 1F). m/z (ESI): 621.2 (M+H)$^+$.

Step 2: To a 250 mL round bottom flask was added ethyl 2-(N-(4-((2-(4,4-difluoropiperidin-1-yl)-6-methylpyrimidin-4-yl)carbamoyl)-3-(6-azaspiro[2.5]octan-6-yl)phenyl)sulfamoyl)propanoate (10.39 g, 16.74 mmol) and lithium borohydride solution, (2.0M in THF, 16.7 mL, 33.5 mmol, Sigma-Aldrich Corporation) in THF (100 mL). Methanol (4.29 mL, 134 mmol) was added slowly over 5 min and the resulting solution was stirred at room temperature for 30 min. 1 N HCl (20 mL) was slowly added followed by EtOAc (20 mL) and the resulting biphasic mixture was transferred to a separatory funnel and the phases were separated. The aqueous layer was extracted with EtOAc (1×25 mL) and the combined extracts were washed with saturated NaHCO$_3$ (1×50 mL), brine (1×50 mL), dried over anhydrous MgSO$_4$, filtered, and concentrated to give 8.9 g racemic mixture. This material was separated by preparative SFC using a Chiral Tech AD column (250×30 mm, 5 mm) with a mobile phase of 85% Liquid CO$_2$ and 15% MeOH with 0.2% TEA using a flowrate of 150 mL/min to give:

Example 5-1: (R)—N-(2-(4,4-difluoropiperidin-1-yl)-6-methylpyrimidin-4-yl)-4-((2-hydroxy-1-methylethyl)sulfonamido)-2-(6-azaspiro[2.5]octan-6-yl)benzamide. First eluting peak (3.50 g, 6.05 mmol, 36.1% yield, >99% ee). $^1$H NMR (400 MHz, DMSO-d$_6$) δ ppm 13.36 (s, 1H) 8.05 (d, J=8.50 Hz, 1H) 7.40 (s, 1H) 7.31 (d, J=1.87 Hz, 1H) 7.17 (dd, J=8.71, 2.07 Hz, 1H) 3.88-3.97 (m, 4H) 3.84 (dd, J=10.99, 4.35 Hz, 1H) 3.37-3.54 (m, 1H) 3.25-3.30 (m, 1H) 2.97 (brt, J=4.77 Hz, 4H) 2.32 (s, 3H) 1.84-2.06 (m, 4H) 1.57-1.84 (br s, 4H) 1.30 (d, J=6.84 Hz, 3H) 0.39 (s, 4H). 2 exchangeable protons not observed. $^{19}$F NMR (376 MHz, DMSO-d$_6$) δ ppm −94.74 (s, 1F). m/z (ESI): 579.2 (M+H)$^+$.

Example 5-2: (S)—N-(2-(4,4-difluoropiperidin-1-yl)-6-methylpyrimidin-4-yl)-4-((2-hydroxy-1-methylethyl)sulfonamido)-2-(6-azaspiro[2.5]octan-6-yl)benzamide. Second eluting peak (2.66 g, 4.60 mmol, 27.5% yield. 98.9% ee). $^1$H NMR (400 MHz, DMSO-d$_6$) δ ppm 13.35 (s, 1H) 8.05 (d, J=8.50 Hz, 1H) 7.40 (s, 1H) 7.31 (d, J=2.07 Hz, 1H) 7.17 (dd, J=8.60, 1.97 Hz, 1H) 3.88-3.97 (m, 4H) 3.84 (dd, J=10.99, 4.35 Hz, 1H) 3.50 (dd, J=10.99, 7.46 Hz, 1H) 3.25-3.32 (m, 1H) 2.97 (br t, J=4.77 Hz, 4H) 2.31 (s, 3H) 1.83-2.06 (m, 4H) 1.73 (br s, 4H) 1.30 (d, J=6.84 Hz, 3H) 0.39 (s, 4H). 2 exchangeable protons not observed. $^{19}$F NMR (376 MHz, DMSO-d$_6$) δ ppm −94.75 (s, 1F). m/z (ESI): 579.2 (M+H)$^+$. The stereochemistry was arbitrarily assigned.

TABLE 8

Examples 6-1 to 6-40 were prepared following a similar procedure for Examples 3 to 5-2:

| Ex. # | Chemical Structure | Name | LRMS: (ESI +ve ion) m/z |
|---|---|---|---|
| 6-1 | 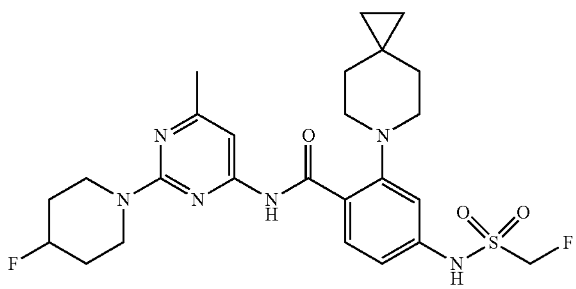 [SMILES: Cc1cc(NC(=O)c2ccc(NS(=O)(=O)CF)cc2N2CCC3(CC2)CC3)nc(N2CCC(F)CC2)n1] | 4-((Fluoromethyl)sulfonamido)-N-(2-(4-fluoropiperidin-1-yl)-6-methylpyrimidin-4-yl)-2-(6-azaspiro[2.5]octan-6-yl)benzamide | 535.3 |
| 6-2 | 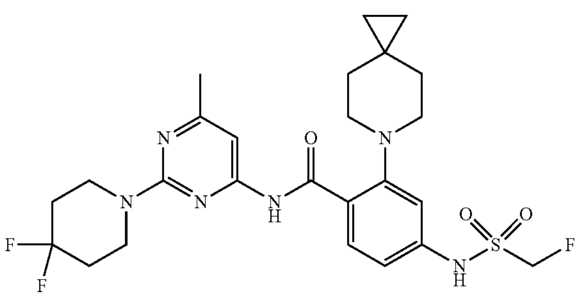 [SMILES: Cc1cc(NC(=O)c2ccc(NS(=O)(=O)CF)cc2N2CCC3(CC2)CC3)nc(N2CCC(F)(F)CC2)n1] | N-(2-(4,4-Difluoropiperidin-1-yl)-6-methylpyrimidin-4-yl)-4-((fluoromethyl)sulfonamido)-2-(6-azaspiro[2.5]octan-6-yl)benzamide | 553.3 |
| 6-3 | 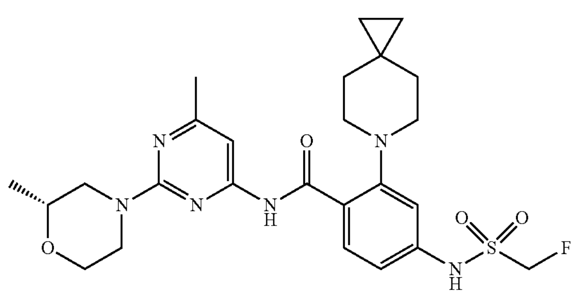 [SMILES: Cc1cc(NC(=O)c2ccc(NS(=O)(=O)CF)cc2N2CCC3(CC2)CC3)nc(N2CCO[C@H](C)C2)n1] | (R)-4-((Fluoromethyl)sulfonamido)-N-(6-methyl-2-(2-methylmorpholino)pyrimidin-4-yl)-2-(6-azaspiro[2.5]octan-6-yl)benzamide | 533.2 |
| 6-4 | 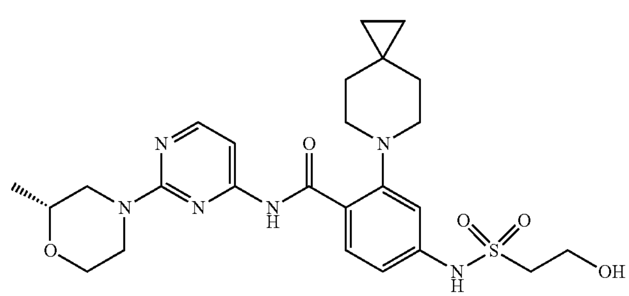 [SMILES: C[C@@H]1CN(c2nccc(NC(=O)c3ccc(NS(=O)(=O)CCO)cc3N3CCC4(CC3)CC4)n2)CCO1] | (R)-4-((2-Hydroxyethyl)sulfonamido)-N-(2-(2-methylmorpholino)pyrimidin-4-yl)-2-(6-azaspiro[2.5]octan-6-yl)benzamide | 531.2 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-5 | 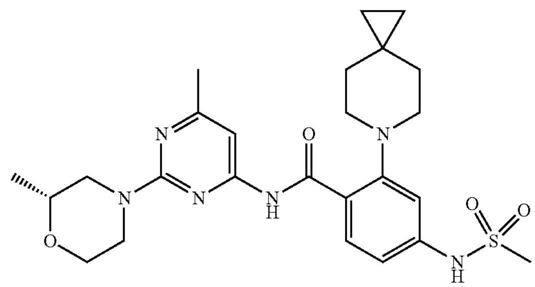 | (R)-N-(6-Methyl-2-(2-methylmorpholino)pyrimidin-4-yl)-4-(methylsulfonamido)-2-(6-azaspiro[2.5]octan-6-yl)benzamide | 515.2 |
| 6-6 | 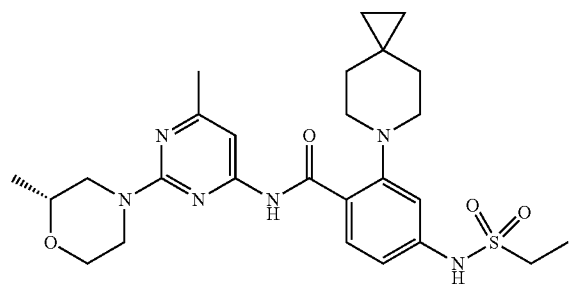 [SMILES: CCS(=O)(=O)Nc1ccc(C(=O)Nc2cc(C)nc(N3CCO[C@H](C)C3)n2)c(N2CCC3(CC2)CC3)c1] | (R)-4-(Ethylsulfonamido)-N-(6-methyl-2-(2-methylmorpholino)pyrimidin-4-yl)-2-(6-azaspiro[2.5]octan-6-yl)benzamide | 529.2 |
| 6-7 | 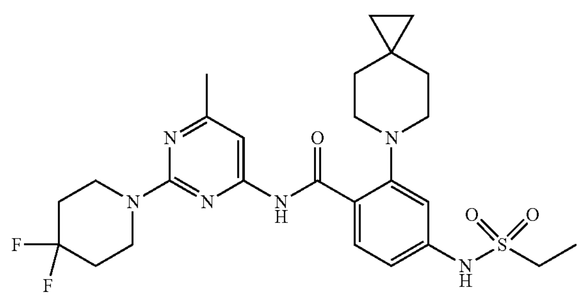 [SMILES: CCS(=O)(=O)Nc1ccc(C(=O)Nc2cc(C)nc(N3CCC(F)(F)CC3)n2)c(N2CCC3(CC2)CC3)c1] | N-(2-(4,4-Difluoropiperidin-1-yl)-6-methylpyrimidin-4-yl)-4-(ethylsulfonamido)-2-(6-azaspiro[2.5]octan-6-yl)benzamide | 549.2 |
| 6-8 | 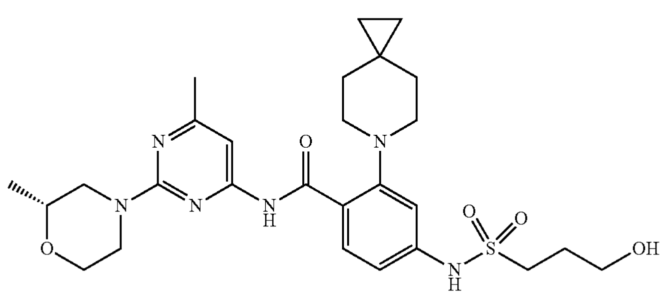 [SMILES: Cc1cc(NC(=O)c2ccc(NS(=O)(=O)CCCO)cc2N2CCC3(CC2)CC3)nc(N2CCO[C@H](C)C2)n1] | (R)-4-((3-Hydroxypropyl)sulfonamido)-N-(6-methyl-2-(2-methylmorpholino)pyrimidin-4-yl)-2-(6-azaspiro[2.5]octan-6-yl)benzamide | 559.2 |
| 6-9 | 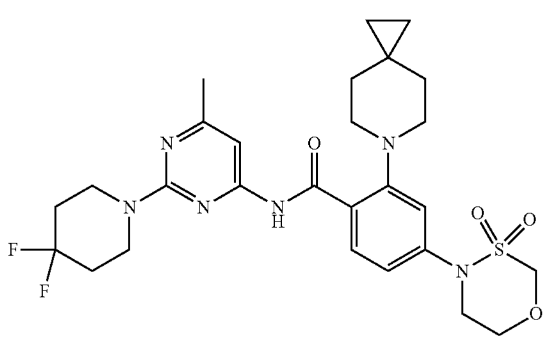 [SMILES: Cc1cc(NC(=O)c2ccc(N3CCOCS3(=O)=O)cc2N2CCC3(CC2)CC3)nc(N2CCC(F)(F)CC2)n1] | N-(2-(4,4-Difluoropiperidin-1-yl)-6-methylpyrimidin-4-yl)-4-(3,3-dioxido-1,3,4-oxathiazinan-4-yl)-2-(6-azaspiro[2.5]octan-6-yl)benzamide | 577.2 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-10 | 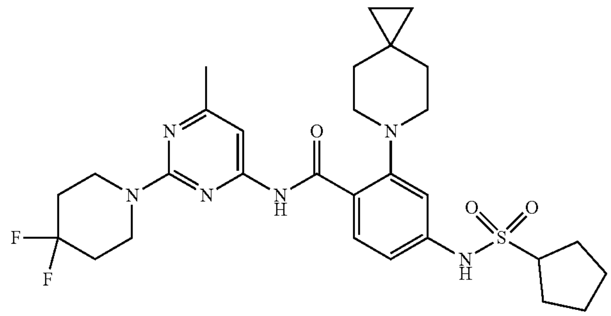 [SMILES: Cc1cc(NC(=O)c2ccc(NS(=O)(=O)C3CCCC3)cc2N2CCC3(CC2)CC3)nc(N2CCC(F)(F)CC2)n1] | 4-(Cyclopentanesulfonamido)-N-(2-(4,4-difluoropiperidin-1-yl)-6-methylpyrimidin-4-yl)-2-(6-azaspiro[2.5]octan-6-yl)benzamide | 589.3 |
| 6-11 | 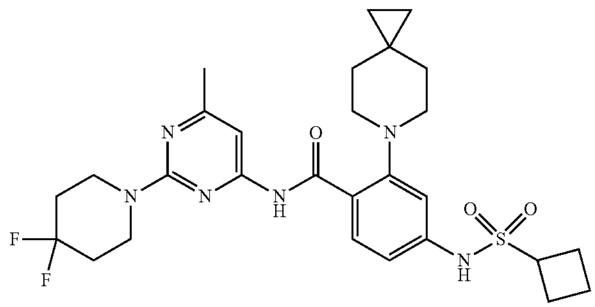 [SMILES: Cc1cc(NC(=O)c2ccc(NS(=O)(=O)C3CCC3)cc2N2CCC3(CC2)CC3)nc(N2CCC(F)(F)CC2)n1] | 4-(Cyclobutanesulfonamido)-N-(2-(4,4-difluoropiperidin-1-yl)-6-methylpyrimidin-4-yl)-2-(6-azaspiro[2.5]octan-6-yl)benzamide | 575.2 |
| 6-12 | 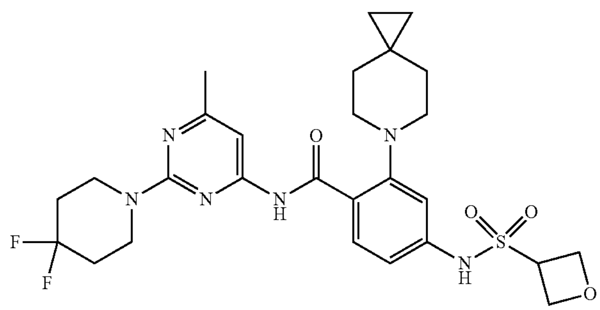 [SMILES: Cc1cc(NC(=O)c2ccc(NS(=O)(=O)C3COC3)cc2N2CCC3(CC2)CC3)nc(N2CCC(F)(F)CC2)n1] | N-(2-(4,4-Difluoropiperidin-1-yl)-6-methylpyrimidin-4-yl)-4-(oxetane-3-sulfonamido)-2-(6-azaspiro[2.5]octan-6-yl)benzamide | 577.2 |
| 6-13 | 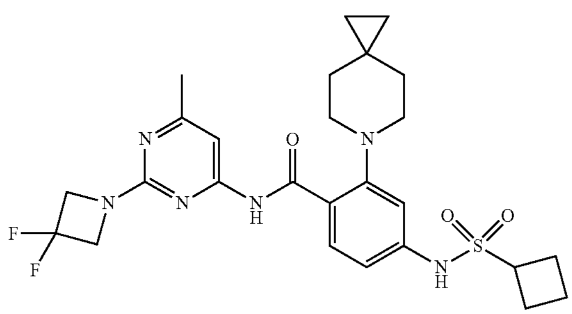 [SMILES: Cc1cc(NC(=O)c2ccc(NS(=O)(=O)C3CCC3)cc2N2CCC3(CC2)CC3)nc(N2CC(F)(F)C2)n1] | 4-(Cyclobutanesulfonamido)-N-(2-(3,3-difluoroazetidin-1-yl)-6-methylpyrimidin-4-yl)-2-(6-azaspiro[2.5]octan-6-yl)benzamide | 547.2 |
| 6-14 | 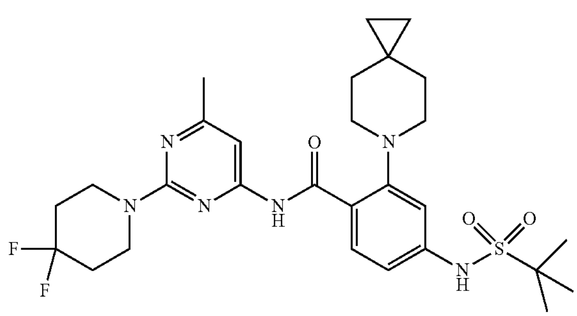 [SMILES: Cc1cc(NC(=O)c2ccc(NS(=O)(=O)C(C)(C)C)cc2N2CCC3(CC2)CC3)nc(N2CCC(F)(F)CC2)n1] | N-(2-(4,4-Difluoropiperidin-1-yl)-6-methylpyrimidin-4-yl)-4-((1,1-dimethylethyl)sulfonamido)-2-(6-azaspiro[2.5]octan-6-yl)benzamide | 577.3 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-15 | 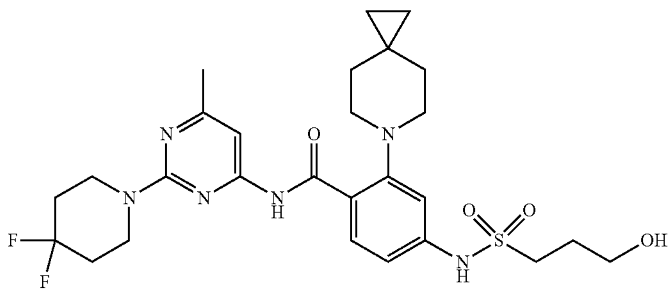 [SMILES: Cc1cc(NC(=O)c2ccc(NS(=O)(=O)CCCO)cc2N2CCC3(CC2)CC3)nc(N2CCC(F)(F)CC2)n1] | N-(2-(4,4-Difluoropiperidin-1-yl)-6-methylpyrimidin-4-yl)-4-((3-hydroxypropyl)sulfonamido)-2-(6-azaspiro[2.5]octan-6-yl)benzamide | 579.2 |
| 6-16 | 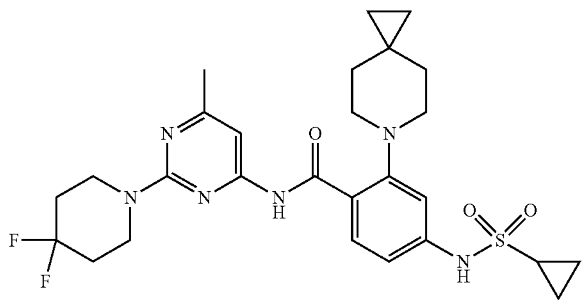 [SMILES: Cc1cc(NC(=O)c2ccc(NS(=O)(=O)C3CC3)cc2N2CCC3(CC2)CC3)nc(N2CCC(F)(F)CC2)n1] | 4-(Cyclopropanesulfonamido)-N-(2-(4,4-difluoropiperidin-1-yl)-6-methylpyrimidin-4-yl)-2-(6-azaspiro[2.5]octan-6-yl)benzamide | 561.2 |
| 6-17 | 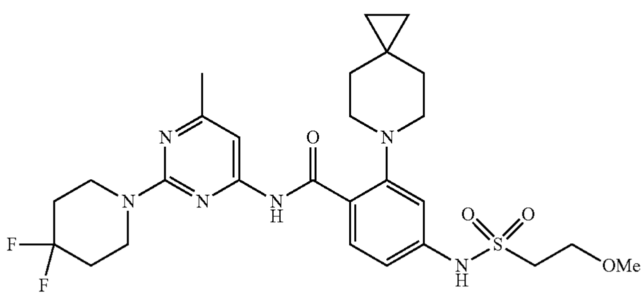 [SMILES: COCCS(=O)(=O)Nc1ccc(C(=O)Nc2cc(C)nc(N3CCC(F)(F)CC3)n2)c(N2CCC3(CC2)CC3)c1] | N-(2-(4,4-Difluoropiperidin-1-yl)-6-methylpyrimidin-4-yl)-4-((2-methoxyethyl)sulfonamido)-2-(6-azaspiro[2.5]octan-6-yl)benzamide | 579.9 |
| 6-18 | 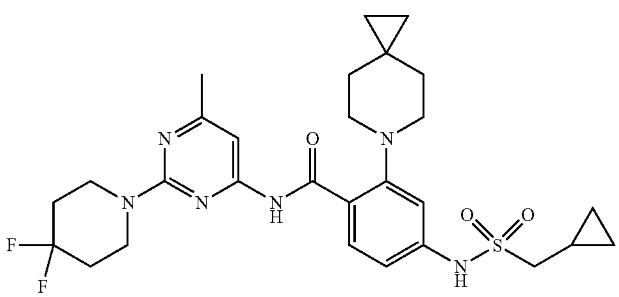 [SMILES: Cc1cc(NC(=O)c2ccc(NS(=O)(=O)CC3CC3)cc2N2CCC3(CC2)CC3)nc(N2CCC(F)(F)CC2)n1] | 4-((Cyclopropyl-methyl)sulfonamido)-N-(2-(4,4-difluoropiperidin-1-yl)-6-methylpyrimidin-4-yl)-2-(6-azaspiro[2.5]octan-6-yl)benzamide | 575.2 |
| 6-19 | 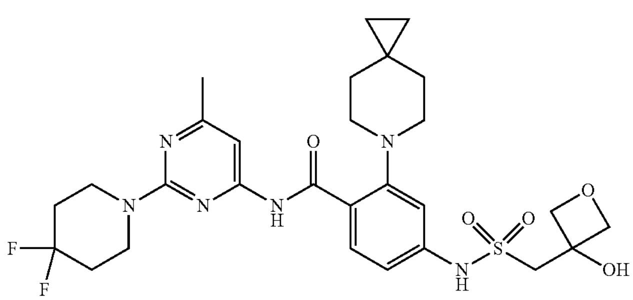 [SMILES: Cc1cc(NC(=O)c2ccc(NS(=O)(=O)CC3(O)COC3)cc2N2CCC3(CC2)CC3)nc(N2CCC(F)(F)CC2)n1] | N-(2-(4,4-Difluoropiperidin-1-yl)-6-methylpyrimidin-4-yl)-4-(((3-hydroxyoxetan-3-yl)methyl)sulfonamido)-2-(6-azaspiro[2.5]octan-6-yl)benzamide | 607.2 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-20 | 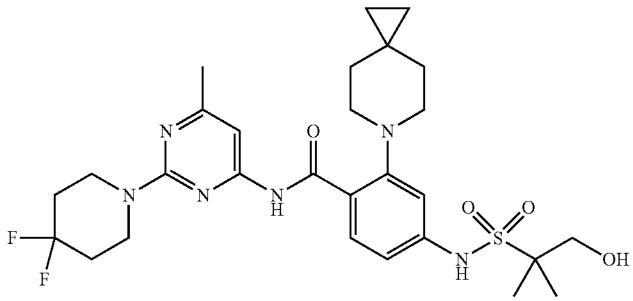 [SMILES: Cc1cc(NC(=O)c2ccc(NS(=O)(=O)C(C)(C)CO)cc2N2CCC3(CC2)CC3)nc(N2CCC(F)(F)CC2)n1] | N-(2-(4,4-Difluoropiperidin-1-yl)-6-methylpyrimidin-4-yl)-4-((2-hydroxy-1,1-dimethylethyl)sulfonamido)-2-(6-azaspiro[2.5]octan-6-yl)benzamide | 593.2 |
| 6-21 | 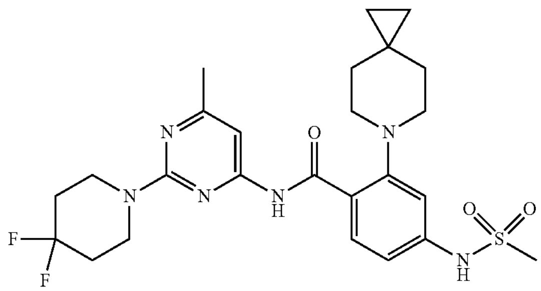 [SMILES: Cc1cc(NC(=O)c2ccc(NS(C)(=O)=O)cc2N2CCC3(CC2)CC3)nc(N2CCC(F)(F)CC2)n1] | N-(2-(4,4-Difluoropiperidin-1-yl)-6-methylpyrimidin-4-yl)-4-(methylsulfonamido)-2-(6-azaspiro[2.5]octan-6-yl)benzamide | 535.2 |
| 6-22 | 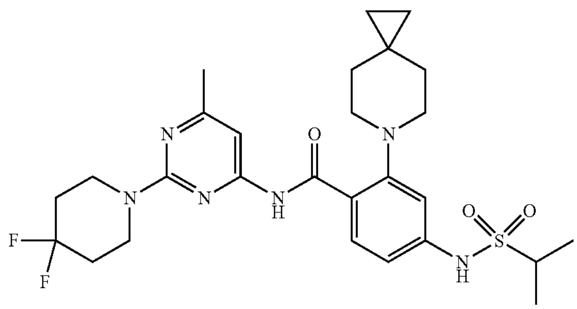 [SMILES: Cc1cc(NC(=O)c2ccc(NS(=O)(=O)C(C)C)cc2N2CCC3(CC2)CC3)nc(N2CCC(F)(F)CC2)n1] | N-(2-(4,4-Difluoropiperidin-1-yl)-6-methylpyrimidin-4-yl)-4-(((1-methylethyl)sulfonamido)-2-(6-azaspiro[2.5]octan-6-yl)benzamide | 563.2 |
| 6-23-1 | 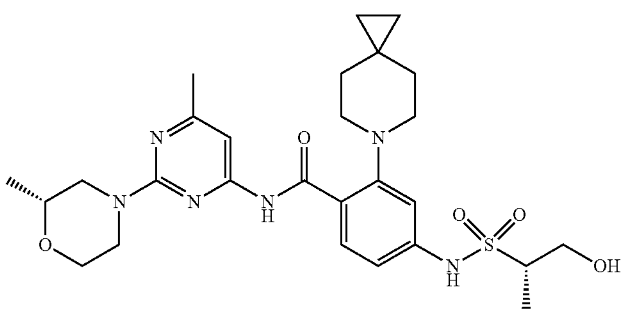 [SMILES: Cc1cc(NC(=O)c2ccc(NS(=O)(=O)[C@@H](C)CO)cc2N2CCC3(CC2)CC3)nc(N2CCO[C@H](C)C2)n1] | 4-(((S)-2-Hydroxy-1-methylethyl)sulfonamido)-N-(6-methyl-2-((R)-2-methylmorpholino)pyrimidin-4-yl)-2-(6-azaspiro[2.5]octan-6-yl)benzamide | 559.2 |
| 6-23-2 | 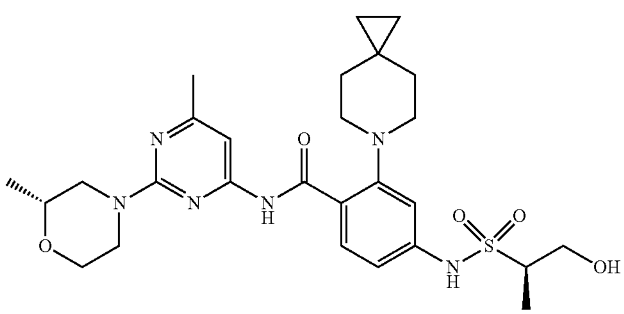 [SMILES: Cc1cc(NC(=O)c2ccc(NS(=O)(=O)[C@H](C)CO)cc2N2CCC3(CC2)CC3)nc(N2CCO[C@H](C)C2)n1] | 4-(((R)-2-Hydroxy-1-methylethyl)sulfonamido)-N-(6-methyl-2-((R)-2-methylmorpholino)pyrimidin-4-yl)-2-(6-azaspiro[2.5]octan-6-yl)benzamide | 559.2 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-24-1 | 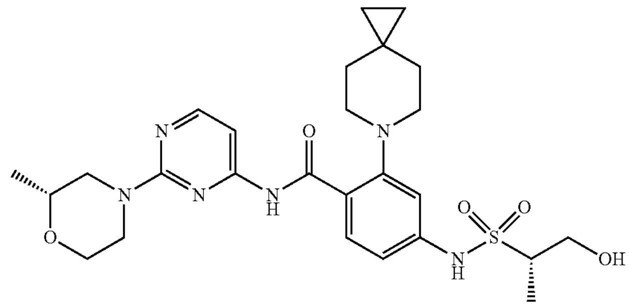 [SMILES: C[C@@H]1CN(c2nccc(NC(=O)c3ccc(NS(=O)(=O)[C@@H](C)CO)cc3N3CCC4(CC3)CC4)n2)CCO1] | 4-(((S)-2-Hydroxy-1-methylethyl)sulfonamido)-N-(2-((R)-2-methylmorpholino)pyrimidin-4-yl)-2-(6-azaspiro[2.5]octan-6-yl)benzamide | 545.2 |
| 6-24-2 | 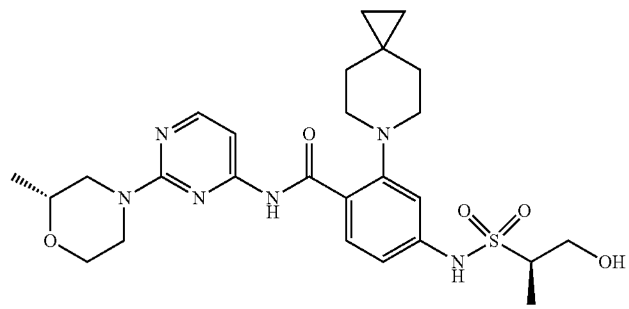 [SMILES: C[C@@H]1CN(c2nccc(NC(=O)c3ccc(NS(=O)(=O)[C@H](C)CO)cc3N3CCC4(CC3)CC4)n2)CCO1] | 4-(((R)-2-hydroxy-1-methylethyl)sulfonamido)-N-(2-((R)-2-methylmorpholino)pyrimidin-4-yl)-2-(6-azaspiro[2.5]octan-6-yl)benzamide | 545.2 |
| 6-25-1 | 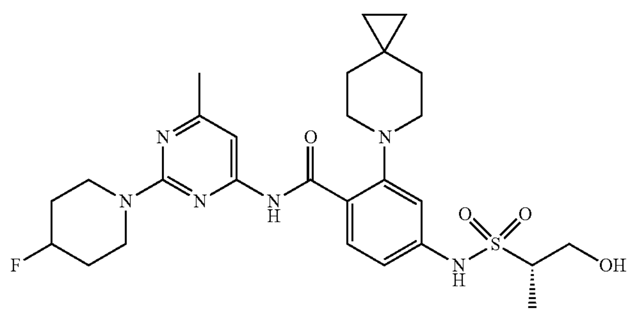 [SMILES: Cc1cc(NC(=O)c2ccc(NS(=O)(=O)[C@@H](C)CO)cc2N2CCC3(CC2)CC3)nc(N2CCC(F)CC2)n1] | (S)-N-(2-(4-fluoropiperidin-1-yl)-6-methylpyrimidin-4-yl)-4-((2-hydroxy-1-methylethyl)sulfonamido)-2-(6-azaspiro[2.5]octan-6-yl)benzamide | 561.2 |
| 6-25-2 | 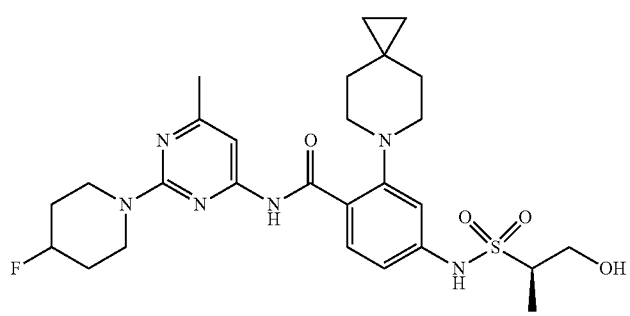 [SMILES: Cc1cc(NC(=O)c2ccc(NS(=O)(=O)[C@H](C)CO)cc2N2CCC3(CC2)CC3)nc(N2CCC(F)CC2)n1] | (R)-N-(2-(4-Fluoropiperidin-1-yl)-6-methylpyrimidin-4-yl)-4-((2-hydroxy-1-methylethyl)sulfonamido)-2-(6-azaspiro[2.5]octan-6-yl)benzamide | 561.2 |
| 6-26-1 | 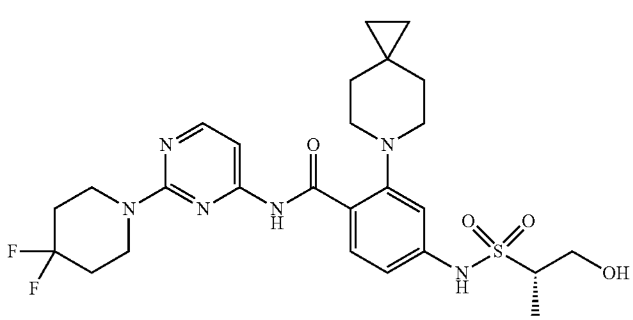 [SMILES: C[C@@H](CO)S(=O)(=O)Nc1ccc(C(=O)Nc2ccnc(N3CCC(F)(F)CC3)n2)c(N2CCC3(CC2)CC3)c1] | (S)-N-(2-(4,4-Difluoropiperidin-1-yl)pyrimidin-4-yl)-4-((2-hydroxy-1-methylethyl)sulfonamido)-2-(6-azaspiro[2.5]octan-6-yl)benzamide | 565.2 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-26-2 | 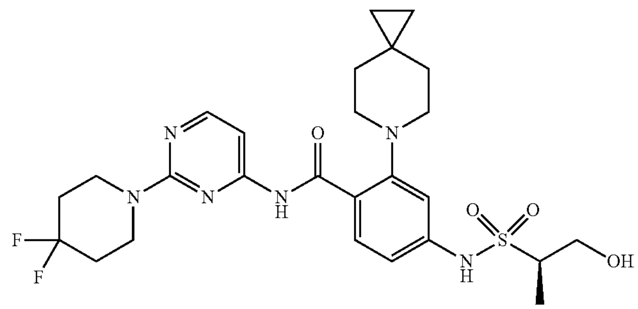 [SMILES: C[C@H](CO)S(=O)(=O)Nc1ccc(C(=O)Nc2ccnc(N3CCC(F)(F)CC3)n2)c(N2CCC3(CC2)CC3)c1] | (R)-N-(2-(4,4-Difluoropiperidin-1-yl)pyrimidin-4-yl)-4-((2-hydroxy-1-methylethyl)sulfonamido)-2-(6-azaspiro[2.5]octan-6-yl)benzamide | 565.2 |
| 6-27-1 | 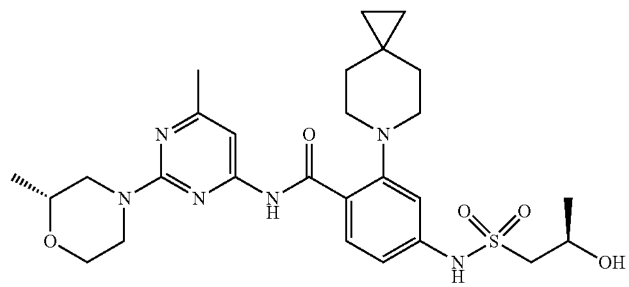 [SMILES: Cc1cc(NC(=O)c2ccc(NS(=O)(=O)C[C@@H](C)O)cc2N2CCC3(CC2)CC3)nc(N2CCO[C@H](C)C2)n1] | 4-(((R)-2-Hydroxypropyl)sulfonamido)-N-(6-methyl-2-((R)-2-methylmorpholino)pyrimidin-4-yl)-2-(6-azaspiro[2.5]octan-6-yl)benzamide | 559.2 |
| 6-27-2 | 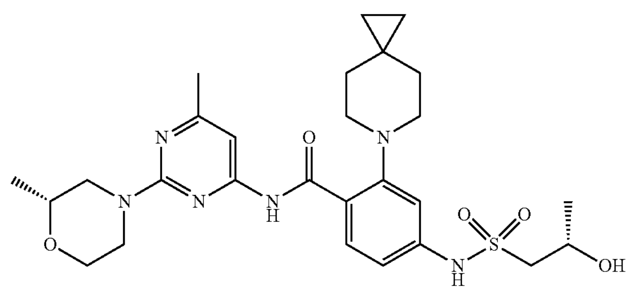 [SMILES: Cc1cc(NC(=O)c2ccc(NS(=O)(=O)C[C@H](C)O)cc2N2CCC3(CC2)CC3)nc(N2CCO[C@H](C)C2)n1] | 4-(((S)-2-Hydroxypropyl)sulfonamido)-N-(6-methyl-2-((R)-2-methylmorpholino)pyrimidin-4-yl)-2-(6-azaspiro[2.5]octan-6-yl)benzamide | 559.2 |
| 6-28-1 | 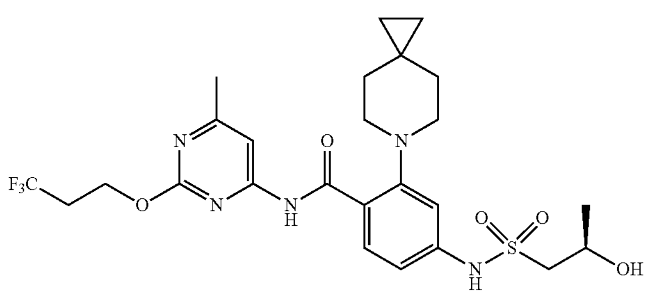 [SMILES: Cc1cc(NC(=O)c2ccc(NS(=O)(=O)C[C@@H](C)O)cc2N2CCC3(CC2)CC3)nc(OCCC(F)(F)F)n1] | (R)-4-((2-Hydroxypropyl)sulfonamido)-N-(6-methyl-2-(3,3,3-trifluoropropoxy)pyrimidin-4-yl)-2-(6-azaspiro[2.5]octan-6-yl)benzamide | 572.2 |
| 6-28-2 | 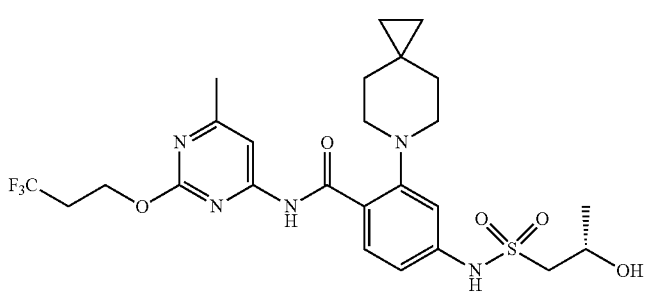 [SMILES: Cc1cc(NC(=O)c2ccc(NS(=O)(=O)C[C@H](C)O)cc2N2CCC3(CC2)CC3)nc(OCCC(F)(F)F)n1] | (S)-4-((2-Hydroxypropyl)sulfonamido)-N-(6-methyl-2-(3,3,3-trifluoropropoxy)pyrimidin-4-yl)-2-(6-azaspiro[2.5]octan-6-yl)benzamide | 572.2 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-29 | 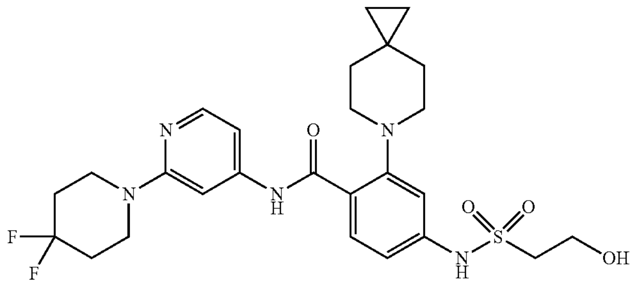 [SMILES: O=C(Nc1ccnc(N2CCC(F)(F)CC2)c1)c1ccc(NS(=O)(=O)CCO)cc1N1CCC2(CC1)CC2] | N-(2-(4,4-Difluoropiperidin-1-yl)pyridin-4-yl)-4-((2-hydroxyethyl)sulfonamido)-2-(6-azaspiro[2.5]octan-6-yl)benzamide | 550.2 |
| 6-30 | 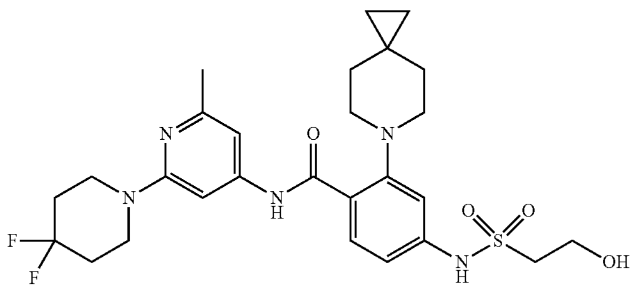 [SMILES: Cc1cc(NC(=O)c2ccc(NS(=O)(=O)CCO)cc2N2CCC3(CC2)CC3)cc(N2CCC(F)(F)CC2)n1] | N-(2-(4,4-Difluoropiperidin-1-yl)-6-methylpyridin-4-yl)-4-((2-hydroxyethyl)sulfonamido)-2-(6-azaspiro[2.5]octan-6-yl)benzamide | 564.2 |
| 6-31-1 | 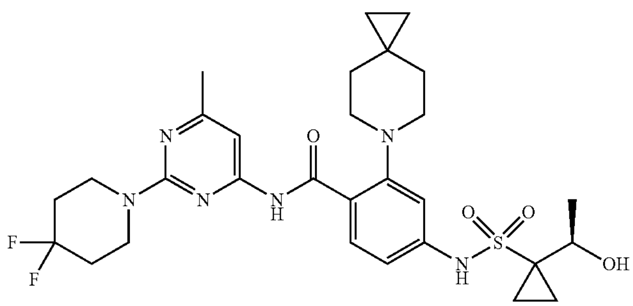 [SMILES: Cc1cc(NC(=O)c2ccc(NS(=O)(=O)C3([C@@H](C)O)CC3)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-((1-(1-hydroxyethyl)cyclopropane)-1-sulfonamido)-2-(6-azaspiro[2.5]octan-6-yl)benzamide | 605.2 |
| 6-31-2 | 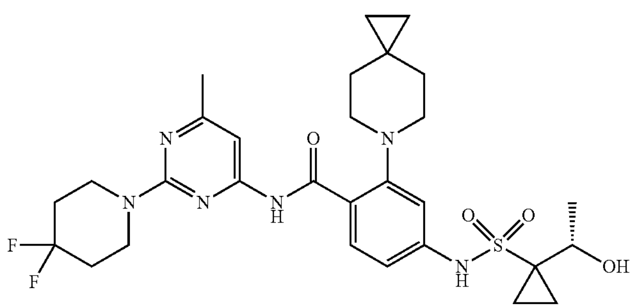 [SMILES: Cc1cc(NC(=O)c2ccc(NS(=O)(=O)C3([C@H](C)O)CC3)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((1-(1-hydroxyethyl)cyclopropane)-1-sulfonamido)-2-(6-azaspiro[2.5]octan-6-yl)benzamide | 605.2 |
| 6-32-1 | 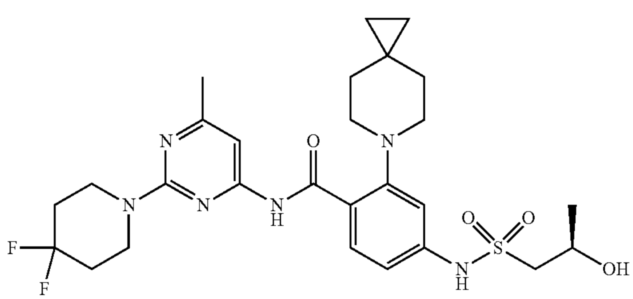 [SMILES: Cc1cc(NC(=O)c2ccc(NS(=O)(=O)C[C@@H](C)O)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-((2-hydroxypropyl)sulfonamido)-2-(6-azaspiro[2.5]octan-6-yl)benzamide | 579.1 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-32-2 | 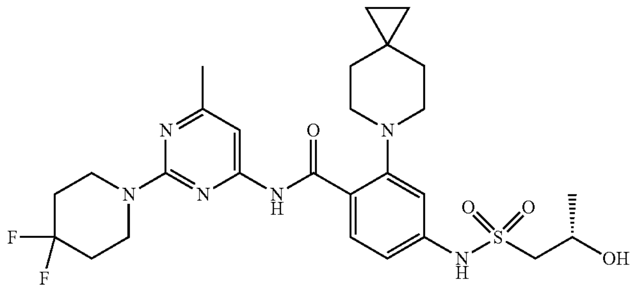 [SMILES: Cc1cc(NC(=O)c2ccc(NS(=O)(=O)C[C@H](C)O)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((2-hydroxypropyl)sulfonamido)-2-(6-azaspiro[2.5]octan-6-yl)benzamide | 579.1 |
| 6-33-1 | 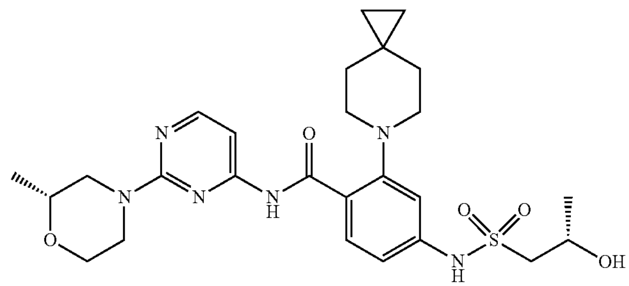 [SMILES: C[C@H](O)CS(=O)(=O)Nc1ccc(C(=O)Nc2ccnc(N3CCO[C@H](C)C3)n2)c(N2CCC3(CC2)CC3)c1] | 4-(((S)-2-Hydroxypropyl)sulfonamido)-N-(2-((R)-2-methylmorpholino)pyrimidin-4-yl)-2-(6-azaspiro[2.5]octan-6-yl)benzamide | 545.2 |
| 6-33-2 | 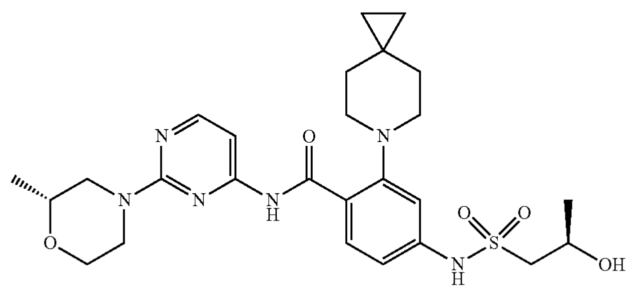 [SMILES: C[C@@H]1CN(c2nccc(NC(=O)c3ccc(NS(=O)(=O)C[C@@H](C)O)cc3N3CCC4(CC3)CC4)n2)CCO1] | 4-(((R)-2-hydroxypropyl)sulfonamido)-N-(2-((R)-2-methylmorpholino)pyrimidin-4-yl)-2-(6-azaspiro[2.5]octan-6-yl)benzamide | 545.2 |
| 6-34 | 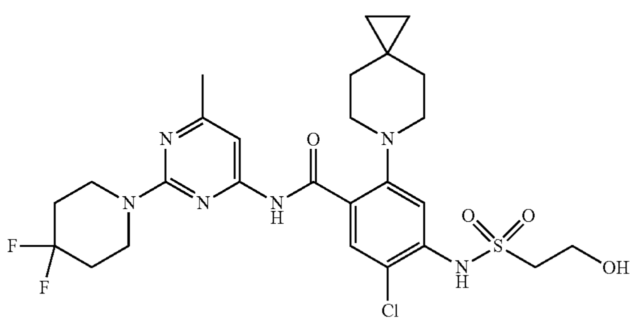 [SMILES: Cc1cc(NC(=O)c2cc(Cl)c(NS(=O)(=O)CCO)cc2N2CCC3(CC2)CC3)nc(N2CCC(F)(F)CC2)n1] | 5-Chloro-N-(2-(4,4-difluoropiperidin-1-yl)-6-methylpyrimidin-4-yl)-4-((2-hydroxyethyl)sulfonamido)-2-(6-azaspiro[2.5]octan-6-yl)benzamide | 599.2 |
| 6-35 | 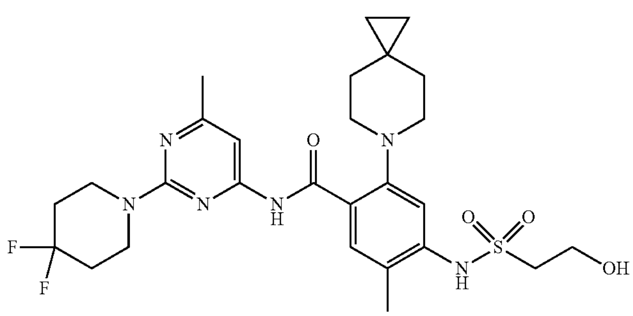 [SMILES: Cc1cc(NC(=O)c2cc(C)c(NS(=O)(=O)CCO)cc2N2CCC3(CC2)CC3)nc(N2CCC(F)(F)CC2)n1] | N-(2-(4,4-Difluoropiperidin-1-yl)-6-methylpyrimidin-4-yl)-4-((2-hydroxyethyl)sulfonamido)-5-methyl-2-(6-azaspiro[2.5]octan-6-yl)benzamide | 579.2 |

TABLE 8-continued

Examples 6-1 to 6-40 were prepared following a similar procedure for Examples 3 to 5-2:

| Ex. # | Chemical Structure | Name | LRMS: (ESI + ve ion) m/z |
|---|---|---|---|
| 6-36 | 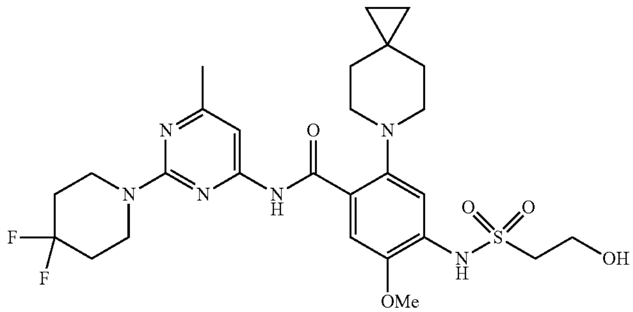 [SMILES: COc1cc(C(=O)Nc2cc(C)nc(N3CCC(F)(F)CC3)n2)c(N2CCC3(CC2)CC3)cc1NS(=O)(=O)CCO] | N-(2-(4,4-Difluoropiperidin-1-yl)-6-methylpyrimidin-4-yl)-4-((2-hydroxyethyl)sulfonamido)-5-methoxy-2-(6-azaspiro[2.5]octan-6-yl)benzamide | 595.2 |
| 6-37 | 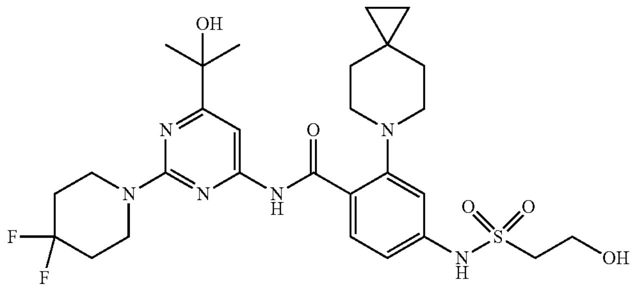 [SMILES: CC(C)(O)c1cc(NC(=O)c2ccc(NS(=O)(=O)CCO)cc2N2CCC3(CC2)CC3)nc(N2CCC(F)(F)CC2)n1] | N-(2-(4,4-Difluoropiperidin-1-yl)-6-(2-hydroxypropan-2-yl)pyrimidin-4-yl)-4-((2-hydroxyethyl)sulfonamido)-2-(6-azaspiro[2.5]octan-6-yl)benzamide | 609.1 |
| 6-38 | 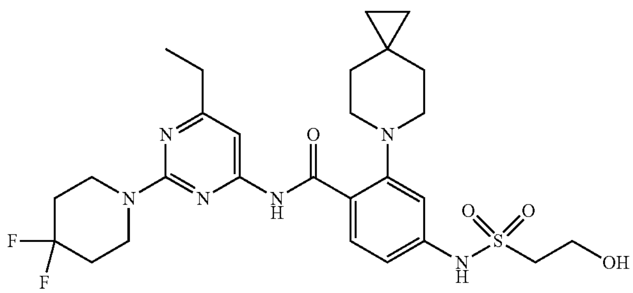 [SMILES: CCc1cc(NC(=O)c2ccc(NS(=O)(=O)CCO)cc2N2CCC3(CC2)CC3)nc(N2CCC(F)(F)CC2)n1] | N-(2-(4,4-Difluoropiperidin-1-yl)-6-ethylpyrimidin-4-yl)-4-((2-hydroxyethyl)sulfonamido)-2-(6-azaspiro[2.5]octan-6-yl)benzamide | 579.2 |
| 6-39 | 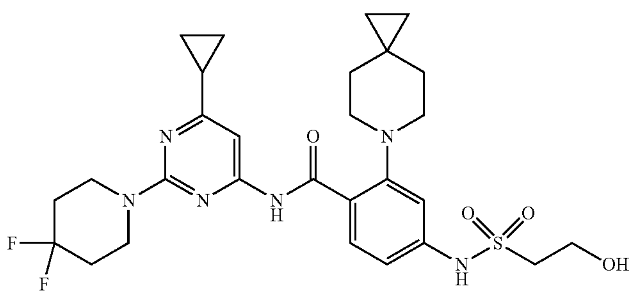 [SMILES: O=C(Nc1cc(C2CC2)nc(N2CCC(F)(F)CC2)n1)c1ccc(NS(=O)(=O)CCO)cc1N1CCC2(CC1)CC2] | N-(6-Cyclopropyl-2-(4,4-difluoropiperidin-1-yl)pyrimidin-4-yl)-4-((2-hydroxyethyl)sulfonamido)-2-(6-azaspiro[2.5]octan-6-yl)benzamide | 591.2 |
| 6-40 | 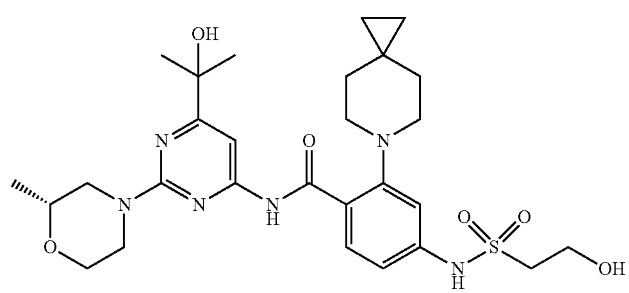 [SMILES: C[C@@H]1CN(c2nc(NC(=O)c3ccc(NS(=O)(=O)CCO)cc3N3CCC4(CC3)CC4)cc(C(C)(C)O)n2)CCO1] | (R)-4-((2-Hydroxyethyl)sulfonamido)-N-(6-(2-hydroxypropan-2-yl)-2-(2-methylmorpholino)pyrimidin-4-yl)-2-(6-azaspiro[2.5]octan-6-yl)benzamide | 589.3 |

Example 7: N-(2-(3,3-Difluoroazetidin-1-yl)-6-methylpyrimidin-4-yl)-4-((2-hydroxyethyl)sulfonamido)-2-(6-azaspiro[2.5]octan-6-yl)benzamide

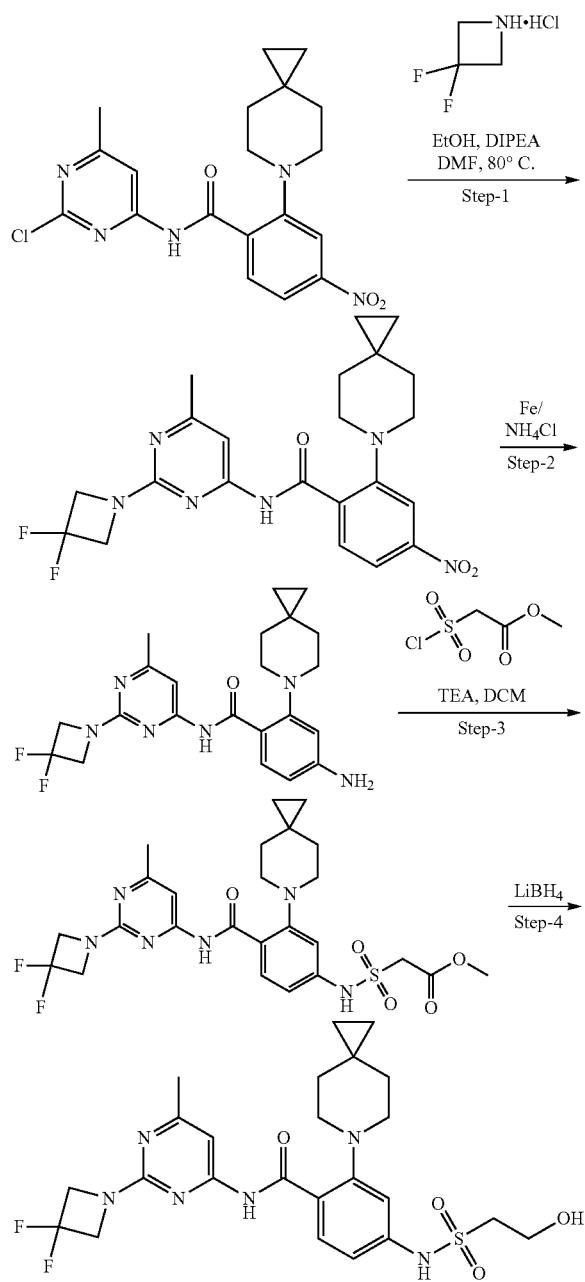

Step 1: A solution of N-(2-chloro-6-methylpyrimidin-4-yl)-4-nitro-2-(6-azaspiro[2.5]octan-6-yl)benzamide (0.3 g, 0.747 mmol, Int. 21-18), 3,3-difluoroazetidine hydrochloride (0.145 g, 1.120 mmol, Combi-Blocks) and DIPEA (0.261 mL, 1.49 mmol) in DMF (0.5 mL) and ethanol (1 mL) was heated at 80° C. for 4 h. Then the reaction mixture was quenched with water (50 mL) and extracted with ethyl acetate (3×50 mL). The combined organic layers were washed with brine (50 mL), dried over $Na_2SO_4$, filtered, and concentrated. The concentrate was purified by flash column chromatography eluting with 30% to 50% ethyl acetate in petroleum ether to provide N-(2-(3,3-difluoroazetidin-1-yl)-6-methylpyrimidin-4-yl)-4-nitro-2-(6-azaspiro[2.5]octan-6-yl)benzamide (180 mg, 0.393 mmol, 52.6% yield) as yellow solid $^1$H NMR (400 MHz, Chloroform-d) δ ppm 8.47 (d, J=8.7 Hz, 1H), 8.25 (d, J=12 Hz, 1H), 8.17 (dd, J=8.7, 2.2 Hz, 1H), 7.68 (s, 1H), 3.79-3.66 (m, 4H), 3.17 (t, J=5.4 Hz, 4H), 2.60 (s, 3H), 1.28 (s, 4H), 0.50 (s, 4H). m/z (ESI): 459.2 (M+H)$^+$.

Step 2: To a solution of N-(2-(3,3-difluoroazetidin-1-yl)-6-methylpyrimidin-4-yl)-4-nitro-2-(6-azaspiro[2.5]octan-6-yl)benzamide (0.18 g, 0.39 mmol) in ethanol (8 mL) and water (8 mL) were added iron powder (0.066 g, 1.18 mmol) and ammonium chloride (0.063 g, 1.18 mmol). Then the mixture was heated at 90° C. for 3 h before it was filtered through a bed of CELITE® and was washed with ethyl acetate (3×100 mL). The filtrate was washed with brine, dried over $Na_2SO_4$, filtered, and concentrated to provide 4-amino-N-(2-(3,3-difluoroazetidin-1-yl)-6-methylpyrimidin-4-yl)-2-(6-azaspiro[2.5]octan-6-yl)benzamide (0.12 g, 0.280 mmol, 71.3% yield) as pale yellow solid. It was used directly for the next step without further purification. m/z (ESI): 429.2 (M+H)$^+$.

Step 3: To a solution of 4-amino-N-(2-(3,3-difluoroazetidin-1-yl)-6-methylpyrimidin-4-yl)-2-(6-azaspiro[2.5]octan-6-yl)benzamide (0.120 g, 0.280 mmol) in DCM (5 mL) were added $Et_3N$ (0.078 mL, 0.560 mmol) and methyl 2-(chlorosulfonyl)acetate (0.058 g, 0.336 mmol, Combi-blocks) at 0° C. The mixture was stirred at room temperature for 4 h before it was quenched with water (50 mL) and was extracted with DCM (3×50 mL). The combined organic layers were washed with brine (50 mL), dried over $Na_2SO_4$, filtered and concentrated to afford methyl 2-(N-(4-((2-(3,3-difluoroazetidin-1-yl)-6-methylpyrimidin-4-yl)carbamoyl)-3-(6-azaspiro[2.5]octan-6-yl)phenyl)sulfamoyl)acetate (140 mg, 0.25 mmol, 89% yield) as pale yellow solid. It was used for the next step without further purification. m/z (ESI): 565.2 (M+H)$^+$.

Step 4: A solution of methyl 2-(N-(4-((2-(3,3-difluoroazetidin-1-yl)-6-methylpyrimidin-4-yl)carbamoyl)-3-(6-azaspiro[2.5]octan-6-yl)phenyl)sulfamoyl)acetate (130 mg, 0.230 mmol) in THF (5 mL) was treated with $LiBH_4$ (230 μl, 0.460 mmol) at −30° C. The reaction mixture was stirred for 30 min at 0° C. before it was quenched with a saturated aqueous solution of $NH_4Cl$ (50 mL) at 0° C. and was extracted with EtOAc (2×10 mL). The combined organic layers were washed with brine (5 mL), dried over $Na_2SO_4$, filtered and concentrated. The concentrate was purified by flash column chromatography eluting with a gradient of 20% to 100% EtOAc in hexanes to provide N-(2-(3,3-difluoroazetidin-1-yl)-6-methylpyrimidin-4-yl)-4-((2-hydroxyethyl)sulfonamido)-2-(6-azaspiro[2.5]octan-6-yl)benzamide (60 mg, 0.112 mmol, 48.6% yield) as white solid. $^1$H NMR (400 MHz, DMSO-$d_6$) δ ppm 13.55 (s, 1H), 10.28 (s, 1H), 8.05 (d, J=8.7 Hz, 1H), 7.51 (s, 1H), 7.28 (d, J=2.2 Hz, 1H), 7.14 (dd, 7=8.6, 2.2 Hz, 1H), 4.95 (s, 1H), 4.45 (d, 7=12.3 Hz, 4H), 3.76 (t, 7=6.4 Hz, 2H), 3.64 (s, 1H), 3.57 (s, 1H), 2.97 (t, 7=5.4 Hz, 4H), 2.34 (s, 3H), 1.74 (br s, 4H), 0.40 (s, 4H). m/z (ESI): 537.2 (M+H)$^+$.

Examples 8-1 and 8-2: (R)—N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide and (S)—N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide

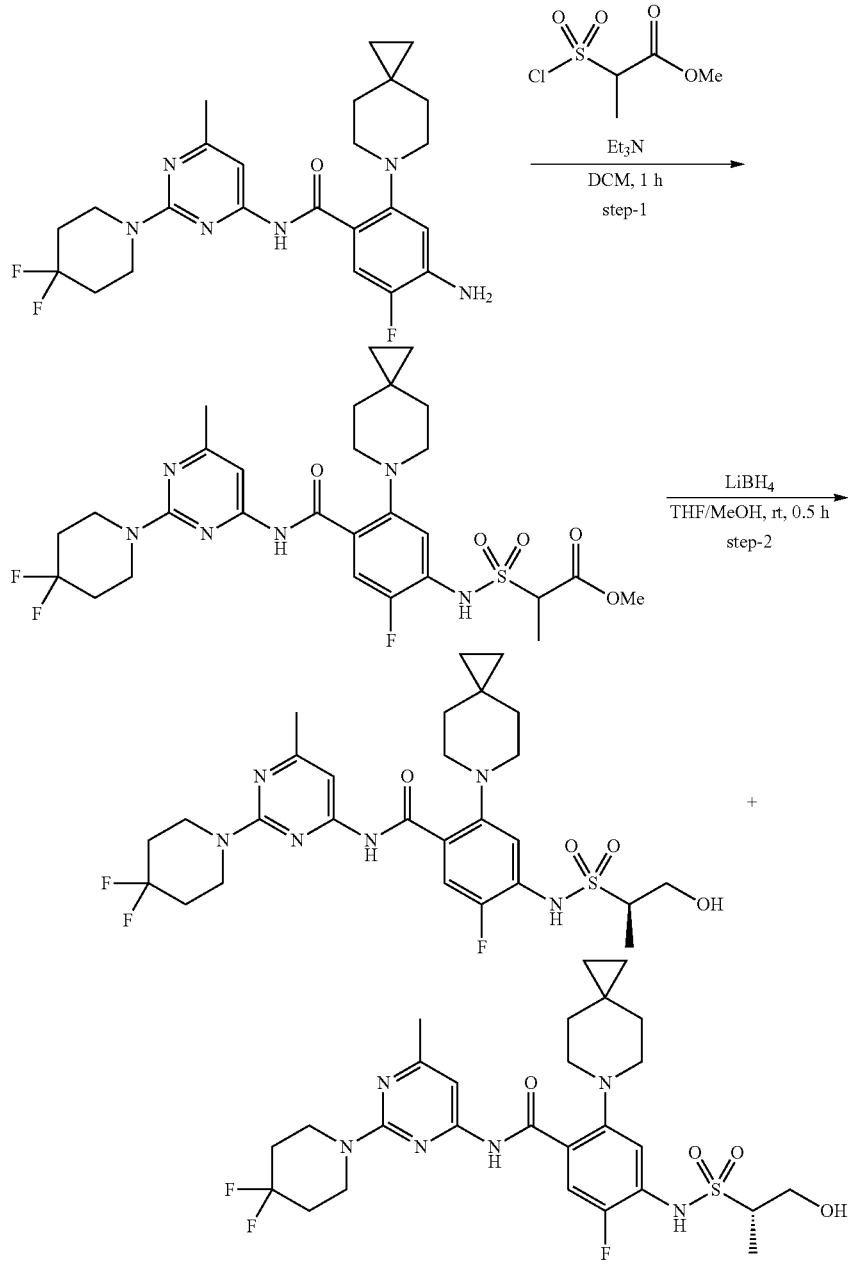

Step 1: Methyl 2-(chlorosulfonyl)propanoate (177 mg, 0.95 mmol, Enamine) was added to a solution of 4-amino-N-(2-(4,4-difluoropiperidin-1-yl)-6-methylpyrimidin-4-yl)-5-fluoro-2-(6-azaspiro[2.5]octan-6-yl)benzamide (0.41 g, 0.86 mmol, Int. 21) and triethylamine (0.18 mL, 1.30 mmol) in DCM (3 mL) at 0° C. The mixture was stirred for 1 h then the mixture was concentrated in vacuo and then purified by silica gel chromatography using a Redi-Sep pre-packed silica gel column (12 g), eluting with 25% EtOAc/heptane gradient, to provide methyl 2-(N-(4-((2-(4,4-difluoropiperidin-1-yl)-6-methylpyrimidin-4-yl)carbamoyl)-2-fluoro-5-(6-azaspiro[2.5]octan-6-yl)phenyl)sulfamoyl)propanoate (0.54 g, 0.48 mmol, 54.8% yield) as a white solid. $^1$H NMR (400 MHz, DMSO-$d_6$) δ ppm 13.71 (s, 1H) 10.66 (brs, 1H) 7.88 (d, J=11.61 Hz, 1H) 7.60 (d, J=7.26 Hz, 1H) 7.39 (s, 1H) 4.38 (d, J=7.05 Hz, 1H) 3.88-3.96 (m, 4H) 3.57 (s, 3H) 2.98 (br t, J=4.56 Hz, 4H) 2.33 (s, 3H) 1.92-2.07 (m, 4H) 1.57-1.91 (m, 4H) 1.52 (d, J=6.84 Hz, 3H) 0.40 (s, 4H). $^{19}$F NMR (376 MHz, DMSO-$d_6$) δ ppm −94.77 (s, 1F) −126.39 (s, 1F). m/z (ESI): 625.2 (M+H)$^+$.

Step 2: Methanol (0.10 mL, 2.52 mmol) was added dropwise to a THF (2.5 mL) solution of methyl 2-(N-(4-((2-(4,4-difluoropiperidin-1-yl)-6-methylpyrimidin-4-yl)carbamoyl)-2-fluoro-5-(6-azaspiro[2.5]octan-6-yl)phenyl)sulfamoyl)propanoate (192 mg, 0.31 mmol) and lithium borohydride (2.0 M in THF, 0.35 mL, 0.69 mmol). The mixture was stirred for 30 minutes and then aqueous NH$_4$Cl was added. The product was extracted into EtOAc (2×), and the combined extracts were dried over anhydrous MgSO$_4$, filtered, and concentrated in vacuo to give racemic product as a solid. This material was separated by preparative SFC using a OD column (250×21 mm, 5 mm) and OD column (150×21 mm, 5 mm) with a mobile phase of 90% Liquid CO$_2$ and 10% EtOH/0.2% triethylamine using a flowrate of 80 mL/min to give:

Example 8-1: (R)—N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide. First eluting peak (94 mg, 0.16 mmol, 33.2% yield, >99% ee). $^1$H NMR (400 MHz, DMSO-d$_6$) δ ppm 13.74 (s, 1H) 7.82 (d, J=11.82 Hz, 1H) 7.58 (d, J=7.26 Hz, 1H) 7.39 (s, 1H) 3.77-3.96 (m, 6H) 3.37-3.54 (m, 1H) 3.22-3.30 (m, 1H) 2.88-3.05 (m, 4H) 2.32 (s, 3H) 1.92-2.05 (m, 4H) 1.73 (brs, 4H) 1.31 (d, J=6.84 Hz, 3H) 0.40 (s, 4H). $^{19}$F NMR (376 MHz, DMSO-d$_6$) δ ppm −94.77 (s, 1F) −127.36 (s, 1F). m/z (ESI): 597.2 (M+H)$^+$.

Example 8-2: (S)—N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide. Second eluting peak (102 mg, 0.17 mmol, 36.1% yield, 98.4% ee). $^1$H NMR (400 MHz, DMSO-d$_6$) δ ppm 13.74 (s, 1H) 7.82 (d, J=11.82 Hz, 1H) 7.58 (d, J=7.26 Hz, 1H) 7.39 (s, 1H) 3.77-3.96 (m, 6H) 3.37-3.54 (m, 1H) 3.22-3.30 (m, 1H) 2.88-3.05 (m, 4H) 2.32 (s, 3H) 1.92-2.05 (m, 4H) 1.73 (brs, 4H) 1.31 (d, 7=6.84 Hz, 3H) 0.40 (s, 4H). $^{19}$F NMR (376 MHz, DMSO-d$_6$) δ ppm −94.76 (s, 1F) −127.73 (s, 1F). m/z (ESI): 597.2 (M+H)$^+$. The stereochemistry was arbitrarily assigned.

Examples 10-1 and 10-2: (R)—N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide and (S)—N-(2-(3,3-difluoroazetidin-1-yl)-6-methylpyrimidin-4-yl)-4-((2-hydroxypropyl)sulfonamido)-2-(6-azaspiro[2.5]octan-6-yl)benzamide

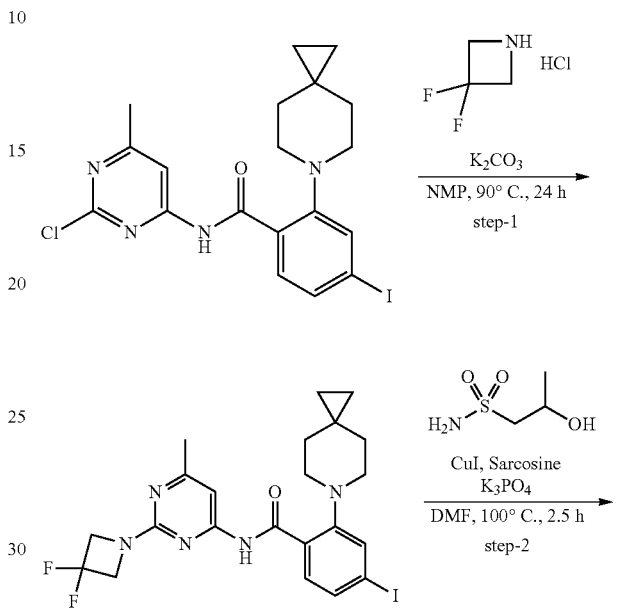

TABLE 9

Examples 9-1 to 9-2 were prepared following similar procedure for Examples 8-1 and 8-2:

| Ex. # | Chemical Structure | Name | LRMS: (ESI + ve ion) m/z |
|---|---|---|---|
| 9-1 | 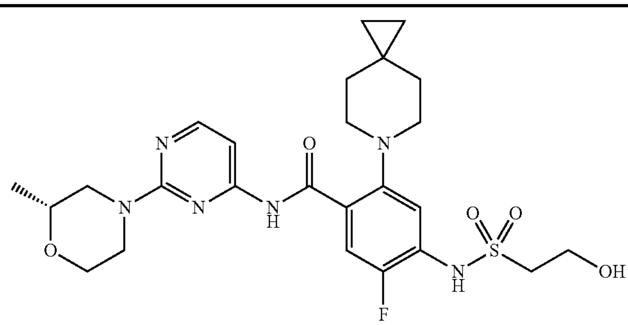 | (R)-5-Fluoro-4-((2-hydroxyethyl)sulfonamido)-N-(2-(2-methylmorpholino)pyrimidin-4-yl)-2-(6-azaspiro[2.5]octan-6-yl)benzamide | 549.2 |
| 9-2 | 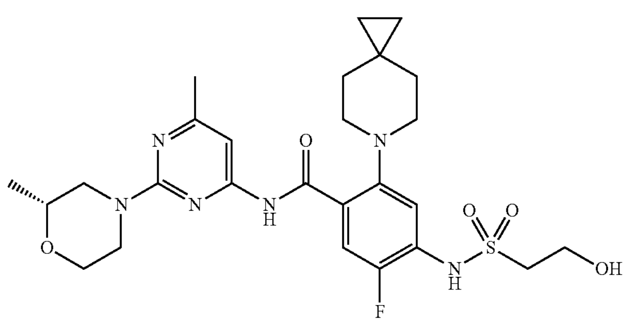 [SMILES: Cc1cc(NC(=O)c2cc(F)c(NS(=O)(=O)CCO)cc2N2CCC3(CC2)CC3)nc(N2CCO[C@H](C)C2)n1] | (R)-5-Fluoro-4-((2-hydroxyethyl)sulfonamido)-N-(6-methyl-2-(2-methylmorpholino)pyrimidin-4-yl)-2-(6-azaspiro[2.5]octan-6-yl)benzamide | 563.2 |

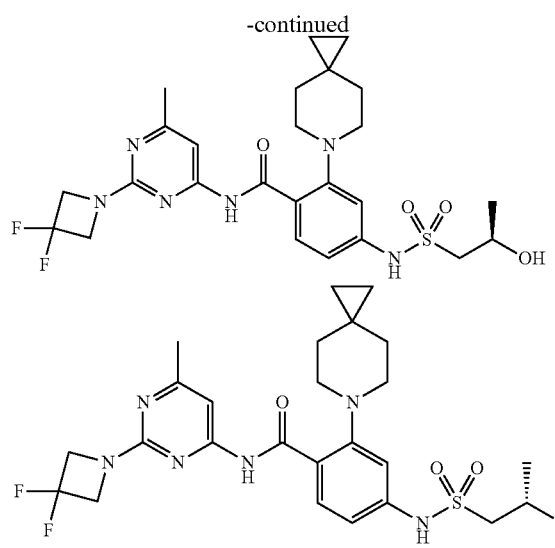

Step 1: A mixture of N-(2-chloro-6-methylpyrimidin-4-yl)-4-iodo-2-(6-azaspiro[2.5]octan-6-yl)benzamide (2.0 g, 4.14 mmol, Int. 17), 3,3-difluoroazetidine hydrochloride (1.07 g, 8.29 mmol, Combi-Blocks Inc.), and potassium carbonate (1.72 g, 12.4 mmol, Combi-Blocks, Inc.) in NMP (10 mL) was heated to 90° C. for 24 h. The mixture was cooled to room temperature, EtOAc (10 mL) was added, and then the mixture was washed with water (1×10 mL), 1N HCl (1×10 mL) and brine (1×10 mL). The mixture was then dried over anhydrous MgSO₄, filtered, and concentrated in vacuo to give a solid. The solid was then suspended in MeOH and filtered, then dried in vacuo to provide N-(2-(3,3-difluoroazetidin-1-yl)-6-methylpyrimidin-4-yl)-4-iodo-2-(6-azaspiro[2.5]octan-6-yl)benzamide (1.16 g, 2.15 mmol, 51.9% yield) as a light brown solid. $^1$H NMR (400 MHz, DMSO-d$_6$) δ ppm 13.53 (br s, 1H) 7.79-7.86 (m, 2H) 7.73-7.77 (m, 1H) 7.49 (s, 1H) 4.43 (t, J=12.44 Hz, 4H) 3.02 (br t, J=5.08 Hz, 4H) 2.31-2.38 (m, 3H) 1.65-1.82 (m, 4H) 0.39 (s, 4H). $^{19}$F NMR (376 MHz, DMSO-d$_6$) δ ppm −99.09 (s, 1F). m/z (ESI): 540.0 (M+H)⁺.

Step 2: A mixture of 2-hydroxypropane-1-sulfonamide (206 mg, 1.48 mmol, Int. 23), copper(I) iodide (71 mg, 0.37 mmol), Sarcosine (66 mg, 0.74 mmol), and potassium phosphate (787 mg, 3.71 mmol) was placed under argon atmosphere, taken up in anhydrous DMF (3 mL), and warmed to 50° C. for 5 min. N-(2-(3,3-difluoroazetidin-1-yl)-6-methylpyrimidin-4-yl)-4-iodo-2-(6-azaspiro[2.5]octan-6-yl)benzamide (0.40 g, 0.74 mmol) was added in one portion and the mixture was heated to 100° C. for 2.5 h, then cooled to room temperature. Water was added, and the product was extracted into EtOAc (2×). The combined extracts were washed with water (2×), 9:1 saturated NH₄Cl/NH₄OH (1×), dried over anhydrous MgSO₄, filtered, and concentrated in vacuo to give racemic product as an oil. This material was separated by preparative SFC using an IF column (250×301 mm, 5 mm) with a mobile phase of 75% Liquid CO₂ and 25% MeOH using a flowrate of 130 mL/min to give:

Example 10-1: (R)—N-(2-(3,3-difluoroazetidin-1-yl)-6-methylpyrimidin-4-yl)-4-((2-hydroxypropyl)sulfonamido)-2-(6-azaspiro[2.5]octan-6-yl)benzamide. First eluting peak (88 mg, 0.16 mmol, 21.6% yield, >99% ee). $^1$H NMR (400 MHz, DMSO-d$_6$) δ ppm 13.54 (s, 1H) 8.05 (d, J=8.71 Hz, 1H) 7.51 (s, 1H) 7.27 (d, J=1.87 Hz, 1H) 7.14 (dd, J=8.71, 1.87 Hz, 1H) 4.44 (t, J=12.44 Hz, 4H) 4.07-4.15 (m, 1H) 3.22-3.29 (m, 2H) 2.97 (br t, J=4.87 Hz, 4H) 2.34 (s, 3H) 1.74 (br s, 4H) 1.19 (d, J=6.22 Hz, 3H) 0.40 (s, 4H). 2 exchangeable protons not observed. $^{19}$F NMR (376 MHz, DMSO-d$_6$) 5 ppm −99.08 (s, 1F). m/z (ESI): 551 (M+H)⁺.

Example 10-2: (S)—N-(2-(3,3-difluoroazetidin-1-yl)-6-methylpyrimidin-4-yl)-4-((2-hydroxypropyl)sulfonamido)-2-(6-azaspiro[2.5]octan-6-yl)benzamide. Second eluting peak (89 mg, 0.162 mmol, 21.8% yield, 99% ee). $^1$H NMR (400 MHz, DMSO-d$_6$) δ ppm 13.55 (s, 1H) 8.05 (d, J=8.71 Hz, 1H) 7.51 (s, 1H) 7.26 (d, J=1.87 Hz, 1H) 7.14 (dd, J=8.71, 1.87 Hz, 1H) 4.43 (t, J=12.44 Hz, 4H) 4.11 (d, J=6.01 Hz, 1H) 3.21-3.31 (m, 2H) 2.97 (br t, J=4.87 Hz, 4H) 2.34 (s, 3H) 1.53-2.01 (m, 4H) 1.19 (d, J=6.43 Hz, 3H) 0.40 (s, 4H). 2 exchangeable protons not observed. $^{19}$F NMR (376 MHz, DMSO-d$_6$) δ ppm −99.09 (s, 1F). m/z (ESI): 551 (M+H)⁺. The stereochemistry was arbitrarily assigned.

TABLE 10

Examples 11-1 to 11-83 were prepared following similar procedures for Example 10:

| Ex. # | Chemical Structure | Name | LRMS: (ESI + ve ion) m/z |
|---|---|---|---|
| 11-1 | 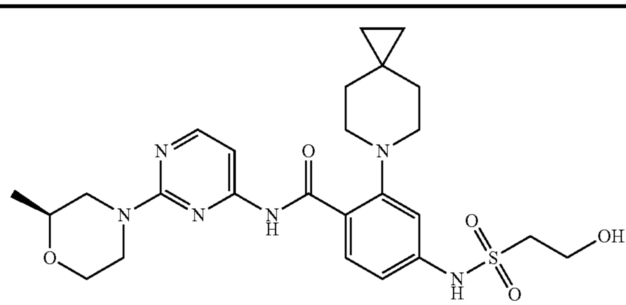 | (S)-4-((2-Hydroxyethyl)sulfonamido)-N-(2-(2-methylmorpholino)pyrimidin-4-yl)-2-(6-azaspiro[2.5]octan-6-yl)benzamide | 531.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-2 | 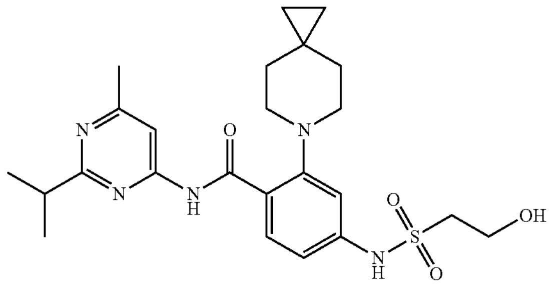 [SMILES: Cc1cc(NC(=O)c2ccc(NS(=O)(=O)CCO)cc2N2CCC3(CC2)CC3)nc(C(C)C)n1] | 4-((2-Hydroxyethyl)sulfonamido)-N-(2-isopropyl-6-methylpyrimidin-4-yl)-2-(6-azaspiro[2.5]octan-6-yl)benzamide | 488.2 |
| 11-3 | 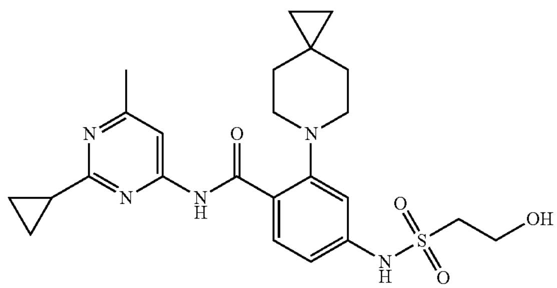 [SMILES: Cc1cc(NC(=O)c2ccc(NS(=O)(=O)CCO)cc2N2CCC3(CC2)CC3)nc(C2CC2)n1] | N-(2-Cyclopropyl-6-methylpyrimidin-4-yl)-4-((2-hydroxyethyl)sulfonamido)-2-(6-azaspiro[2.5]octan-6-yl)benzamide | 486.1 |
| 11-4 | 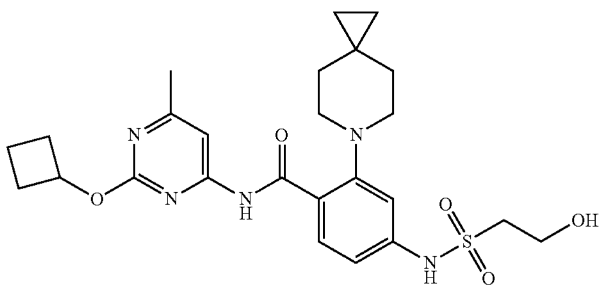 [SMILES: Cc1cc(NC(=O)c2ccc(NS(=O)(=O)CCO)cc2N2CCC3(CC2)CC3)nc(OC2CCC2)n1] | N-(2-Cyclobutoxy-6-methylpyrimidin-4-yl)-4-((2-hydroxyethyl)sulfonamido)-2-(6-azaspiro[2.5]octan-6-yl)benzamide | 516.2 |
| 11-5 | 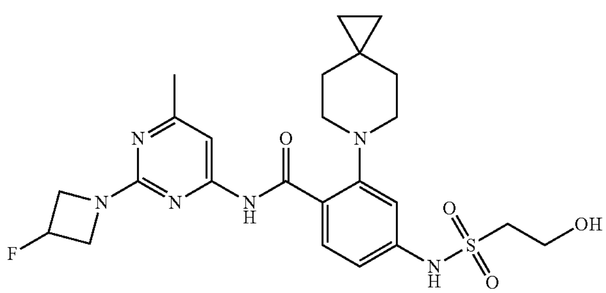 [SMILES: Cc1cc(NC(=O)c2ccc(NS(=O)(=O)CCO)cc2N2CCC3(CC2)CC3)nc(N2CC(F)C2)n1] | N-(2-(3-Fluoroazetidin-1-yl)-6-methylpyrimidin-4-yl)-4-((2-hydroxyethyl)sulfonamido)-2-(6-azaspiro[2.5]octan-6-yl)benzamide | 519.2 |
| 11-6 | 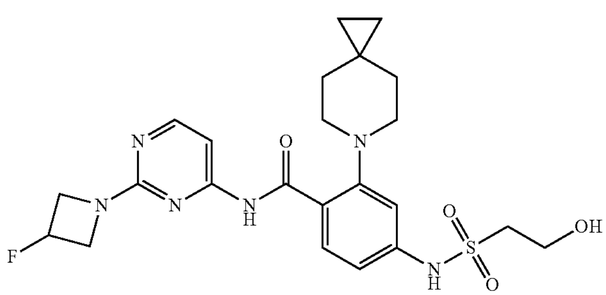 [SMILES: O=C(Nc1ccnc(N2CC(F)C2)n1)c1ccc(NS(=O)(=O)CCO)cc1N1CCC2(CC1)CC2] | N-(2-(3-Fluoroazetidin-1-yl)pyrimidin-4-yl)-4-((2-hydroxyethyl)sulfonamido)-2-(6-azaspiro[2.5]octan-6-yl)benzamide | 505.1 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-7 | 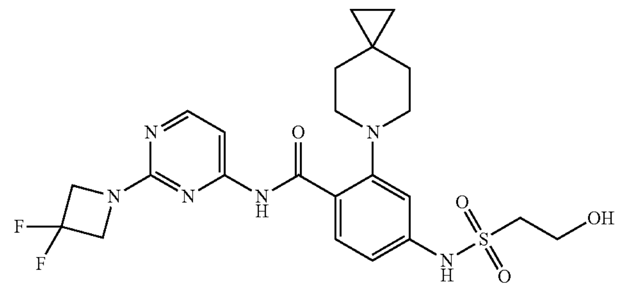 [SMILES: O=C(Nc1ccnc(N2CC(F)(F)C2)n1)c1ccc(NS(=O)(=O)CCO)cc1N1CCC2(CC1)CC2] | N-(2-(3,3-Difluoroazetidin-1-yl)pyrimidin-4-yl)-4-((2-hydroxyethyl)sulfonamido)-2-(6-azaspiro[2.5]octan-6-yl)benzamide | 523.1 |
| 11-8 | 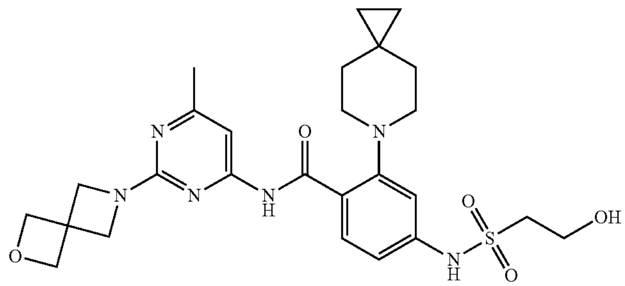 [SMILES: Cc1cc(NC(=O)c2ccc(NS(=O)(=O)CCO)cc2N2CCC3(CC2)CC3)nc(N2CC3(COC3)C2)n1] | 4-((2-Hydroxyethyl)sulfonamido)-N-(6-methyl-2-(2-oxa-6-azaspiro[3.3]heptan-6-yl)pyrimidin-4-yl)-2-(6-azaspiro[2.5]octan-6-yl)benzamide | 543.2 |
| 11-9 | 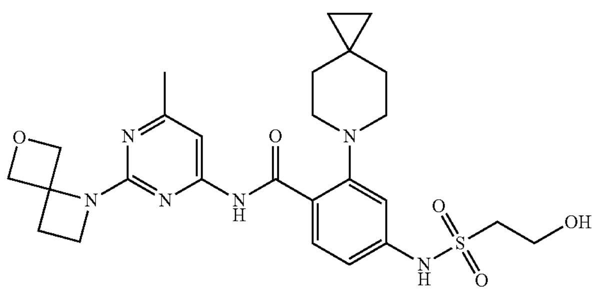 [SMILES: Cc1cc(NC(=O)c2ccc(NS(=O)(=O)CCO)cc2N2CCC3(CC2)CC3)nc(N2CCC23COC3)n1] | 4-((2-Hydroxyethyl)sulfonamido)-N-(6-methyl-2-(6-oxa-1-azaspiro[3.3]heptan-1-yl)pyrimidin-4-yl)-2-(6-azaspiro[2.5]octan-6-yl)benzamide | 543.2 |
| 11-10 | 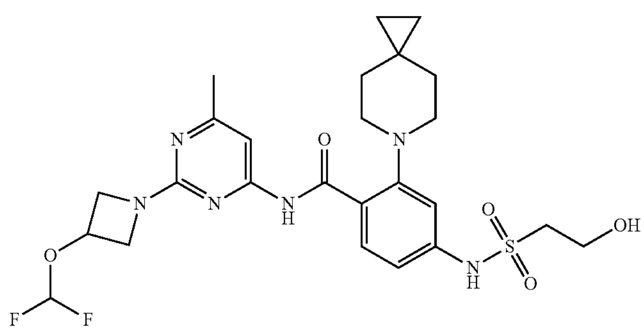 [SMILES: Cc1cc(NC(=O)c2ccc(NS(=O)(=O)CCO)cc2N2CCC3(CC2)CC3)nc(N2CC(OC(F)F)C2)n1] | N-(2-(3-(Difluoromethoxy)azetidin-1-yl)-6-methylpyrimidin-4-yl)-4-((2-hydroxyethyl)sulfonamido)-2-(6-azaspiro[2.5]octan-6-yl)benzamide | 567.2 |
| 11-11 | 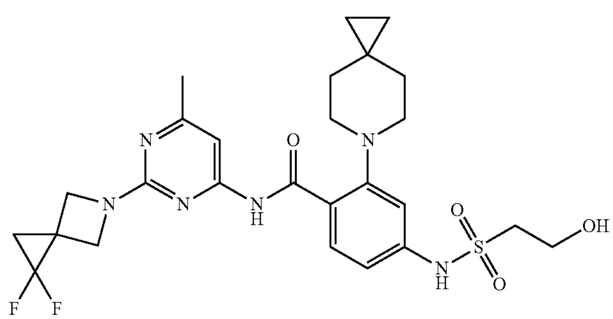 [SMILES: Cc1cc(NC(=O)c2ccc(NS(=O)(=O)CCO)cc2N2CCC3(CC2)CC3)nc(N2CC3(C2)CC3(F)F)n1] | N-(2-(1,1-Difluoro-5-azaspiro[2.3]hexan-5-yl)-6-methylpyrimidin-4-yl)-4-((2-hydroxyethyl)sulfonamido)-2-(6-azaspiro[2.5]octan-6-yl)benzamide | 563.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-12 | 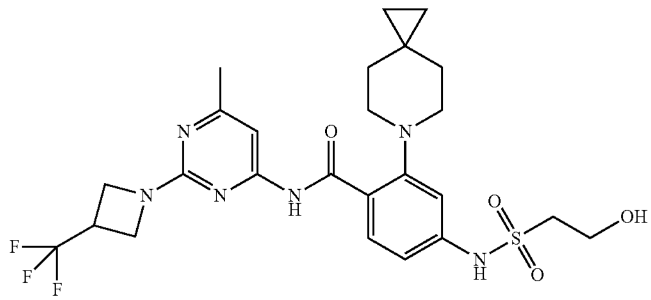 [SMILES: Cc1cc(NC(=O)c2ccc(NS(=O)(=O)CCO)cc2N2CCC3(CC2)CC3)nc(N2CC(C(F)(F)F)C2)n1] | 4-((2-Hydroxyethyl)sulfonamido)-N-(6-methyl-2-(3-(trifluoromethyl)azetidin-1-yl)pyrimidin-4-yl)-2-(6-azaspiro[2.5]octan-6-yl)benzamide | 569.2 |
| 11-13 | 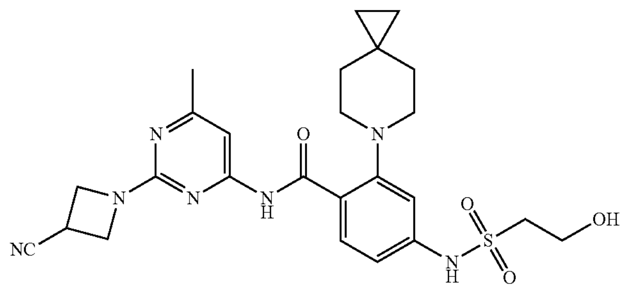 [SMILES: Cc1cc(NC(=O)c2ccc(NS(=O)(=O)CCO)cc2N2CCC3(CC2)CC3)nc(N2CC(C#N)C2)n1] | N-(2-(3-Cyanoazetidin-1-yl)-6-methylpyrimidin-4-yl)-4-((2-hydroxyethyl)sulfonamido)-2-(6-azaspiro[2.5]octan-6-yl)benzamide | 526.2 |
| 11-14 | 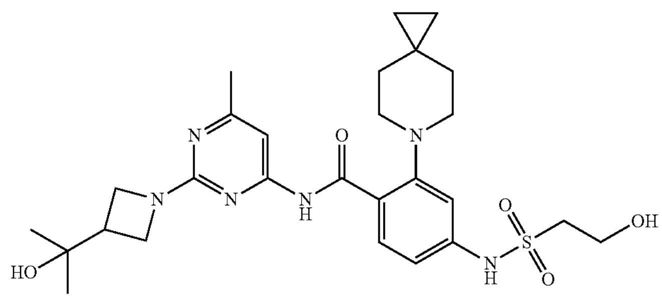 [SMILES: Cc1cc(NC(=O)c2ccc(NS(=O)(=O)CCO)cc2N2CCC3(CC2)CC3)nc(N2CC(C(C)(C)O)C2)n1] | 4-((2-Hydroxyethyl)sulfonamido)-N-(2-(3-(2-hydroxypropan-2-yl)azetidin-1-yl)-6-methylpyrimidin-4-yl)-2-(6-azaspiro[2.5]octan-6-yl)benzamide | 559.2 |
| 11-15 | 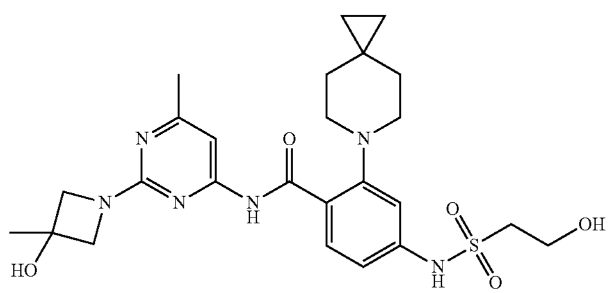 [SMILES: Cc1cc(NC(=O)c2ccc(NS(=O)(=O)CCO)cc2N2CCC3(CC2)CC3)nc(N2CC(C)(O)C2)n1] | N-(2-(3-Hydroxy-3-methylazetidin-1-yl)-6-methylpyrimidin-4-yl)-4-((2-hydroxyethyl)sulfonamido)-2-(6-azaspiro[2.5]octan-6-yl)benzamide | 531.2 |
| 11-16 | 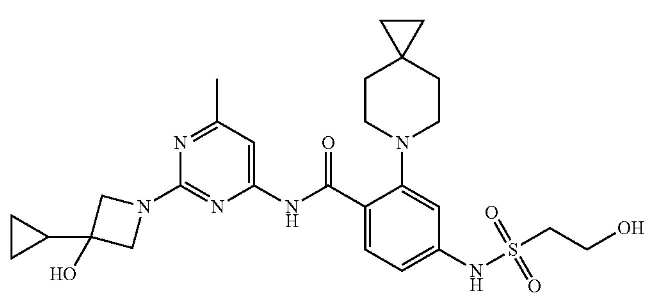 [SMILES: Cc1cc(NC(=O)c2ccc(NS(=O)(=O)CCO)cc2N2CCC3(CC2)CC3)nc(N2CC(O)(C3CC3)C2)n1] | N-(2-(3-Cyclopropyl-3-hydroxyazetidin-1-yl)-6-methylpyrimidin-4-yl)-4-((2-hydroxyethyl)sulfonamido)-2-(6-azaspiro[2.5]octan-6-yl)benzamide | 557.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-17 | 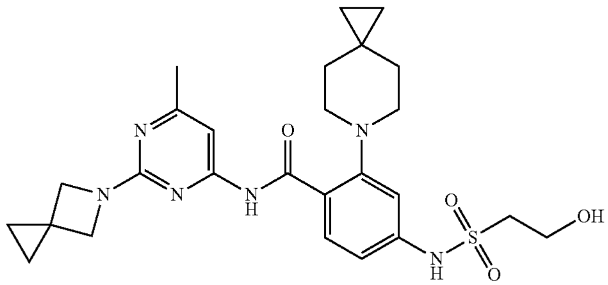 [SMILES: Cc1cc(NC(=O)c2ccc(NS(=O)(=O)CCO)cc2N2CCC3(CC2)CC3)nc(N2CC3(CC3)C2)n1] | 4-((2-Hydroxyethyl)sulfonamido)-N-(6-methyl-2-(5-azaspiro[2.3]hexan-5-yl)pyrimidin-4-yl)-2-(6-azaspiro[2.5]octan-6-yl)benzamide | 527.2 |
| 11-18 | 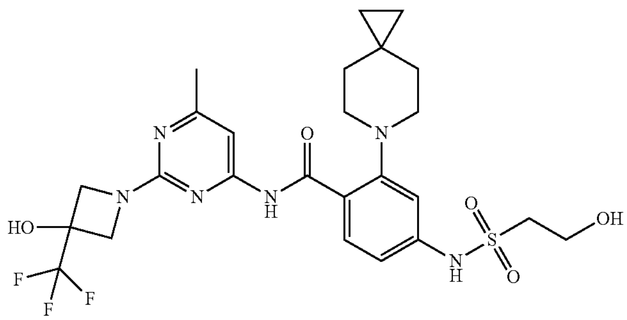 [SMILES: Cc1cc(NC(=O)c2ccc(NS(=O)(=O)CCO)cc2N2CCC3(CC2)CC3)nc(N2CC(O)(C(F)(F)F)C2)n1] | N-(2-(3-Hydroxy-3-(trifluoromethyl)azetidin-1-yl)-6-methylpyrimidin-4-yl)-4-((2-hydroxyethyl)sulfonamido)-2-(6-azaspiro[2.5]octan-6-yl)benzamide | 585.2 |
| 11-19 | 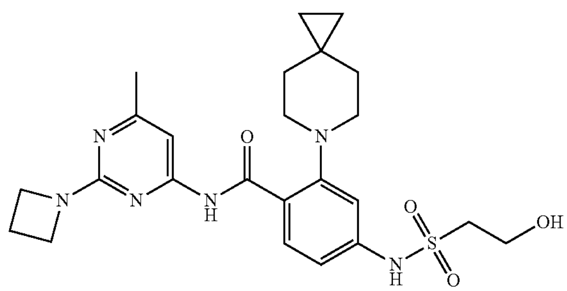 [SMILES: Cc1cc(NC(=O)c2ccc(NS(=O)(=O)CCO)cc2N2CCC3(CC2)CC3)nc(N2CCC2)n1] | N-(2-(Azetidin-1-yl)-6-methylpyrimidin-4-yl)-4-((2-hydroxyethyl)sulfonamido)-2-(6-azaspiro[2.5]octan-6-yl)benzamide | 501.2 |
| 11-20 | 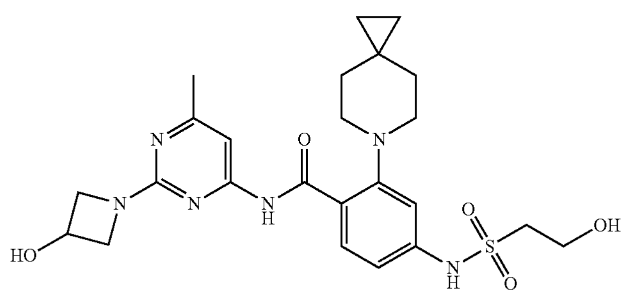 | N-(2-(3-Hydroxyazetidin-1-yl)-6-methylpyrimidin-4-yl)-4-((2-hydroxyethyl)sulfonamido)-2-(6-azaspiro[2.5]octan-6-yl)benzamide | 517.2 |
| 11-21 | 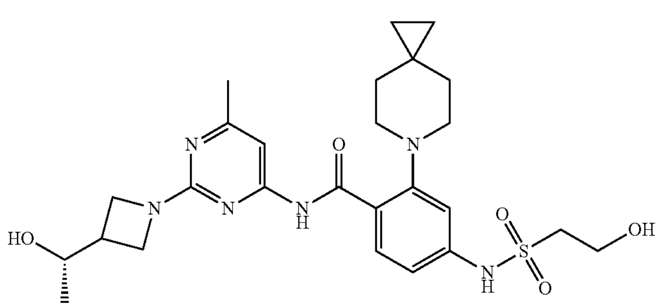 [SMILES: Cc1cc(NC(=O)c2ccc(NS(=O)(=O)CCO)cc2N2CCC3(CC2)CC3)nc(N2CC([C@H](C)O)C2)n1] | (S)-N-(2-(3-(1-Hydroxyethyl)azetidin-1-yl)-6-methylpyrimidin-4-yl)-4-((2-hydroxyethyl)sulfonamido)-2-(6-azaspiro[2.5]octan-6-yl)benzamide | 545.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-22 | 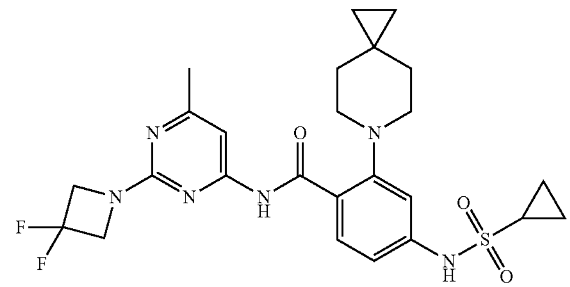 [SMILES: Cc1cc(NC(=O)c2ccc(NS(=O)(=O)C3CC3)cc2N2CCC3(CC2)CC3)nc(N2CC(F)(F)C2)n1] | 4-(Cyclopropanesulfonamido)-N-(2-(3,3-difluoroazetidin-1-yl)-6-methylpyrimidin-4-yl)-2-(6-azaspiro[2.5]octan-6-yl)benzamide | 533.2 |
| 11-23 | 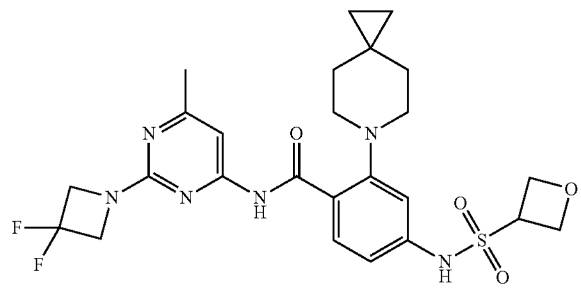 [SMILES: Cc1cc(NC(=O)c2ccc(NS(=O)(=O)C3COC3)cc2N2CCC3(CC2)CC3)nc(N2CC(F)(F)C2)n1] | N-(2-(3,3-Difluoroazetidin-1-yl)-6-methylpyrimidin-4-yl)-4-(oxetane-3-sulfonamido)-2-(6-azaspiro[2.5]octan-6-yl)benzamide | 549.2 |
| 11-24 | 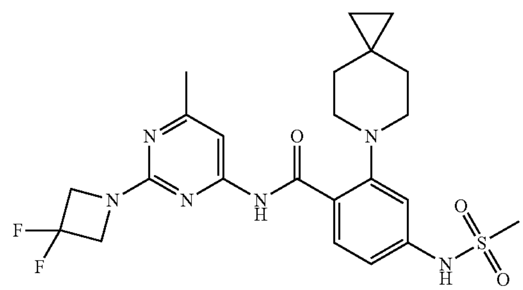 [SMILES: Cc1cc(NC(=O)c2ccc(NS(C)(=O)=O)cc2N2CCC3(CC2)CC3)nc(N2CC(F)(F)C2)n1] | N-(2-(3,3-Difluoroazetidin-1-yl)-6-methylpyrimidin-4-yl)-4-(methylsulfonamido)-2-(6-azaspiro[2.5]octan-6-yl)benzamide | 507.1 |
| 11-25 | 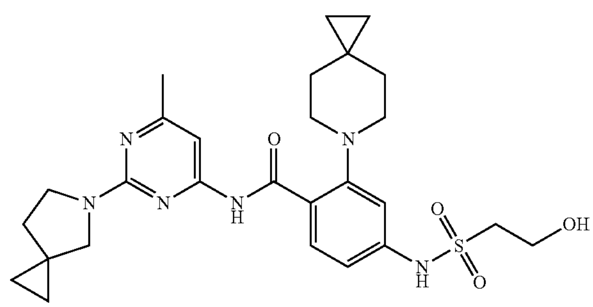 [SMILES: Cc1cc(NC(=O)c2ccc(NS(=O)(=O)CCO)cc2N2CCC3(CC2)CC3)nc(N2CCC3(CC3)C2)n1] | 4-((2-Hydroxyethyl)sulfonamido)-N-(6-methyl-2-(5-azaspiro[2.4]heptan-5-yl)pyrimidin-4-yl)-2-(6-azaspiro[2.5]octan-6-yl)benzamide | 541.2 |
| 11-26 | 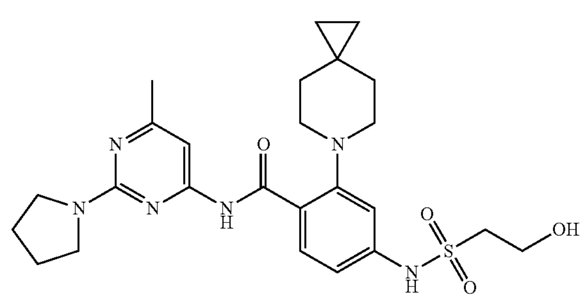 [SMILES: Cc1cc(NC(=O)c2ccc(NS(=O)(=O)CCO)cc2N2CCC3(CC2)CC3)nc(N2CCCC2)n1] | 4-((2-Hydroxyethyl)sulfonamido)-N-(6-methyl-2-(pyrrolidin-1-yl)pyrimidin-4-yl)-2-(6-azaspiro[2.5]octan-6-yl)benzamide | 515.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-27 | 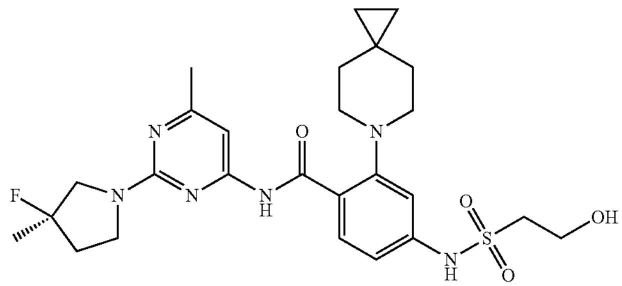 [SMILES: Cc1cc(NC(=O)c2ccc(NS(=O)(=O)CCO)cc2N2CCC3(CC2)CC3)nc(N2CC[C@@](C)(F)C2)n1] | (R)-N-(2-(3-Fluoro-3-methylpyrrolidin-1-yl)-6-methylpyrimidin-4-yl)-4-((2-hydroxyethyl)sulfonamido)-2-(6-azaspiro[2.5]octan-6-yl)benzamide | 547.3 |
| 11-28 | 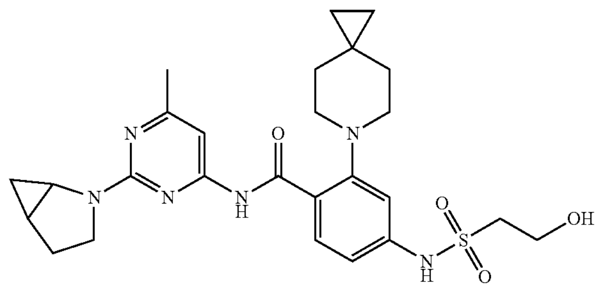 [SMILES: Cc1cc(NC(=O)c2ccc(NS(=O)(=O)CCO)cc2N2CCC3(CC2)CC3)nc(N2CCC3CC32)n1] | N-(2-(2-Azabicyclo[3.1.0]hexan-2-yl)-6-methylpyrimidin-4-yl)-4-((2-hydroxyethyl)sulfonamido)-2-(6-azaspiro[2.5]octan-6-yl)benzamide | 527.2 |
| 11-29 | 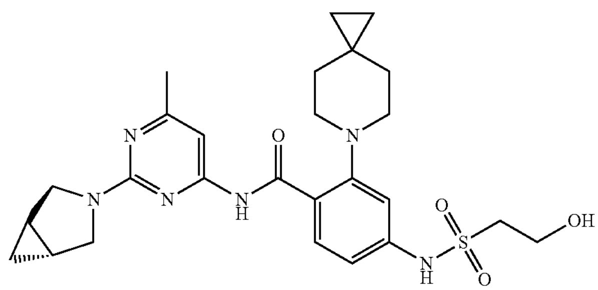 | N-(2-((1R,5S)-3-Azabicyclo[3.1.0]hexan-3-yl)-6-methylpyrimidin-4-yl)-4-((2-hydroxyethyl)sulfonamido)-2-(6-azaspiro[2.5]octan-6-yl)benzamide | 527.2 |
| 11-30 | 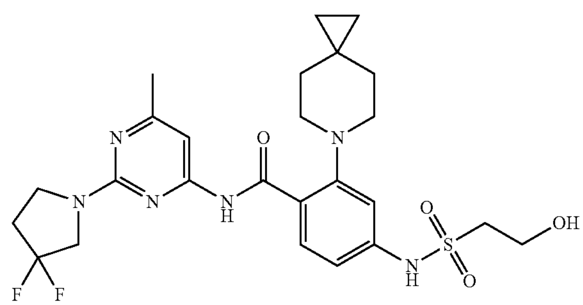 [SMILES: Cc1cc(NC(=O)c2ccc(NS(=O)(=O)CCO)cc2N2CCC3(CC2)CC3)nc(N2CCC(F)(F)C2)n1] | N-(2-(3,3-Difluoropyrrolidin-1-yl)-6-methylpyrimidin-4-yl)-4-((2-hydroxyethyl)sulfonamido)-2-(6-azaspiro[2.5]octan-6-yl)benzamide | 551.2 |
| 11-31 | 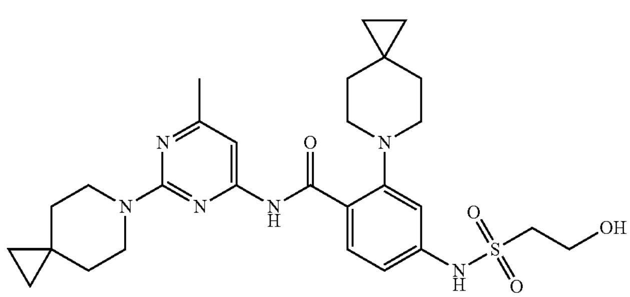 [SMILES: Cc1cc(NC(=O)c2ccc(NS(=O)(=O)CCO)cc2N2CCC3(CC2)CC3)nc(N2CCC3(CC2)CC3)n1] | 4-((2-Hydroxyethyl)sulfonamido)-N-(6-methyl-2-(6-azaspiro[2.5]octan-6-yl)pyrimidin-4-yl)-2-(6-azaspiro[2.5]octan-6-yl)benzamide | 555.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-32 | 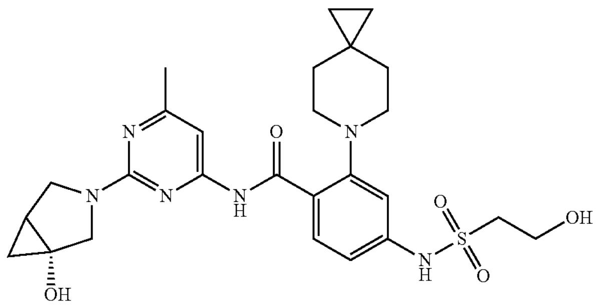 [SMILES: Cc1cc(NC(=O)c2ccc(NS(=O)(=O)CCO)cc2N2CCC3(CC2)CC3)nc(N2CC3C[C@]3(O)C2)n1] | N-(2-((1R)-1-Hydroxy-3-azabicyclo[3.1.0]hexan-3-yl)-6-methylpyrimidin-4-yl)-4-((2-hydroxyethyl)sulfonamido)-2-(6-azaspiro[2.5]octan-6-yl)benzamide | 543.2 |
| 11-33 | 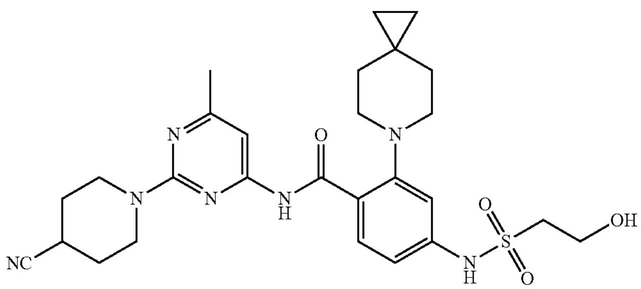 [SMILES: Cc1cc(NC(=O)c2ccc(NS(=O)(=O)CCO)cc2N2CCC3(CC2)CC3)nc(N2CCC(C#N)CC2)n1] | N-(2-(4-Cyanopiperidin-1-yl)-6-methylpyrimidin-4-yl)-4-((2-hydroxyethyl)sulfonamido)-2-(6-azaspiro[2.5]octan-6-yl)benzamide | 554.2 |
| 11-34 | 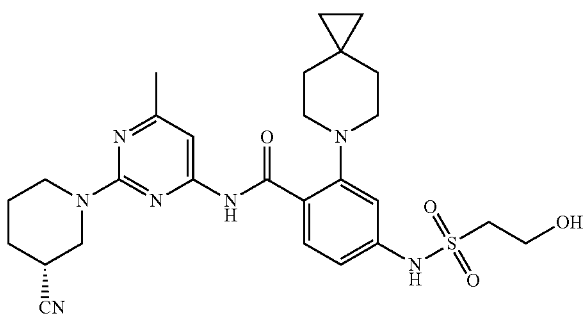 [SMILES: Cc1cc(NC(=O)c2ccc(NS(=O)(=O)CCO)cc2N2CCC3(CC2)CC3)nc(N2CCC[C@@H](C#N)C2)n1] | (R)-N-(2-(3-Cyanopiperidin-1-yl)-6-methylpyrimidin-4-yl)-4-((2-hydroxyethyl)sulfonamido)-2-(6-azaspiro[2.5]octan-6-yl)benzamide | 554.2 |
| 11-35 | 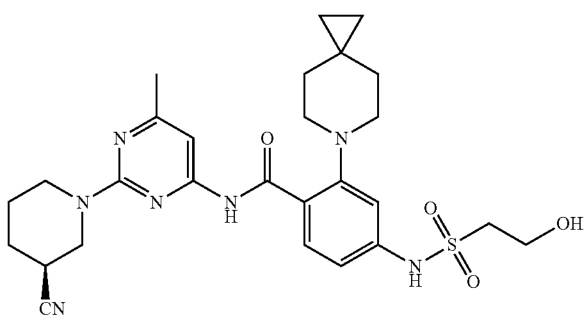 [SMILES: Cc1cc(NC(=O)c2ccc(NS(=O)(=O)CCO)cc2N2CCC3(CC2)CC3)nc(N2CCC[C@H](C#N)C2)n1] | (S)-N-(2-(3-Cyanopiperidin-1-yl)-6-methylpyrimidin-4-yl)-4-((2-hydroxyethyl)sulfonamido)-2-(6-azaspiro[2.5]octan-6-yl)benzamide | 554.2 |
| 11-36 | 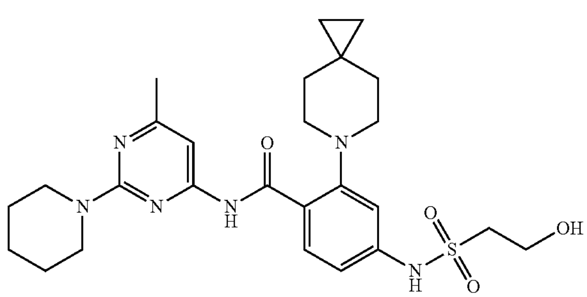 [SMILES: Cc1cc(NC(=O)c2ccc(NS(=O)(=O)CCO)cc2N2CCC3(CC2)CC3)nc(N2CCCCC2)n1] | 4-((2-Hydroxyethyl)sulfonamido)-N-(6-methyl-2-(piperidin-1-yl)pyrimidin-4-yl)-2-(6-azaspiro[2.5]octan-6-yl)benzamide | 529.3 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-37 | 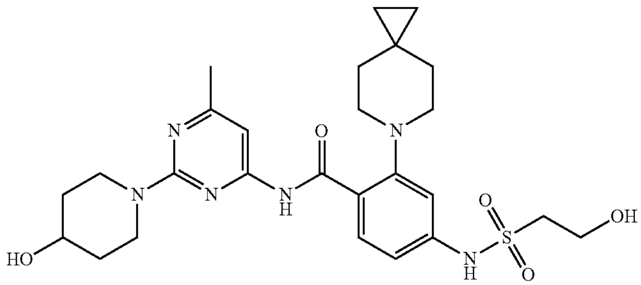 | 4-((2-Hydroxyethyl)sulfonamido)-N-(2-(4-hydroxypiperidin-1-yl)-6-methylpyrimidin-4-yl)-2-(6-azaspiro[2.5]octaii-6-yl)benzamide | 545.2 |
| 11-38 | 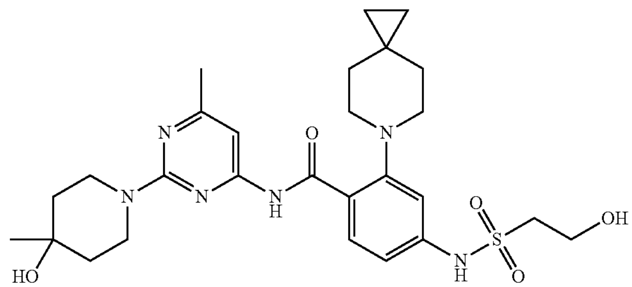 [SMILES: Cc1cc(NC(=O)c2ccc(NS(=O)(=O)CCO)cc2N2CCC3(CC2)CC3)nc(N2CCC(C)(O)CC2)n1] | N-(2-(4-Hydroxy-4-methylpiperidin-1-yl)-6-methylpyrimidin-4-yl)-4-((2-hydroxyethyl)sulfonamido)-2-(6-azaspiro[2.5]octan-6-yl)benzamide | 559.2 |
| 11-39 | 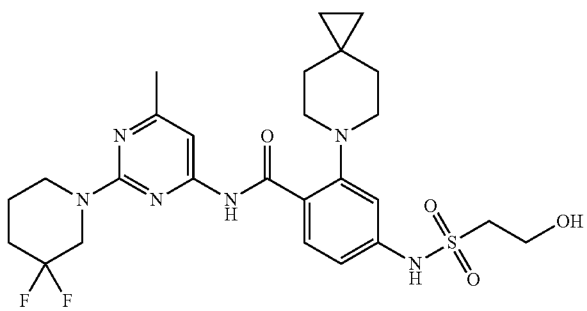 [SMILES: Cc1cc(NC(=O)c2ccc(NS(=O)(=O)CCO)cc2N2CCC3(CC2)CC3)nc(N2CCCC(F)(F)C2)n1] | N-(2-(3,3-Difluoropiperidin-1-yl)-6-methylpyrimidin-4-yl)-4-((2-hydroxyethyl)sulfonamido)-2-(6-azaspiro[2.5]octan-6-yl)benzamide | 565.2 |
| 11-40 | 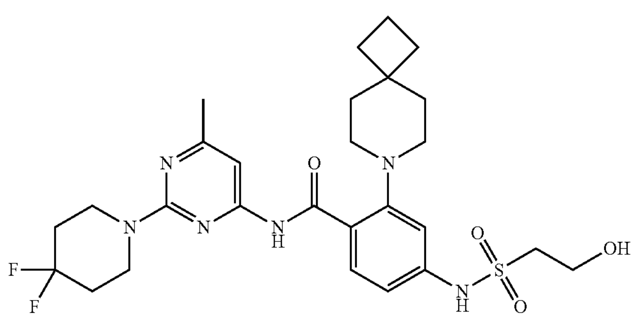 [SMILES: Cc1cc(NC(=O)c2ccc(NS(=O)(=O)CCO)cc2N2CCC3(CCC3)CC2)nc(N2CCC(F)(F)CC2)n1] | N-(2-(4,4-Difluoropiperidin-1-yl)-6-methylpyrimidin-4-yl)-4-((2-hydroxyethyl)sulfonamido)-2-(7-azaspiro[3.5]nonan-7-yl)benzamide | 579.2 |
| 11-41 | 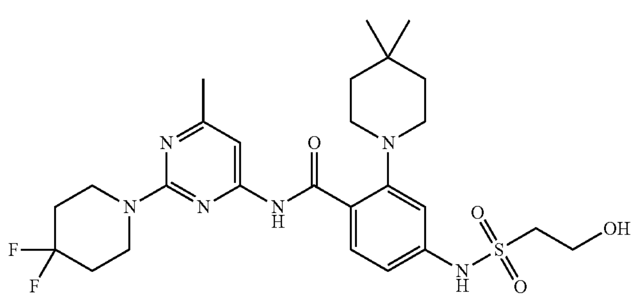 [SMILES: Cc1cc(NC(=O)c2ccc(NS(=O)(=O)CCO)cc2N2CCC(C)(C)CC2)nc(N2CCC(F)(F)CC2)n1] | N-(2-(4,4-Difluoropiperidin-1-yl)-6-methylpyrimidin-4-yl)-2-(4,4-dimethylpiperidin-1-yl)-4-((2-hydroxyethyl)sulfonamido)benzamide | 567.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-42 | 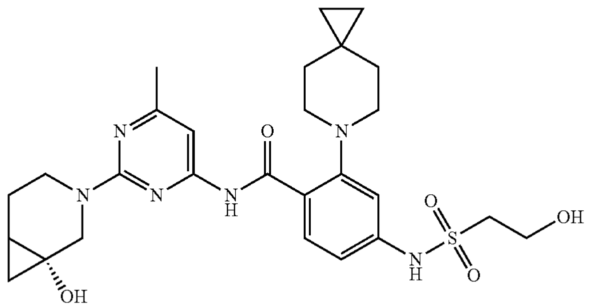 [SMILES: Cc1cc(NC(=O)c2ccc(NS(=O)(=O)CCO)cc2N2CCC3(CC2)CC3)nc(N2CCC3C[C@]3(O)C2)n1] | N-(2-((1R)-1-Hydroxy-3-azabicyclo[4.1.0]heptan-3-yl)-6-methylpyrimidin-4-yl)-4-((2-hydroxyethyl)sulfonamido)-2-(6-azaspiro[2.5]octan-6-yl)benzamide | 557.2 |
| 11-43 | 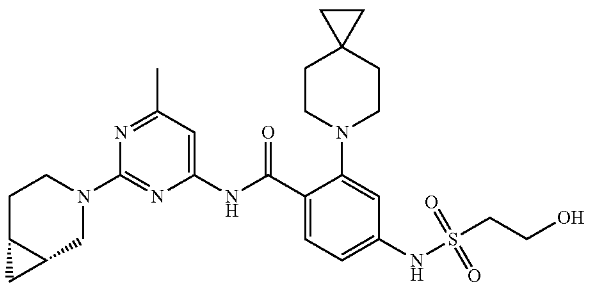 [SMILES: Cc1cc(NC(=O)c2ccc(NS(=O)(=O)CCO)cc2N2CCC3(CC2)CC3)nc(N2CC[C@H]3C[C@H]3C2)n1] | N-(2-((1R,6R)-3-Azabicyclo[4.1.0]heptan-3-yl)-6-methylpyrimidin-4-yl)-4-((2-hydroxyethyl)sulfonamido)-2-(6-azaspiro[2.5]octan-6-yl)benzamide | 541.2 |
| 11-44 | 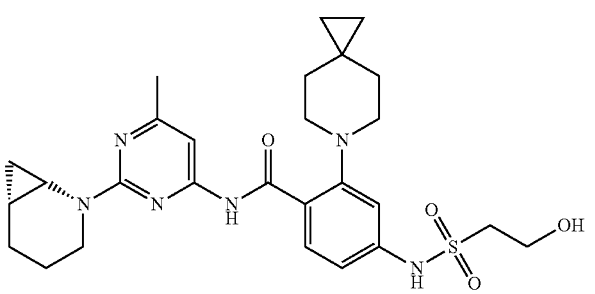 | N-(2-((1S,6R)-2-Azabicyclo[4.1.0]heptan-2-yl)-6-methylpyrimidin-4-yl)-4-((2-hydroxyethyl)sulfonamido)-2-(6-azaspiro[2.5]octan-6-yl)benzamide | 541.2 |
| 11-45 | 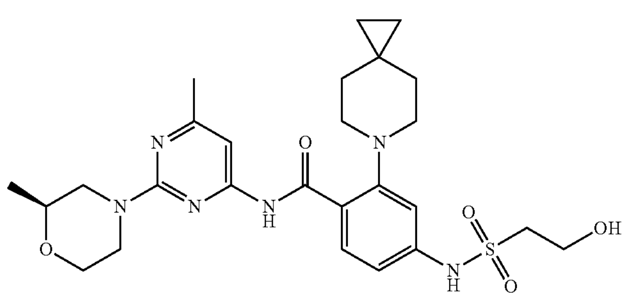 [SMILES: Cc1cc(NC(=O)c2ccc(NS(=O)(=O)CCO)cc2N2CCC3(CC2)CC3)nc(N2CCO[C@@H](C)C2)n1] | (S)-4-((2-Hydroxyethyl)sulfonamido)-N-(6-methyl-2-(2-methylmorpholino)pyrimidin-4-yl)-2-(6-azaspiro[2.5]octan-6-yl)benzamide | 545.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-46 | 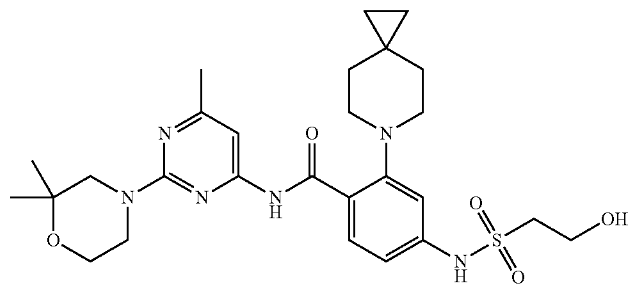 | N-(2-(2,2-Dimethylmorpholino)-6-methylpyrimidin-4-yl)-4-((2-hydroxyethyl)sulfonamido)-2-(6-azaspiro[2.5]octan-6-yl)benzamide | 559.3 |
| 11-47 | 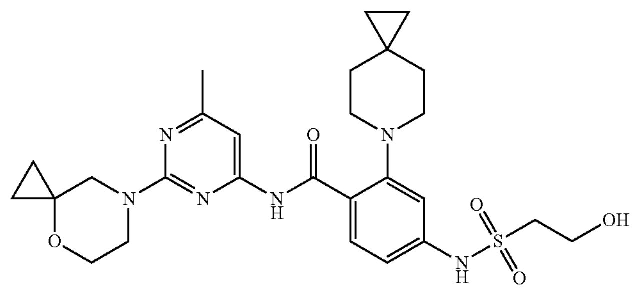 [SMILES: Cc1cc(NC(=O)c2ccc(NS(=O)(=O)CCO)cc2N2CCC3(CC2)CC3)nc(N2CCOC3(CC3)C2)n1] | 4-((2-Hydroxyethyl)sulfonamido)-N-(6-methyl-2-(4-oxa-7-azaspiro[2.5]octan-7-yl)pyrimidin-4-yl)-2-(6-azaspiro[2.5]octan-6-yl)benzamide | 557.3 |
| 11-48 | 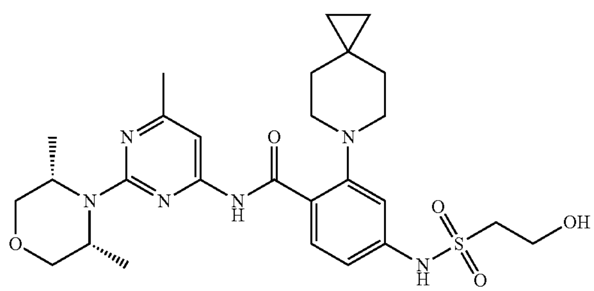 [SMILES: Cc1cc(NC(=O)c2ccc(NS(=O)(=O)CCO)cc2N2CCC3(CC2)CC3)nc(N2[C@H](C)COC[C@@H]2C)n1] | N-(2-((3S,5R)-3,5-Dimethylmorpholino)-6-methylpyrimidin-4-yl)-4-((2-hydroxyethyl)sulfonamido)-2-(6-azaspiro[2.5]octan-6-yl)benzamide | 559.3 |
| 11-49 | 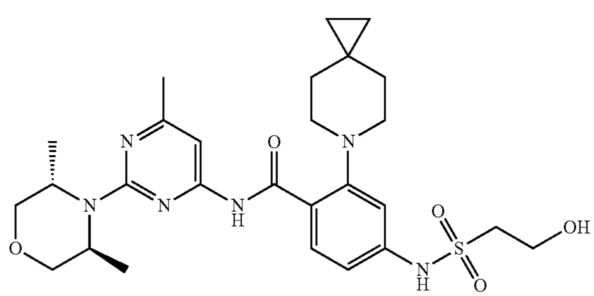 [SMILES: Cc1cc(NC(=O)c2ccc(NS(=O)(=O)CCO)cc2N2CCC3(CC2)CC3)nc(N2[C@@H](C)COC[C@@H]2C)n1] | N-(2-((3S,5S)-3,5-Dimethylmorpholino)-6-methylpyrimidin-4-yl)-4-((2-hydroxyethyl)sulfonamido)-2-(6-azaspiro[2.5]octan-6-yl)benzamide | 559.3 |
| 11-50 | 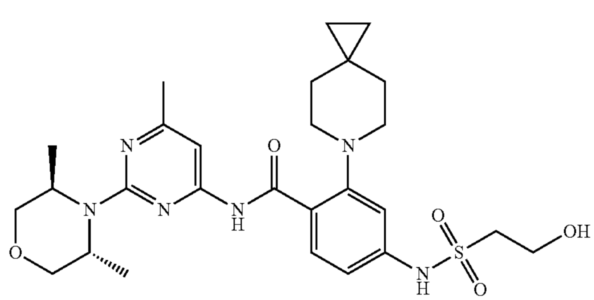 [SMILES: Cc1cc(NC(=O)c2ccc(NS(=O)(=O)CCO)cc2N2CCC3(CC2)CC3)nc(N2[C@H](C)COC[C@H]2C)n1] | N-(2-((3R,5R)-3,5-Dimethylmorpholino)-6-methylpyrimidin-4-yl)-4-((2-hydroxyethyl)sulfonamido)-2-(6-azaspiro[2.5]octan-6-yl)benzamide | 559.3 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-51 | 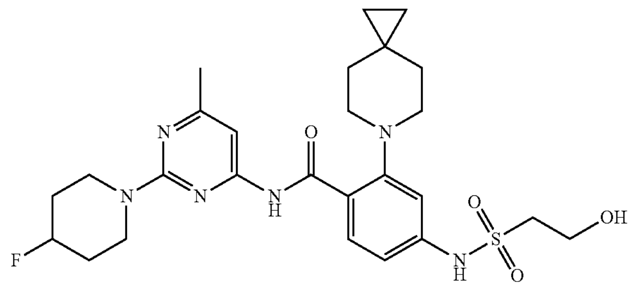 [SMILES: Cc1cc(NC(=O)c2ccc(NS(=O)(=O)CCO)cc2N2CCC3(CC2)CC3)nc(N2CCC(F)CC2)n1] | N-(2-(4-Fluoropiperidin-1-yl)-6-methylpyrimidin-4-yl)-4-((2-hydroxyethyl)sulfonamido)-2-(6-azaspiro[2.5]octan-6-yl)benzamide | 547.2 |
| 11-52 | 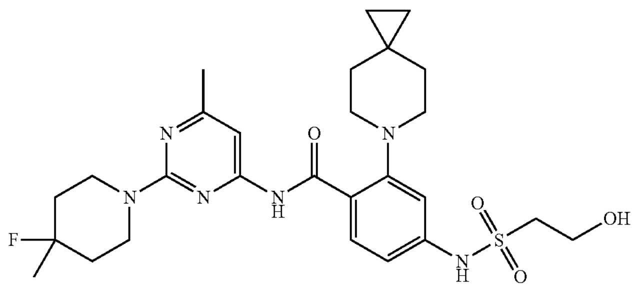 [SMILES: Cc1cc(NC(=O)c2ccc(NS(=O)(=O)CCO)cc2N2CCC3(CC2)CC3)nc(N2CCC(C)(F)CC2)n1] | N-(2-(4-Fluoro-4-methylpiperidin-1-yl)-6-methylpyrimidin-4-yl)-4-((2-hydroxyethyl)sulfonamido)-2-(6-azaspiro[2.5]octan-6-yl)benzamide | 561.3 |
| 11-53 | 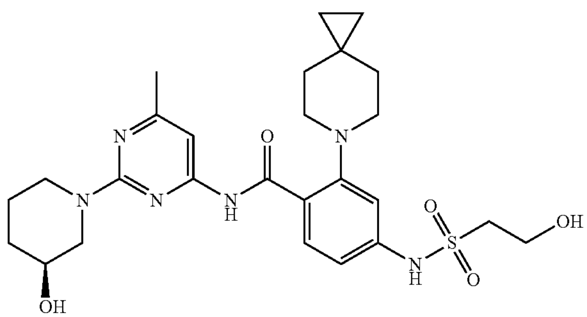 [SMILES: Cc1cc(NC(=O)c2ccc(NS(=O)(=O)CCO)cc2N2CCC3(CC2)CC3)nc(N2CCC[C@H](O)C2)n1] | (S)-4-((2-Hydroxyethyl)sulfonamido)-N-(2-(3-hydroxypiperidin-1-yl)-6-methylpyrimidin-4-yl)-2-(6-azaspiro[2.5]octan-6-yl)benzamide | 545.2 |
| 11-54 | 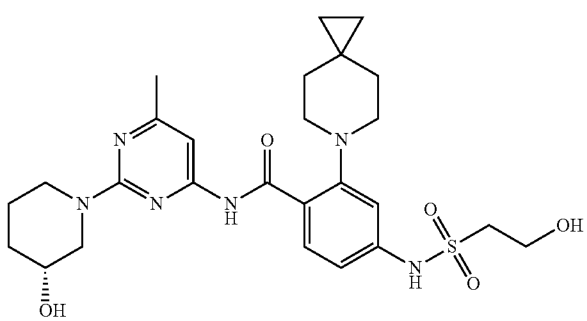 | (R)-4-((2-Hydroxyethyl)sulfonamido)-N-(2-(3-hydroxypiperidin-1-yl)-6-methylpyrimidin-4-yl)-2-(6-azaspiro[2.5]octan-6-yl)benzamide | 545.2 |
| 11-55 | 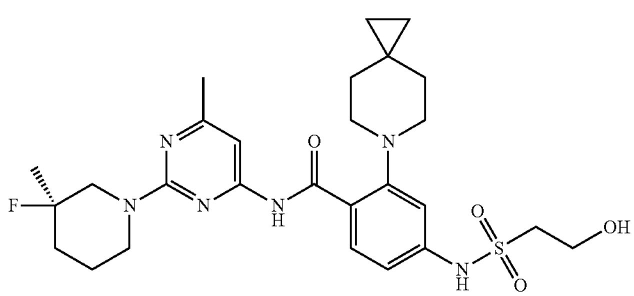 [SMILES: Cc1cc(NC(=O)c2ccc(NS(=O)(=O)CCO)cc2N2CCC3(CC2)CC3)nc(N2CCC[C@@](C)(F)C2)n1] | (R)-N-(2-(3-Fluoro-3-methylpiperidin-1-yl)-6-methylpyrimidin-4-yl)-4-((2-hydroxyethyl)sulfonamido)-2-(6-azaspiro[2.5]octan-6-yl)benzamide | 561.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-56 | 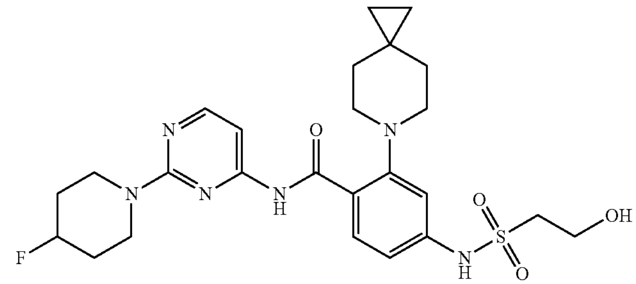 [SMILES: O=C(Nc1ccnc(N2CCC(F)CC2)n1)c1ccc(NS(=O)(=O)CCO)cc1N1CCC2(CC1)CC2] | N-(2-(4-Fluoropiperidin-1-yl)pyrimidin-4-yl)-4-((2-hydroxyethyl)sulfonamido)-2-(6-azaspiro[2.5]octan-6-yl)benzamide | 533.2 |
| 11-57 | 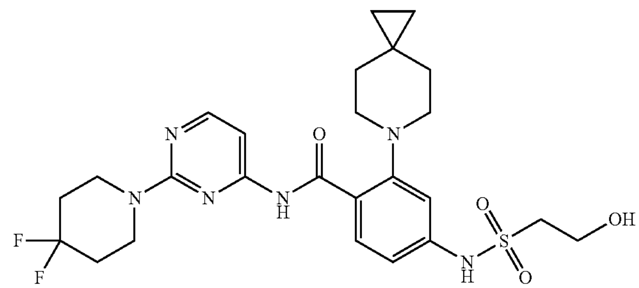 [SMILES: O=C(Nc1ccnc(N2CCC(F)(F)CC2)n1)c1ccc(NS(=O)(=O)CCO)cc1N1CCC2(CC1)CC2] | N-(2-(4,4-Difluoropiperidin-1-yl)pyrimidin-4-yl)-4-((2-hydroxyethyl)sulfonamido)-2-(6-azaspiro[2.5]octan-6-yl)benzamide | 551.2 |
| 11-58 | 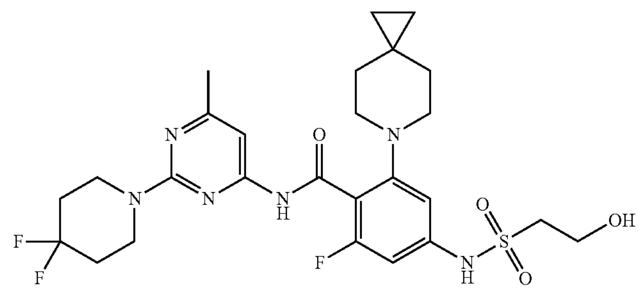 [SMILES: Cc1cc(NC(=O)c2c(F)cc(NS(=O)(=O)CCO)cc2N2CCC3(CC2)CC3)nc(N2CCC(F)(F)CC2)n1] | N-(2-(4,4-Difluoropiperidin-1-yl)-6-methylpyrimidin-4-yl)-2-fluoro-4-((2-hydroxyethyl)sulfonamido)-6-(6-azaspiro[2.5]octan-6-yl)benzamide | 583.2 |
| 11-59 | 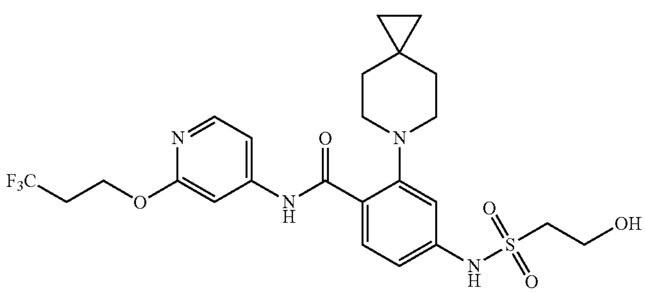 [SMILES: O=C(Nc1ccnc(OCCC(F)(F)F)c1)c1ccc(NS(=O)(=O)CCO)cc1N1CCC2(CC1)CC2] | 4-((2-Hydroxyethyl)sulfonamido)-2-(6-azaspiro[2.5]octan-6-yl)-N-(2-(3,3,3-trifluoropropoxy)pyridin-4-yl)benzamide | 543.2 |
| 11-60 | 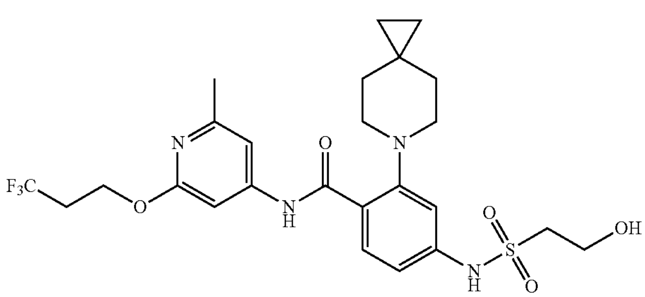 [SMILES: Cc1cc(NC(=O)c2ccc(NS(=O)(=O)CCO)cc2N2CCC3(CC2)CC3)cc(OCCC(F)(F)F)n1] | 4-((2-Hydroxyethyl)sulfonamido)-N-(2-methyl-6-(3,3,3-trifluoropropoxy)pyridin-4-yl)-2-(6-azaspiro[2.5]octan-6-yl)benzamide | 557.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-61 | 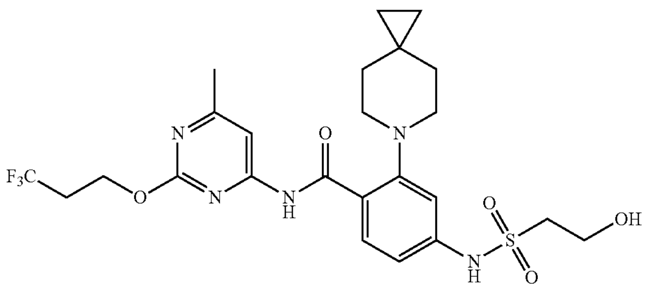 [SMILES: Cc1cc(NC(=O)c2ccc(NS(=O)(=O)CCO)cc2N2CCC3(CC2)CC3)nc(OCCC(F)(F)F)n1] | 4-((2-Hydroxyethyl)sulfonamido)-N-(6-methyl-2-(3,3,3-trifluoropropoxy)pyrimidin-4-yl)-2-(6-azaspiro[2.5]octan-6-yl)benzamide | 558.2 |
| 11-62 | 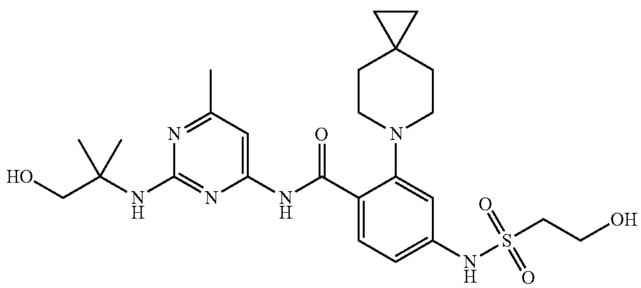 [SMILES: Cc1cc(NC(=O)c2ccc(NS(=O)(=O)CCO)cc2N2CCC3(CC2)CC3)nc(NC(C)(C)CO)n1] | N-(2-((1-Hydroxy-2-methylpropan-2-yl)amino)-6-methylpyrimidin-4-yl)-4-((2-hydroxyethyl)sulfonamido)-2-(6-azaspiro[2.5]octan-6-yl)benzamide | 533.2 |
| 11-63 | 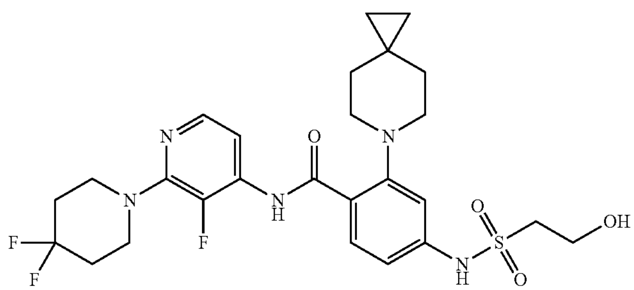 [SMILES: O=C(Nc1ccnc(N2CCC(F)(F)CC2)c1F)c1ccc(NS(=O)(=O)CCO)cc1N1CCC2(CC1)CC2] | N-(2-(4,4-Difluoropiperidin-1-yl)-3-fluoropyridin-4-yl)-4-((2-hydroxyethyl)sulfonamido)-2-(6-azaspiro[2.5]octan-6-yl)benzamide | 568.2 |
| 11-64 | 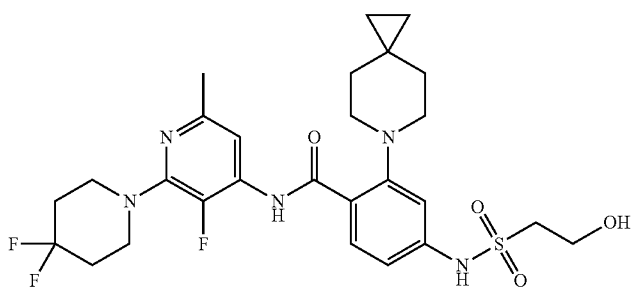 | N-(2-(4,4-Difluoropiperidin-1-yl)-3-fluoro-6-methylpyridin-4-yl)-4-((2-hydroxyethyl)sulfonamido)-2-(6-azaspiro[2.5]octan-6-yl)benzamide | 582.2 |
| 11-65 | 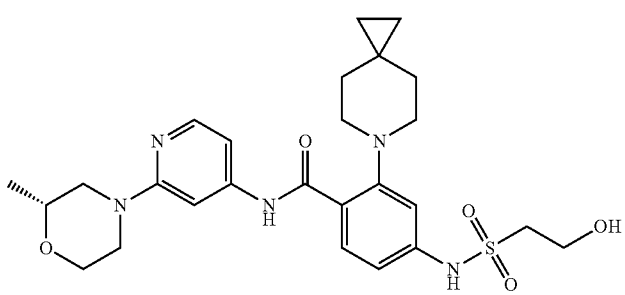 [SMILES: C[C@@H]1CN(c2cc(NC(=O)c3ccc(NS(=O)(=O)CCO)cc3N3CCC4(CC3)CC4)ccn2)CCO1] | (R)-4-((2-Hydroxyethyl)sulfonamido)-N-(2-(2-methylmorpholino)pyridin-4-yl)-2-(6-azaspiro[2.5]octan-6-yl)benzamide | 530.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-66 | 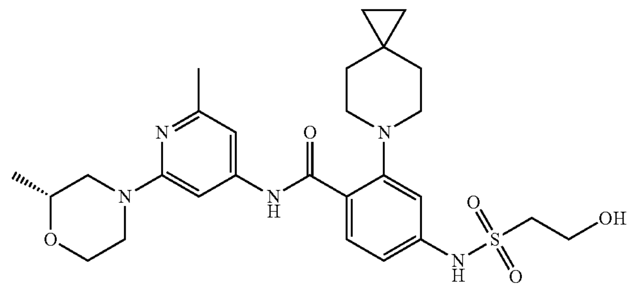 | (R)-4-((2-Hydroxyethyl)sulfonamido)-N-(2-methyl-6-(2-methylmorpholino)pyridin-4-yl)-2-(6-azaspiro[2.5]octan-6-yl)benzamide | 544.3 |
| 11-67 | 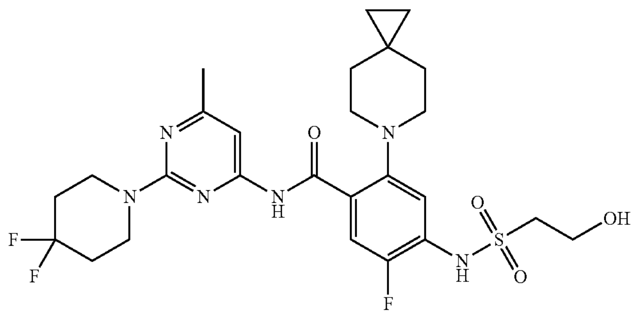 [SMILES: Cc1cc(NC(=O)c2cc(F)c(NS(=O)(=O)CCO)cc2N2CCC3(CC2)CC3)nc(N2CCC(F)(F)CC2)n1] | N-(2-(4,4-Difluoropiperidin-1-yl)-6-methylpyrimidin-4-yl)-5-fluoro-4-((2-hydroxyethyl)sulfonamido)-2-(6-azaspiro[2.5]octan-6-yl)benzamide | 583.4 |
| 11-68 | 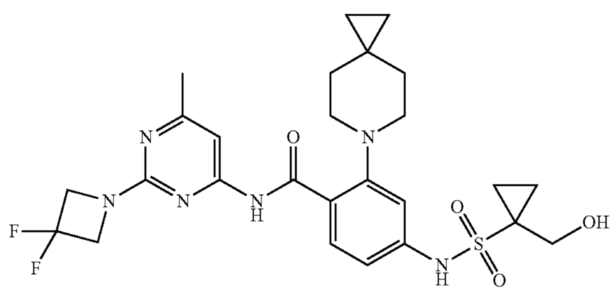 [SMILES: Cc1cc(NC(=O)c2ccc(NS(=O)(=O)C3(CO)CC3)cc2N2CCC3(CC2)CC3)nc(N2CC(F)(F)C2)n1] | N-(2-(3,3-Difluoroazetidin-1-yl)-6-methylpyrimidin-4-yl)-4-((1-(hydroxymethyl)cyclopropane)-1-sulfonamido)-2-(6-azaspiro[2.5]octan-6-yl)benzamide | 563.2 |
| 11-69 | 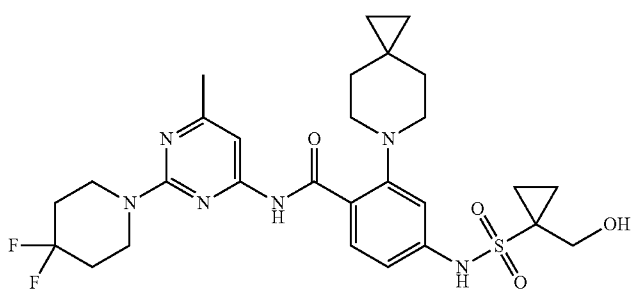 [SMILES: Cc1cc(NC(=O)c2ccc(NS(=O)(=O)C3(CO)CC3)cc2N2CCC3(CC2)CC3)nc(N2CCC(F)(F)CC2)n1] | N-(2-(4,4-Difluoropiperidin-1-yl)-6-methylpyrimidin-4-yl)-4-((1-(hydroxymethyl)cyclopropane)-1-sulfonamido)-2-(6-azaspiro[2.5]octan-6-yl)benzamide | 591.2 |
| 11-70 | 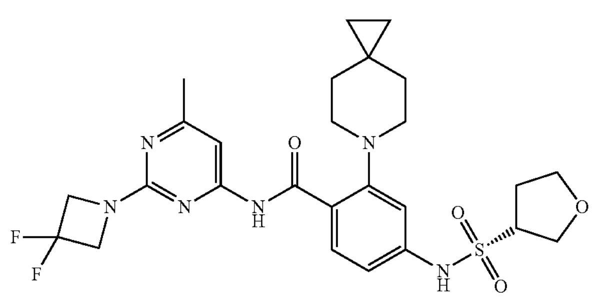 | (S)-N-(2-(3,3-Difluoroazetidin-1-yl)-6-methylpyrimidin-4-yl)-2-(6-azaspiro[2.5]octan-6-yl)-4-((tetrahydrofuran)-3-sulfonamido)benzamide | 563.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-71 | 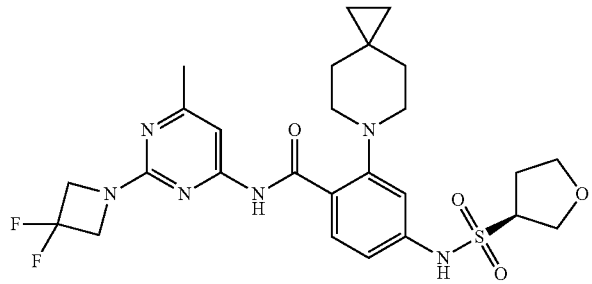 [SMILES: Cc1cc(NC(=O)c2ccc(NS(=O)(=O)[C@H]3CCOC3)cc2N2CCC3(CC2)CC3)nc(N2CC(F)(F)C2)n1] | (R)-N-(2-(3,3-Difluoroazetidin-1-yl)-6-methylpyrimidin-4-yl)-2-(6-azaspiro[2.5]octan-6-yl)-4-((tetrahydrofuran)-3-sulfonamido)benzamide | 563.2 |
| 11-72 | 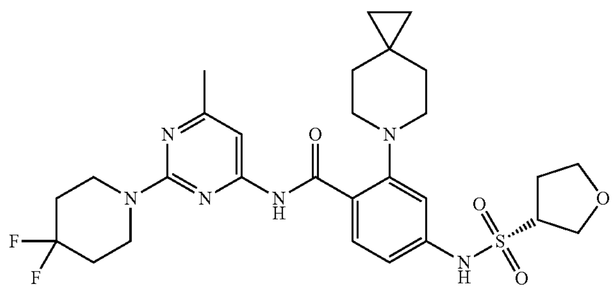 | (S)-N-(2-(4,4-Difluoropiperidin-1-yl)-6-methylpyrimidin-4-yl)-2-(6-azaspiro[2.5]octan-6-yl)-4-((tetrahydrofuran)-3-sulfonamido)benzamide | 591.3 |
| 11-73 | 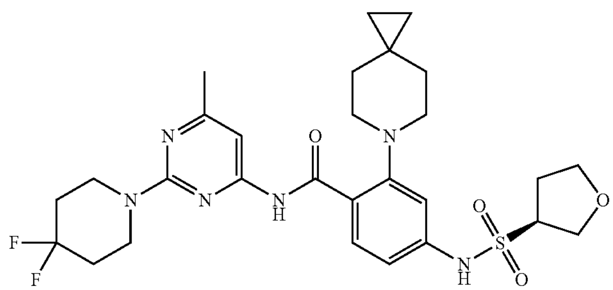 [SMILES: Cc1cc(NC(=O)c2ccc(NS(=O)(=O)[C@H]3CCOC3)cc2N2CCC3(CC2)CC3)nc(N2CCC(F)(F)CC2)n1] | (R)-N-(2-(4,4-Difluoropiperidin-1-yl)-6-methylpyrimidin-4-yl)-2-(6-azaspiro[2.5]octan-6-yl)-4-((tetrahydrofuran)-3-sulfonamido)benzamide | 591.3 |
| 11-74 | 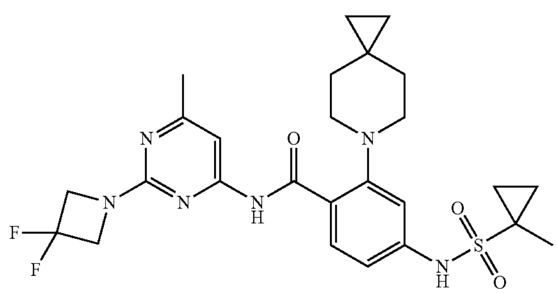 [SMILES: Cc1cc(NC(=O)c2ccc(NS(=O)(=O)C3(C)CC3)cc2N2CCC3(CC2)CC3)nc(N2CC(F)(F)C2)n1] | N-(2-(3,3-Difluoroazetidin-1-yl)-6-methylpyrimidin-4-yl)-4-((1-methylcyclopropane)-1-sulfonamido)-2-(6-azaspiro[2.5]octan-6-yl)benzamide | 547.2 |
| 11-75 | 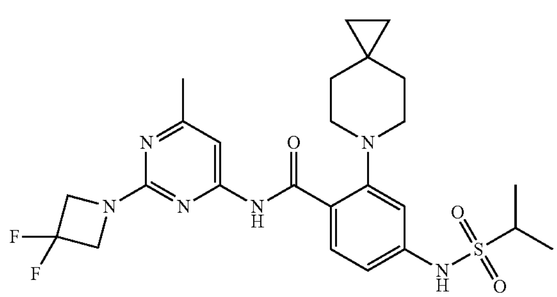 [SMILES: Cc1cc(NC(=O)c2ccc(NS(=O)(=O)C(C)C)cc2N2CCC3(CC2)CC3)nc(N2CC(F)(F)C2)n1] | N-(2-(3,3-Difluoroazetidin-1-yl)-6-methylpyrimidin-4-yl)-4-((1-methylethyl)sulfonamido)-2-(6-azaspiro[2.5]octan-6-yl)benzamide | 535.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-76 | 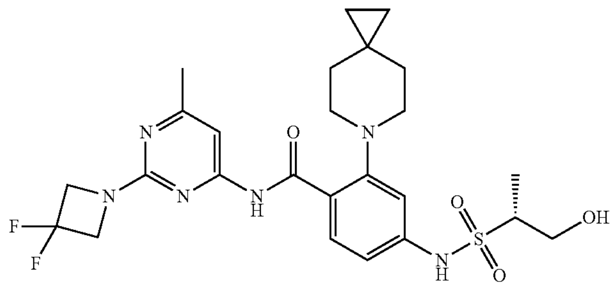 [SMILES: Cc1cc(NC(=O)c2ccc(NS(=O)(=O)[C@H](C)CO)cc2N2CCC3(CC2)CC3)nc(N2CC(F)(F)C2)n1] | (R)-N-(2-(3,3-Difluoroazetidin-1-yl)-6-methylpyrimidin-4-yl)-4-((2-hydroxy-1-methylethyl)sulfonamido)-2-(6-azaspiro[2.5]octan-6-yl)benzamide | 551.2 |
| 11-77 | 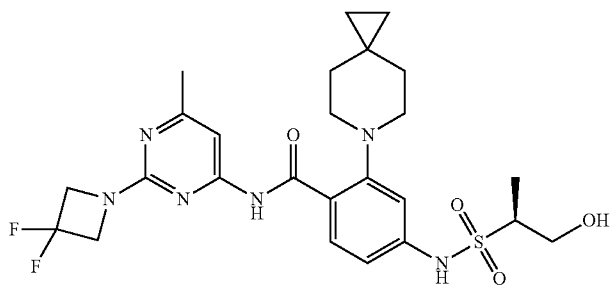 [SMILES: Cc1cc(NC(=O)c2ccc(NS(=O)(=O)[C@@H](C)CO)cc2N2CCC3(CC2)CC3)nc(N2CC(F)(F)C2)n1] | (S)-N-(2-(3,3-Difluoroazetidin-1-yl)-6-methylpyrimidin-4-yl)-4-((2-hydroxy-1-methylethyl)sulfonamido)-2-(6-azaspiro[2.5]octan-6-yl)benzamide | 551.2 |
| 11-78 | 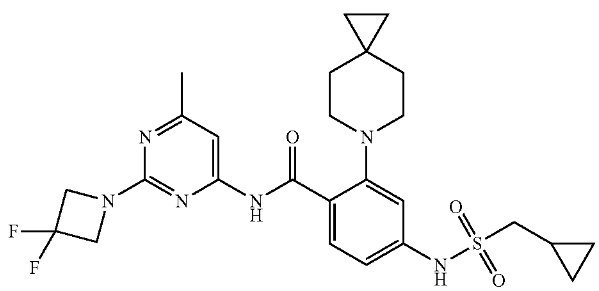 [SMILES: Cc1cc(NC(=O)c2ccc(NS(=O)(=O)CC3CC3)cc2N2CCC3(CC2)CC3)nc(N2CC(F)(F)C2)n1] | 4-((Cyclopropylmethyl)sulfonamido)-N-(2-(3,3-difluoroazetidin-1-yl)-6-methylpyrimidin-4-yl)-2-(6-azaspiro[2.5]octan-6-yl)benzamide | 547.2 |
| 11-79 | 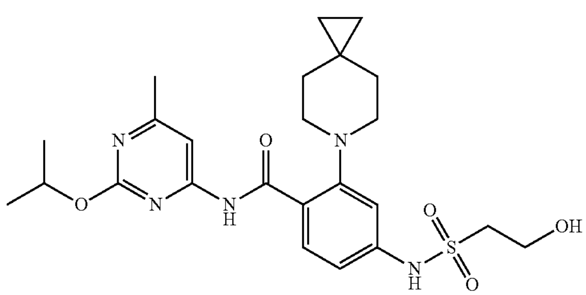 [SMILES: Cc1cc(NC(=O)c2ccc(NS(=O)(=O)CCO)cc2N2CCC3(CC2)CC3)nc(OC(C)C)n1] | 4-((2-Hydroxyethyl)sulfonarnido)-N-(2-isopropoxy-6-methylpyrimidin-4-yl)-2-(6-azaspiro[2.5]octan-6-yl)benzamide | 504.2 |
| 11-80 | 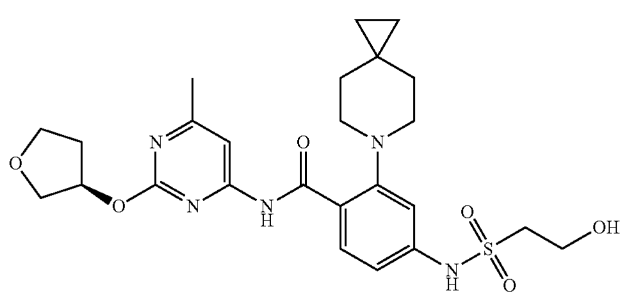 [SMILES: Cc1cc(NC(=O)c2ccc(NS(=O)(=O)CCO)cc2N2CCC3(CC2)CC3)nc(O[C@@H]2CCOC2)n1] | (R)-4-((2-Hydroxyethyl)sulfonamido)-N-(6-methyl-2-((tetrahydrofuran-3-yl)oxy)pyrimidin-4-yl)-2-(6-azaspiro[2.5]octan-6-yl)benzamide | 532.2 |

TABLE 10-continued

Examples 11-1 to 11-83 were prepared following similar procedures for Example 10:

| Ex. # | Chemical Structure | Name | LRMS: (ESI + ve ion) m/z |
|---|---|---|---|
| 11-81 | 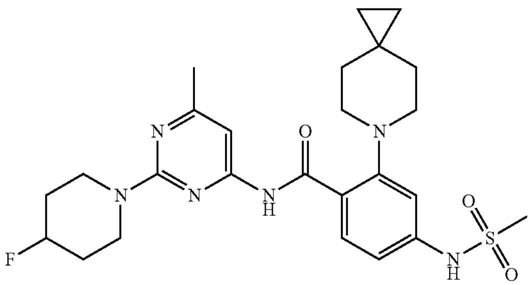 [SMILES: Cc1cc(NC(=O)c2ccc(NS(C)(=O)=O)cc2N2CCC3(CC2)CC3)nc(N2CCC(F)CC2)n1] | N-(2-(4-Fluoropiperidin-1-yl)-6-methylpyrimidin-4-yl)-4-(methylsulfonamido)-2-(6-azaspiro[2.5]octan-6-yl)benzamide | 517.2 |
| 11-82 | 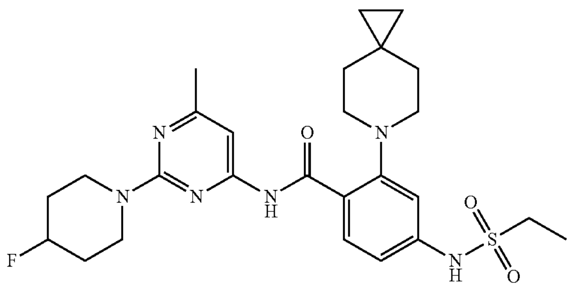 [SMILES: CCS(=O)(=O)Nc1ccc(C(=O)Nc2cc(C)nc(N3CCC(F)CC3)n2)c(N2CCC3(CC2)CC3)c1] | 4-(Ethylsulfonamido)-N-(2-(4-fluoropiperidin-1-yl)-6-methylpyrimidin-4-yl)-2-(6-azaspiro[2.5]octan-6-yl)benzamide | 531.2 |
| 11-83 | 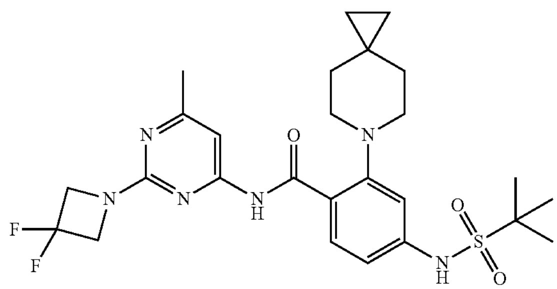 [SMILES: Cc1cc(NC(=O)c2ccc(NS(=O)(=O)C(C)(C)C)cc2N2CCC3(CC2)CC3)nc(N2CC(F)(F)C2)n1] | N-(2-(3,3-Difluoroazetidin-1-yl)-6-methylpyrimidin-4-yl)-4-((1,1-dimethylethyl)sulfonamido)-2-(6-azaspiro[2.5]octan-6-yl)benzamide | 549.2 |

Example 12: N-(2-(4,4-difluoropiperidin-1-yl)-6-methylpyrimidin-4-yl)-4-((2-hydroxyethyl)sulfonyl)-2-(6-azaspiro[2.5]octan-6-yl)benzamide

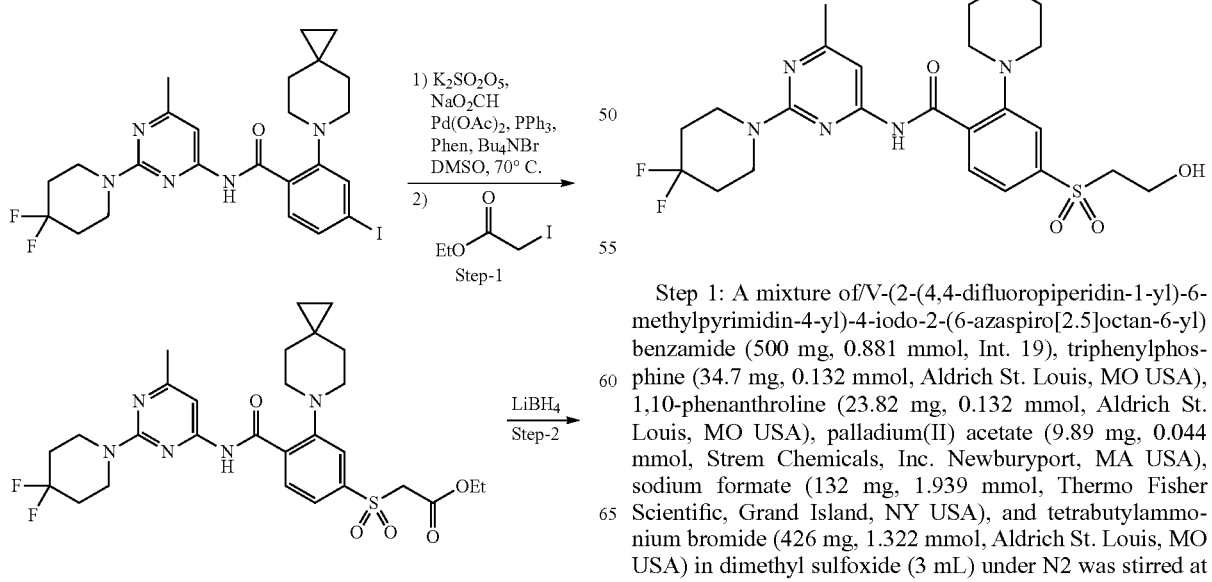

Step 1: A mixture of N-(2-(4,4-difluoropiperidin-1-yl)-6-methylpyrimidin-4-yl)-4-iodo-2-(6-azaspiro[2.5]octan-6-yl)benzamide (500 mg, 0.881 mmol, Int. 19), triphenylphosphine (34.7 mg, 0.132 mmol, Aldrich St. Louis, MO USA), 1,10-phenanthroline (23.82 mg, 0.132 mmol, Aldrich St. Louis, MO USA), palladium(II) acetate (9.89 mg, 0.044 mmol, Strem Chemicals, Inc. Newburyport, MA USA), sodium formate (132 mg, 1.939 mmol, Thermo Fisher Scientific, Grand Island, NY USA), and tetrabutylammonium bromide (426 mg, 1.322 mmol, Aldrich St. Louis, MO USA) in dimethyl sulfoxide (3 mL) under N2 was stirred at 70° C. for 45 min. Then, the mixture was cooled to room temperature and ethyl iodoacetate (0.157 mL, 1.322 mmol, Aldrich St. Louis, MO USA) was added. The mixture was then stirred at room temperature for 10 min. Then, the mixture was diluted with water (20 mL) and was then extracted with EtOAc (2×40 mL). The combined organic extracts were then dried over MgSO₄ and concentrated. Chromatographic purification of the residue (silica gel, 0%-100% EtOAc/heptane) provided ethyl 2-((4-((2-(4,4-difluoropiperidin-1-yl)-6-methylpyrimidin-4-yl)carbamoyl)-3-(6-azaspiro[2.5]octan-6-yl)phenyl)sulfonyl)acetate (330 mg, 0.558 mmol) as a light yellow solid. $^1$H NMR (DMSO-d$_6$) δ 13.14 (brs, 1H), 8.27 (br d, J=8.1 Hz, 1H), 7.97 (s, 1H), 7.84 (br d, J=1.1 Hz, 1H), 7.40 (s, 1H), 4.80 (s, 2H), 4.05 (q, J=7.2 Hz, 2H), 3.92 (brs, 4H), 3.03-3.13 (m, 4H), 2.34 (s, 3H), 1.90-2.07 (m, 4H), 1.71 (brs, 4H), 1.07 (t, J=7.0 Hz, 3H), 0.39 (s, 4H). m/z (ESI): 592.3 (M+H)+.

Step 2: To a solution of ethyl 2-((4-((2-(4,4-difluoropiperidin-1-yl)-6-methylpyrimidin-4-yl)carbamoyl)-3-(6-azaspiro[2.5]octan-6-yl)phenyl)sulfonyl)acetate (320 mg, 0.541 mmol) in 2-methyltetrahydrofuran (3.5 mL) under N$_2$ at 0° C. was added lithium borohydride solution (2.0M in tetrahydrofuran 0.541 mL, 1.082 mmol, Aldrich St. Louis, MO USA) dropwise. After addition, the mixture was stirred at room temperature overnight. Then, the mixture was quenched with saturated NH₄Cl (18 mL) and was stirred at room temperature for 15 min. The mixture was then extracted with EtOAc (2×30 mL). The combined organic extracts were then dried over MgSO₄ and concentrated. Chromatographic purification of the residue (silica gel, 0%-100% EtOAc/heptane) provided N-(2-(4,4-difluoropiperidin-1-yl)-6-methylpyrimidin-4-yl)-4-((2-hydroxyethyl)sulfonyl)-2-(6-azaspiro[2.5]octan-6-yl)benzamide (60 mg, 0.109 mmol, 20% yield) provided N-(2-(4,4-difluoropiperidin-1-yl)-6-methylpyrimidin-4-yl)-4-((2-hydroxyethyl)sulfonyl)-2-(6-azaspiro[2.5]octan-6-yl)benzamide (60 mg, 0.109 mmol) as a white solid. $^1$H NMR (DMSO-d$_6$) δ ppm 13.17 (brs, 1H), 8.25 (br d, J=8.3 Hz, 1H), 7.93 (brs, 1H), 7.82 (brd, J=8.3 Hz, 1H), 7.40 (brs, 1H), 4.91 (br t, J=5.0 Hz, 1H), 3.92 (brs, 4H), 3.68-3.77 (m, 2H), 3.52-3.60 (m, 2H), 3.09 (brs, 4H), 2.34 (s, 3H), 1.87-2.08 (m, 4H), 1.70 (br d, J=1.0 Hz, 4H), 0.39 (s, 4H). $^{19}$F NMR (DMSO-d$_6$) δ ppm −94.76 (s, 2F). m/z (ESI): 550.1 (M+H)+.

Examples 13-1 and 13-2: (S)—N-(2-(4,4-Difluoropiperidin-1-yl)-6-methylpyrimidin-4-yl)-4-((1-hydroxypropan-2-yl)sulfonyl)-2-(6-azaspiro[2.5]octan-6-yl)benzamide and (R)—N-(2-(4,4-difluoropiperidin-1-yl)-6-methylpyrimidin-4-yl)-4-((1-hydroxypropan-2-yl)sulfonyl)-2-(6-azaspiro[2.5]octan-6-yl)benzamide

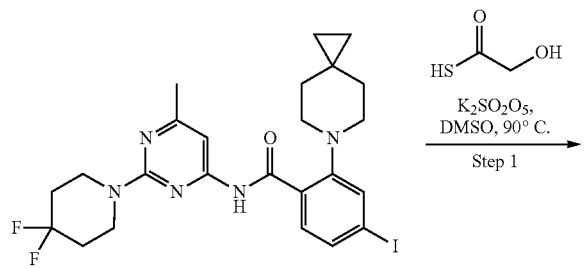

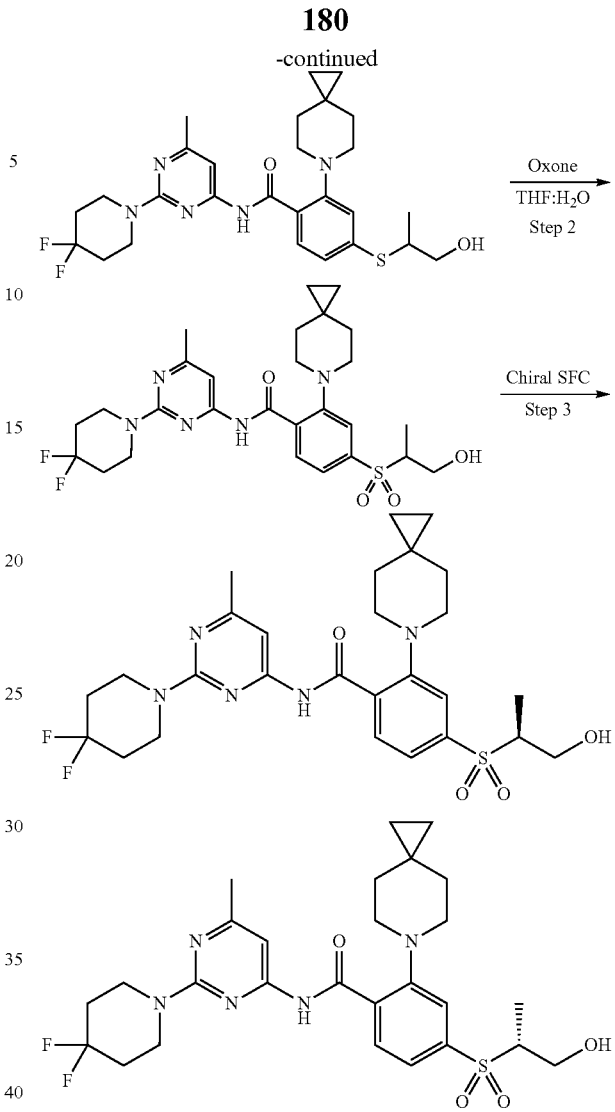

Step 1: N-(2-(4,4-difluoropiperidin-1-yl)-6-methylpyrimidin-4-yl)-4-iodo-2-(6-azaspiro[2.5]octan-6-yl)benzamide (1.08 g, 1.90 mmol, Int. 19), 2-mercaptopropan-1-ol (0.48 g, 5.21 mmol, Enamine), and potassium carbonate (0.237 mL, 3.91 mmol) in 4 mL DMSO were heated at 90° C. in a sealed vial for 4 h. The mixture was cooled to RT, added 50 mL ethyl acetate and 10 mL brine. The organic layer was separated, washed with brine, dried, and evaporated. The resulting product was adsorbed onto a plug of silica gel and purified by silica gel chromatography (0-30% of EtOAc in heptane) to give N-(2-(4,4-difluoropiperidin-1-yl)-6-methylpyrimidin-4-yl)-4-((1-hydroxypropan-2-yl)thio)-2-(6-azaspiro[2.5]octan-6-yl)benzamide as a yellow solid. $^1$H NMR (400 MHz, CHLOROFORM-d) δ ppm 0.39-0.44 (m, 4H) 1.37-1.43 (m, 3H) 1.55-1.60 (m, 4H) 1.96-2.04 (m, 4H) 2.35-2.41 (m, 3H) 3.01-3.11 (m, 4H) 3.46-3.78 (m, 3H) 3.96-4.05 (m, 4H) 7.28-7.36 (m, 2H) 7.48-7.53 (m, 1H) 8.12-8.32 (m, 1H) 13.01-13.37 (m, 1H). m/z (ESI): 531.4 (M+H)$^+$.

Step 2: To N-(2-(4,4-difluoropiperidin-1-yl)-6-methylpyrimidin-4-yl)-4-((1-hydroxypropan-2-yl)thio)-2-(6-azaspiro[2.5]octan-6-yl)benzamide (0.62 g, 1.17 mmol) in 15 mL THF was added oxone(r) monopersulfate compound (0.72 g, 1.17 mmol) in 5 mL water. After stirring for 1.5 h, LCMS showed a mixture of sulfone and sulfoxide formed. Additional 0.4 g of oxone in 3 mL water was added. After stirring for additional 2 h, EtOAc (50 mL) and brine (20 mL) were added to the reaction mixture and the organic layer was taken, washed with brine, dried, and evaporated. The crude product was purified via preparative SFC using an (S,S) Whelk-01 (250×21 mm, 5 mm) column with a mobile phase of 60% Liquid $CO_2$ and 40% MeOH, flowrate of 80 mL/min. to give N-2-(4,4-difluoropiperidin-1-yl)-6-methylpyrimidin-4-yl)-4-((1-hydroxypropan-2-yl)sulfonyl)-2-(6-azaspiro[2.5]octan-6-yl)benzamide (337 mg, 0.58 mmol, 50% yield). $^1$H NMR (400 MHz, CHLOROFORM-d) δ ppm 0.30-0.57 (m, 4H) 1.27-1.37 (m, 3H) 1.59-1.72 (m, 4H) 1.94-2.10 (m, 4H) 2.40-2.54 (m, 3H) 2.55-2.97 (m, 1H) 3.05-3.23 (m, 4H) 3.28-3.41 (m, 1H) 3.84-4.06 (m, 6H) 7.63-7.86 (m, 2H) 8.13-8.37 (m, 1H) 11.08-11.59 (m, 1H). m/z (ESI): 598.3 $(M+H)^+$. This racemic mixture was separated by preparative SFC using an OD (250×21 mm, 5 mm) with a mobile phase of 85% Liquid $CO_2$ and 15% iPrOH and a flowrate of 90 mL/min to generate:

Example 13-1: (S)—N-(2-(4,4-difluoropiperidin-1-yl)-6-methylpyrimidin-4-yl)-4-((1-hydroxypropan-2-yl)sulfonyl)-2-(6-azaspiro[2.5]octan-6-yl)benzamide. First eluting peak (85 mg, ee>99%). $^1$H NMR (400 MHz, CHLOROFORM-d) δ ppm 12.74-13.01 (m, 1H), 8.36-8.54 (m, 1H), 7.69-8.03 (m, 2H), 7.41-7.58 (m, 1H), 3.83-4.06 (m, 6H), 3.25-3.43 (m, 1H), 3.03-3.17 (m, 4H), 2.50-2.81 (m, 1H), 2.31-2.42 (m, 3H), 1.93-2.10 (m, 4H), 1.61-1.90 (m, 4H), 1.28-1.36 (m, 3H), 0.35-0.50 (m, 4H). m/z (ESI): 563.2 $(M+H)^+$.

Example 13-2: (R)—N-(2-(4,4-difluoropiperidin-1-yl)-6-methylpyrimidin-4-yl)-4-((1-hydroxypropan-2-yl)sulfonyl)-2-(6-azaspiro[2.5]octan-6-yl)benzamide. Second eluting peak (84 mg, ee 97%). $^1$H NMR (400 MHz, CHLOROFORM-d) δ ppm 12.71-13.05 (m, 1H), 8.39-8.56 (m, 1H), 7.74-8.03 (m, 2H), 7.38-7.54 (m, 1H), 3.81-4.04 (m, 6H), 3.26-3.39 (m, 1H), 3.03-3.19 (m, 4H), 2.48-2.83 (m, 1H), 2.33-2.41 (m, 3H), 1.92-2.10 (m, 4H), 1.60-1.90 (m, 4H), 1.28-1.33 (m, 3H), 0.36-0.46 (m, 4H). m/z (ESI): 563.2 $(M+H)^+$. The stereochemistry was arbitrary assigned.

Example 14: N-(2-(4,4-difluoropiperidin-1-yl)-6-methylpyrimidin-4-yl)-4-((1-hydroxy-2-methylpropan-2-yl) sulfonyl)-2-(6-azaspiro[2.5]octan-6-yl) benzamide

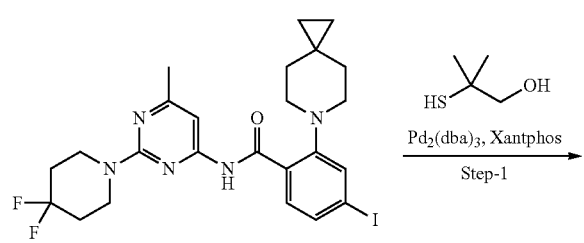

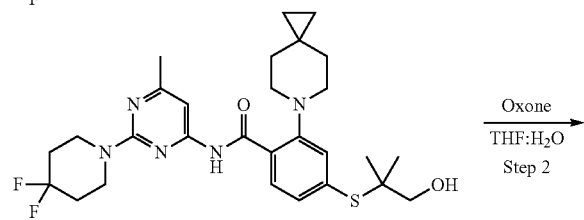

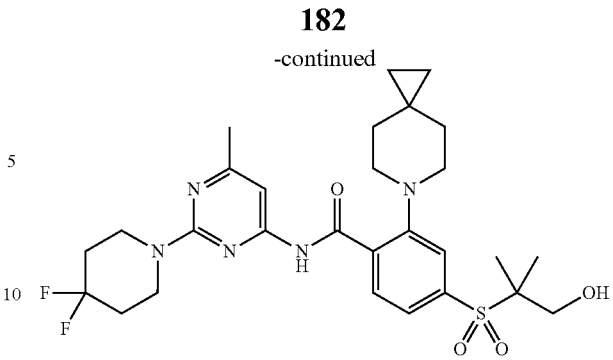

Step 1: N-(2-(4,4-difluoropiperidin-1-yl)-6-methylpyrimidin-4-yl)-4-iodo-2-(6-azaspiro[2.5]octan-6-yl)benzamide (0.55 g, 0.967 mmol, Int. 19), 4,5-bis(diphenylphosphino)-9,9-dimethyl-xanthene (0.034 g, 0.058 mmol), tris (dibenzylideneacetone)dipalladium (0) chloroform adduct (0.035 g, 0.034 mmol), DIPEA (0.4 mL, 2.29 mmol), and 2-mercapto-2-methylpropan-1-ol (0.134 g, 1.29 mmol) in 3 mL dioxane were passed through $N_2$ for 5 min in a sealed tube. The mixture was heated at 90° C. for 3 h and cooled to RT. The resulting crude product was adsorbed onto a plug of silica gel and purified by silica gel chromatography (0-7% EtOAc in DCM) to give N-(2-(4,4-difluoropiperidin-1-yl)-6-methylpyrimidin-4-yl)-4-((1-hydroxy-2-methylpropan-2-yl)thio)-2-(6-azaspiro[2.5]octan-6-yl)benzamide. $^1$H NMR (400 MHz, CHLOROFORM-d) δ ppm 0.38-0.47 (m, 4H) 1.25-1.31 (m, 6H) 1.56-1.56 (m, 4H) 1.94-2.04 (m, 4H) 2.35-2.41 (m, 3H) 3.03-3.12 (m, 4H) 3.31-3.38 (m, 2H) 3.95-4.04 (m, 4H) 7.41-7.47 (m, 2H) 7.48-7.52 (m, 1H) 8.14-8.32 (m, 1H) 12.96-13.41 (m, 1H). 4H overlapped with water peak, m/z (ESI): 546.2 $(M+H)^+$.

Step 2: To N-(2-(4,4-difluoropiperidin-1-yl)-6-methylpyrimidin-4-yl)-4-((1-hydroxy-2-methylpropan-2-yl)thio)-2-(6-azaspiro[2.5]octan-6-yl)benzamide (0.36 g, 0.66 mmol) in THF (15 mL) cooled to 0° C. was added oxone(r) monopersulfate compound (0.52 g, 0.85 mmol) in water (5 mL). The mixture was stirred for 2.5 h from 0° C. to RT. Additional 0.35 g oxone was added. After 1 h 1 cms showed the sulfoxide was almost consumed. Ethyl acetate (40 mL) and brine (20 mL) were added and organic layer was separated, dried and evaporated. The crude mixture was purified via preparative SFC using an (S,S) Whelk-01 (250× 21 mm, 5 mm) with a mobile phase of 60% Liquid $CO_2$ and 40% MeOH using a flowrate of 80 mL/min to give N-(2-(4,4-difluoropiperidin-1-yl)-6-methylpyrimidin-4-yl)-4-((1-hydroxy-2-methylpropan-2-yl)sulfonyl)-2-(6-azaspiro[2.5]octan-6-yl)benzamide. $^1$H NMR (400 MHz, CHLOROFORM-d) δ ppm 8.15-8.73 (m, 1H), 7.64-7.90 (m, 2H), 7.41-7.52 (m, 1H), 3.94-4.07 (m, 4H), 3.70-3.83 (m, 2H), 3.04-3.20 (m, 4H), 2.34-2.47 (m, 3H), 1.96-2.12 (m, 4H), 1.47-1.95 (m, 4H), 1.30-1.41 (m, 6H), 0.37-0.52 (m, 4H). $^{19}$F NMR (376 MHz, CHLOROFORM-d) δ ppm −96.68 (br s, 1F). m/z (ESI): 578.2 $(M+H)^+$.

TABLE 11

Examples 14-1 to 14-9 were prepared following similar procedures for Examples 12 to 14:

| Ex. # | Chemical Structure | Name | LRMS: (ESI + ve ion) m/z |
|---|---|---|---|
| 14-1 | 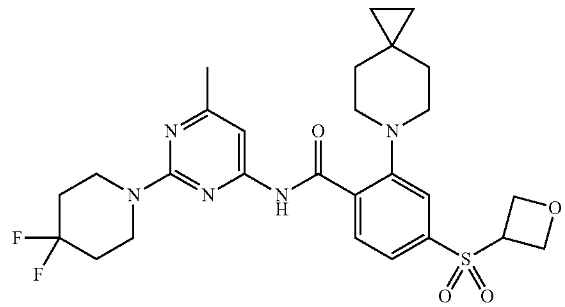 [SMILES: Cc1cc(NC(=O)c2ccc(S(=O)(=O)C3COC3)cc2N2CCC3(CC2)CC3)nc(N2CCC(F)(F)CC2)n1] | N-(2-(4,4-Difluoropiperidin-1-yl)-6-methylpyrimidin-4-yl)-4-(oxetan-3-ylsulfonyl)-2-(6-azaspiro[2.5]octan-6-yl)benzamide | 562.3 |
| 14-2 | 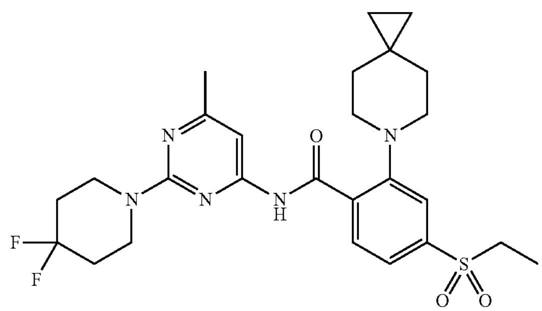 [SMILES: CCS(=O)(=O)c1ccc(C(=O)Nc2cc(C)nc(N3CCC(F)(F)CC3)n2)c(N2CCC3(CC2)CC3)c1] | N-(2-(4,4-Difluoropiperidin-1-yl)-6-methylpyrimidin-4-yl)-4-(ethylsulfonyl)-2-(6-azaspiro[2.5]octan-6-yl)benzamide | 534.2 |
| 14-3 | 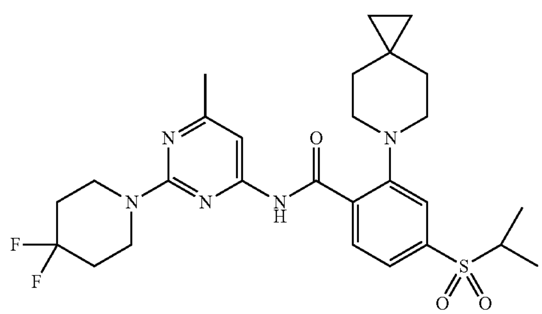 [SMILES: Cc1cc(NC(=O)c2ccc(S(=O)(=O)C(C)C)cc2N2CCC3(CC2)CC3)nc(N2CCC(F)(F)CC2)n1] | N-(2-(4,4-Difluoropiperidin-1-yl)-6-methylpyrimidin-4-yl)-4-(isopropylsulfonyl)-2-(6-azaspiro[2.5]octan-6-yl)benzamide | 548.2 |
| 14-4 | 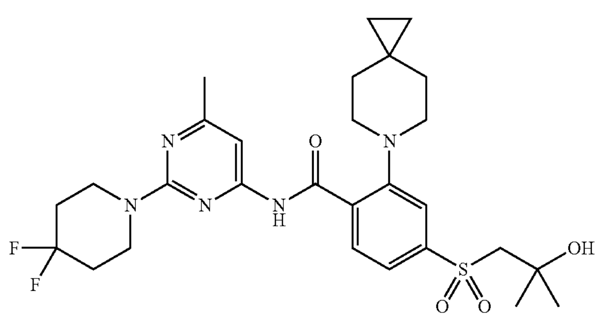 [SMILES: Cc1cc(NC(=O)c2ccc(S(=O)(=O)CC(C)(C)O)cc2N2CCC3(CC2)CC3)nc(N2CCC(F)(F)CC2)n1] | N-(2-(4,4-Difluoropiperidin-1-yl)-6-methylpyrimidin-4-yl)-4-((2-hydroxy-2-methylpropyl)sulfonyl)-2-(6-azaspiro[2.5]octan-6-yl)benzamide | 578.2 |

TABLE 11-continued

Examples 14-1 to 14-9 were prepared following similar procedures for Examples 12 to 14:

| Ex. # | Chemical Structure | Name | LRMS: (ESI + ve ion) m/z |
|---|---|---|---|
| 14-5 | 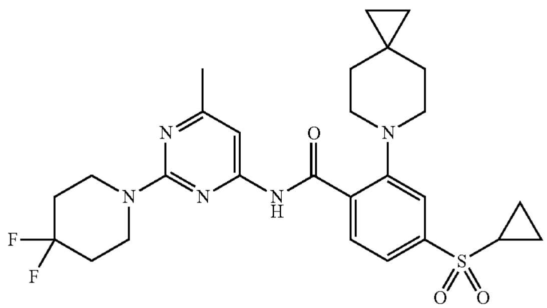 [SMILES: Cc1cc(NC(=O)c2ccc(S(=O)(=O)C3CC3)cc2N2CCC3(CC2)CC3)nc(N2CCC(F)(F)CC2)n1] | 4-(Cyclopropylsulfonyl)-N-(2-(4,4-difluoropiperidin-1-yl)-6-methylpyrimidin-4-yl)-2-(6-azaspiro[2.5]octan-6-yl)benzamide | 546.2 |
| 14-6 | 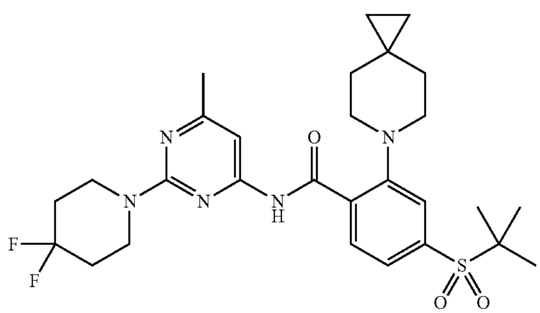 [SMILES: Cc1cc(NC(=O)c2ccc(S(=O)(=O)C(C)(C)C)cc2N2CCC3(CC2)CC3)nc(N2CCC(F)(F)CC2)n1] | 4-(tert-Butylsulfonyl)-N-(2-(4,4-difluoropiperidin-1-yl)-6-methylpyrimidin-4-yl)-2-(6-azaspiro[2.5]octan-6-yl)benzamide | 562.3 |
| 14-7 | 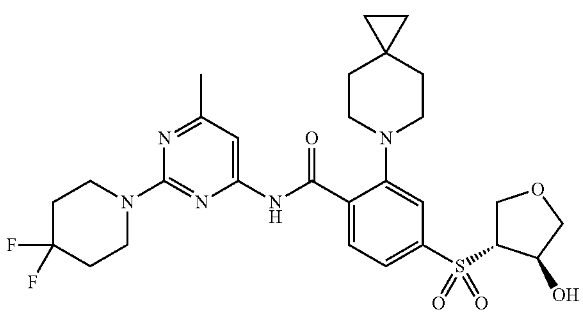 [SMILES: Cc1cc(NC(=O)c2ccc(S(=O)(=O)[C@@H]3COC[C@H]3O)cc2N2CCC3(CC2)CC3)nc(N2CCC(F)(F)CC2)n1] | N-(2-(4,4-Difluoropiperidin-1-yl)-6-methylpyrimidin-4-yl)-4-(((3R,4R)-4-hydroxytetrahydrofuran-3-yl)sulfonyl)-2-(6-azaspiro[2.5]octan-6-yl)benzamide | 592.2 |
| 14-8 | 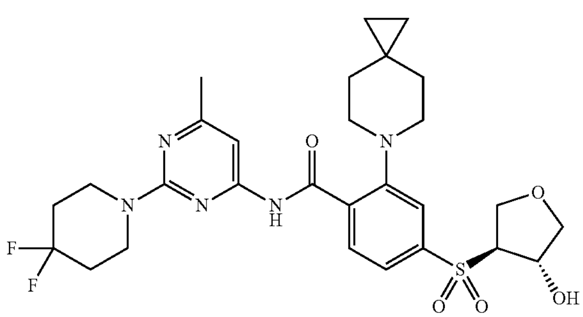 [SMILES: Cc1cc(NC(=O)c2ccc(S(=O)(=O)[C@H]3COC[C@@H]3O)cc2N2CCC3(CC2)CC3)nc(N2CCC(F)(F)CC2)n1] | N-(2-(4,4-Difluoropiperidin-1-yl)-6-methylpyrimidin-4-yl)-4-(((3S,4S)-4-hydroxytetrahydrofuran-3-yl)sulfonyl)-2-(6-azaspiro[2.5]octan-6-yl)benzamide | 592.2 |

TABLE 11-continued

Examples 14-1 to 14-9 were prepared following similar procedures for Examples 12 to 14:

| Ex. # | Chemical Structure | Name | LRMS: (ESI + ve ion) m/z |
|---|---|---|---|
| 14-9 | 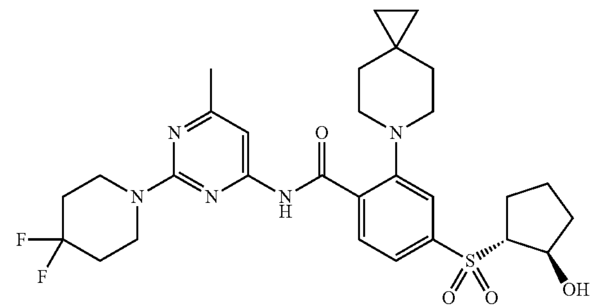 [SMILES: Cc1cc(NC(=O)c2ccc(S(=O)(=O)[C@@H]3CCC[C@H]3O)cc2N2CCC3(CC2)CC3)nc(N2CCC(F)(F)CC2)n1] | N-(2-(4,4-Difluoropiperidin-1-yl)-6-methylpyrimidin-4-yl)-4-(((1R,2R)-2-hydroxycyclopentyl)sulfonyl)-2-(6-azaspiro[2.5]octan-6-yl)benzamide | 590.2 |

Example 15: N-(2-(4,4-Difluorocyclohexyl)-6-methylpyrimidin-4-yl)-4-((2-hydroxyethyl)sulfonamido)-2-(6-azaspiro[2.5]octan-6-yl)benzamide A mixture of 4-bromo-N-(2-(4,4-difluorocyclohexyl)-6-methylpyrimidin-4-yl)-2-(6-azaspiro[2.5]octan-6-yl)benzamide (0.055 g, 0.106 mmol, Int. 21-13), 2-hydroxyethane-1-sulfonamide (0.020 g, 0.159 mmol, Wuxi), potassium phosphate tribasic (0.045 g, 0.212 mmol), copper(I) iodide (0.020 g, 0.106 mmol) and (1R,2R)—N,N'-dimethyl-1,2-cyclohexanediamine (7.53 mg, 0.053 mmol, Combi-Blocks) in DMF (1.5 mL) was heated at 90° C. for 16 h. Then the reaction mixture was filtered through a pad of CELITE® pad and filtrate was diluted with EtOAc. The resulting solution was washed with water and brine, dried over $Na_2SO_4$, filtered and concentrated. The residue was purified by reverse phase HPLC using a gradient of 60% ACN in water (0.1% TFA) to afford N-(2-(4,4-difluorocyclohexyl)-6-methylpyrimidin-4-yl)-4-((2-hydroxyethyl)sulfonamido)-2-(6-azaspiro[2.5]octan-6-yl)benzamide (0.025 g, 0.044 mmol, 42% yield) as white solid. $^1$H NMR (400 MHz, DMSO-$d_6$) δ ppm 13.70 (s, 1H), 8.04 (d, 2=8.8 Hz, 1H), 7.92 (s, 1H), 7.25 (d, 2=2.2 Hz, 1H), 7.16-7.08 (m, 1H), 3.75 (t, 2=6.3 Hz, 2H), 3.03-2.85 (m, 6H), 2.44 (d, 2=4.5 Hz, 5H), 2.05 (s, 5H), 1.92 (d, 2=11.7 Hz, 4H), 1.72 (s, 4H), 0.38 (s, 4H). m/z (ESI): 564.1 (M+H)$^+$.

Example 16-1 and 16-2: (S)—N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide and (R)—N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide

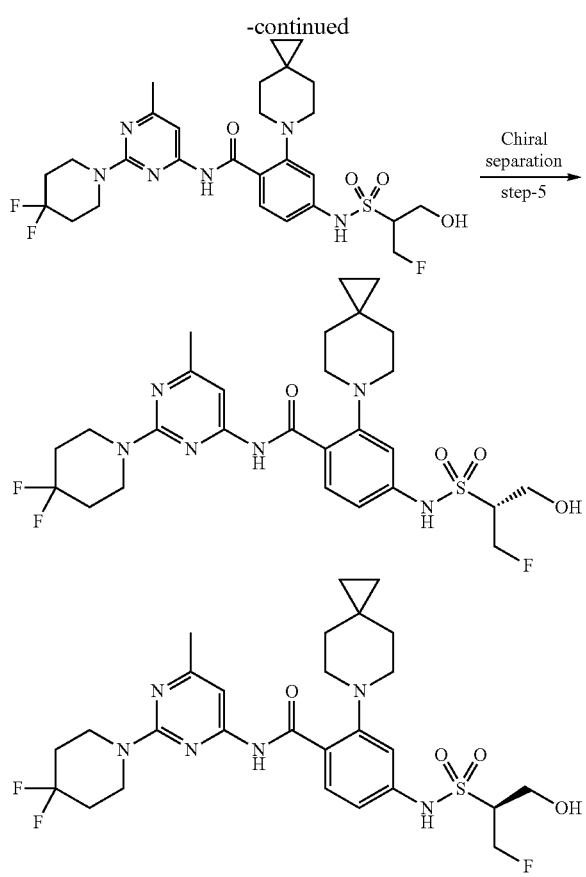

Step 1: To a solution of 1-(benzyloxy)-3-((tert-butyldimethylsilyl)oxy)propane-2-sulfonamide (0.803 g, 2.23 mmol) in THF was added tetrabutylammonium fluoride solution (2.75 mL, 2.75 mmol, 1M in THF) at RT. The reaction was stirred for 1 hour and then concentrated under reduced pressure. The resulting material was used immediately in the next step.

Step 2: To a pressure relief vial charged with the sulfonamide from the previous step was added copper(I) iodide (0.196 g, 1.03 mmol), methyl glycine (0.128 g, 1.440 mmol), potassium phosphate, tribasic (0.934 g, 4.40 mmol), and N-(2-(4,4-difluoropiperidin-1-yl)-6-methylpyrimidin-4-yl)-4-iodo-2-(6-azaspiro[2.5]octan-6-yl)benzamide (0.975 g, 1.72 mmol, Int. 19). The vial was sealed and evacuated/backfilled with nitrogen and then DMF (7 mL) was added. The cap was replaced, and the reaction was stirred in a pre-heated 100° C. oil bath for 16 h. The reaction mixture was partitioned between satd. NH$_4$Cl:NH$_4$OH (9:1) and EtOAc. The organic phase was separated, washed with brine, and concentrated in vacuo. The material was purified by silica gel chromatography (20-100% EtOAc in heptane) to afford 4-((2-(benzyloxy)-1-(hydroxymethyl)ethyl)sulfonamido)-N-(2-(4,4-difluoropiperidin-1-yl)-6-methylpyrimidin-4-yl)-2-(6-azaspiro[2.5]octan-6-yl)benzamide (0.635 g, 0.927 mmol, 54.0% yield). $^1$H NMR (400 MHz, CHLOROFORM-d) δ ppm 13.11 (br dd, J=4.66, 2.38 Hz, 1H) 8.14 (d, J=8.50 Hz, 1H) 7.49 (br s, 1H) 7.31-7.44 (m, 5H) 7.13 (d, J=1.87 Hz, 1H) 6.83 (dd, J=8.60, 2.18 Hz, 2H) 4.49-4.62 (m, 2H) 4.08 (dt, J=11.77, 5.83 Hz, 1H) 3.94-4.03 (m, 5H) 3.88-3.93 (m, 1H) 3.95 (br s, 1H) 3.45-3.55 (m, 1H) 2.96 (br t, J=4.98 Hz, 4H) 2.29-2.49 (m, 4H) 1.95-2.07 (m, 4H) 1.57 (brs, 4H) 1.18-1.35 (m, 2H) 0.85-0.91 (m, 1H) 0.40 (s, 4H). m/z (ESI, +ve ion): 683.8 (M+H)$^+$.

Step 3: To a solution of xtalfluor-m (0.351 g, 1.446 mmol) in DCM (6 mL) in a brine/ice bath was added triethylamine trihydrofluoride (0.262 mL, 1.61 mmol) followed by a solution of 4-((2-(benzyloxy)-1-(hydroxymethyl)ethyl)sulfonamido)-7V-(2-(4,4-difluoropiperidin-1-yl)-6-methylpyrimidin-4-yl)-2-(6-azaspiro[2.5]octan-6-yl)benzamide (0.55 g, 0.803 mmol) in DCM (10 mL) dropwise via addition funnel. The reaction was gradually warmed to RT and stirred for 16 h. The reaction was quenched with saturated sodium bicarbonate (aq) and diluted with water and DCM. The organic phase was separated, washed with brine, dried over magnesium sulfate, and concentrated in vacuo. The crude material was purified by silica gel chromatography (20-100% EtOAc in heptane) to afford a 1:0.8 mixture of rac-4-((2-(benzyloxy)-1-(fluoromethyl)ethyl)sulfonamido)-N-(2-(4,4-difluoropiperidin-1-yl)-6-methylpyrimidin-4-yl)-2-(6-azaspiro[2.5]octan-6-yl)benzamide and 4-((1-((benzyloxy)methyl)vinyl)sulfonamido)-N-(2-(4, 4-difluoropiperidin-1-yl)-6-methylpyrimidin-4-yl)-2-(6-azaspiro[2.5]octan-6-yl)benzamide (265 mg). The mixture was carried forward without further purification.

Step 4: To a suspension of 265 mg of the product mixture from the previous step and palladium hydroxide on carbon (0.135 g, 0.193 mmol), in EtOH (20 mL) was added and AcOH (0.033 mL, 0.579 mmol). The reaction was hydrogenated under 55 psi hydrogen at room temperature for 24 hours. After flushing the reaction with Nitrogen, an additional portion of palladium hydroxide on carbon (0.135 mL, 0.193 mmol) was added followed by additional AcOH (0.033 mL, 0.579 mmol). The reaction vessel was flushed with N$_2$ before replacing the atmosphere with 55 psi hydrogen. The reaction was continued at room temperature for an additional 48 hours. The reaction was flushed with nitrogen then filtered over CELITE® and the filtrate was concentrated in vacuo. The racemic mixture was purified by preparative SFC using an IE (250×21 mm, 5 mm) with a mobile phase of 80% Liquid CO$^2$ and 20% MeOH (flowrate of 80 mL/min) to give:

Example 16-1: (S)—N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide. First eluting peak $^1$H NMR (400 MHz, DMSO-d$_6$) δ ppm 13.35 (s, 1H), 10.21-10.84 (m, 1H), 8.06 (d, J=8.50 Hz, 1H) 7.40 (s, 1H), 7.29 (d, J=2.07 Hz, 1H), 7.16 (dd, J=8.50, 2.07 Hz, 1H), 5.12-5.38 (m, 1H), 4.88-4.97 (m, 1H) 4.71-4.84 (m, 1H), 3.85-4.01 (m, 5H), 3.74 (dd, J=11.30, 7.98 Hz, 1H), 3.51-3.63 (m, 1H) 2.98 (br t, J=4.77 Hz, 4H), 2.32 (s, 3H), 1.93-2.07 (m, 4H), 1.51-1.91 (m, 4H), 0.40 (s, 4H). m/z (ESI, +ve ion): 597.2 (M+H)$^+$.

Example 16-2: (R)—N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide. Second eluting peak. $^1$H NMR (400 MHz, DMSO-d$_6$) δ ppm 13.35 (s, 1H) 10.32-10.70 (m, 1H) 8.05 (d, J=8.71 Hz, 1H), 7.40 (s, 1H) 7.29 (d, J=2.07 Hz, 1H) 7.16 (dd, J=8.71, 2.07 Hz, 1H) 5.14-5.40 (m, 1H) 4.85-4.97 (m, 1H) 4.73-4.84 (m, 1H) 3.87-3.98 (m, 5H), 3.74 (dd, J=11.09, 7.98 Hz, 1H) 3.48. m/z (ESI, +ve ion): 597.2 (M+H)$^+$. The stereochemistry was arbitrarily assigned

Example 17: N-(2-(4,4-Difluoropiperidin-1-yl)pyridin-4-yl)-4-(N-(2-hydroxyethyl)sulfamoyl)-2-(6-azaspiro[2.5]octan-6-yl)benzamide

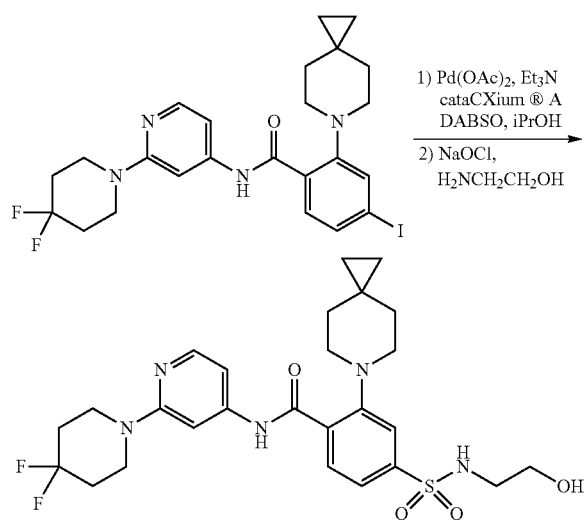

A mixture of N-(2-(4,4-difluoropiperidin-1-yl)pyridin-4-yl)-4-iodo-2-(6-azaspiro[2.5]octan-6-yl)benzamide (212 mg, 0.384 mmol, Int. 21-14), 1,4-diazabicyclo[2.2.2]octane bis(sulfur dioxide) adduct (DABSO) (55 mg, 0.23 mmol, Sigma-Aldrich), diacetoxypalladium (13 mg, 0.06 mmol, Strem), rac-((3R,5R,7R)-adamantan-1-yl)((3S,5S,7S)-adamantan-1-yl)(butyl)phosphane (cataCXium® A) (28 mg, 0.08 mmol, Strem), and triethylamine (107 uL, 0.77 mmol) in IPA (3 mL) in a glass tube was degassed for 3 min. The tube was sealed then heated at 85° C. in an oil bath for 3 h. The heterogeneous mixture was cooled to RT and treated with 2-aminoethan-1-ol (47 mg, 0.77 mmol, Sigma-Aldrich) followed by sodium hypochlorite solution (10% wt., 571 mg, 0.77 mmol, Sigma-Aldrich) and stirred at RT for 18 h. The mixture was treated with 2-aminoethan-1-ol (23 mg) followed by sodium hypochlorite solution (10% wt., 275 mg) then stirred at RT for 5 h. EtOAc (20 mL) and water (5 mL) were added to the heterogeneous mixture and the insoluble solid was filtered off. The filter cake was washed with water (2×2 mL) followed by EtOAc (2×4 mL). The organic solution was taken and concentrated under vacuum. The residue was purified by silica gel chromatography (10% to 60% EtOAc in heptane) to give N-(2-(4,4-difluoropiperidin-1-yl)pyridin-4-yl)-4-(N-(2-hydroxyethyl)sulfamoyl)-2-(6-azaspiro[2.5]octan-6-yl)benzamide (100 mg, 0.18 mmol, 47% yield) as an off-white solid. $^1$H NMR (400 MHz, METHANOL-$d_4$) δ ppm 7.99-8.14 (m, 2H), 7.79 (s, 1H), 7.68 (d, J=7.88 Hz, 1H), 7.47 (s, 1H), 7.01 (d, J=4.77 Hz, 1H), 3.76 (t, J=5.29 Hz, 4H), 3.58 (t, J=5.91 Hz, 2H), 3.16 (t, J=5.08 Hz, 4H), 3.02 (t, J=5.80 Hz, 2H), 1.98-2.11 (m, 4H), 1.62 (s, 4H), 0.42 (s, 4H). m/z (ESI): (M+H)$^+$550.1.

TABLE 12

Examples 17-1 to 17-8 were prepared following similar procedures for Example 17:

| Ex. # | Chemical Structure | Name | LRMS: (ESI + ve ion) m/z |
|---|---|---|---|
| 17-1 | 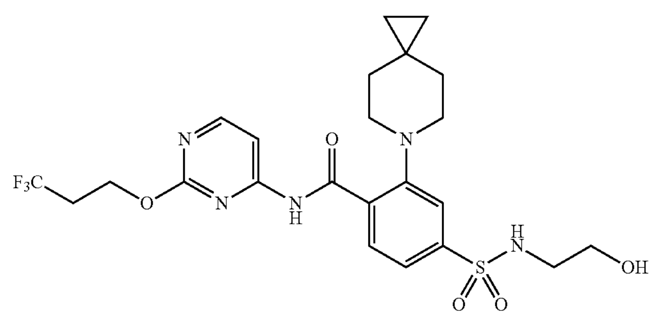 [SMILES: O=C(Nc1ccnc(OCCC(F)(F)F)n1)c1ccc(S(=O)(=O)NCCO)cc1N1CCC2(CC1)CC2] | 4-(N-(2-Hydroxyethyl)sulfamoyl)-2-(6-azaspiro[2.5]octan-6-yl)-N-(2-(3,3,3-trifluoropropoxy)pyrimidin-4-yl)benzamide | 544.2 |
| 17-2 | 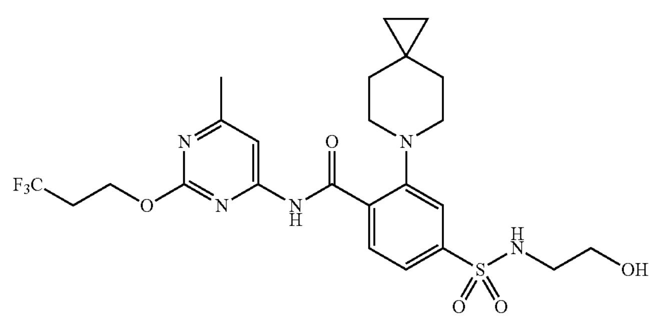 [SMILES: Cc1cc(NC(=O)c2ccc(S(=O)(=O)NCCO)cc2N2CCC3(CC2)CC3)nc(OCCC(F)(F)F)n1] | 4-(N-(2-Hydroxyethyl)sulfamoyl)-N-(6-methyl-2-(3,3,3-trifluoropropoxy)pyrimidin-4-yl)-2-(6-azaspiro[2.5]octan-6-yl)benzamide | 558.2 |

TABLE 12-continued

Examples 17-1 to 17-8 were prepared following similar procedures for Example 17:

| Ex. # | Chemical Structure | Name | LRMS: (ESI + ve ion) m/z |
|---|---|---|---|
| 17-3 | 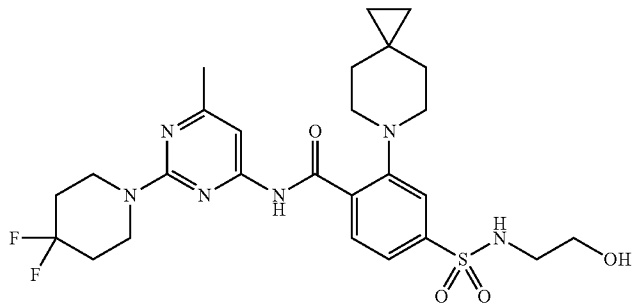 [SMILES: Cc1cc(NC(=O)c2ccc(S(=O)(=O)NCCO)cc2N2CCC3(CC2)CC3)nc(N2CCC(F)(F)CC2)n1] | N-(2-(4,4-Difluoropiperidin-1-yl)-6-methylpyrimidin-4-yl)-4-(N-(2-hydroxyethyl)sulfamoyl)-2-(6-azaspiro[2.5]octan-6-yl)benzamide | 565.2 |
| 17-4 | 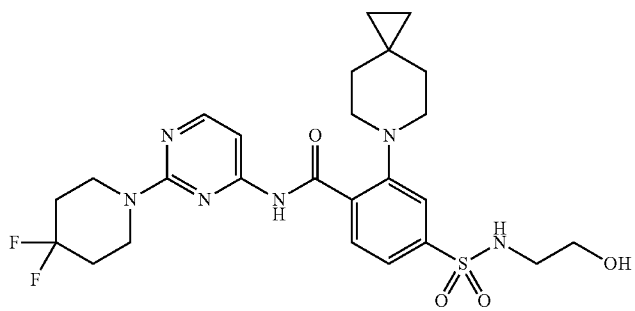 [SMILES: O=C(Nc1ccnc(N2CCC(F)(F)CC2)n1)c1ccc(S(=O)(=O)NCCO)cc1N1CCC2(CC1)CC2] | N-(2-(4,4-Difluoropiperidin-1-yl)pyrimidin-4-yl)-4-(N-(2-hydroxyethyl)sulfamoyl)-2-(6-azaspiro[2.5]octan-6-yl)benzamide | 551.2 |
| 17-5 | 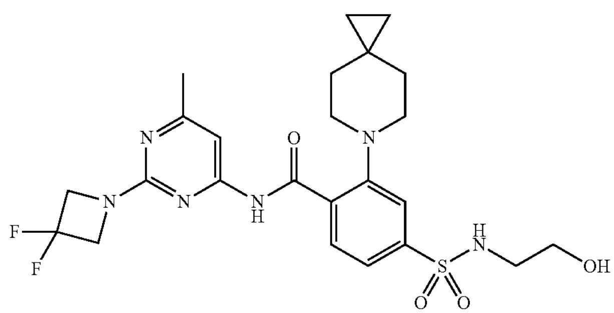 [SMILES: Cc1cc(NC(=O)c2ccc(S(=O)(=O)NCCO)cc2N2CCC3(CC2)CC3)nc(N2CC(F)(F)C2)n1] | N-(2-(3,3-Difluoroazetidin-1-yl)-6-methylpyrimidin-4-yl)-4-(N-(2-hydroxyethyl)sulfamoyl)-2-(6-azaspiro[2.5]octan-6-yl)benzamide | 537.2 |
| 17-6 | 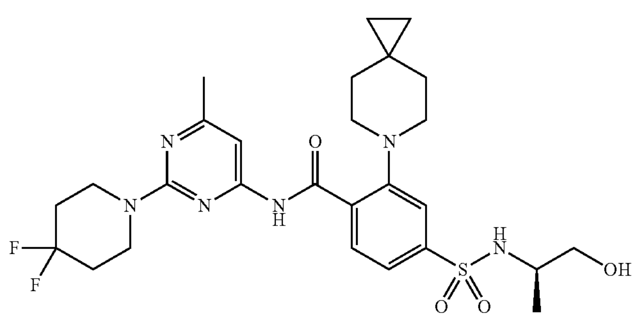 [SMILES: Cc1cc(NC(=O)c2ccc(S(=O)(=O)N[C@H](C)CO)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-(N-(1-hydroxypropan-2-yl)sulfamoyl)-2-(6-azaspiro[2.5]octan-6-yl)benzamide | 579.4 |

TABLE 12-continued

Examples 17-1 to 17-8 were prepared following similar procedures for Example 17:

| Ex. # | Chemical Structure | Name | LRMS: (ESI + ve ion) m/z |
|---|---|---|---|
| 17-7 | 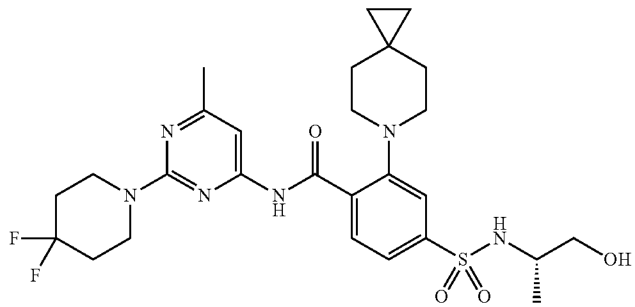 [SMILES: Cc1cc(NC(=O)c2ccc(S(=O)(=O)N[C@@H](C)CO)cc2N2CCC3(CC2)CC3)nc(N2CCC(F)(F)CC2)n1] | ((S)-N-(2-(4,4-Difluoropiperidin-1-yl)-6-methylpyrimidin-4-yl)-4-(N-(1-hydroxypropan-2-yl)sulfamoyl)-2-(6-azaspiro[2.5]octan-6-yl)benzamide | 579.4 |
| 17-8 | 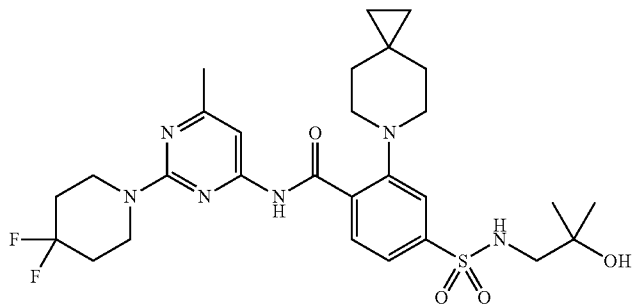 [SMILES: Cc1cc(NC(=O)c2ccc(S(=O)(=O)NCC(C)(C)O)cc2N2CCC3(CC2)CC3)nc(N2CCC(F)(F)CC2)n1] | N-(2-(4,4-Difluoropiperidin-1-yl)-6-methylpyrimidin-4-yl)-4-(N-(2-hydroxy-2-methylpropyl)sulfamoyl)-2-(6-azaspiro[2.5]octan-6-yl)benzamide | 593.4 |

Examples 18-1 and 18-2: 2-(6-Azaspiro[2.5]octan-6-yl)-4-(R-cyclopropylsulfonimidoyl)-N-(2-(4,4-difluoro-1-piperidinyl)-6-methyl-4-pyrimidinyl)benzamide and 2-(6-azaspiro[2.5]octan-6-yl)-4-(S-cyclopropylsulfonimidoyl)-N-(2-(4,4-difluoro-1-piperidinyl)-6-methyl-4-pyrimidinyl)benzamide

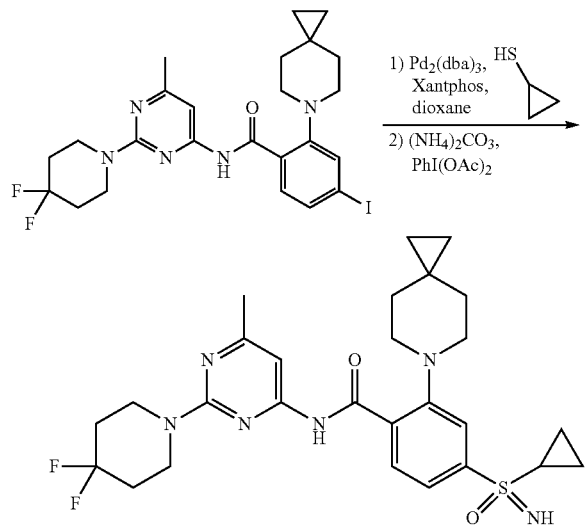

Step 1: Into a 20 mL microwave vessel were placed N-(2-(4,4-difluoropiperidin-1-yl)-6-methylpyrimidin-4-yl)-4-iodo-2-(6-azaspiro[2.5]octan-6-yl)benzamide (1.00 g, 1.762 mmol, Int. 19), tris (dibenzylideneacetone) dipalladium (0) (0.161 g, 0.176 mmol) and 4,5-bis(diphenylphosphino)-9,9-dimethyl-xanthene (0.102 g, 0.176 mmol) followed by 1,4-dioxane (10 mL). The resulting mixture was stirred and purged with nitrogen for 5 min before 1,1'-dimethyltriethylamine (0.616 mL, 3.52 mmol) was added under nitrogen followed by cyclopropanethiol (0.142 mL, 1.939 mmol). The vessel was sealed and subjected to microwave condition (10 h, 90° C.). The crude mixture was directly loaded onto a silica gel precolumn and subjected to combi-flash column chromatography on a 40-g ISCO gold column eluting with MeOH/DCM (5 min at 0% and 25 min from 0 to 6%) twice to give 4-(cyclopropylthio)-N-(2-(4,4-difluoropiperidin-1-yl)-6-methylpyrimidin-4-yl)-2-(6-azaspiro[2.5]octan-6-yl)benzamide (0.92 g, 1.791 mmol, 102% yield) as an off-white solid. $^1$H NMR (400 MHz, DICHLOROMETHANE-$d_2$) δ ppm 13.33 (s, 1H), 8.15 (d, J=8.29 Hz, 1H), 7.48 (s, 1H), 7.22-7.35 (m, 2H), 3.91-4.09 (m, 4H), 3.06 (brt, J=5.18 Hz, 4H), 2.35 (s, 3H), 2.17-2.28 (m, 1H), 1.62-2.10 (m, 6H), 1.52 (s, 2H), 1.13-1.21 (m, 2H), 0.68-0.76 (m, 2H), 0.40 (s, 4H). m/z (ESI): 514.1 (M+H)$^+$.

Step 2: To a stirred solution of 4-(cyclopropylthio)-N-(2-(4,4-difluoropiperidin-1-yl)-6-methylpyrimidin-4-yl)-2-(6-azaspiro[2.5]octan-6-yl)benzamide (0.89 g, 1.733 mmol) and ammonium carbonate (0.250 g, 2.60 mmol) in MeOH (4.5 mL) and dichloromethane (9.0 mL) was added (acetyloxy)(phenyl)-iodanyl acetate (1.284 g, 3.99 mmol) in one portion as a solid. The resulting mixture was stirred in open air at rt for 18 h. The resulting mixture was directly loaded onto silica gel precolumn (25 g) and subjected to combi-flash column chromatography on a 40-g ISCO gold column eluting with MeOH/DCM (3 min at 0% and 25 min from 0 to 14%) to give a racemic mixture of 4-(cyclopropanesulfonimidoyl)-N-(2-(4,4-difluoropiperidin-1-yl)-6-methylpyrimidin-4-yl)-2-(6-azaspiro[2.5]octan-6-yl)benzamide (0.95 g, 1.744 mmol, 101% yield) as an off-white solid. The enantiomers were separated via preparative SFC using a Regis (S,S) Whelk-01 (250×21 mm, 5 mm) with a mobile phase of 50% Liquid $CO_2$ and 50% MeOH using a flow rate of 60 mL/min to generate:

Example 18-1: 2-(6-Azaspiro[2.5]octan-6-yl)-4-(R-cyclopropylsulfonimidoyl)-N-(2-(4,4-difluoro-1-piperidinyl)-6-methyl-4-pyrimidinyl)benzamide. First eluting peak, $^1$H NMR (400 MHz, CHLOROFORM-d) δ ppm 13.20 (br d, J=3.73 Hz, 1H), 8.44 (d, J=8.29 Hz, 1H), 7.96 (d, J=1.45 Hz, 1H), 7.87 (dd, J=1.66, 8.29 Hz, 1H), 7.52 (s, 1H), 4.03 (br s, 4H), 3.14 (t, J=5.29 Hz, 4H), 2.53-2.63 (m, 1H), 2.44 (br s, 3H), 1.95-2.10 (m, 4H), 1.53-1.89 (m, 5H), 1.45 (tdd, J=5.08, 6.92, 10.29 Hz, 1H), 1.20-1.30 (m, 1H), 1.07-1.17 (m, 1H), 0.93-1.03 (m, 1H), 0.44 (s, 4H). m/z (ESI): 545.2 (M+H)$^+$.

Example 18-2: 2-(6-Azaspiro[2.5]octan-6-yl)-4-(S-cyclopropylsulfonimidoyl)-N-(2-(4,4-difluoro-1-piperidinyl)-6-methyl-4-pyrimidinyl)benzamide. Second eluting peak. $^1$H NMR (400 MHz, CHLOROFORM-d) δ ppm 13.20 (br d, J=3.73 Hz, 1H), 8.44 (d, J=8.29 Hz, 1H), 7.96 (d, J=1.45 Hz, 1H), 7.87 (dd, J=1.66, 8.29 Hz, 1H), 7.52 (s, 1H), 4.03 (br s, 4H), 3.14 (t, J=5.29 Hz, 4H), 2.53-2.63 (m, 1H), 2.44 (br s, 3H), 1.95-2.10 (m, 4H), 1.53-1.89 (m, 5H), 1.45 (tdd, J=5.08, 6.92, 10.29 Hz, 1H), 1.20-1.30 (m, 1H), 1.07-1.17 (m, 1H), 0.93-1.03 (m, 1H), 0.44 (s, 4H). m/z (ESI): 545.2 (M+H)$^+$. The stereochemistry assignments were arbitrary.

TABLE 13

Examples 19-1 to 19-9 were prepared following the procedure described for Examples 18-1 and 18-2:

| Ex. # | Chemical Structure | Name | LRMS: (ESI + ve ion) m/z |
|---|---|---|---|
| 19-1 | 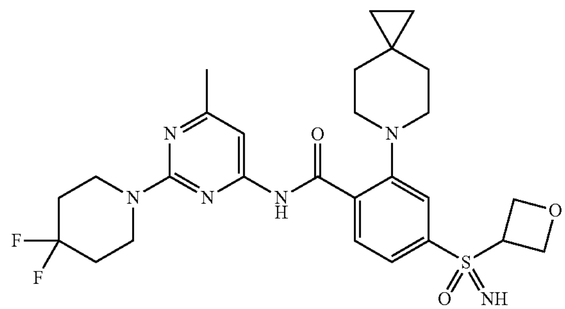 [SMILES: Cc1cc(NC(=O)c2ccc(S(=N)(=O)C3COC3)cc2N2CCC3(CC2)CC3)nc(N2CCC(F)(F)CC2)n1] | N-(2-(4,4-Difluoropiperidin-1-yl)-6-methylpyrimidin-4-yl)-4-(oxetane-3-sulfonimidoyl)-2-(6-azaspiro[2.5]octan-6-yl)benzamide | 561.2 |
| 19-2 | 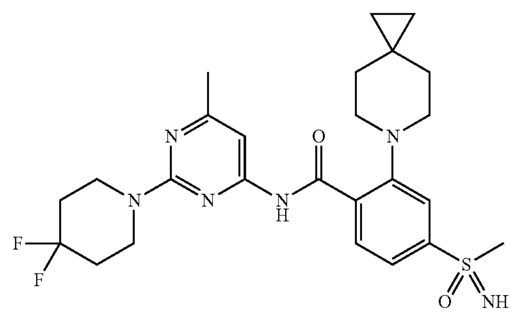 [SMILES: Cc1cc(NC(=O)c2ccc(S(C)(=N)=O)cc2N2CCC3(CC2)CC3)nc(N2CCC(F)(F)CC2)n1] | N-(2-(4,4-Difluoropiperidin-1-yl)-6-methylpyrimidin-4-yl)-4-(methylsulfonimidoyl)-2-(6-azaspiro[2.5]octan-6-yl)benzamide | 519.2 |
| 19-3 | 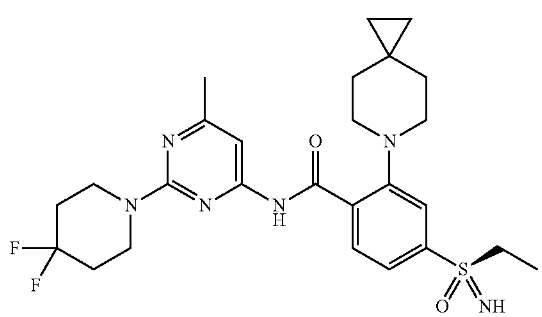 [SMILES: CC[S@@](=N)(=O)c1ccc(C(=O)Nc2cc(C)nc(N3CCC(F)(F)CC3)n2)c(N2CCC3(CC2)CC3)c1] | 2-(6-Azaspiro[2.5]octan-6-yl)-N-(2-(4,4-difluoro-1-pieridinyl)-6-methyl-4-pyrimidinyl)-4-(S-ethylsulfonimidoyl)benzamide | 533.2 |

TABLE 13-continued

Examples 19-1 to 19-9 were prepared following the procedure described for Examples 18-1 and 18-2:

| Ex. # | Chemical Structure | Name | LRMS: (ESI + ve ion) m/z |
|---|---|---|---|
| 19-4 | 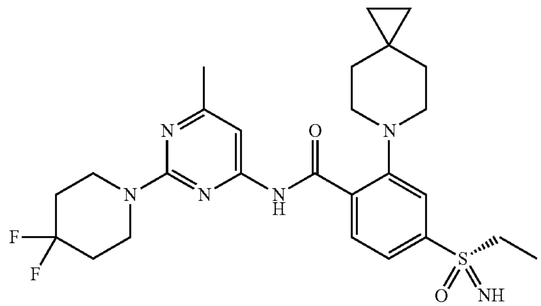 [SMILES: CC[S@](=N)(=O)c1ccc(C(=O)Nc2cc(C)nc(N3CCC(F)(F)CC3)n2)c(N2CCC3(CC2)CC3)c1] | 2-(6-Azaspiro[2.5]octan-6-yl)-N-(2-(4,4-difluoro-1-pieridinyl)-6-methyl-4-pyrimidinyl)-4-(R-ethylsulfonimidoyl)benzamide | 533.2 |
| 19-5 | 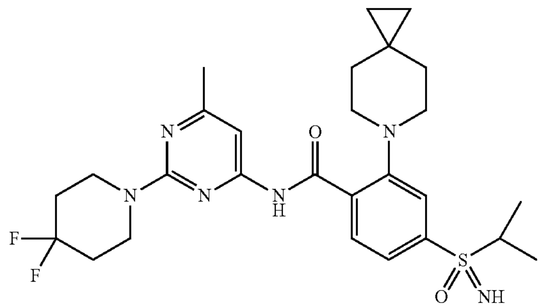 [SMILES: Cc1cc(NC(=O)c2ccc(S(=N)(=O)C(C)C)cc2N2CCC3(CC2)CC3)nc(N2CCC(F)(F)CC2)n1] | N-(2-(4,4-Difluoropiperidin-1-yl)-6-methylpyrimidin-4-yl)-4-(propan-2-ylsulfonimidoyl)-2-(6-azaspiro[2.5]octan-6-yl)benzamide | 547.3 |
| 19-6 | 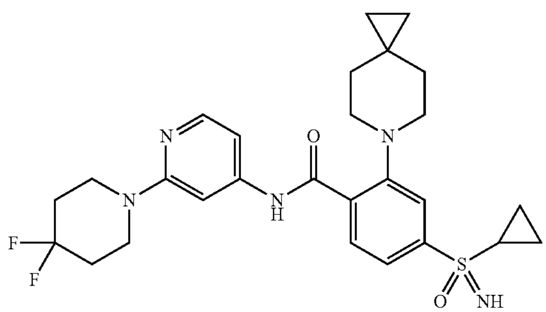 [SMILES: N=S(=O)(c1ccc(C(=O)Nc2ccnc(N3CCC(F)(F)CC3)c2)c(N2CCC3(CC2)CC3)c1)C1CC1] | 4-(Cyclopropanesulfonimidoyl)-N-(2-(4,4-difluoropiperidin-1-yl)pyridin-4-yl)-2-(6-azaspiro[2.5]octan-6-yl)benzamide | 530.0 |
| 19-7 | 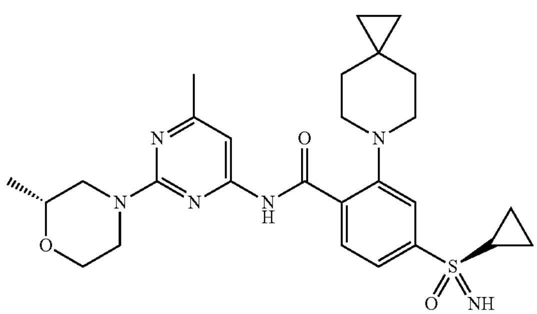 [SMILES: Cc1cc(NC(=O)c2ccc([S@](=N)(=O)C3CC3)cc2N2CCC3(CC2)CC3)nc(N2CCO[C@H](C)C2)n1] | 2-(6-Azaspiro[2.5]octan-6-yl)-4-(S-cyclopropylsulfonimidoyl)-N-(6-methy-2-((2R)-2-methyl-4-moprpholinyl)-4-pyrimidinyl)benzamide | 525.2 |
| 19-8 | 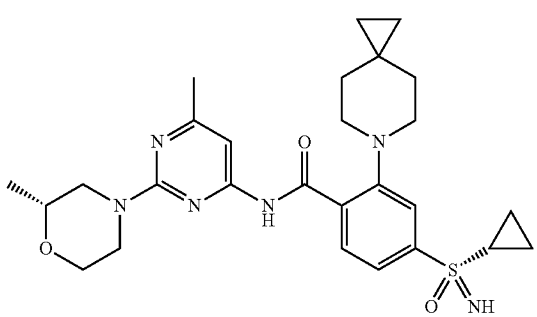 [SMILES: Cc1cc(NC(=O)c2ccc([S@@](=N)(=O)C3CC3)cc2N2CCC3(CC2)CC3)nc(N2CCO[C@H](C)C2)n1] | 2-(6-Azaspiro[2.5]octan-6-yl)-4-(R-cyclopropylsulfonimidoyl)-N-(6-methy-2-((2R)-2-methyl-4-moprpholinyl)-4-pyrimidinyl)benzamide | 525.2 |

TABLE 13-continued

Examples 19-1 to 19-9 were prepared following the procedure described for Examples 18-1 and 18-2:

| Ex. # | Chemical Structure | Name | LRMS: (ESI + ve ion) m/z |
|---|---|---|---|
| 19-9 | 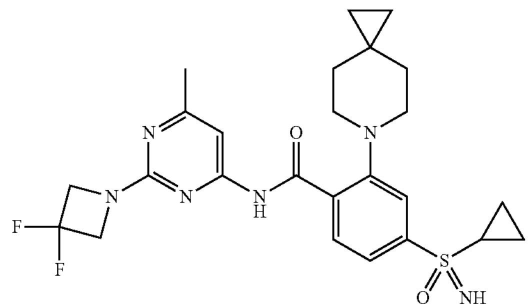 [SMILES: Cc1cc(NC(=O)c2ccc(S(=N)(=O)C3CC3)cc2N2CCC3(CC2)CC3)nc(N2CC(F)(F)C2)n1] | 4-(Cyclopropanesulfonimidoyl)-N-(2-(3,3-difluoroazetidin-1-yl)-6-methylpyrimidin-4-yl)-2-(6-azaspiro[2.5]octan-6-yl)benzamide | 517.3 |

Example 20: ($N^1$-(2-(4,4-Difluoropiperidin-1-yl)-6-methylpyrimidin-4-yl)-2-(6-azaspiro[2.5]octan-6-yl) terephthalamide

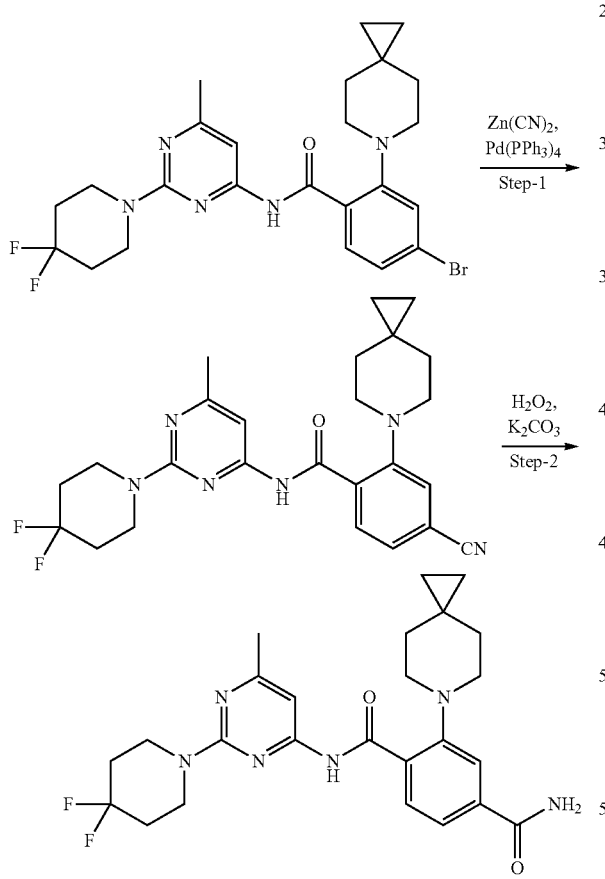

Step 1: To a solution of 4-bromo-N-(2-(4,4-difluoropiperidin-1-yl)-6-methylpyrimidin-4-yl)-2-(6-azaspiro[2.5]octan-6-yl)benzamide (250 mg, 0.48 mmol, Int. 21-3) in DMF (2.5 mL) was added Pd(PPh$_3$)$_4$ (6 mg, 4.8 μmol) and Zn(CN)$_2$ (113 mg, 0.961 mmol) and the reaction mixture was stirred at 100° C. for 16 h. Then the reaction mixture was diluted with EtOAc and filtered through a CELITE® bed. The filtrate was washed with water and brine, dried over Na$_2$SO$_4$, filtered, concentrated and purified by flash column chromatography using a gradient of 30% EtOAc in petroleum ether to provide 4-cyano-N-(2-(4,4-difluoropiperidin-1-yl)-6-methylpyrimidin-4-yl)-2-(6-azaspiro[2.5]octan-6-yl)benzamide (160 mg, 0.343 mmol, 71.4% yield) as an off white solid. $^1$H NMR (400 MHz, DMSO-d$_6$) δ ppm 13.20 (s, 1H), 8.18 (d, J=8.1 Hz, 1H), 8.03 (s, 1H), 7.79 (d, J=8.1 Hz, 1H), 7.39 (s, 1H), 4.00-3.80 (m, 4H), 3.07 (t, J=5.2 Hz, 4H), 2.34 (s, 3H), 1.99 (tt, J=13.3, 5.7 Hz, 4H), 1.69 (s, 4H), 0.38 (s, 4H). m/z (ESI): 467.2 (M+H)$^+$.

Step 2: To a solution of 4-cyano-N-(2-(4,4-difluoropiperidin-1-yl)-6-methylpyrimidin-4-yl)-2-(6-azaspiro[2.5]octan-6-yl)benzamide (110 mg, 0.236 mmol) in dimethyl sulfoxide (2 mL) were added K$_2$CO$_3$ (6.52 mg, 0.047 mmol) and H$_2$O$_2$ (103 μL, 1.179 mmol) at 0° C. and the reaction mixture was stirred for 1 h before it was quenched with water and was extracted with EtOAc (2×20 mL). The combined organic layers were washed with brine, dried over Na$_2$SO$_4$, filtered, concentrated and purified by flash column chromatography using a gradient of 10% methanol in dichloromethane to provide $N^1$-(2-(4,4-difluoropiperidin-1-yl)-6-methylpyrimidin-4-yl)-2-(6-azaspiro[2.5]octan-6-yl) terephthalamide (108 mg, 0.223 mmol, 95% yield) as off white solid. $^1$H NMR (400 MHz, DMSO-d$_6$) δ ppm 13.75 (s, 1H), 8.26 (m, 1H), 8.17 (m, 1H), 8.00 (s, 1H), 7.89-7.78 (m, 1H), 7.61 (s, 1H), 7.42 (s, 1H), 3.94 (d, J=5.8 Hz, 4H), 3.06 (d, J=6.0 Hz, 4H), 2.34 (d, J=2.3 Hz, 3H), 2.01 (q, J=8.5, 8.1 Hz, 4H), 1.74 (s, 4H), 0.41 (d, J=2.3 Hz, 4H). m/z (ESI): 485.2 (M+H)$^+$.

Example 21: 4-(Azetidin-3-ylsulfonyl)-N-(2-(4,4-difluoropiperidin-1-yl)-6-methylpyrimidin-4-yl)-2-(6-azaspiro[2.5]octan-6-yl)benzamide

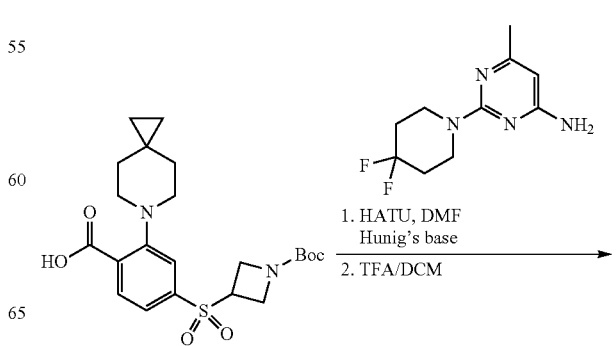

-continued

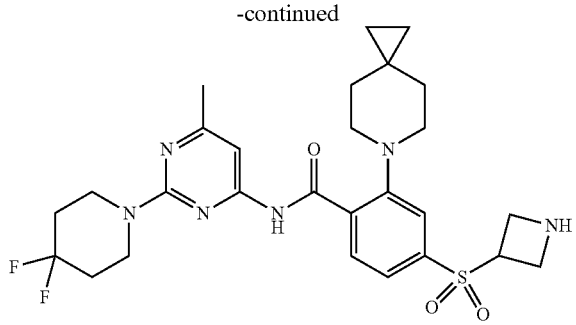

To a solution of 4-((1-(tert-butoxycarbonyl)azetidin-3-yl)sulfonyl)-2-(6-azaspiro[2.5]octan-6-yl)benzoic acid (2.54 g, 5.64 mmol, Int. 16) and HATU (3.22 g, 8.46 mmol, ChemPep) in DMF (35 mL), was added 2-(4,4-difluoropiperidin-1-yl)-6-methylpyrimidin-4-amine (1.93 g, 8.46 mmol, Int. 4) and DIPEA (2.46 mL, 14.09 mmol). The mixture was stirred at room temperature for 18 h. The mixture was diluted with saturated $Na_2CO_3$ and EtOAc. The organic was separated and washed with $Na_2CO_3$, water and brine, dried over $Na_2SO_4$ and concentrated in vacuo. The crude was purified by silica gel chromatography: 0-30%-60% EtOAc in heptane, m/z (ESI): 661.3 $(M+H)^+$. The residue was treated with DCM (8 mL) and TFA (4 mL) at room temperature for 30 min and concentrated in vacuo. The solid obtained was suspended in EtOAc and washed with 1N NaOH solution and the mixture was extracted with EtOAc. The organic extracts were washed with water and brine, dried over $Na_2SO_4$ and concentrated in vacuo. The crude was purified by silica gel chromatography: 0-20% MeOH in DCM with 2% NH4OH to give the title compound as a white solid. $^1$H NMR (400 MHz, METHANOL-$d_4$) δ ppm 8.35 (d, J=8.09 Hz, 1H), 7.90 (d, J=1.24 Hz, 1H), 7.81 (dd, J=1.66, 8.09 Hz, 1H), 7.46 (s, 1H), 4.46-4.60 (m, 1H), 3.97-4.06 (m, 6H), 3.76-3.86 (m, 2H), 3.10-3.21 (m, 4H), 2.37 (s, 3H), 1.93-2.01 (m, 4H), 1.73-1.88 (m, 4H), 0.45 (s, 4H). m/z (ESI): 561.2 $(M+H)^+$.

Example 22: 4-N-(2-(4,4-Difluoropiperidin-1-yl)-6-methylpyrimidin-4-yl)-4-((1-methylazetidin-3-yl)sulfonyl)-2-(6-azaspiro[2.5]octan-6-yl)benzamide

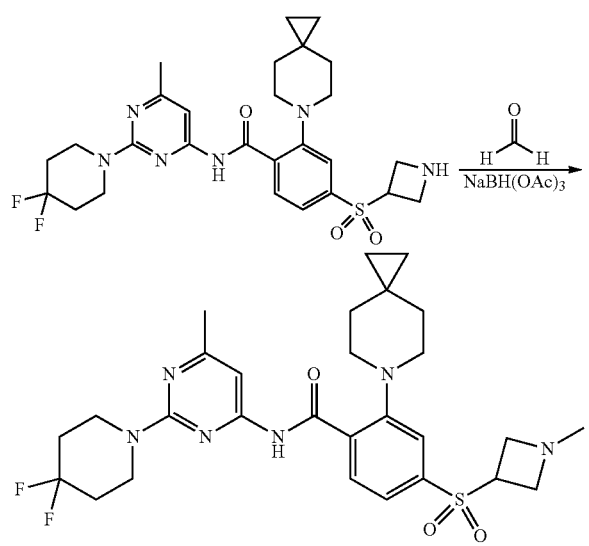

To a mixture of 4-(azetidin-3-ylsulfonyl)-N-(2-(4,4-difluoropiperidin-1-yl)-6-methylpyrimidin-4-yl)-2-(6-azaspiro[2.5]octan-6-yl)benzamide (0.045 g, 0.080 mmol, ex. 21), MeOH (1 mL), and formaldehyde with 10-15% MeOH (0.016 g, 0.482 mmol, Fisher) was added AcOH (0.037 mL, 0.642 mmol, Aldrich), followed by sodium triacetoxyborohydride (0.204 g, 0.963 mmol, Aldrich). The mixture was stirred at room temperature for 18 h and concentrated in vacuo. The acid was neutralized with 1N NaOH solution and the mixture was extracted with EtOAc. The organic phase was washed with water and brine, dried over $Na_2SO_4$ and concentrated in vacuo. Purification by silica gel chromatography: 0-100% EtOAc/EtOH (3/1) in heptane gave the title compound as a white solid. $^1$H NMR (400 MHz, CHLOROFORM-d) δ ppm 12.82 (br s, 1H), 8.44 (d, J=8.29 Hz, 1H), 7.82 (d, J=1.66 Hz, 1H), 7.73 (dd, J=1.76, 8.19 Hz, 1H), 7.46 (s, 1H), 3.97-4.11 (m, 5H), 3.60-3.90 (m, 4H), 3.12 (t, J=5.29 Hz, 4H), 2.44-2.57 (m, 3H), 2.39 (s, 3H), 1.68-2.06 (m, 8H), 0.43 (s, 4H). m/z (ESI): 575.3 $(M+H)^+$.

BIOLOGICAL EXAMPLES

The following assays were used in testing the exemplary compounds of the invention. Data for those examples tested in accordance with the procedures described below are presented in Table A below.

KIF18A Enzyme Assay: Microtubule-stimulated ATPase activity assay is used to measure KIF18A enzyme activity after treatment with compound. Compounds were 2-fold serially diluted in DMSO (Sigma Inc) over 22-point concentration range. Recombinant human KIF18A (1-467 His-tagged) protein was expressed using a baculovirus system and purified by affinity chromatography by Amgen Inc. Concentrations of KIF18A protein, microtubules (MT), and ATP in the reaction were optimized for standardized homogenous enzyme assay using ADP-Glo™ Kinase/ATPase Assay Kit (Promega Inc). The assay measures ADP formed from the ATPase reaction. Prepare reaction buffer [(15 mM Tris, pH 7.5 (Teknova Inc), 10 mM MgCl2 (JT Baker Inc), 0.01% Pluronic F-68 (Life Technologies Inc), 1 µM Taxol (Cytoskeleton Inc), and 30 µg/mL pig microtubules (Cytoskeleton Inc)]. Add compound and KIF18A protein (30 nM) to prepared reaction buffer and incubated for 15 minutes at room temperature, next add ATP (at $K_m$, 75 µM) to the reaction mixture and incubated for an additional 15 minutes at room temperature. Mix 5 µl of ADP-Glo™ Reagent and 2.5 µl of the reaction mixture and incubate for 40 minutes at room temperature. Add 10 µl ADP-Glo™ Detection Reagent and incubate for 40 minutes at room temperature. Read luminescence using EnVision microplate reader with ultraluminescence module (Perkin Elmer Inc). Concentration-response curve-fitting and $IC_{50}$ determination was performed using Genedata Screener Software (Standard 15.0.1, Genedata Inc) with a four-parameter logistic regression fit model.

Table A provides data for compounds exemplified in the present application and priority document thereof, as representative compounds of the present invention, as follows: compound name and biological data. ($IC_{50}$ in uM, where available. Ex. # refers to Example No.)

TABLE A

BIOLOGICAL DATA

| Ex. # | Compound Name | KIF18A ATPase IC$_{50}$ (μM) |
|---|---|---|
| 1 | N-(2-((1-Hydroxy-2-methylpropan-2-yl)amino)-6-methylpyrimidin-4-yl)-4-(methylsulfonyl)-2-(6-azaspiro[2.5]octan-6-yl)benzamide | 0.186 |
| 1-1 | (R)-N-(2-((1-Hydroxypropan-2-yl)amino)-6-methylpyrimidin-4-yl)-4-(methylsulfonyl)-2-(6-azaspiro[2.5]octan-6-yl)benzamide | 0.216 |
| 1-2 | (S)-N-(2-((1-Hydroxypropan-2-yl)amino)-6-methylpyrimidin-4-yl)-4-(methylsulfonyl)-2-(6-azaspiro[2.5]octan-6-yl)benzamide | 0.491 |
| 1-3 | N-(2-((2-Hydroxyethyl)amino)-6-methylpyrimidin-4-yl)-4-(methylsulfonyl)-2-(6-azaspiro[2.5]octan-6-yl)benzamide | 0.849 |
| 1-4 | (R)-N-(2-((2-Hydroxypropyl)amino)-6-methylpyrimidin-4-yl)-4-(methylsulfonyl)-2-(6-azaspiro[2.5]octan-6-yl)benzamide | 0.580 |
| 1-5 | (S)-N-(2-((2-Hydroxypropyl)amino)-6-methylpyrimidin-4-yl)-4-(methylsulfonyl)-2-(6-azaspiro[2.5]octan-6-yl)benzamide | 0.451 |
| 1-6 | N-(6-Methyl-2-(3,3,3-trifluoropropoxy)pyrimidin-4-yl)-4-(N-(3-methyloxetan-3-yl)sulfamoyl)-2-(6-azaspiro[2.5]octan-6-yl)benzamide | 0.032 |
| 1-7 | N-(2-((1-hydroxy-2-methylpropan-2-yl)amino)-6-methylpyrimidin-4-yl)-4-(N-(3-methyloxetan-3-yl)sulfamoyl)-2-(6-azaspiro[2.5]octan-6-yl)benzamide | 0.168 |
| 2 | N-(2-(2-Hydroxypropan-2-yl)pyrimidin-4-yl)-4-(N-(3-methyloxetan-3-yl)sulfamoyl)-2-(6-azaspiro[2.5]octan-6-yl)benzamide | 0.143 |
| 2-1 | N-(2-(2-Hydroxypropan-2-yl)-6-methylpyrimidin-4-yl)-4-(N-(3-methyloxetan-3-yl)sulfamoyl)-2-(6-azaspiro[2.5]octan-6-yl)benzamide | 0.065 |
| 2-2 | (R)-N-(2-(2-methylmorpholino)pyrimidin-4-yl)-4-(N-(3-methyloxetan-3-yl)sulfamoyl)-2-(6-azaspiro[2.5]octan-6-yl)benzamide | 0.068 |
| 2-3 | (R)-N-(6-Methyl-2-(2-methylmorpholino)pyrimidin-4-yl)-4-(N-(3-methyloxetan-3-yl)sulfamoyl)-2-(6-azaspiro[2.5]octan-6-yl)benzamide | 0.115 |
| 2-4 | N-(2-(4,4-Difluoropiperidin-1-yl)pyridin-4-yl)-4-(N-(3-methyloxetan-3-yl)sulfamoyl)-2-(6-azaspiro[2.5]octan-6-yl)benzamide | 0.029 |
| 2-5 | N-(2-(4,4-Difluoropiperidin-1-yl)-6-methylpyrimidin-4-yl)-4-(N-(3-methyloxetan-3-yl)sulfamoyl)-2-(6-azaspiro[2.5]octan-6-yl)benzamide | 0.103 |
| 2-6 | N-(2-(4,4-Difluoropiperidin-1-yl)-6-methylpyrimidin-4-yl)-4-(methylsulfonyl)-2-(6-azaspiro[2.5]octan-6-yl)benzamide | 0.260 |
| 2-7 | (R)-N-(2-(2-Methylmorpholino)pyrimidin-4-yl)-4-(methylsulfonyl)-2-(6-azaspiro[2.5]octan-6-yl)benzamide | 0.240 |
| 2-8 | N-(2-(4,4-Difluoropiperidin-1-yl)-6-methylpyrimidin-4-yl)-4-((1-methylcyclopropane)-1-sulfonamido)-2-(6-azaspiro[2.5]octan-6-yl)benzamide | 0.713 |
| 3 | (R)-4-((2-Hydroxyethyl)sulfonamido)-N-(6-methyl-2-(2-methylmorpholino)pyrimidin-4-yl)-2-(6-azaspiro[2.5]octan-6-yl)benzamide | 0.057 |
| 4 | N-(2-(4,4-Difluoropiperidin-1-yl)-6-methylpyrimidin-4-yl)-4-((2-hydroxyethyl)sulfonamido)-2-(6-azaspiro[2.5]octan-6-yl)benzamide | 0.071 |
| 5-1 | (R)-N-(2-(4,4-difluoropiperidin-1-yl)-6-methylpyrimidin-4-yl)-4-((2-hydroxy-1-methylethyl)sulfonamido)-2-(6-azaspiro[2.5]octan-6-yl)benzamide | 0.062 |
| 5-2 | (S)-N-(2-(4,4-difluoropiperidin-1-yl)-6-methylpyrimidin-4-yl)-4-((2-hydroxy-1-methylethyl)sulfonamido)-2-(6-azaspiro[2.5]octan-6-yl)benzamide | 0.070 |
| 6-1 | 4-((Fluoromethyl)sulfonamido)-N-(2-(4-fluoropiperidin-1-yl)-6-methylpyrimidin-4-yl)-2-(6-azaspiro[2.5]octan-6-yl)benzamide | 0.062 |
| 6-2 | N-(2-(4,4-Difluoropiperidin-1-yl)-6-methylpyrimidin-4-yl)-4-((fluoromethyl)sulfonamido)-2-(6-azaspiro[2.5]octan-6-yl)benzamide | 0.042 |
| 6-3 | (R)-4-((Fluoromethyl)sulfonamido)-N-(6-methyl-2-(2-methylmorpholino)pyrimidin-4-yl)-2-(6-azaspiro[2.5]octan-6-yl)benzamide | 0.079 |
| 6-4 | (R)-4-((2-Hydroxyethyl)sulfonamido)-N-(2-(2-methylmorpholino)pyrimidin-4-yl)-2-(6-azaspiro[2.5]octan-6-yl)benzamide | 0.032 |
| 6-5 | (R)-N-(6-Methyl-2-(2-methylmorpholino)pyrimidin-4-yl)-4-(methylsulfonamido)-2-(6-azaspiro[2.5]octan-6-yl)benzamide | 0.120 |
| 6-6 | (R)-4-(Ethylsulfonamido)-N-(6-methyl-2-(2-methylmorpholino)pyrimidin-4-yl)-2-(6-azaspiro[2.5]octan-6-yl)benzamide | 0.067 |
| 6-7 | N-(2-(4,4-Difluoropiperidin-1-yl)-6-methylpyrimidin-4-yl)-4-(ethylsulfonamido)-2-(6-azaspiro[2.5]octan-6-yl)benzamide | 0.122 |
| 6-8 | (R)-4-((3-Hydroxypropyl)sulfonamido)-N-(6-methyl-2-(2-methylmorpholino)pyrimidin-4-yl)-2-(6-azaspiro[2.5]octan-6-yl)benzamide | 0.107 |
| 6-9 | N-(2-(4,4-Difluoropiperidin-1-yl)-6-methylpyrimidin-4-yl)-4-(3,3-dioxido-1,3,4-oxathiazinan-4-yl)-2-(6-azaspiro[2.5]octan-6-yl)benzamide | 0.246 |
| 6-10 | 4-(Cyclopentanesulfonamido)-N-(2-(4,4-difluoropiperidin-1-yl)-6-methylpyrimidin-4-yl)-2-(6-azaspiro[2.5]octan-6-yl)benzamide | 2.42 |
| 6-11 | 4-(Cyclobutanesulfonamido)-N-(2-(4,4-difluoropiperidin-1-yl)-6-methylpyrimidin-4-yl)-2-(6-azaspiro[2.5]octan-6-yl)benzamide | 0.127 |
| 6-12 | N-(2-(4,4-Difluoropiperidin-1-yl)-6-methylpyrimidin-4-yl)-4-(oxetane-3-sulfonamido)-2-(6-azaspiro[2.5]octan-6-yl)benzamide | 0.040 |

TABLE A-continued

BIOLOGICAL DATA

| Ex. # | Compound Name | KIF18A ATPase IC$_{50}$ (μM) |
|---|---|---|
| 6-13 | 4-(Cyclobutanesulfonamido)-N-(2-(3,3-difluoroazetidin-1-yl)-6-methylpyrimidin-4-yl)-2-(6-azaspiro[2.5]octan-6-yl)benzamide | 0.052 |
| 6-14 | N-(2-(4,4-Difluoropiperidin-1-yl)-6-methylpyrimidin-4-yl)-4-((1,1-dimethylethyl)sulfonamido)-2-(6-azaspiro[2.5]octan-6-yl)benzamide | 0.413 |
| 6-15 | N-(2-(4,4-Difluoropiperidin-1-yl)-6-methylpyrimidin-4-yl)-4-((3-hydroxypropyl)sulfonamido)-2-(6-azaspiro[2.5]octan-6-yl)benzamide | 0.086 |
| 6-16 | 4-(Cyclopropanesulfonamido)-N-(2-(4,4-difluoropiperidin-1-yl)-6-methylpyrimidin-4-yl)-2-(6-azaspiro[2.5]octan-6-yl)benzamide | 0.052 |
| 6-17 | N-(2-(4,4-Difluoropiperidin-1-yl)-6-methylpyrimidin-4-yl)-4-((2-methoxyethyl)sulfonamido)-2-(6-azaspiro[2.5]octan-6-yl)benzamide | 0.032 |
| 6-18 | 4-((Cyclopropylmethyl)sulfonamido)-N-(2-(4,4-difluoropiperidin-1-yl)-6-methylpyrimidin-4-yl)-2-(6-azaspiro[2.5]octan-6-yl)benzamide | 0.085 |
| 6-19 | N-(2-(4,4-Difluoropiperidin-1-yl)-6-methylpyrimidin-4-yl)-4-(((3-hydroxyoxetan-3-yl)methyl)sulfonamido)-2-(6-azaspiro[2.5]octan-6-yl)benzamide | 0.039 |
| 6-20 | N-(2-(4,4-Difluoropiperidin-1-yl)-6-methylpyrimidin-4-yl)-4-((2-hydroxy-1,1-dimethylethyl)sulfonamido)-2-(6-azaspiro[2.5]octan-6-yl)benzamide | 0.049 |
| 6-21 | N-(2-(4,4-Difluoropiperidin-1-yl)-6-methylpyrimidin-4-yl)-4-(methylsulfonamido)-2-(6-azaspiro[2.5]octan-6-yl)benzamide | 0.039 |
| 6-22 | N-(2-(4,4-Difluoropiperidin-1-yl)-6-methylpyrimidin-4-yl)-4-((1-methylethyl)sulfonamido)-2-(6-azaspiro[2.5]octan-6-yl)benzamide | 0.151 |
| 6-23-1 | 4-(((S)-2-Hydroxy-1-methylethyl)sulfonamido)-N-(6-methyl-2-((R)-2-methylmorpholino)pyrimidin-4-yl)-2-(6-azaspiro[2.5]octan-6-yl)benzamide | 0.039 |
| 6-23-2 | 4-(((R)-2-Hydroxy-1-methylethyl)sulfonamido)-N-(6-methyl-2-((R)-2-methylmorpholino)pyrimidin-4-yl)-2-(6-azaspiro[2.5]octan-6-yl)benzamide | 0.0373 |
| 6-24-1 | 4-(((S)-2-Hydroxy-1-methylethyl)sulfonamido)-N-(2-((R)-2-methylmorpholino)pyrimidin-4-yl)-2-(6-azaspiro[2.5]octan-6-yl)benzamide | 0.0174 |
| 6-24-2 | 4-(((R)-2-hydroxy-1-methylethyl)sulfonamido)-N-(2-((R)-2-methylmorpholino)pyrimidin-4-yl)-2-(6-azaspiro[2.5]octan-6-yl)benzamide | 0.028 |
| 6-25-1 | (S)-N-(2-(4-fluoropiperidin-1-yl)-6-methylpyrimidin-4-yl)-4-((2-hydroxy-1-methylethyl)sulfonamido)-2-(6-azaspiro[2.5]octan-6-yl)benzamide | 0.047 |
| 6-25-2 | (R)-N-(2-(4-Fluoropiperidin-1-yl)-6-methylpyrimidin-4-yl)-4-((2-hydroxy-1-methylethyl)sulfonamido)-2-(6-azaspiro[2.5]octan-6-yl)benzamide | 0.041 |
| 6-26-1 | (S)-N-(2-(4,4-Difluoropiperidin-1-yl)pyrimidin-4-yl)-4-((2-hydroxy-1-methylethyl)sulfonamido)-2-(6-azaspiro[2.5]octan-6-yl)benzamide | 0.031 |
| 6-26-2 | (R)-N-(2-(4,4-Difluoropiperidin-1-yl)pyrimidin-4-yl)-4-((2-hydroxy-1-methylethyl)sulfonamido)-2-(6-azaspiro[2.5]octan-6-yl)benzamide | 0.021 |
| 6-27-1 | 4-(((R)-2-Hydroxypropyl)sulfonamido)-N-(6-methyl-2-((R)-2-methylmorpholino)pyrimidin-4-yl)-2-(6-azaspiro[2.5]octan-6-yl)benzamide | 0.162 |
| 6-27-2 | 4-(((S)-2-Hydroxypropyl)sulfonamido)-N-(6-methyl-2((R)-2-methylmorpholino)pyrimidin-4-yl)-2-(6-azaspiro[2.5]octan-6-yl)benzamide | 0.151 |
| 6-28-1 | (R)-4-((2-Hydroxypropyl)sulfonamido)-N-(6-methyl-2-(3,3,3-trifluoropropoxy)pyrimidin-4-yl)-2-(6-azaspiro[2.5]octan-6-yl)benzamide | 0.068 |
| 6-28-2 | (S)-4-((2-Hydroxypropyl)sulfonamido)-N-(6-methyl-2-(3,3,3-trifluoropropoxy)pyrimidin-4-yl)-2-(6-azaspiro[2.5]octan-6-yl)benzamide | 0.071 |
| 6-29 | N-(2-(4,4-Difluoropiperidin-1-yl)pyridin-4-yl)-4-((2-hydroxyethyl)sulfonamido)-2-(6-azaspiro[2.5]octan-6-yl)benzamide | 0.017 |
| 6-30 | N-(2-(4,4-Difluoropiperidin-1-yl)-6-methylpyridin-4-yl)-4-((2-hydroxyethyl)sulfonamido)-2-(6-azaspiro[2.5]octan-6-yl)benzamide | 0.0384 |
| 6-31-1 | (R)-N-(2-(4,4-Difluoropiperidin-1-yl)-6-methylpyrimidin-4-yl)-4-((1-(1-hydroxyethyl)cyclopropane)-1-sulfonamido)-2-(6-azaspiro[2.5]octan-6-yl)benzamide | 0.324 |
| 6-31-2 | (S)-N-(2-(4,4-Difluoropiperidin-1-yl)-6-methylpyrimidin-4-yl)-4-((1-(1-hydroxyethyl)cyclopropane)-1-sulfonamido)-2-(6-azaspiro[2.5]octan-6-yl)benzamide | 0.281 |
| 6-32-1 | (R)-N-(2-(4,4-Difluoropiperidin-1-yl)-6-methylpyrimidin-4-yl)-4-((2-hydroxypropyl)sulfonamido)-2-(6-azaspiro[2.5]octan-6-yl)benzamide | 0.112 |
| 6-32-2 | (S)-N-(2-(4,4-Difluoropiperidin-1-yl)-6-methylpyrimidin-4-yl)-4-((2-hydroxypropyl)sulfonamido)-2-(6-azaspiro[2.5]octan-6-yl)benzamide | 0.141 |
| 6-33-1 | 4-(((S)-2-Hydroxypropyl)sulfonamido)-N-(2-((R)-2-methylmorpholino)pyrimidin-4-yl)-2-(6-azaspiro[2.5]octan-6-yl)benzamide | 0.115 |
| 6-33-2 | 4-(((R)-2-hydroxypropyl)sulfonamido)-N-(2-((R)-2-methylmorpholino)pyrimidin-4-yl)-2-(6-azaspiro[2.5]octan-6-yl)benzamide | 0.086 |
| 6-34 | 5-Chloro-N-(2-(4,4-difluoropiperidin-1-yl)-6-methylpyrimidin-4-yl)-4-((2-hydroxyethyl)sulfonamido)-2-(6-azaspiro[2.5]octan-6-yl)benzamide | 0.0922 |

TABLE A-continued

BIOLOGICAL DATA

| Ex. # | Compound Name | KIF18A ATPase IC$_{50}$ (μM) |
|---|---|---|
| 6-35 | N-(2-(4,4-Difluoropiperidin-1-yl)-6-methylpyrimidin-4-yl)-4-((2-hydroxyethyl)sulfonamido)-5-methyl-2-(6-azaspiro[2.5]octan-6-yl)benzamide | 0.144 |
| 6-36 | N-(2-(4,4-Difluoropiperidin-1-yl)-6-methylpyrimidin-4-yl)-4-((2-hydroxyethyl)sulfonamido)-5-methoxy-2-(6-azaspiro[2.5]octan-6-yl)benzamide | 0.114 |
| 6-37 | N-(2-(4,4-Difluoropiperidin-1-yl)-6-(2-hydroxypropan-2-yl)pyrimidin-4-yl)-4-((2-hydroxyethyl)sulfonamido)-2-(6-azaspiro[2.5]octan-6-yl)benzamide | 0.125 |
| 6-38 | N-(2-(4,4-Difluoropiperidin-1-yl)-6-ethylpyrimidin-4-yl)-4-((2-hydroxyethyl)sulfonamido)-2-(6-azaspiro[2.5]octan-6-yl)benzamide | 0.060 |
| 6-39 | N-(6-Cyclopropyl-2-(4,4-difluoropiperidin-1-yl)pyrimidin-4-yl)-4-((2-hydroxyethyl)sulfonamido)-2-(6-azaspiro[2.5]octan-6-yl)benzamide | 0.225 |
| 6-40 | (R)-4-((2-Hydroxyethyl)sulfonamido)-N-(6-(2-hydroxypropan-2-yl)-2-(2-methylmorpholino)pyrimidin-4-yl)-2-(6-azaspiro[2.5]octan-6-yl)benzamide | 0.161 |
| 7 | N-(2-(3,3-Difluoroazetidin-1-yl)-6-methylpyrimidin-4-yl)-4-((2-hydroxyethyl)sulfonamido)-2-(6-azaspiro[2.5]octan-6-yl)benzamide | 0.023 |
| 8-1 | (R)-N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide | 0.091 |
| 8-2 | (S)-N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide | 0.073 |
| 9-1 | (R)-5-Fluoro-4-((2-hydroxyethyl)sulfonamido)-N-(2-(2-methylmorpholino)pyrimidin-4-yl)-2-(6-azaspiro[2.5]octan-6-yl)benzamide | 0.078 |
| 9-2 | (R)-5-Fluoro-4-((2-hydroxyethyl)sulfonamido)-N-(6-methyl-2-(2-methylmorpholino)pyrimidin-4-yl)-2-(6-azaspiro[2.5]octan-6-yl)benzamide | 0.158 |
| 10-1 | (R)-N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide | 0.083 |
| 10-2 | (S)-N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide | 0.073 |
| 11-1 | (S)-4-((2-Hydroxyethyl)sulfonamido)-N-(2-(2-methylmorpholino)pyrimidin-4-yl)-2-(6-azaspiro[2.5]octan-6-yl)benzamide | 0.037 |
| 11-2 | 4-((2-Hydroxyethyl)sulfonamido)-N-(2-isopropyl-6-methylpyrimidin-4-yl)-2-(6-azaspiro[2.5]octan-6-yl)benzamide | 0.027 |
| 11-3 | N-(2-Cyclopropyl-6-methylpyrimidin-4-yl)-4-((2-hydroxyethyl)sulfonamido)-2-(6-azaspiro[2.5]octan-6-yl)benzamide | 0.049 |
| 11-4 | N-(2-Cyclobutoxy-6-methylpyrimidin-4-yl)-4-((2-hydroxyethyl)sulfonamido)-2-(6-azaspiro[2.5]octan-6-yl)benzamide | 0.018 |
| 11-5 | N-(2-(3-Fluoroazetidin-1-yl)-6-methylpyrimidin-4-yl)-4-((2-hydroxyethyl)sulfonamido)-2-(6-azaspiro[2.5]octan-6-yl)benzamide | 0.032 |
| 11-6 | N-(2-(3-Fluoroazetidin-1-yl)pyrimidin-4-yl)-4-((2-hydroxyethyl)sulfonamido)-2-(6-azaspiro[2.5]octan-6-yl)benzamide | 0.068 |
| 11-7 | N-(2-(3,3-Difluoroazetidin-1-yl)pyrimidin-4-yl)-4-((2-hydroxyethyl)sulfonamido)-2-(6-azaspiro[2.5]octan-6-yl)benzamide | 0.023 |
| 11-8 | 4-((2-Hydroxyethyl)sulfonamido)-N-(6-methyl-2-(2-oxa-6-azaspiro[3.3]heptan-6-yl)pyrimidin-4-yl)-2-(6-azaspiro[2.5]octan-6-yl)benzamide | 0.640 |
| 11-9 | 4-((2-Hydroxyethyl)sulfonamido)-N-(6-methyl-2-(6-oxa-1-azaspiro[3.3]heptan-1-yl)pyrimidin-4-yl)-2-(6-azaspiro[2.5]octan-6-yl)benzamide | 0.128 |
| 11-10 | N-(2-(3-(Difluoromethoxy)azetidin-1-yl)-6-methylpyrimidin-4-yl)-4-((2-hydroxyethyl)sulfonamido)-2-(6-azaspiro[2.5]octan-6-yl)benzamide | 0.192 |
| 11-12 | N-(2-(1,1-Difluoro-5-azaspiro[2.3]hexan-5-yl)-6-methylpyrimidin-4-yl)-4-((2-hydroxyethyl)sulfonamido)-2-(6-azaspiro[2.5]octan-6-yl)benzamide | 0.093 |
| 11-13 | 4-((2-Hydroxyethyl)sulfonamido)-N-(6-methyl-2-(3-(trifluoromethyl)azetidin-1-yl)pyrimidin-4-yl)-2-(6-azaspiro[2.5]octan-6-yl)benzamide | 0.067 |
| 11-14 | N-(2-(3-Cyanoazetidin-1-yl)-6-methylpyrimidin-4-yl)-4-((2-hydroxyethyl)sulfonamido)-2-(6-azaspiro[2.5]octan-6-yl)benzamide | 0.172 |
| 11-15 | 4-((2-Hydroxyethyl)sulfonamido)-N-(2-(3-(2-hydroxypropan-2-yl)azetidin-1-yl)-6-methylpyrimidin-4-yl)-2-(6-azaspiro[2.5]octan-6-yl)benzamide | 0.935 |
| 11-16 | N-(2-(3-Hydroxy-3-methylazetidin-1-yl)-6-methylpyrimidin-4-yl)-4-((2-hydroxyethyl)sulfonamido)-2-(6-azaspiro[2.5]octan-6-yl)benzamide | 1.01 |
| 11-17 | N-(2-(3-Cyclopropyl-3-hydroxyazetidin-1-yl)-6-methylpyrimidin-4-yl)-4-((2-hydroxyethyl)sulfonamido)-2-(6-azaspiro[2.5]octan-6-yl)benzamide | 1.09 |
| 11-18 | 4-((2-Hydroxyethyl)sulfonamido)-N-(6-methyl-2-(5-azaspiro[2.3]hexan-5-yl)pyrimidin-4-yl)-2-(6-azaspiro[2.5]octan-6-yl)benzamide | 0.064 |

TABLE A-continued

BIOLOGICAL DATA

| Ex. # | Compound Name | KIF18A ATPase IC$_{50}$ (μM) |
|---|---|---|
| 11-19 | N-(2-(3-Hydroxy-3-(trifluoromethyl)azetidin-1-yl)-6-methylpyrimidin-4-yl)-4-((2-hydroxyethyl)sulfonamido)-2-(6-azaspiro[2.5]octan-6-yl)benzamide | 0.205 |
| 11-20 | N-(2-(Azetidin-1-yl)-6-methylpyrimidin-4-yl)-4-((2-hydroxyethyl)sulfonamido)-2-(6-azaspiro[2.5]octan-6-yl)benzamide | 0.0483 |
| 11-21 | (S)-N-(2-(3-(1-Hydroxyethyl)azetidin-1-yl)-6-methylpyrimidin-4-yl)-4-((2-hydroxyethyl)sulfonamido)-2-(6-azaspiro[2.5]octan-6-yl)benzamide | 0.704 |
| 11-22 | 4-(Cyclopropanesulfonamido)-N-(2-(3,3-difluoroazetidin-1-yl)-6-methylpyrimidin-4-yl)-2-(6-azaspiro[2.5]octan-6-yl)benzamide | 0.788 |
| 11-23 | N-(2-(3,3-Difluoroazetidin-1-yl)-6-methylpyrimidin-4-yl)-4-(oxetane-3-sulfonamido)-2-(6-azaspiro[2.5]octan-6-yl)benzamide | 0.0489 |
| 11-24 | N-(2-(3,3-Difluoroazetidin-1-yl)-6-methylpyrimidin-4-yl)-4-(methylsulfonamido)-2-(6-azaspiro[2.5]octan-6-yl)benzamide | 0.0551 |
| 11-25 | 4-((2-Hydroxyethyl)sulfonamido)-N-(6-methyl-2-(5-azaspiro[2.4]heptan-5-yl)pyrimidin-4-yl)-2-(6-azaspiro[2.5]octan-6-yl)benzamide | 0.0176 |
| 11-26 | 4-((2-Hydroxyethyl)sulfonamido)-N-(6-methyl-2-(pyrrolidin-1-yl)pyrimidin-4-yl)-2-(6-azaspiro[2.5]octan-6-yl)benzamide | 0.0716 |
| 11-27 | (R)-N-(2-(3-Fluoro-3-methylpyrrolidin-1-yl)-6-methylpyrimidin-4-yl)-4-((2-hydroxyethyl)sulfonamido)-2-(6-azaspiro[2.5]octan-6-yl)benzamide | 0.020 |
| 11-28 | N-(2-(2-Azabicyclo[3.1.0]hexan-2-yl)-6-methylpyrimidin-4-yl)-4-((2-hydroxyethyl)sulfonamido)-2-(6-azaspiro[2.5]octan-6-yl)benzamide | 0.059 |
| 11-29 | N-(2-((1R,5S)-3-Azabicyclo[3.1.0]hexan-3-yl)-6-methylpyrimidin-4-yl)-4-((2-hydroxyethyl)sulfonamido)-2-(6-azaspiro[2.5]octan-6-yl)benzamide | 0.020 |
| 11-30 | N-(2-(3,3-Difluoropyrrolidin-1-yl)-6-methylpyrimidin-4-yl)-4-((2-hydroxyethyl)sulfonamido)-2-(6-azaspiro[2.5]octan-6-yl)benzamide | 0.033 |
| 11-31 | 4-((2-Hydroxyethyl)sulfonamido)-N-(6-methyl-2-(6-azaspiro[2.5]octan-6-yl)pyrimidin-4-yl)-2-(6-azaspiro[2.5]octan-6-yl)benzamide | 0.146 |
| 11-32 | N-(2-((1R)-1-Hydroxy-3-azabicyclo[3.1.0]hexan-3-yl)-6-methylpyrimidin-4-yl)-4-((2-hydroxyethyl)sulfonamido)-2-(6-azaspiro[2.5]octan-6-yl)benzamide | 0.193 |
| 11-33 | N-(2-(4-Cyanopiperidin-1-yl)-6-methylpyrimidin-4-yl)-4-((2-hydroxyethyl)sulfonamido)-2-(6-azaspiro[2.5]octan-6-yl)benzamide | 0.088 |
| 11-34 | (R)-N-(2-(3-Cyanopiperidin-1-yl)-6-methylpyrimidin-4-yl)-4-((2-hydroxyethyl)sulfonamido)-2-(6-azaspiro[2.5]octan-6-yl)benzamide | 0.092 |
| 11-35 | (S)-N-(2-(3-Cyanopiperidin-1-yl)-6-methylpyrimidin-4-yl)-4-((2-hydroxyethyl)sulfonamido)-2-(6-azaspiro[2.5]octan-6-yl)benzamide | 0.043 |
| 11-36 | 4-((2-Hydroxyethyl)sulfonamido)-N-(6-methyl-2-(piperidin-1-yl)pyrimidin-4-yl)-2-(6-azaspiro[2.5]octan-6-yl)benzamide | 0.082 |
| 11-37 | 4-((2-Hydroxyethyl)sulfonamido)-N-(2-(4-hydroxypiperidin-1-yl)-6-methylpyrimidin-4-yl)-2-(6-azaspiro[2.5]octan-6-yl)benzamide | 0.144 |
| 11-38 | N-(2-(4-Hydroxy-4-methylpiperidin-1-yl)-6-methylpyrimidin-4-yl)-4-((2-hydroxyethyl)sulfonamido)-2-(6-azaspiro[2.5]octan-6-yl)benzamide | 0.065 |
| 11-39 | N-(2-(3,3-Difluoropiperidin-1-yl)-6-methylpyrimidin-4-yl)-4-((2-hydroxyethyl)sulfonamido)-2-(6-azaspiro[2.5]octan-6-yl)benzamide | 0.045 |
| 11-40 | N-(2-(4,4-Difluoropiperidin-1-yl)-6-methylpyrimidin-4-yl)-4-((2-hydroxyethyl)sulfonamido)-2-(7-azaspiro[3.5]nonan-7-yl)benzamide | 0.109 |
| 11-41 | N-(2-(4,4-Difluoropiperidin-1-yl)-6-methylpyrimidin-4-yl)-2-(4,4-dimethylpiperidin-1-yl)-4-((2-hydroxyethyl)sulfonamido)benzamide | 0.127 |
| 11-42 | N-(2-((1R)-1-Hydroxy-3-azabicyclo[4.1.0]heptan-3-yl)-6-methylpyrimidin-4-yl)-4-((2-hydroxyethyl)sulfonamido)-2-(6-azaspiro[2.5]octan-6-yl)benzamide | 0.034 |
| 11-43 | N-(2-((1R,6R)-3-Azabicyclo[4.1.0]heptan-3-yl)-6-methylpyrimidin-4-yl)-4-((2-hydroxyethyl)sulfonamido)-2-(6-azaspiro[2.5]octan-6-yl)benzamide | 0.035 |
| 11-44 | N-(2-((1S,6R)-2-Azabicyclo[4.1.0]heptan-2-yl)-6-methylpyrimidin-4-yl)-4-((2-hydroxyethyl)sulfonamido)-2-(6-azaspiro[2.5]octan-6-yl)benzamide | 0.033 |
| 11-45 | (S)-4-((2-Hydroxyethyl)sulfonamido)-N-(6-methyl-2-(2-methylmorpholino)pyrimidin-4-yl)-2-(6-azaspiro[2.5]octan-6-yl)benzamide | 0.035 |
| 11-46 | N-(2-(2,2-Dimethylmorpholino)-6-methylpyrimidin-4-yl)-4-((2-hydroxyethyl)sulfonamido)-2-(6-azaspiro[2.5]octan-6-yl)benzamide | 0.150 |
| 11-47 | 4-((2-Hydroxyethyl)sulfonamido)-N-(6-methyl-2-(4-oxa-7-azaspiro[2.5]octan-7-yl)pyrimidin-4-yl)-2-(6-azaspiro[2.5]octan-6-yl)benzamide | 0.095 |
| 11-48 | N-(2-((3S,5R)-3,5-Dimethylmorpholino)-6-methylpyrimidin-4-yl)-4-((2-hydroxyethyl)sulfonamido)-2-(6-azaspiro[2.5]octan-6-yl)benzamide | 0.095 |
| 11-49 | N-(2-((3S,5S)-3,5-Dimethylmorpholino)-6-methylpyrimidin-4-yl)-4-((2-hydroxyethyl)sulfonamido)-2-(6-azaspiro[2.5]octan-6-yl)benzamide | 0.245 |
| 11-50 | N-(2-((3R,5R)-3,5-Dimethylmorpholino)-6-methylpyrimidin-4-yl)-4-((2-hydroxyethyl)sulfonamido)-2-(6-azaspiro[2.5]octan-6-yl)benzamide | 0.187 |
| 11-51 | N-(2-(4-Fluoropiperidin-1-yl)-6-methylpyrimidin-4-yl)-4-((2-hydroxyethyl)sulfonamido)-2-(6-azaspiro[2.5]octan-6-yl)benzamide | 0.020 |
| 11-52 | N-(2-(4-Fluoro-4-methylpiperidin-1-yl)-6-methylpyrimidin-4-yl)-4-((2-hydroxyethyl)sulfonamido)-2-(6-azaspiro[2.5]octan-6-yl)benzamide | 0.063 |
| 11-53 | (S)-4-((2-Hydroxyethyl)sulfonamido)-N-(2-(3-hydroxypiperidin-1-yl)-6-methylpyrimidin-4-yl)-2-(6-azaspiro[2.5]octan-6-yl)benzamide | 0.105 |

TABLE A-continued

BIOLOGICAL DATA

| Ex. # | Compound Name | KIF18A ATPase IC$_{50}$ (μM) |
|---|---|---|
| 11-54 | (R)-4-((2-Hydroxyethyl)sulfonamido)-N-(2-(3-hydroxypiperidin-1-yl)-6-methylpyrimidin-4-yl)-2-(6-azaspiro[2.5]octan-6-yl)benzamide | 0.074 |
| 11-55 | (R)-N-(2-(3-Fluoro-3-methylpiperidin-1-yl)-6-methylpyrimidin-4-yl)-4-((2-hydroxyethyl)sulfonamido)-2-(6-azaspiro[2.5]octan-6-yl)benzamide | 0.041 |
| 11-56 | N-(2-(4-Fluoropiperidin-1-yl)pyrimidin-4-yl)-4-((2-hydroxyethyl)sulfonamido)-2-(6-azaspiro[2.5]octan-6-yl)benzamide | 0.022 |
| 11-57 | N-(2-(4,4-Difluoropiperidin-1-yl)pyrimidin-4-yl)-4-((2-hydroxyethyl)sulfonamido)-2-(6-azaspiro[2.5]octan-6-yl)benzamide | 0.022 |
| 11-58 | N-(2-(4,4-Difluoropiperidin-1-yl)-6-methylpyrimidin-4-yl)-2-fluoro-4-((2-hydroxyethyl)sulfonamido)-6-(6-azaspiro[2.5]octan-6-yl)benzamide | 0.071 |
| 11-59 | 4-((2-Hydroxyethyl)sulfonamido)-2-(6-azaspiro[2.5]octan-6-yl)-N-(2-(3,3,3-trifluoropropoxy)pyridin-4-yl)benzamide | 0.058 |
| 11-60 | 4-((2-Hydroxyethyl)sulfonamido)-N-(2-methyl-6-(3,3,3-trifluoropropoxy)pyridin-4-yl)-2-(6-azaspiro[2.5]octan-6-yl)benzamide | 0.084 |
| 11-61 | 4-((2-Hydroxyethyl)sulfonamido)-N-(6-methyl-2-(3,3,3-trifluoropropoxy)pyrimidin-4-yl)-2-(6-azaspiro[2.5]octan-6-yl)benzamide | 0.070 |
| 11-62 | N-(2-((1-Hydroxy-2-methylpropan-2-yl)amino)-6-methylpyrimidin-4-yl)-4-((2-hydroxyethyl)sulfonamido)-2-(6-azaspiro[2.5]octan-6-yl)benzamide | 0.018 |
| 11-63 | N-(2-(4,4-Difluoropiperidin-1-yl)-3-fluoropyridin-4-yl)-4-((2-hydroxyethyl)sulfonamido)-2-(6-azaspiro[2.5]octan-6-yl)benzamide | 0.022 |
| 11-64 | N-(2-(4,4-Difluoropiperidin-1-yl)-3-fluoro-6-methylpyridin-4-yl)-4-((2-hydroxyethyl)sulfonamido)-2-(6-azaspiro[2.5]octan-6-yl)benzamide | 0.054 |
| 11-65 | (R)-4-((2-Hydroxyethyl)sulfonamido)-N-(2-(2-methylmorpholino)pyridin-4-yl)-2-(6-azaspiro[2.5]octan-6-yl)benzamide | 0.151 |
| 11-66 | (R)-4-((2-Hydroxyethyl)sulfonamido)-N-(2-methyl-6-(2-methylmorpholino)pyridin-4-yl)-2-(6-azaspiro[2.5]octan-6-yl)benzamide | 0.148 |
| 11-67 | N-(2-(4,4-Difluoropiperidin-1-yl)-6-methylpyrimidin-4-yl)-5-fluoro-4-((2-hydroxyethyl)sulfonamido)-2-(6-azaspiro[2.5]octan-6-yl)benzamide | 0.034 |
| 11-68 | N-(2-(3,3-Difluoroazetidin-1-yl)-6-methylpyrimidin-4-yl)-4-((1-(hydroxymethyl)cyclopropane)-1-sulfonamido)-2-(6-azaspiro[2.5]octan-6-yl)benzamide | 0.053 |
| 11-69 | N-(2-(4,4-Difluoropiperidin-1-yl)-6-methylpyrimidin-4-yl)-4-((1-(hydroxymethyl)cyclopropane)-1-sulfonamido)-2-(6-azaspiro[2.5]octan-6-yl)benzamide | 0.099 |
| 11-70 | (S)-N-(2-(3,3-Difluoroazetidin-1-yl)-6-methylpyrimidin-4-yl)-2-(6-azaspiro[2.5]octan-6-yl)-4-((tetrahydrofuran)-3-sulfonamido)benzamide | 0.072 |
| 11-71 | (R)-N-(2-(3,3-Difluoroazetidin-1-yl)-6-methylpyrimidin-4-yl)-2-(6-azaspiro[2.5]octan-6-yl)-4-((tetrahydrofuran)-3-sulfonamido)benzamide | 0.042 |
| 11-72 | (S)-N-(2-(4,4-Difluoropiperidin-1-yl)-6-methylpyrimidin-4-yl)-2-(6-azaspiro[2.5]octan-6-yl)-4-((tetrahydrofuran)-3-sulfonamido)benzamide | 0.135 |
| 11-73 | (R)-N-(2-(4,4-Difluoropiperidin-1-yl)-6-methylpyrimidin-4-yl)-2-(6-azaspiro[2.5]octan-6-yl)-4-((tetrahydrofuran)-3-sulfonamido)benzamide | 0.079 |
| 11-74 | N-(2-(3,3-Difluoroazetidin-1-yl)-6-methylpyrimidin-4-yl)-4-((1-methylcyclopropane)-1-sulfonamido)-2-(6-azaspiro[2.5]octan-6-yl)benzamide | 0.094 |
| 11-75 | N-(2-(3,3-Difluoroazetidin-1-yl)-6-methylpyrimidin-4-yl)-4-((1-methylethyl)sulfonamido)-2-(6-azaspiro[2.5]octan-6-yl)benzamide | 0.056 |
| 11-76 | (R)-N-(2-(3,3-Difluoroazetidin-1-yl)-6-methylpyrimidin-4-yl)-4-((2-hydroxy-1-methylethyl)sulfonamido)-2-(6-azaspiro[2.5]octan-6-yl)benzamide | 0.020 |
| 11-77 | (S)-N-(2-(3,3-Difluoroazetidin-1-yl)-6-methylpyrimidin-4-yl)-4-((2-hydroxy-1-methylethyl)sulfonamido)-2-(6-azaspiro[2.5]octan-6-yl)benzamide | 0.034 |
| 11-78 | 4-((Cyclopropylmethyl)sulfonamido)-N-(2-(3,3-difluoroazetidin-1-yl)-6-methylpyrimidin-4-yl)-2-(6-azaspiro[2.5]octan-6-yl)benzamide | 0.125 |
| 11-79 | 4-((2-Hydroxyethyl)sulfonamido)-N-(2-isopropoxy-6-methylpyrimidin-4-yl)-2-(6-azaspiro[2.5]octan-6-yl)benzamide | 0.057 |
| 11-80 | (R)-4-((2-Hydroxyethyl)sulfonamido)-N-(6-methyl-2-((tetrahydrofuran-3-yl)oxy)pyrimidin-4-yl)-2-(6-azaspiro[2.5]octan-6-yl)benzamide | 0.117 |
| 11-81 | N-(2-(4-Fluoropiperidin-1-yl)-6-methylpyrimidin-4-yl)-4-(methylsulfonamido)-2-(6-azaspiro[2.5]octan-6-yl)benzamide | 0.060 |
| 11-82 | 4-(Ethylsulfonamido)-N-(2-(4-fluoropiperidin-1-yl)-6-methylpyrimidin-4-yl)-2-(6-azaspiro[2.5]octan-6-yl)benzamide | 0.051 |
| 11-83 | N-(2-(3,3-Difluoroazetidin-1-yl)-6-methylpyrimidin-4-yl)-4-((1,1-dimethylethyl)sulfonamido)-2-(6-azaspiro[2.5]octan-6-yl)benzamide | 0.098 |
| 12 | N-(2-(4,4-Difluoropiperidin-1-yl)-6-methylpyrimidin-4-yl)-4-((2-hydroxyethyl)sulfonyl)-2-(6-azaspiro[2.5]octan-6-yl)benzamide | 0.076 |
| 13-1 | (S)-N-(2-(4,4-Difluoropiperidin-1-yl)-6-methylpyrimidin-4-yl)-4-((1-hydroxypropan-2-yl)sulfonyl)-2-(6-azaspiro[2.5]octan-6-yl)benzamide | 0.057 |
| 13-2 | (R)-N-(2-(4,4-difluoropiperidin-1-yl)-6-methylpyrimidin-4-yl)-4-((1-hydroxypropan-2-yl)sulfonyl)-2-(6-azaspiro[2.5]octan-6-yl)benzamide | 0.064 |
| 14 | N-(2-(4,4-Difluoropiperidin-1-yl)-6-methylpyrimidin-4-yl)-4-((1-hydroxy-2-methylpropan-2-yl)sulfonyl)-2-(6-azaspiro[2.5]octan-6-yl)benzamide | 0.122 |

TABLE A-continued

BIOLOGICAL DATA

| Ex. # | Compound Name | KIF18A ATPase IC$_{50}$ (μM) |
|---|---|---|
| 14-1 | N-(2-(4,4-Difluoropiperidin-1-yl)-6-methylpyrimidin-4-yl)-4-(oxetan-3-ylsulfonyl)-2-(6-azaspiro[2.5]octan-6-yl)benzamide | 0.182 |
| 14-2 | N-(2-(4,4-Difluoropiperidin-1-yl)-6-methylpyrimidin-4-yl)-4-(ethylsulfonyl)-2-(6-azaspiro[2.5]octan-6-yl)benzamide | 0.108 |
| 14-3 | N-(2-(4,4-Difluoropiperidin-1-yl)-6-methylpyrimidin-4-yl)-4-(isopropylsulfonyl)-2-(6-azaspiro[2.5]octan-6-yl)benzamide | 0.128 |
| 14-4 | N-(2-(4,4-Difluoropiperidin-1-yl)-6-methylpyrimidin-4-yl)-4-((2-hydroxy-2-methylpropyl)sulfonyl)-2-(6-azaspiro[2.5]octan-6-yl)benzamide | 0.806 |
| 14-5 | 4-(Cyclopropylsulfonyl)-N-(2-(4,4-difluoropiperidin-1-yl)-6-methylpyrimidin-4-yl)-2-(6-azaspiro[2.5]octan-6-yl)benzamide | 0.826 |
| 14-6 | 4-(tert-Butylsulfonyl)-N-(2-(4,4-difluoropiperidin-1-yl)-6-methylpyrimidin-4-yl)-2-(6-azaspiro[2.5]octan-6-yl)benzamide | 1.88 |
| 14-7 | N-(2-(4,4-Difluoropiperidin-1-yl)-6-methylpyrimidin-4-yl)-4-(((3R,4R)-4-hydroxytetrahydrofuran-3-yl)sulfonyl)-2-(6-azaspiro[2.5]octan-6-yl)benzamide | 0.094 |
| 14-8 | N-(2-(4,4-Difluoropiperidin-1-yl)-6-methylpyrimidin-4-yl)-4-(((3S,4S)-4-hydroxytetrahydrofuran-3-yl)sulfonyl)-2-(6-azaspiro[2.5]octan-6-yl)benzamide | 0.097 |
| 14-9 | N-(2-(4,4-Difluoropiperidin-1-yl)-6-methylpyrimidin-4-yl)-4-(((1R,2R)-2-hydroxycyclopentyl)sulfonyl)-2-(6-azaspiro[2.5]octan-6-yl)bezamide | 0.195 |
| 15 | N-(2-(4,4-Difluorocyclohexyl)-6-methylpyrimidin-4-yl)-4-((2-hydroxyethyl)sulfonamido)-2-(6-azaspiro[2.5]octan-6-yl)benzamide | 0.017 |
| 16-1 | (R)-N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide | 0.089 |
| 16-2 | (S)-N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide | 0.096 |
| 17 | N-(2-(4,4-Difluoropiperidin-1-yl)pyridin-4-yl)-4-(N-(2-hydroxyethyl)sulfamoyl)-2-(6-azaspiro[2.5]octan-6-yl)benzamide | 0.023 |
| 17-1 | 4-(N-(2-Hydroxyethyl)sulfamoyl)-2-(6-azaspiro[2.5]octan-6-yl)-N-(2-(3,3,3-trifluoropropoxy)pyrimidin-4-yl)benzamide | 0.027 |
| 17-2 | 4-(N-(2-Hydroxyethyl)sulfamoyl)-N-(6-methyl-2-(3,3,3-trifluoropropoxy)pyrimidin-4-yl)-2-(6-azaspiro[2.5]octan-6-yl)benzamide | 0.042 |
| 17-3 | N-(2-(4,4-Difluoropiperidin-1-yl)-6-methylpyrimidin-4-yl)-4-(N-(2-hydroxyethyl)sulfamoyl)-2-(6-azaspiro[2.5]octan-6-yl)benzamide | 0.063 |
| 17-4 | N-(2-(4,4-Difluoropiperidin-1-yl)pyrimidin-4-yl)-4-(N-(2-hydroxyethyl)sulfamoyl)-2-(6-azaspiro[2.5]octan-6-yl)benzamide | 0.023 |
| 17-5 | N-(2-(3,3-Difluoroazetidin-1-yl)-6-methylpyrimidin-4-yl)-4-(N-(2-hydroxyethyl)sulfamoyl)-2-(6-azaspiro[2.5]octan-6-yl)benzamide | 0.133 |
| 17-6 | (R)-N-(2-(4,4-Difluoropiperidin-1-yl)-6-methylpyrimidin-4-yl)-4-(N-(1-hydroxypropan-2-yl)sulfamoyl)-2-(6-azaspiro[2.5]octan-6-yl)benzamide | 0.127 |
| 17-7 | (S)-N-(2-(4,4-Difluoropiperidin-1-yl)-6-methylpyrimidin-4-yl)-4-(N-(1-hydroxypropan-2-yl)sulfamoyl)-2-(6-azaspiro[2.5]octan-6-yl)benzamide | 0.147 |
| 17-8 | N-(2-(4,4-Difluoropiperidin-1-yl)-6-methylpyrimidin-4-yl)-4-(N-(2-hydroxy-2-methylpropyl)sulfamoyl)-2-(6-azaspiro[2.5]octan-6-yl)benzamide | 0.286 |
| 18-1 | 2-(6-Azaspiro[2.5]octan-6-yl)-4-(R-cyclopropylsulfonimidoyl)-N-(2-(4,4-difluoro-1-piperidinyl)-6-methyl-4-pyrimidinyl)benzamide | 0.064 |
| 18-2 | 2-(6-azaspiro[2.5]octan-6-yl)-4-(S-cyclopropylsulfonimidoyl)-N-(2-(4,4-difluoro-1-piperidinyl)-6-methyl-4-pyrimidinyl)benzamide | 0.057 |
| 19-1 | N-(2-(4,4-Difluoropiperidin-1-yl)-6-methylpyrimidin-4-yl)-4-(oxetane-3-sulfonimidoyl)-2-(6-azaspiro[2.5]octan-6-yl)benzamide | 0.163 |
| 19-2 | N-(2-(4,4-Difluoropiperidin-1-yl)-6-methylpyrimidin-4-yl)-4-(S-methylsulfonimidoyl)-2-(6-azaspiro[2.5]octan-6-yl)benzamide | 0.438 |
| 19-3 | 2-(6-Azaspiro[2.5]octan-6-yl)-N-(2-(4,4-difluoro-1-pieridinyl)-6-methyl-4-pyrimidinyl)-4-(S-ethylsulfonimidoyl)benzamide | 0.078 |
| 19-4 | 2-(6-Azaspiro[2.5]octan-6-yl)-N-(2-(4,4-difluoro-1-pieridinyl)-6-methyl-4-pyrimidinyl)-4-(R-ethylsulfonimidoyl)benzamide | 0.035 |
| 19-5 | N-(2-(4,4-Difluoropiperidin-1-yl)-6-methylpyrimidin-4-yl)-4-(propan-2-ylsulfonimidoyl)-2-(6-azaspiro[2.5]octan-6-yl)benzamide | 0.175 |
| 19-6 | 4-(Cyclopropanesulfonimidoyl)-N-(2-(4,4-difluoropiperidin-1-yl)pyridin-4-yl)-2-(6-azaspiro[2.5]octan-6-yl)benzamide | 0.042 |
| 19-7 | 2-(6-Azaspiro[2.5]octan-6-yl)-4-(S-cyclopropylsulfonimidoyl)-N-(6-methy-2-((2R)-2-methyl-4-moprpholinyl)-4-pyrimidinyl)benzamide | 0.195 |
| 19-8 | 2-(6-Azaspiro[2.5]octan-6-yl)-4-(R-cyclopropylsulfonimidoyl)-N-(6-methy-2-((2R)-2-methyl-4-moprpholinyl)-4-pyrimidinyl)benzamide | 0.078 |
| 19-9 | 4-(Cyclopropanesulfonimidoyl)-N-(2-(3,3-difluoroazetidin-1-yl)-6-methylpyrimidin-4-yl)-2-(6-azaspiro[2.5]octan-6-yl)benzamide | 0.069 |
| 20 | (N$^1$-(2-(4,4-Difluoropiperidin-1-yl)-6-methylpyrimidin-4-yl)-2-(6-azaspiro[2.5]octan-6-yl)terephthalamide | 0.119 |
| 21 | 4-(Azetidin-3-ylsulfonyl)-N-(2-(4,4-difluoropiperidin-1-yl)-6-methylpyrimidin-4-yl)-2-(6-azaspiro[2.5]octan-6-yl)benzamide | 0.040 |

TABLE A-continued

BIOLOGICAL DATA

| Ex. # | Compound Name | KIF18A ATPase IC$_{50}$ (μM) |
|---|---|---|
| 22 | 4-N-(2-(4,4-Difluoropiperidin-1-yl)-6-methylpyrimidin-4-yl)-4-((1-methylazetidin-3-yl)sulfonyl)-2-(6-azaspiro[2.5]octan-6-yl)benzamide | 0.406 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

The invention claimed is:

1. A compound of formula (I):

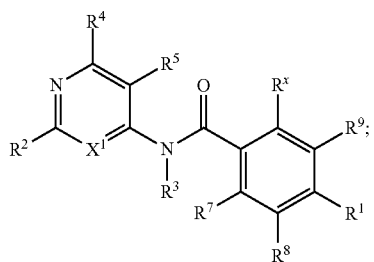

(I)

or any pharmaceutically-acceptable salt thereof, wherein:

$X^1$ is N;

$R^1$ is —CN, or a group —Z—$R^{12}$ wherein Z is —$C_{0-4}$alk-, —$NR^{11}$—, —$NR^{11}SO_2$—, —$SO_2NR^{11}$—, —$NR^{11}$—S(=O)(=NH), —S(=O)(=NH)—, —S—, —S(=O)—, —$SO_2$—, $C_{0-4}$alk-O—, —(C=O)—, —(C=O)$NR^{11}$—, —C=N(OH)—, or —$NR^{11}$(C=O); or the group —Z—$R^{12}$ is —N=S(=O)—($R^{12}$)$_2$, wherein the two $R^{12}$ pair alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from the group consisting of O and S;

$R^2$ is halo or a group —Y—$R^{13}$, wherein Y is —$C_{0-4}$alk-, —NH—$(CH_2)_{0-4}$—, —C(=O)$NR^a(C_{1-4}$alk), —O—$C_{0-4}$alk-, S, S=O, S(=O)$_2$, —$SO_2NR^{13}$, or —S(=O)(=NH)—;

$R^3$ is H, $C_{1-4}$alk, or $C_{1-4}$haloalk;

$R^4$ is H, halo, $R^{4a}$ or $R^{4a}$;

$R^5$ is H, halo, $C_{1-8}$alk, or $C_{1-4}$haloalk;

$R^7$ is H, halo, $C_{1-8}$alk, or $C_{1-4}$haloalk;

$R^8$ is H, halo, $C_{1-8}$alk, $C_{1-4}$haloalk, —OH, —O—$R^{8a}$, or —O—$R^{8b}$;

$R^9$ is H, halo, $C_{1-8}$alk, or $C_{1-4}$haloalk;

$R^x$ is selected from the group consisting of

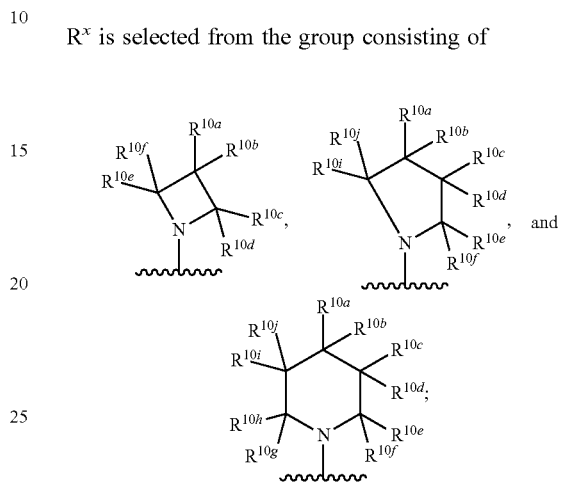

each of $R^{10a}$, $R^{10b}$, $R^{10c}$, $R^{10d}$, $R^{10e}$, $R^{10f}$, $R^{10g}$, $R^{10h}$, $R^{10i}$, and $R^{10j}$ is H, halo, $R^{10k}$, or $R^{10l}$;

or alternatively, each of $R^{10a}$ and $R^{10b}$ pair, $R^{10c}$ and $R^{10d}$ pair, $R^{10e}$ and $R^{10f}$ pair, $R^{10g}$ and $R^{10h}$ pair, or $R^{10i}$ and $R^{10j}$ pair, independently, can combine with the carbon atom attached to each of them to form a saturated or partially-saturated 3-, 4-, 5-, 6-membered monocyclic ring spiro to the $R^x$ ring; wherein said 3-, 4-, 5-, 6-membered monocyclic ring contains 0, 1, 2 or 3 N atoms and 0, 1, or 2 atoms selected from the group consisting of O and S, and further wherein said 3-, 4-, 5-, 6-membered monocyclic ring is substituted by 0, 1, 2 or 3 group(s) selected from the group consisting of F, Cl, Br, $C_{1-6}$alk, $C_{1-4}$haloalk, —$OR^a$, —$OC_{1-4}$haloalk, CN, —$NR^aR^a$, and oxo;

$R^{11}$ is H, $R^{11a}$, or $R^{11b}$;

$R^{12}$ is H, $R^{12a}$, or $R^{12b}$;

$R^{13}$ is $R^{13a}$ or $R^{13b}$;

$R^{4a}$, $R^{8a}$, $R^{10k}$, $R^{11a}$, $R^{12a}$, and $R^{13a}$ is independently, at each instance, a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from the group consisting of O and S, which is substituted by 0, 1, 2 or 3 group(s) selected from the group consisting of F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^{14}$, and oxo;

$R^{4b}$, $R^{8b}$, $R^{10l}$, $R^{11b}$, $R^{12b}$, and $R^{13b}$ is independently, at each instance, $C_{1-6}$alk substituted by 0, 1, 2, 3, 4, or 5 group(s) selected from the group consisting of F, Cl, Br, —OR$^a$, —OC$_{1-4}$haloalk, and CN;

$R^{14}$ is independently, at each instance, a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from the group consisting of O and S, which is substituted by 0, 1, 2 or 3 group(s) selected from the group consisting of F, Cl, Br, $C_{1-6}$alk, $C_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O) R$^b$, —C$_{1-6}$alkC(=O)NR$^a$R$^a$, —C$_{1-6}$alkC(=O)OR$^a$, and oxo;

R$^a$ is independently, at each instance, H or R$^b$; and

R$^b$ is independently, at each instance, $C_{1-6}$alk, phenyl, or benzyl, wherein the $C_{1-6}$alk is substituted by 0, 1, 2 or 3 substituents selected from the group consisting of halo, —OH, —OC$_{1-4}$alk, —NH$_2$, —NHC$_{1-4}$alk, —OC(=O)C$_{1-4}$alk, and —N(C$_{1-4}$alk)C$_{1-4}$alk; and the phenyl or benzyl is substituted by 0, 1, 2 or 3 substituents selected from the group consisting of halo, C$_{1-4}$alk, C$_{1-3}$haloalk, —OH, —OC$_{1-4}$alk, —NH$_2$, —NHC$_{1-4}$alk, —OC(=O)C$_{1-4}$alk, and —N(C$_{1-4}$alk)C$_{1-4}$alk.

2. The compound of claim 1, or the pharmaceutically-acceptable salt thereof, wherein $X^1$ is N; having the formula (Ia):

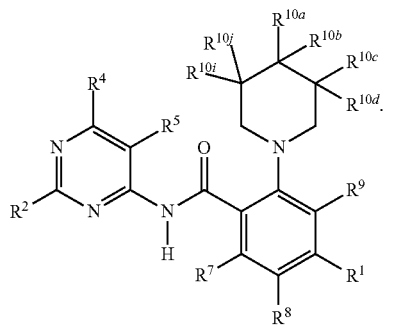

3. The compound of claim 1, or the pharmaceutically-acceptable salt thereof, wherein R$^3$ is H or methyl.

4. The compound of claim 1, or the pharmaceutically-acceptable salt thereof, wherein each of R$^{10c}$, R$^{10d}$, R$^{10e}$, R$^{10f}$, R$^{10g}$, R$^{10h}$, R$^{10i}$, and R$^{10j}$ is H, halo, C$_{1-6}$alk, or C$_{1-4}$haloalk; and each of R$^{10a}$ and R$^{10b}$ pair combine with the carbon atom attached to each of them form a saturated 3-, 4-, or 5-membered monocyclic ring spiro to the R$^x$ ring; wherein said ring contains 0, 1, 2 or 3 N atoms and 0, 1, or 2 atoms selected from the group consisting of O and S.

5. The compound of claim 1, or the pharmaceutically-acceptable salt thereof, wherein each of R$^{10c}$, R$^{10d}$, R$^{10e}$, R$^{10f}$, R$^{10g}$, R$^{10h}$, R$^{10i}$, and R$^{10j}$ is H, methyl, or ethyl; and each of R$^{10a}$ and R$^{10b}$ pair combine with the carbon atom attached to each of them form a cyclopropyl, cyclobutyl, or cyclopentyl ring spiro to the R$^x$ ring.

6. The compound of claim 1, or the pharmaceutically-acceptable salt thereof, wherein the group

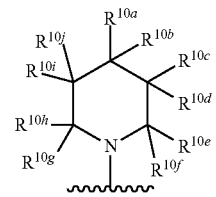

is:

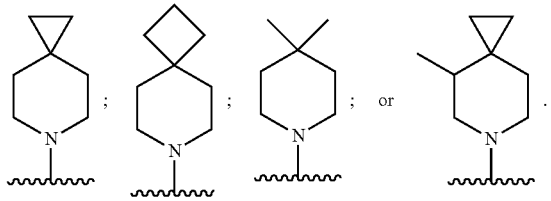

7. The compound of claim 1, or the pharmaceutically-acceptable salt thereof, wherein the group

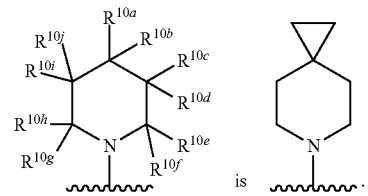

8. The compound of claim 1, or the pharmaceutically-acceptable salt thereof, wherein R$^1$ is —CN, or a group —Z—R$^{12}$, wherein Z is a bond, —NH—, —NHSO$_2$—, —SO$_2$NH—, —S(=O)(=NH)—, —S—, —S(=O)—, —SO$_2$—, —(C=O)—, —(C=O)NH—, or —NH(C=O)—; and R$^{12}$ is:

(a) H;

(b) cyclopropyl, cyclobutyl, cyclopentyl, cyclohexyl, oxiranyl, oxetanyl, tetrahydrofuranyl, azetidinyl, imidazolyl, morpholinyl, pyrrolidinyl, piperazinyl,

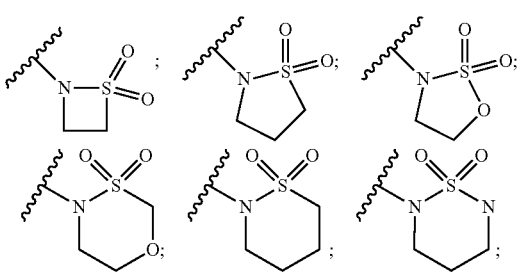

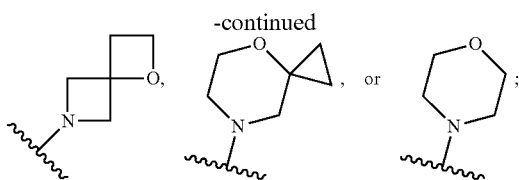

wherein each ring is substituted by 0, 1, 2 or 3 group(s) selected from the group consisting of OH, F, methyl, —CH$_2$OH, —C(=O)OCH$_3$, —C(=O)OC(CH$_3$)$_3$, NH$_2$, CN, and oxo; or (c) C$_{1-6}$alk substituted by 0, 1, 2 or 3 OH or F, C(=O)OCH$_3$, NH$_2$, NH(CH$_3$), or N(CH$_3$)$_2$.

9. The compound of claim 1, or the pharmaceutically-acceptable salt thereof, wherein R$^1$ is —CN, or a group —Z—R$^{12}$, wherein Z is a bond, —NH—, —NHSO$_2$—, —SO$_2$NH—, —S(=O)(=NH)—, —S—, —S(=O)—, —SO$_2$—, —(C=O)—, —(C=O)NH—, or —NH(C=O)—; and (a) R$^{12}$ is H;
(b) R$^{12}$ is oxetanyl or cyclopropyl; or
(c) R$^{12}$ is C$_{1-6}$alk substituted by 0, 1, 2 or 3 OH group(s).

10. The compound of claim 1, or the pharmaceutically-acceptable salt thereof, wherein the group —Z—R$^{12}$ is —N=S(=O)—(R$^{12}$)$_2$, wherein the two R$^{12}$ pair combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from the group consisting of O and S; which is selected from the group consisting of:

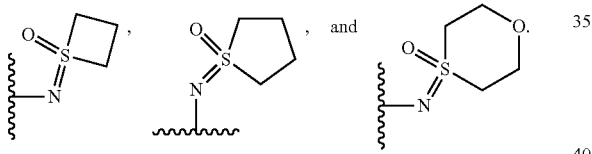

11. The compound of claim 1, or the pharmaceutically-acceptable salt thereof, wherein R$^1$ is a group —Z—R$^{12}$, wherein Z is —NHSO$_2$— or —SO$_2$NH—; and R$^{12}$ is oxetanyl, cyclopropyl, or R$^{12}$ is C$_{1-6}$alk substituted by 0, 1, 2 or 3 OH group(s).

12. The compound of claim 1, or the pharmaceutically-acceptable salt thereof, wherein R$^1$ is a group —Z—R$^{12}$, wherein Z is —NHSO$_2$— and R$^{12}$ is —CH$_2$—CH$_2$—OH.

13. The compound of claim 1, or the pharmaceutically-acceptable salt thereof, wherein R$^2$ is halo or a group —Y—R$^{13}$, wherein Y is a bond, —NH—(CH$_2$)$_{0-4}$—, or —O—(CH$_2$)$_{0-4}$; and R$^{13}$ is a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0 or 1 atoms selected from the group consisting of O and S, which is substituted by 0, 1, 2 or 3 group(s) selected from the group consisting of F, Cl, Br, C$_{1-6}$alk, C$_{1-4}$haloalk, —OH, —OC$_{1-4}$haloalk, CN, R$^{14}$, and oxo; or R$^{13}$ is C$_{1-6}$alk substituted by 0, 1, 2, 3, 4, or 5 group(s) selected from the group consisting of F, Cl, Br, —OH, —OC$_{1-4}$haloalk, and CN.

14. The compound of claim 1, or the pharmaceutically-acceptable salt thereof, wherein R$^2$ is a saturated 5- or 6-membered monocyclic ring wherein each said ring contains 0, 1, or 2 N atoms and 0 or 1 O atom, and wherein each said ring is substituted by 0, 1, 2 or 3 group(s) selected from the group consisting of F, Cl, Br, C$_{1-6}$alk, C$_{1-4}$haloalk, —OH, —OC$_{1-4}$haloalk, CN, R$^{14}$, and oxo.

15. The compound of claim 1, or the pharmaceutically-acceptable salt thereof, wherein R$^2$ is (a) halo; (b) a group —Y—R$^{13}$, wherein Y is a bond; and R$^{13}$ is morpholinyl, piperidinyl, azetidinyl, pyrrolidinyl, cyclopropyl, cyclobutyl, cyclopentyl, cyclohexyl, piperazinyl, tetrahydrofuranyl,

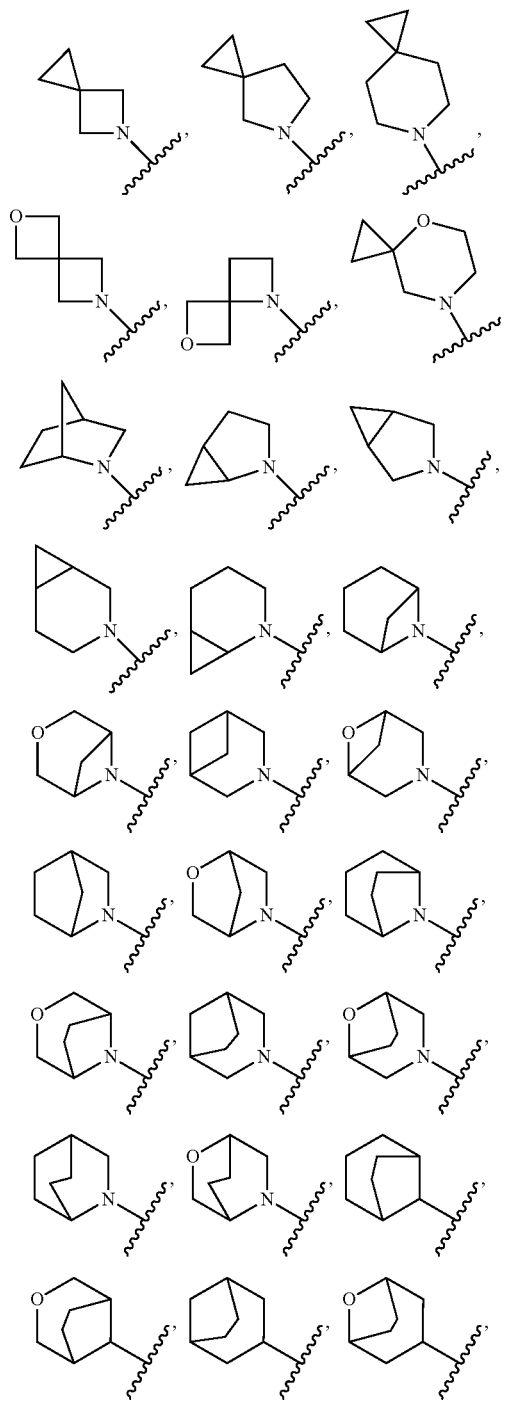

223

-continued

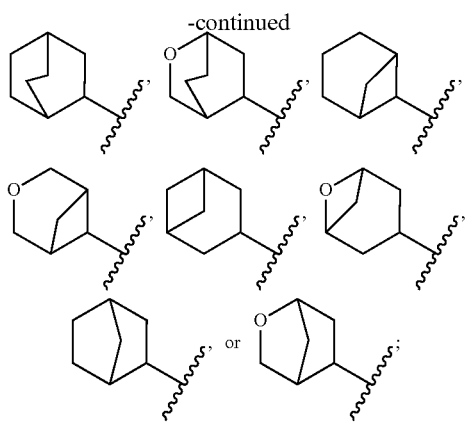

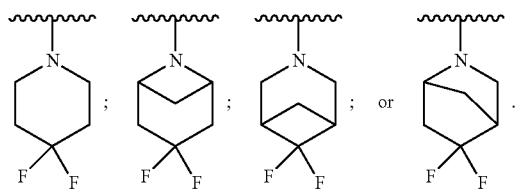

wherein each said ring is substituted by 0, 1, 2 or 3 group(s) selected from the group consisting of F, Cl, Br, methyl, CF₃, —OH, —OCHF₂, CN, and oxo; or
  (c) a group —Y—R¹³, wherein Y is NH, —O—, —O—(CH₂)—, —O—(CH₂)—(CH₂)—, or —O—(CH₂)—(CH₂)—(CH₂)—, and wherein R¹³ is

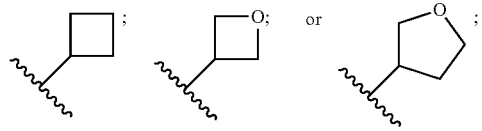 [SMILES: *C1CCC1 ; *C1COC1 ; *C1CCOC1]

or R¹³ is $C_{1-6}$alk substituted by 0, 1, 2, 3, 4, or 5 group(s) selected from the group consisting of F, Cl, Br, methyl, CF₃, —OH, and CN.

16. The compound of claim 1, or the pharmaceutically-acceptable salt thereof, wherein R² is morpholinyl or piperidinyl, wherein each said ring is substituted by 0, 1, 2 or 3 group(s) selected from the group consisting of F, Cl, Br, methyl, CF₃, —OH, —OCHF₂, CN, and oxo.

17. The compound of claim 16, or the pharmaceutically-acceptable salt thereof, wherein R² is morpholinyl substituted by 1, 2 or 3 methyl group(s).

18. The compound of claim 16, or the pharmaceutically-acceptable salt thereof, wherein R² is piperidinyl substituted by 1, 2 or 3 fluoro group(s).

19. The compound of claim 1, or the pharmaceutically-acceptable salt thereof, wherein R² is 20. The compound of claim 1, or the pharmaceutically-acceptable salt thereof, wherein Z is a bond, —NH—, —NHSO₂—, —SO₂NH—, —S(=O)(=NH)—, —S—, —S(=O)—, —SO₂—, —(C=O)—, —(C=O)NH—, or —NH(C=O)—.

21. The compound of claim 1, or the pharmaceutically-acceptable salt thereof, wherein R¹² is (a) H; (b) $C_{1-6}$alk substituted by 0, 1, 2 or 3 group(s) selected from the group consisting of F, Cl, Br, —OH, and —OCH₃, and cyclopropyl; or (c) a saturated, partially-saturated or unsaturated 3-, 4-, 5-, 6-, or 7-membered monocyclic ring containing 0, 1, 2 or 3 N atoms and 0 or 1 atoms selected from the group consisting of O and S, which is substituted by 0, 1, 2 or 3 group(s) selected from the group consisting of F, Cl, Br, $C_{1-6}$alk, $C_{1-4}$haloalk, —$C_{1-6}$alkOH, —OH, —OCH₃, —NH₂, and oxo.

22. The compound of claim 21, or the pharmaceutically-acceptable salt thereof, wherein R¹² is cyclopropyl, cyclobutyl, cyclopentyl, oxetanyl, azetidinyl, tetrahydrofuranyl, or 1,3,4-oxathiazinanyl.

23. The compound of claim 1, or the pharmaceutically-acceptable salt thereof, wherein R⁴ is (a) H; (b) $C_{1-6}$alk substituted by 0, 1, 2 or 3 OH group(s); or (c) cyclopropyl.

24. The compound of claim 23, or the pharmaceutically-acceptable salt thereof, wherein R⁴ is H or methyl.

25. The compound of claim 1, or the pharmaceutically-acceptable salt thereof, wherein R⁵ is H.

26. The compound of claim 1, or the pharmaceutically-acceptable salt thereof, wherein R⁷ is H or F.

27. The compound of claim 1, or the pharmaceutically-acceptable salt thereof, wherein R⁸ is H.

28. The compound of claim 1, or the pharmaceutically-acceptable salt thereof, wherein R⁹ is H.

29. The compound of claim 1, selected from the group consisting of:

| Ex. # | Chemical Structure | Name |
|---|---|---|
| 1 | 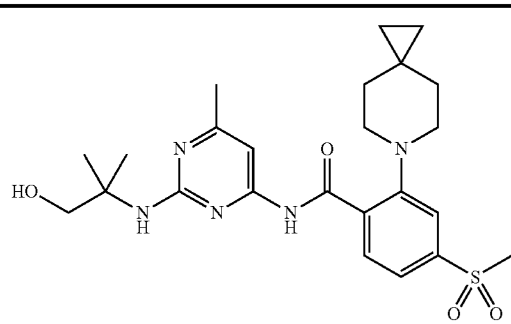 | N-(2-((1-Hydroxy-2-methylpropan-2-yl)amino)-6-methylpyrimidin-4-yl)-4-(methylsulfonyl)-2-(6-azaspiro[2.5]octan-6-yl)benzamide, |

| Ex. # | Chemical Structure | Name |
|---|---|---|
| 1-7 | 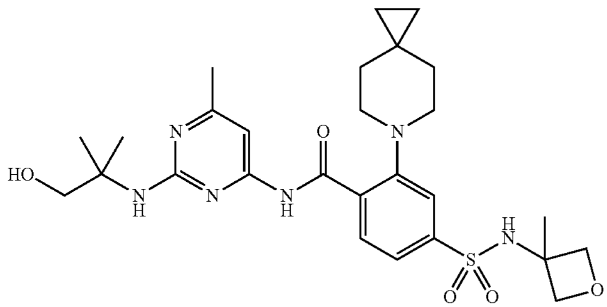 [SMILES: Cc1cc(NC(=O)c2ccc(S(=O)(=O)NC3(C)COC3)cc2N2CCC3(CC2)CC3)nc(NC(C)(C)CO)n1] | N-(2-((1-hydroxy-2-methylpropan-2-yl)amino)-6-methylpyrimidin-4-yl)-4-(N-(3-methyloxetan-3-yl)sulfamoyl)-2-(6-azaspiro[2.5]octan-6-yl)benzamide, |
| 2 | 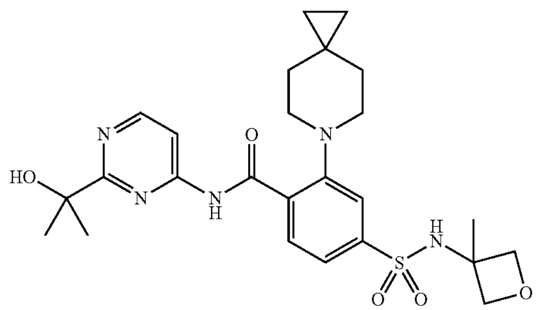 [SMILES: CC1(NS(=O)(=O)c2ccc(C(=O)Nc3ccnc(C(C)(C)O)n3)c(N3CCC4(CC3)CC4)c2)COC1] | N-(2-(2-Hydroxypropan-2-yl)pyrimidin-4-yl)-4-(N-(3-methyloxetan-3-yl)sulfamoyl)-2-(6-azaspiro[2,5]octan-6-yl)benzamide, |
| 2-8 | 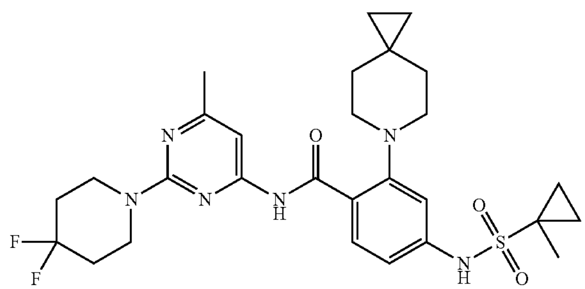 [SMILES: Cc1cc(NC(=O)c2ccc(NS(=O)(=O)C3(C)CC3)cc2N2CCC3(CC2)CC3)nc(N2CCC(F)(F)CC2)n1] | N-(2-(4,4-Difluoropiperidin-1-yl)-6-methylpyrimidin-4-yl)-4-((1-methylcyclopropane)-1-sulfonamido)-2-(6-azaspiro[2.5]octan-6-yl)benzamide, |
| 3 | 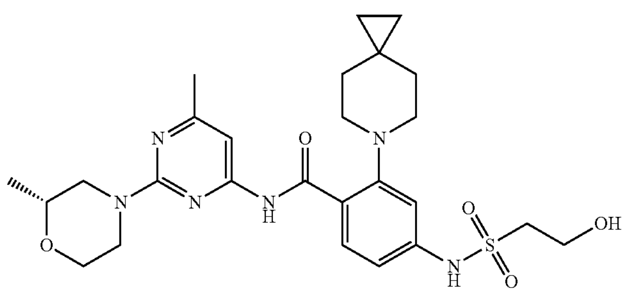 [SMILES: Cc1cc(NC(=O)c2ccc(NS(=O)(=O)CCO)cc2N2CCC3(CC2)CC3)nc(N2CCO[C@H](C)C2)n1] | (R)-4-((2-Hydroxyethyl)sulfonamido)-N-(6-methyl-2-(2-methylmorpholino)pyrimidin-4-yl)-2-(6-azaspiro[2.5]octan-6-yl)benzamide, |
| 4 | 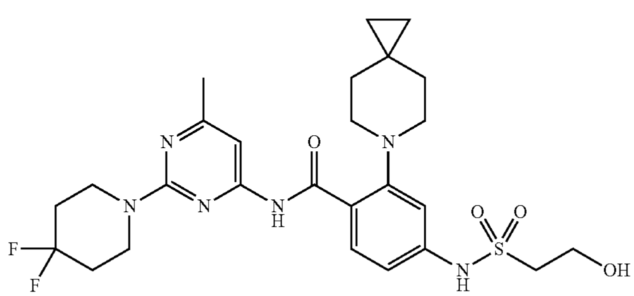 [SMILES: Cc1cc(NC(=O)c2ccc(NS(=O)(=O)CCO)cc2N2CCC3(CC2)CC3)nc(N2CCC(F)(F)CC2)n1] | N-(2-(4,4-Difluoropiperidin-1-yl)-6-methylpyrimidin-4-yl)-4-((2-hydroxyethyl)sulfonamido)-2-(6-azaspiro[2.5]octan-6-yl)benzamide, |

-continued

| Ex. # | Chemical Structure | Name |
|---|---|---|
| 5-1 | 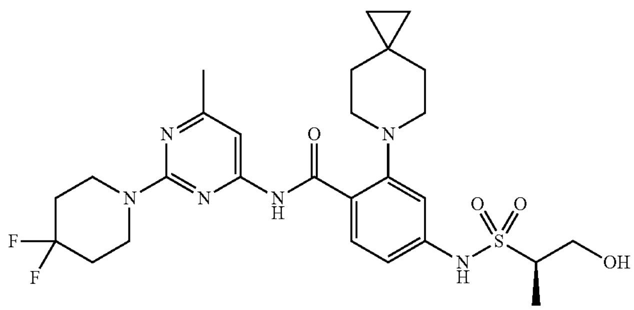 [SMILES: Cc1cc(NC(=O)c2ccc(NS(=O)(=O)[C@H](C)CO)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide, |
| 5-2 | 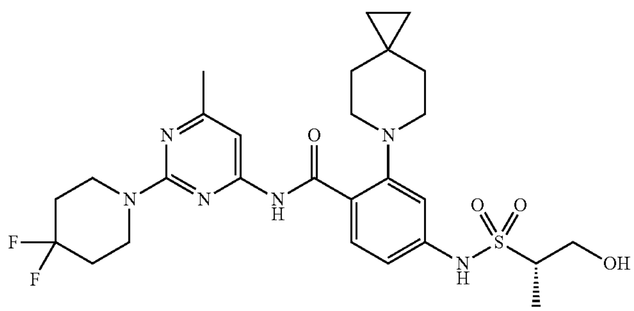 [SMILES: Cc1cc(NC(=O)c2ccc(NS(=O)(=O)[C@@H](C)CO)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide, |
| 6-7 | 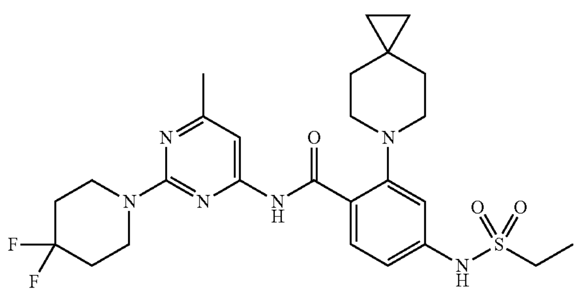 [SMILES: CCS(=O)(=O)Nc1ccc(C(=O)Nc2cc(C)nc(N3CCC(F)(F)CC3)n2)c(N2CCC3(CC2)CC3)c1] | N-(2-(4,4-Difluoropiperidin-1-yl)-6-methylpyrimidin-4-yl)-4-(ethylsulfonamido)-2-(6-azaspiro[2.5]octan-6-yl)benzamide, |
| 6-35 | 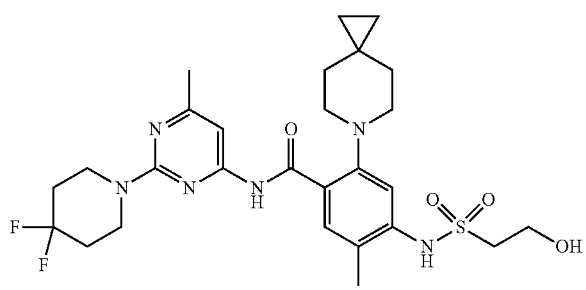 [SMILES: Cc1cc(NC(=O)c2cc(C)c(NS(=O)(=O)CCO)cc2N2CCC3(CC2)CC3)nc(N2CCC(F)(F)CC2)n1] | N-(2-(4,4-Difluoropiperidin-1-yl)-6-methylpyrimidin-4-yl)-4-((2-hydroxyethyl)sulfonamido)-5-methyl-2-(6-azaspiro[2.5]octan-6-yl)benzamide, |
| 7 | 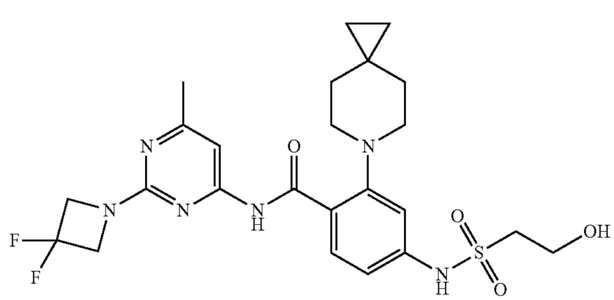 [SMILES: Cc1cc(NC(=O)c2ccc(NS(=O)(=O)CCO)cc2N2CCC3(CC2)CC3)nc(N2CC(F)(F)C2)n1] | N-(2-(3,3-Difluoroazetidin-1-yl)-6-methylpyrimidin-4-yl)-4-((2-hydroxyethyl)sulfonamido)-2-(6-azaspiro[2.5]octan-6-yl)benzamide, |

| Ex. # | Chemical Structure | Name |
|---|---|---|
| 8-1 | 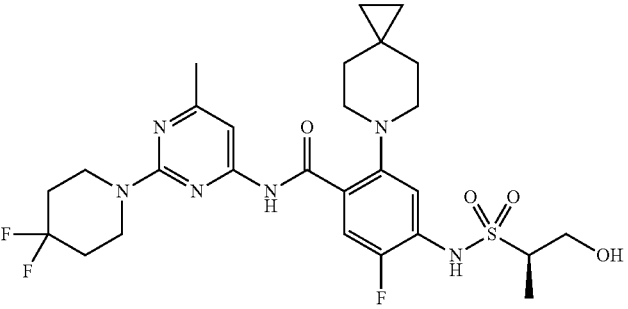 [SMILES: Cc1cc(NC(=O)c2cc(F)c(NS(=O)(=O)[C@H](C)CO)cc2N2CCC3(CC2)CC3)nc(N2CCC(F)(F)CC2)n1] | (R)-N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide, |
| 8-2 | 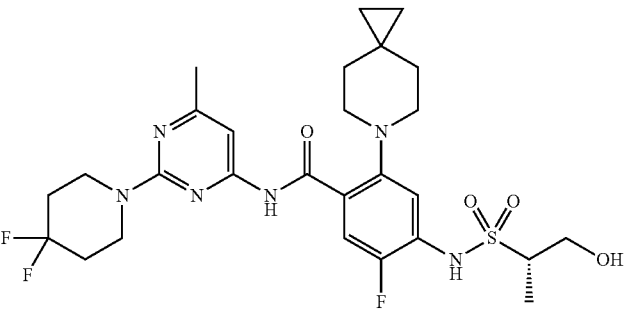 [SMILES: Cc1cc(NC(=O)c2cc(F)c(NS(=O)(=O)[C@@H](C)CO)cc2N2CCC3(CC2)CC3)nc(N2CCC(F)(F)CC2)n1] | (S)-N-(2-(4,4-Difluoropiperidin-1-yl)-6-methylpyrimidin-4-yl)-5-fluoro-4-((2-hydroxy-1-methylethyl)sulfonamido)-2-(6-azaspiro[2.5]octan-6-yl)benzamide, |
| 10-1 | 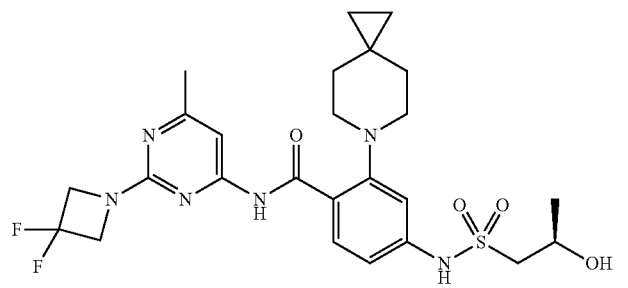 [SMILES: Cc1cc(NC(=O)c2ccc(NS(=O)(=O)C[C@@H](C)O)cc2N2CCC3(CC2)CC3)nc(N2CC(F)(F)C2)n1] | (R)-N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide, |
| 10-2 | 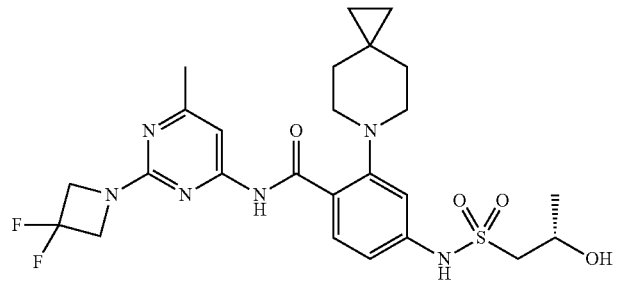 [SMILES: Cc1cc(NC(=O)c2ccc(NS(=O)(=O)C[C@H](C)O)cc2N2CCC3(CC2)CC3)nc(N2CC(F)(F)C2)n1] | (S)-N-(2-(3,3-Difluoroazetidin-1-yl)-6-methylpyrimidin-4-yl)-4-((2-hydroxypropyl)sulfonamido)-2-(6-azaspiro[2.5]octan-6-yl)benzamide, |
| 12 | 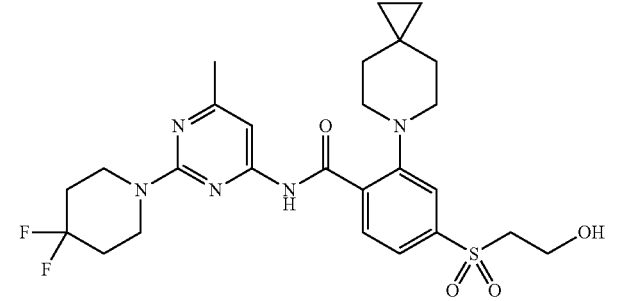 [SMILES: Cc1cc(NC(=O)c2ccc(S(=O)(=O)CCO)cc2N2CCC3(CC2)CC3)nc(N2CCC(F)(F)CC2)n1] | N-(2-(4,4-difluoropiperidin-1-yl)-6-methylpyrimidin-4-yl)-4-((2-hydroxyethyl)sulfonyl)-2-(6-azaspiro[2.5]octan-6-yl)benzamide, |

| Ex. # | Chemical Structure | Name |
|---|---|---|
| 13-1 | 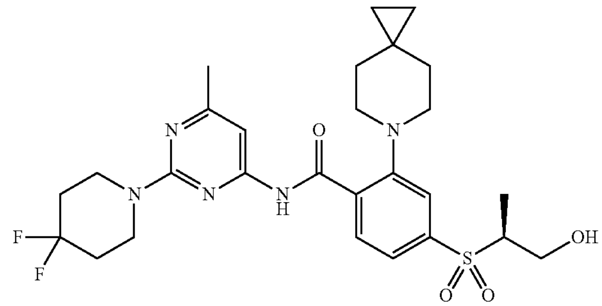 [SMILES: Cc1cc(NC(=O)c2ccc(S(=O)(=O)[C@@H](C)CO)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((1-hydroxypropan-2-yl)sulfonyl)-2-(6-azaspiro[2.5]octan-6-yl)benzamide, |
| 13-2 | 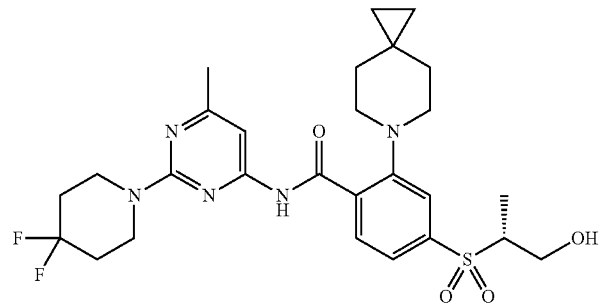 [SMILES: Cc1cc(NC(=O)c2ccc(S(=O)(=O)[C@H](C)CO)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-((1-hydroxypropan-2-yl)sulfonyl)-2-(6-azaspiro[2.5]octan-6-yl)benzamide, |
| 14 | 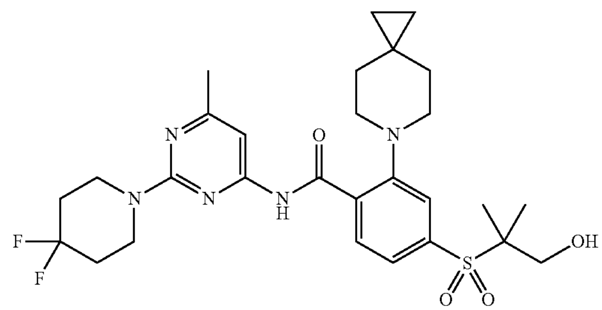 [SMILES: Cc1cc(NC(=O)c2ccc(S(=O)(=O)C(C)(C)CO)cc2N2CCC3(CC2)CC3)nc(N2CCC(F)(F)CC2)n1] | N-(2-(4,4-Difluoropiperidin-1-yl)-6-methylpyrimidin-4-yl)-4-((1-hydroxy-2-methylpropan-2-yl)sulfonyl)-2-(6-azaspiro[2.5]octan-6-yl)benzamide, |
| 15 | 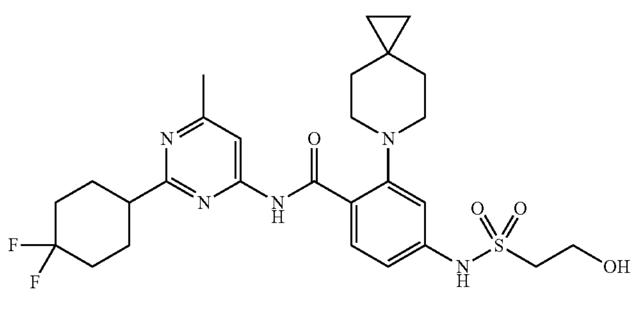 | N-(2-(4,4-Difluorocyclohexyl)-6-methylpyrimidin-4-yl)-4-((2-hydroxyethyl)sulfonamido)-2-(6-azaspiro[2.5]octan-6-yl)benzamide, |
| 16-1 | 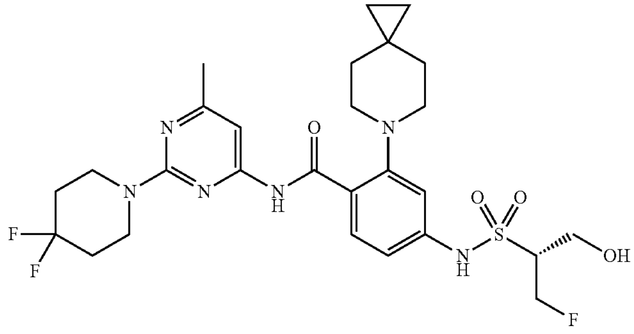 [SMILES: Cc1cc(NC(=O)c2ccc(NS(=O)(=O)[C@H](CO)CF)cc2N2CCC3(CC2)CC3)nc(N2CCC(F)(F)CC2)n1] | (R)-N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide, |

-continued

| Ex. # | Chemical Structure | Name |
|---|---|---|
| 16-2 | 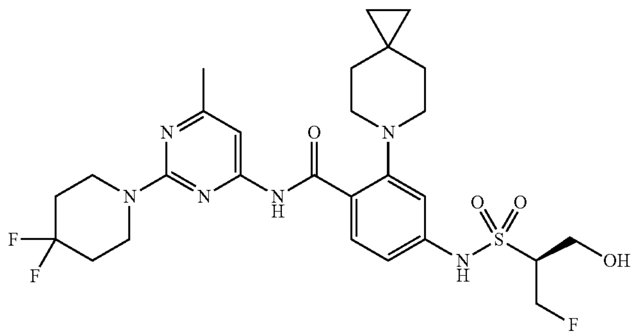 [SMILES: Cc1cc(NC(=O)c2ccc(NS(=O)(=O)[C@@H](CO)CF)cc2N2CCC3(CC2)CC3)nc(N2CCC(F)(F)CC2)n1] | (S)-N-(2-(4,4-Difluoropiperidin-1-yl)-6-methylpyrimidin-4-yl)-4-((2-fluoro-1-(hydroxymethyl)ethyl)sulfonamido)-2-(6-azaspiro[2.5]octan-6-yl)benzamide, |
| 18-1 | 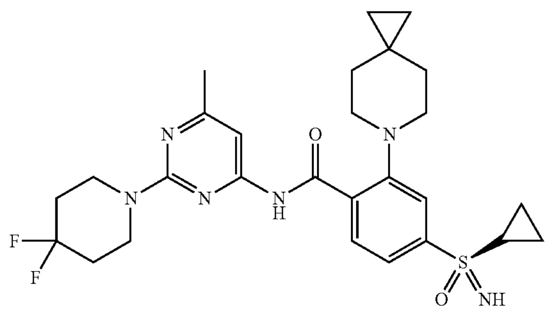 [SMILES: Cc1cc(NC(=O)c2ccc([S@](=N)(=O)C3CC3)cc2N2CCC3(CC2)CC3)nc(N2CCC(F)(F)CC2)n1] | 2-(6-Azaspiro[2.5]octan-6-yl)-4-(R-cyclopropylsulfonimidoyl)-N-(2-(4,4-difluoro-1-piperidinyl)-6-methyl-4-pyrimidinyl)benzamide, |
| 18-2 | 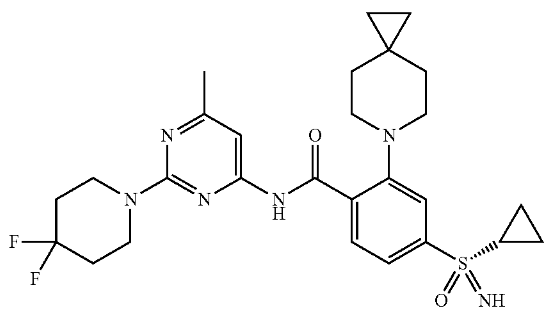 [SMILES: Cc1cc(NC(=O)c2ccc([S@@](=N)(=O)C3CC3)cc2N2CCC3(CC2)CC3)nc(N2CCC(F)(F)CC2)n1] | 2-(6-Azaspiro[2.5]octan-6-yl)-4-(S-cyclopropylsulfonimidoyl)-N-(2-(4,4-difluoro-1-piperidinyl)-6-methyl-4-pyrimidinyl)benzamide, |
| 20 | 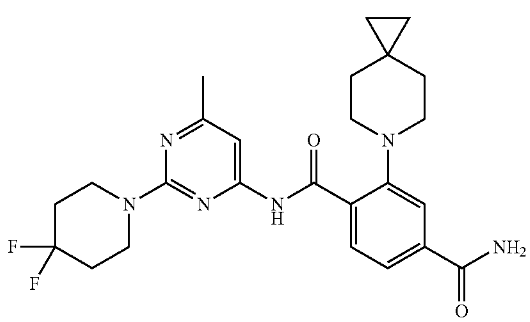 [SMILES: Cc1cc(NC(=O)c2ccc(C(N)=O)cc2N2CCC3(CC2)CC3)nc(N2CCC(F)(F)CC2)n1] | ($N^1$-(2-(4,4-Difluoropiperidin-1-yl)-6-methylpyrimidin-4-yl)-2-(6-azaspiro[2.5]octan-6-yl)terephthalamide, |
| 21 | 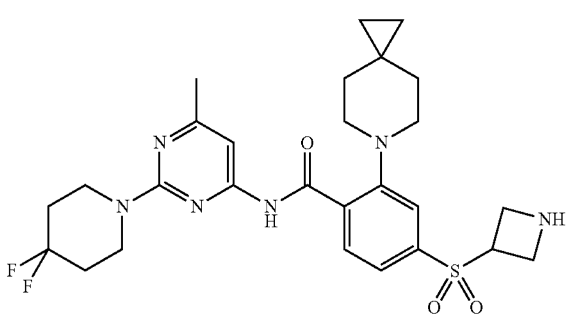 [SMILES: Cc1cc(NC(=O)c2ccc(S(=O)(=O)C3CNC3)cc2N2CCC3(CC2)CC3)nc(N2CCC(F)(F)CC2)n1] | 4-(Azetidin-3-ylsulfonyl)-N-(2-(4,4-difluoropiperidin-1-yl)-6-methylpyrimidin-4-yl)-2-(6-azaspiro[2.5]octan-6-yl)benzamide, and |

-continued

| Ex. # | Chemical Structure | Name |
|---|---|---|
| 22 | | N-(2-(4,4-difluoropiperidin-1-yl)-6-methylpyrimidin-4-yl)-4-((1-methylazetidin-3-yl)sulfonyl)-2-(6-azaspiro[2.5]octan-6-yl)benzamide; | or any pharmaceutically-acceptable salt thereof.

30. A pharmaceutical composition comprising the compound according to claim 1, or the pharmaceutically acceptable salt thereof, and a pharmaceutically-acceptable diluent or carrier.

31. A method of inhibiting KIF18A in a cell, comprising contacting the cell with a compound, or pharmaceutically acceptable salts thereof, in accordance with claim 1, or the pharmaceutically acceptable salt thereof, or the composition according to claim 30.

* * * * *

UNITED STATES PATENT AND TRADEMARK OFFICE
CERTIFICATE OF CORRECTION

PATENT NO. : 12,054,476 B2
APPLICATION NO. : 17/551105
DATED : August 6, 2024
INVENTOR(S) : Nuria A. Tamayo et al.

It is certified that error appears in the above-identified patent and that said Letters Patent is hereby corrected as shown below:

In the Specification

At Column 14, Line numbers 7-11: please replace:
"R)-N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide"
With:
--(R)-N-(2-(4,4-Difluoropiperidin-1-yl)-6-methylpyrimidin-4-yl)-4-((2-hydroxy-1-methylethyl)sulfonamido)-2-(6-azaspiro[2.5]octan-6-yl)benzamide--;

In the Claims

At Column 217, Claim number 1, Line number 62: please replace:
"$R^{4a}$"
With:
--$R^{4b}$--;

At Column 219, Claim number 1, Line number 22: please replace:
"(=O) $R^b$,"
With:
--(=O)$R^b$,--;

At Column 219, Claim number 4, Line number 56: please replace:
"claim 1,"
With:
--claim 1 or 3,--;

At Column 221, Claim number 8, Line numbers 14-15: please replace:
"F, C(=O)OCH$_3$, NH$_2$, NH(CH$_3$), or N(CH$_3$)$_2$"
With:
--F--;

Signed and Sealed this
First Day of July, 2025

Coke Morgan Stewart
*Acting Director of the United States Patent and Trademark Office*

CERTIFICATE OF CORRECTION (continued)
U.S. Pat. No. 12,054,476 B2

At Column 224, Claim number 21, Line number 20-21: please replace:
"-OCH3, and cyclopropyl;"
With:
-- -OCH$_3$;--;

At Column 225-226, Claim number 29, Line number 10: please replace:
"[2,5]"
With:
--[2.5]--;

At Column 229-230, Claim number 29, Line number 11: please replace:
"bcnzamide,"
With:
--benzamide,--;

At Column 233-234, Claim number 29, Line number 9: please replace:
"(R-cyclopropylsulfommidoyl)"
With:
--(R-cyclopropylsulfonimidoyl)--.